United States Patent
Ogita et al.

(10) Patent No.: US 9,553,273 B2
(45) Date of Patent: *Jan. 24, 2017

(54) FLUORENE DERIVATIVE, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Kaori Ogita, Kanagawa (JP); Tsunenori Suzuki, Kanagawa (JP); Harue Osaka, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 318 days.

This patent is subject to a terminal disclaimer.

(21) Appl. No.: 14/161,847

(22) Filed: Jan. 23, 2014

(65) Prior Publication Data

US 2014/0131697 A1    May 15, 2014

Related U.S. Application Data

(63) Continuation of application No. 12/907,699, filed on Oct. 19, 2010, now Pat. No. 8,642,190.

(30) Foreign Application Priority Data

Oct. 22, 2009  (JP) ................ 2009-243646
Nov. 19, 2009  (JP) ................ 2009-264300
Jul. 26, 2010  (JP) ................ 2010-167352

(51) Int. Cl.
    H01L 51/00    (2006.01)
    H01L 51/50    (2006.01)
    (Continued)

(52) U.S. Cl.
    CPC .......... *H01L 51/006* (2013.01); *C07C 211/61* (2013.01); *C09K 11/06* (2013.01); *H01L 51/0058* (2013.01);
    (Continued)

(58) Field of Classification Search
    None
    See application file for complete search history.

(56) References Cited

U.S. PATENT DOCUMENTS 5,312,707 A   5/1994  Ota
5,420,288 A   5/1995  Ohta
(Continued)

FOREIGN PATENT DOCUMENTS

CN    001416301 A   5/2003
CN    001535089 A   10/2004
(Continued)

OTHER PUBLICATIONS

Machine translation for JP 2005-120030 A (publication date: May 2005).*

(Continued)

*Primary Examiner* — Dawn Garrett
(74) *Attorney, Agent, or Firm* — Fish & Richardson P.C.

(57) ABSTRACT

An object is to provide a new fluorene derivative as a good light-emitting material for organic EL elements. A fluorene derivative represented by General Formula (G1) is provided.

(Continued)

US 9,553,273 B2

Page 2

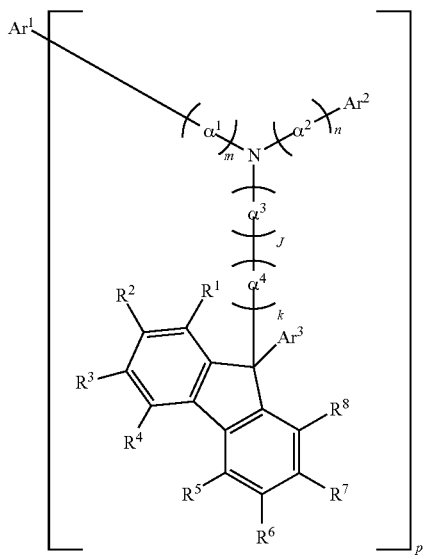

(G1)

In the formula, $R^1$ to $R^8$ separately represent a hydrogen atom, an alkyl group having 1 to 6 carbon atoms, a substituted or unsubstituted phenyl group, or a substituted or unsubstituted biphenyl group. Further, $\alpha^1$ to $\alpha^4$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Further, j, m, and n separately represent 0 or 1, and p represents 1 or 2.

20 Claims, 67 Drawing Sheets

(51) Int. Cl.
  *C07C 211/61* (2006.01)
  *C09K 11/06* (2006.01)
  *H05B 33/10* (2006.01)
(52) U.S. Cl.
  CPC ........... *H01L 51/5012* (2013.01); *H05B 33/10* (2013.01); *C09K 2211/1007* (2013.01); *C09K 2211/1011* (2013.01); *C09K 2211/1014* (2013.01); *H01L 51/0054* (2013.01)

(56) References Cited

U.S. PATENT DOCUMENTS

| | | | |
|---|---|---|---|
| 5,597,925 A | 1/1997 | Ohta | |
| 5,610,309 A | 3/1997 | Ohta | |
| 5,656,401 A | 8/1997 | Ohta | |
| 6,280,859 B1 | 8/2001 | Onikubo et al. | |
| 6,517,957 B1 | 2/2003 | Senoo et al. | |
| 6,858,325 B2 | 2/2005 | Senoo et al. | |
| 6,905,788 B2 | 6/2005 | Tyan | |
| 7,507,485 B2 | 3/2009 | Oh | |
| 7,651,786 B2 | 1/2010 | Matsuura | |
| 7,700,201 B2 | 4/2010 | Seo | |
| 7,732,063 B2 | 6/2010 | Matsuura | |
| 7,919,773 B2 | 4/2011 | Kawakami | |
| 7,927,720 B2 * | 4/2011 | Nomura | C09K 11/06 313/504 |
| 8,436,344 B2 | 5/2013 | Seo | |
| 8,642,190 B2 * | 2/2014 | Ogita | C07C 211/61 313/504 |
| 2001/0033944 A1 | 10/2001 | Onikubo et al. | |
| 2003/0118866 A1 | 6/2003 | Oh | |
| 2004/0110958 A1 | 6/2004 | Nishiyama | |
| 2004/0137274 A1 | 7/2004 | Igarashi | |
| 2005/0221124 A1 | 10/2005 | Hwang | |
| 2006/0033421 A1 | 2/2006 | Matsuura | |
| 2006/0180812 A1 | 8/2006 | Sakata | |
| 2007/0009758 A1 | 1/2007 | Funahashi | |
| 2007/0215867 A1 | 9/2007 | Kawakami | |
| 2007/0215889 A1 | 9/2007 | Kawakami | |
| 2007/0252511 A1 | 11/2007 | Funahashi | |
| 2008/0015399 A1 | 1/2008 | Funahashi | |
| 2008/0122345 A1 | 5/2008 | Sakata | |
| 2008/0124572 A1 | 5/2008 | Mizuki | |
| 2008/0206598 A1 | 8/2008 | Ohsawa | |
| 2010/0155714 A1 | 6/2010 | Seo | |
| 2010/0230666 A1 | 9/2010 | Ohuchi | |
| 2010/0270913 A1 | 10/2010 | Matsuura | |
| 2010/0277061 A1 | 11/2010 | Matsuura | |
| 2010/0301744 A1 | 12/2010 | Osaka | |
| 2010/0314612 A1 | 12/2010 | Lee | |
| 2010/0314615 A1 | 12/2010 | Mizuki et al. | |
| 2011/0156016 A1 | 6/2011 | Kawamura et al. | |
| 2012/0112169 A1 | 5/2012 | Mizuki et al. | |

FOREIGN PATENT DOCUMENTS

| | | |
|---|---|---|
| CN | 001769269 A | 5/2006 |
| CN | 101343234 A | 1/2009 |
| CN | 101494276 A | 7/2009 |
| EP | 0866110 A | 9/1998 |
| EP | 0879868 A | 11/1998 |
| EP | 0934992 A | 8/1999 |
| EP | 1 317 005 A2 | 6/2003 |
| EP | 1 437 395 A2 | 7/2004 |
| EP | 1 604 974 A1 | 12/2005 |
| EP | 2 216 356 A1 | 8/2010 |
| EP | 2314565 A | 4/2011 |
| JP | 06-065569 A | 3/1994 |
| JP | 06-089039 A | 3/1994 |
| JP | 06-107605 A | 4/1994 |
| JP | 06-220437 A | 8/1994 |
| JP | 10-251633 A | 9/1998 |
| JP | 11-035532 A | 2/1999 |
| JP | 2002-179630 A | 6/2002 |
| JP | 2004-204238 A | 7/2004 |
| JP | 2005-120030 A | 5/2005 |
| JP | 2007-015933 A | 1/2007 |
| JP | 2007-153776 A | 6/2007 |
| JP | 3983215 B2 | 9/2007 |
| JP | 2008-205491 A | 9/2008 |
| JP | 2009-149850 A | 7/2009 |
| JP | 5268207 | 8/2013 |
| JP | 5657729 | 1/2015 |
| JP | 5700771 | 4/2015 |
| JP | 5732602 | 6/2015 |
| WO | WO-2005/108348 | 11/2005 |
| WO | WO 2009/069523 A1 | 4/2009 |
| WO | WO 2009/069523 A1 | 6/2009 |
| WO | WO-2009/084512 | 7/2009 |
| WO | WO-2010/013675 | 2/2010 |
| WO | WO-2010/013676 | 2/2010 |
| WO | WO-2010/122810 | 10/2010 |

OTHER PUBLICATIONS

Ping-I Shih et al.; "A Novel Fluorene-Triphenylamine Hybrid That is a Highly Efficient Host Material for Blue-, Green-, and Red-Light-Emitting Electrophopsphorescent Devices"; Advanced Functional Materials; 2007; pp. 3514-3520; vol. 17.

(56) References Cited

OTHER PUBLICATIONS

Goldsmith.C et al., "C—H Bond Activation by a Ferric Methoxide Complex: Modeling the Rate-Determining Step in the Mechanism of Lipoxygenase," J. Am. Chem. Soc. (Journal of the American Chemical Society), 2002, vol. 124, No. 1, pp. 83-96.
Onishi T. et al., "A Method of Measuring an Energy Level," High Molecular EL Materials—Development of Light-Emitting High Molecular Compounds, Dec. 25, 2004, pp. 64-67, Kyoritsu Shuppan.
European Search Report (European Application No. 10188228.0) dated Feb. 16, 2011, 6 pages.
Chihaya Adachi et al.; "Durability Characteristics of Aminopyrene Dimer Molecules as an Emitter in Organic Multilayered Electroluminescent Diodes"; Jpn. J. Appl. Phys. (Japanese Journal of Applied Physics); Jun. 11, 1996; pp. 4819-4825; vol. 35, No. 9A.
Office Action, Chinese Application No. 201010532920.X, dated Sep. 6, 2013, 27 pages with full English translation.

* cited by examiner

FLUORENE DERIVATIVE, LIGHT-EMITTING ELEMENT, LIGHT-EMITTING DEVICE, ELECTRONIC DEVICE, AND LIGHTING DEVICE

CROSS-REFERENCE TO RELATED APPLICATIONS

This application is a continuation of U.S. application Ser. No. 12/907,699, filed Oct. 19, 2010, now allowed, which claims the benefit of foreign priority applications filed in Japan as Serial No. 2009-243646 on Oct. 22, 2009, Serial No. 2009-264300 on Nov. 19, 2009, and Serial No. 2010-167352 on Jul. 26, 2010, all of which are incorporated by reference.

BACKGROUND OF THE INVENTION

1. Field of the Invention

The present invention relates to a novel material applicable to a light-emitting element at least part of which includes an organic compound, and also relates to a light-emitting element, a light-emitting device, an electronic device, and a lighting device using the material.

2. Description of the Related Art

In recent years, research and development have been extensively conducted on light-emitting elements using electroluminescence (EL). In a basic structure of such a light-emitting element, a layer which includes a light-emitting substance is interposed between a pair of electrodes. By voltage application to this element, light emission can be obtained from the light-emitting substance having a light-emitting property.

Since such a light-emitting element is of self-light-emitting type, it is thought that the light-emitting element has advantages over a liquid crystal display in that visibility of pixels is high, backlight is not required, and so on and is therefore suitable as flat panel display elements. Besides, such a light-emitting element has advantages in that it can be formed to be thin and lightweight, and has quite fast response speed.

Furthermore, since such a light-emitting element can be formed in a film form, planar light emission can be easily obtained by formation of an element having a large area. This is a feature that is difficult to obtain with point light sources typified by an incandescent lamp and an LED or linear light sources typified by a fluorescent lamp. Accordingly, the light-emitting element is extremely effective for use as a surface light source applicable to lighting and the like.

Light-emitting elements utilizing electroluminescence are broadly classified according to whether they use an organic compound or an inorganic compound as a light-emitting substance. In an organic EL element using an organic compound as a light-emitting substance, by voltage application to a light-emitting element, electrons and holes are injected from a pair of electrodes into a layer including the light-emitting organic compound, and a current flows. Then, both the electrons and holes recombine to form an excited state in the light-emitting organic compound, and the excited state returns to a ground state, whereby luminescence occurs.

Having such a mechanism, the above-described light-emitting element is called a current-excitation light-emitting element. Note that the excited state generated by an organic compound can be a singlet excited state or a triplet excited state. Luminescence from the singlet excited state is referred to as fluorescence, and luminescence from the triplet excited state is referred to as phosphorescence.

In addition to light emission by recombination of carriers excited with a current, there is also a method of light emission in which excitation energy is transferred from an organic compound excited with a current to another organic compound and accordingly the latter organic compound is excited to emit light. This method is effective against an emission efficiency reduction (concentration quenching) due to stacking interaction caused by a high concentration of organic molecules that are desired to emit light. In organic EL elements, the method is generally applied to the element structure in which a light-emitting material is dispersed in a light-emitting layer (a light-emitting layer is doped with a light-emitting material). Doping a host material with organic molecules that are desired to emit light suppresses the stacking interaction, whereby efficiency of a light-emitting element can be increased. In such a light-emitting element, excitation energy is transferred from a host material excited by current excitation to a dopant material, making the dopant material emit light. Note that when Substance A is dispersed in a matrix formed of Substance B, Substance B forming the matrix is called a host material while Substance A dispersed in the matrix is called a dopant material.

Light emitted from a light-emitting material is peculiar to the material. It is very difficult to obtain light-emitting elements that emit light of good color and to fulfill important conditions such as lifetime and power consumption. The significant performances on lifetime, power consumption, and the like of light-emitting elements depend not only on substances that emit light but also largely on layers other than a light-emitting layer, element structures, compatibility between a light-emitting substance and a host, etc. Therefore, materials having various molecular structures have been proposed as light-emitting element materials (e.g., see Patent Document 1).

Further, commercialization of light-emitting elements makes a lifetime increase an important issue. In addition, light-emitting elements have been expected to exhibit improved properties.

REFERENCE

[Patent Document 1] Japanese Published Patent Application No. 2007-015933

SUMMARY OF THE INVENTION

In view of the foregoing, an object of one embodiment of the present invention is to provide a novel fluorene derivative as a good light-emitting material for an organic EL element.

Another object is to provide a light-emitting element, a light-emitting device, a lighting device, and an electronic device using the above novel fluorene derivative.

Through detailed studies, the inventors have succeeded in the synthesis of a fluorene derivative represented by Structural Formula (F1) below which has a unit in which a fluorene skeleton and an amine compound are bonded through a sigma bond, as a substance preferably applicable to a light-emitting element material.

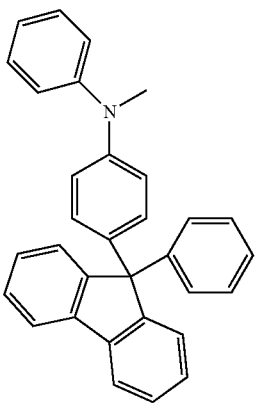
(F1)

Thus, a fluorene derivative of one embodiment of the present invention is the fluorene derivative represented by General Formula (G1) below.

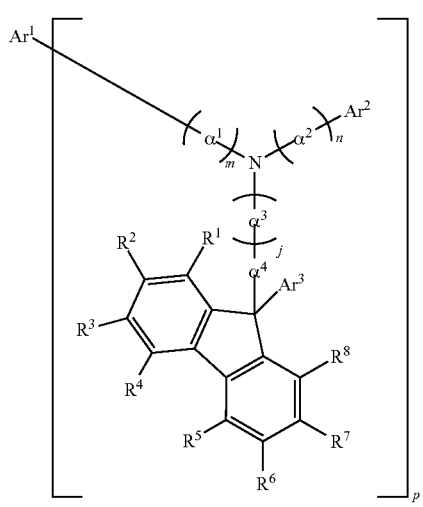
(G1)

In General Formula (G1), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $\alpha^1$ to $\alpha^4$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Further, j, m, and n separately represent 0 or 1, and p represents 1 or 2.

In addition, examples of $Ar^1$ in General Formula (G1) include a substituted or unsubstituted phenanthryl group, a substituted or unsubstituted pyrenyl group, a substituted or unsubstituted triphenylenyl group, a substituted or unsubstituted chrysenyl group, a substituted or unsubstituted anthryl group, a substituted or unsubstituted pentacenyl group, and a substituted or unsubstituted tetracenyl group.

Specifically, $Ar^1$ in General Formula (G1) is preferably a substituent represented by any of General Formulas (Ar1-1) to (Ar1-4) below.

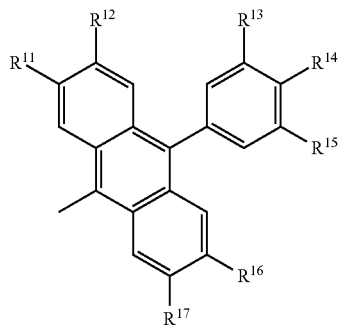
(Ar1-1)

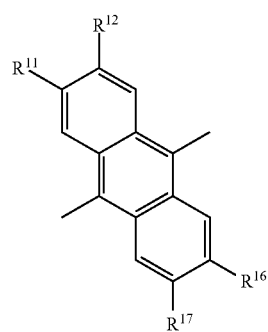
(Ar1-2)

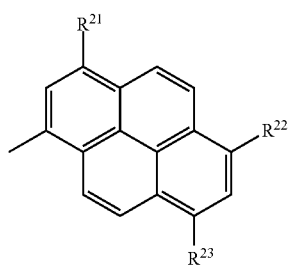
(Ar1-3)

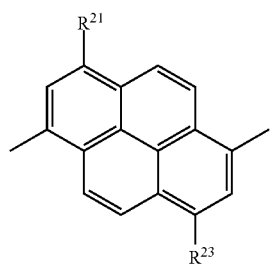
(Ar1-4)

In General Formulas (Ar1-1) to (Ar1-4), $R^{11}$ to $R^{17}$ and $R^{21}$ to $R^{23}$ each separately represent a hydrogen atom or an alkyl group having 1 to 6 carbon atoms. In General Formula (G1), p is 1 when $Ar^1$ is represented by General Formula (Ar1-1) or (Ar1-3), and p is 2 when $Ar^1$ is represented by General Formula (Ar1-2) or (Ar1-4).

Further, a fluorene derivative of another embodiment of the present invention is the fluorene derivative represented by General Formula (G2) below.

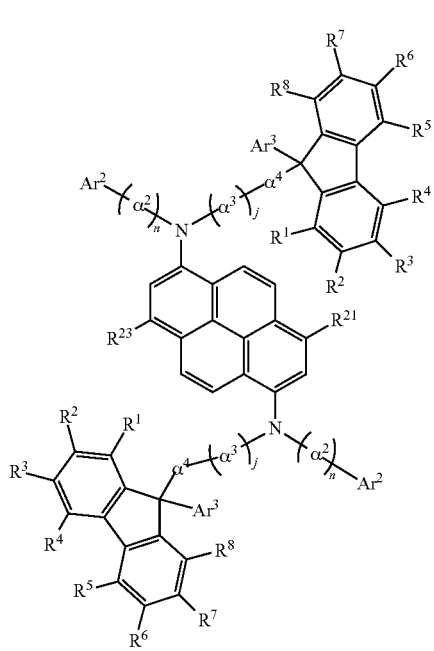

(G2)

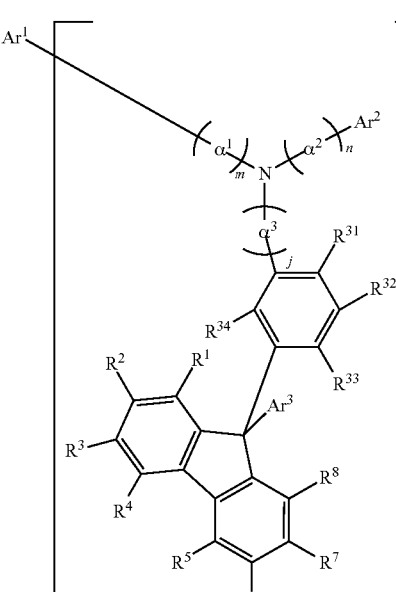

(G3)

In General Formula (G2), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $R^{21}$ to $R^{23}$ each separately represent a hydrogen atom or an alkyl group having 1 to 6 carbon atoms. Furthermore, $\alpha^2$ to $\alpha^4$ separately represent a substituted or unsubstituted phenylene group. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Furthermore, j and n separately represent 0 or 1.

It is preferable that $\alpha^1$ to $\alpha^4$ in the above General Formulas (G1) and (G2) be separately represented by any of Structural Formulas ($\alpha$-1) to ($\alpha$-3) below.

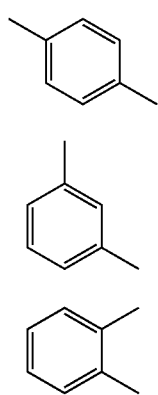

($\alpha$-1)

($\alpha$-2)

($\alpha$-3)

Further, a fluorene derivative of still another embodiment of the present invention is the fluorene derivative represented by General Formula (G3) below.

In General Formula (G3), $R^1$ to $R^8$ and $R^{31}$ to $R^{34}$ separately represent any of a hydrogen atom, an alkyl group having 1 to 6 carbon atoms, a substituted or unsubstituted phenyl group, or a substituted or unsubstituted biphenyl group. Further, $\alpha^1$ to $\alpha^3$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Further, j, m, and n separately represent 0 or 1, and p represents 1 or 2.

Further, a fluorene derivative of yet another embodiment of the present invention is the fluorene derivative represented by General Formula (G4) below.

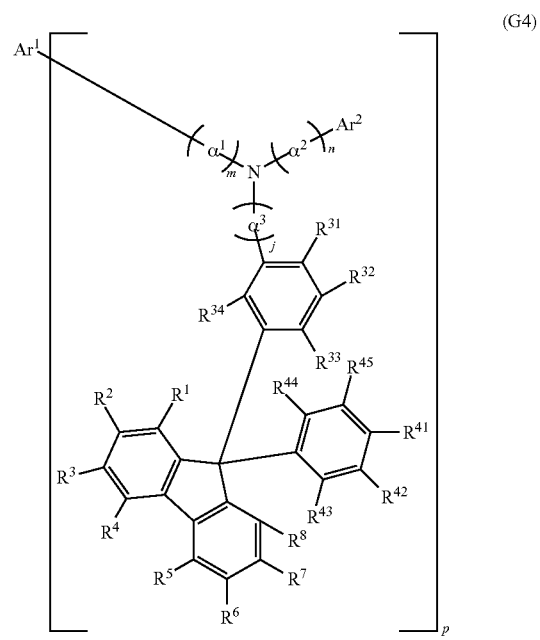

(G4)

In General Formula (G4), $R^1$ to $R^8$, $R^{31}$ to $R^{34}$, and $R^{41}$ to $R^{45}$ separately represent any of a hydrogen atom, an alkyl group having 1 to 6 carbon atoms, a substituted or unsubstituted phenyl group, or a substituted or unsubstituted biphenyl group. Further, $\alpha^1$ to $\alpha^3$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. Further, j, m, and n separately represent 0 or 1, and p represents 1 or 2.

It is preferable that $Ar^2$ in the above General Formulas (G1) to (G4) be represented by any of Structural Formulas (Ar2-1) to (Ar2-6) below.

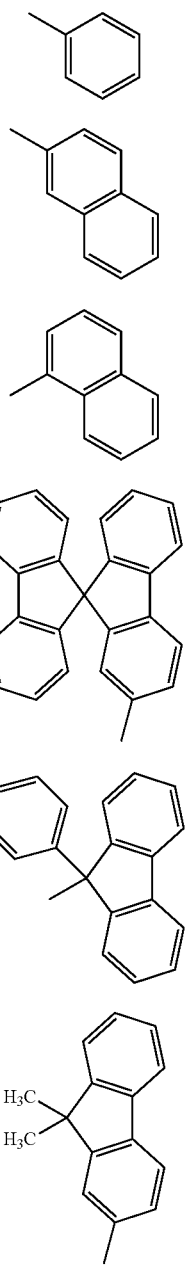

It is also preferable that $Ar^3$ in the above General Formulas (G1) to (G4) is represented by any of Structural Formulas (Ar3-1) to (Ar3-8) below.

(Ar3-1)

(Ar3-2)

(Ar3-3)

(Ar3-4)

(Ar3-5)

(Ar3-6)

(Ar3-7)

(Ar3-8)

Further, it is preferable that $R^1$ to $R^8$ in the above General Formulas (G1) to (G4) be separately represented by any of Structural Formulas (R-1) to (R-9) below.

(R-1)

(R-2)

(R-3)

(R-4)

(R-5)

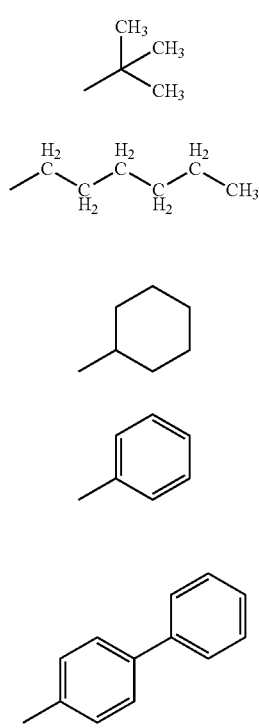

(R-6)

(R-7)

(R-8)

(R-9)

Another embodiment of the present invention is the fluorene derivative represented by Structural Formula (124) below.

(124)

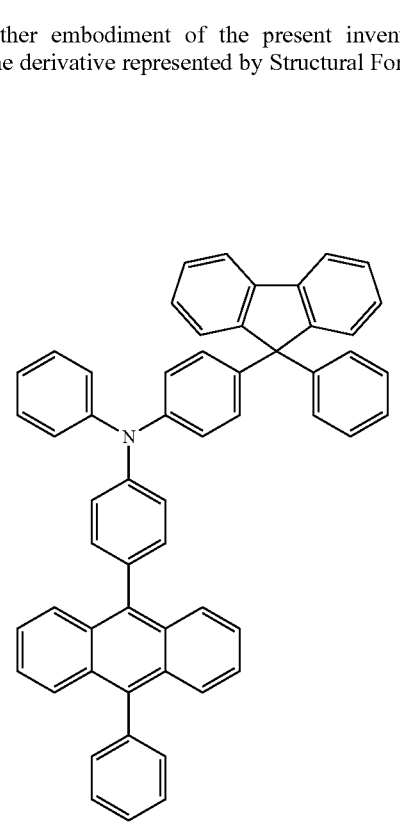

Still another embodiment of the present invention is the fluorene derivative represented by Structural Formula (100) below.

(100)

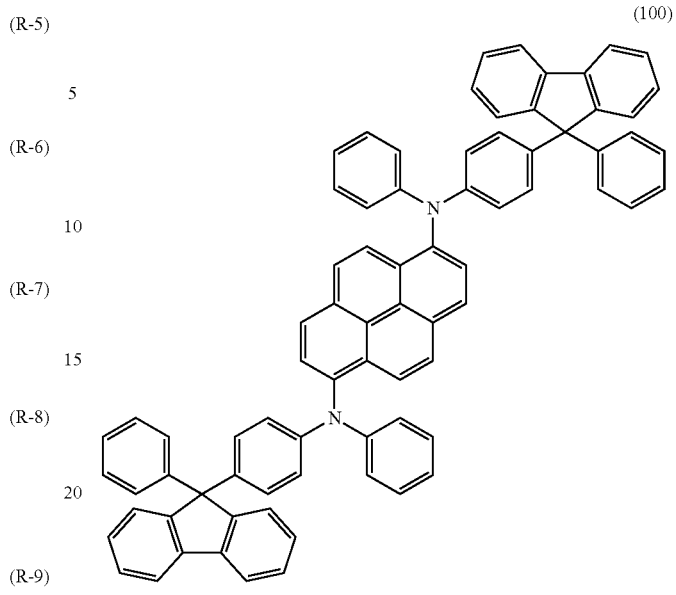

Yet another embodiment of the present invention is the fluorene derivative represented by Structural Formula (102) below.

(102)

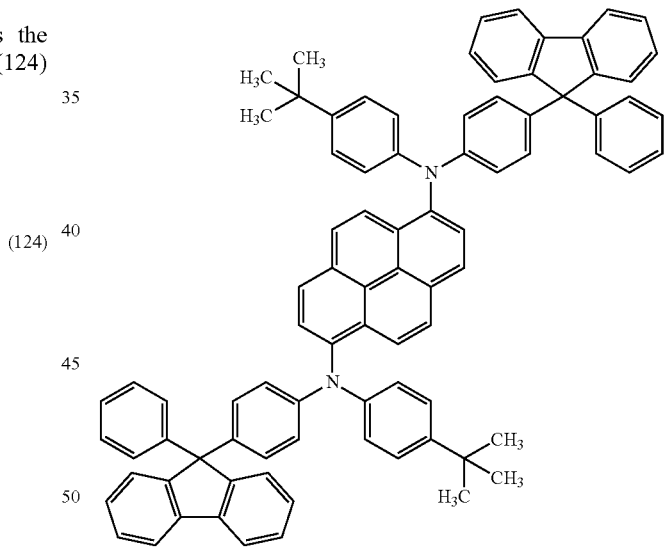

Further, another embodiment of the present invention is a light-emitting element including an EL layer between a pair of electrodes. The EL layer includes at least a light-emitting layer and the light-emitting layer includes any of the above fluorene derivatives.

Furthermore, another embodiment of the present invention is a light-emitting device formed using the above light-emitting element. Still another embodiment of the present invention is an electronic device formed using the light-emitting device. Yet another embodiment of the present invention is a lighting device formed using the light-emitting device The light-emitting device of one embodiment of the present invention is a light-emitting device including the above light-emitting element and a control unit which controls the light emission from the light-emitting element. Note that the light-emitting device in this specification includes image display devices, light-emitting devices, or light sources (including lighting devices). In addition, the light-emitting device includes the following modules in its category: a module in which a connector such as an flexible printed circuit (FPC), a tape automated bonding (TAB) tape, or a tape carrier package (TCP) is attached to a panel; a module having a TAB tape or a TCP provided with a printed wiring board at the end thereof; and a module having an integrated circuit (IC) directly mounted on a light-emitting element by a chip on glass (COG) method.

The present invention also covers an electronic device in which its display portion has the light-emitting device of one embodiment of the present invention. Thus, an electronic device of one embodiment of the present invention has a display portion, in which the display portion includes the above light-emitting device.

Furthermore, the present invention covers a lighting device using the light-emitting device of one embodiment of the present invention. Therefore, a lighting device of one embodiment of the present invention includes the above light-emitting device.

A fluorene derivative of one embodiment of the present invention can emit light with a short wavelength; the fluorene derivative can provide blue light emission with high color purity.

In addition, the fluorene derivative of one embodiment of the present invention is used to form a light-emitting element, whereby the light-emitting element achieves high emission efficiency and high reliability.

Furthermore, by use of such a light-emitting element, a light-emitting device, an electronic device, and a lighting device with high reliability can be obtained.

DETAILED DESCRIPTION OF THE INVENTION

Figure 1A:
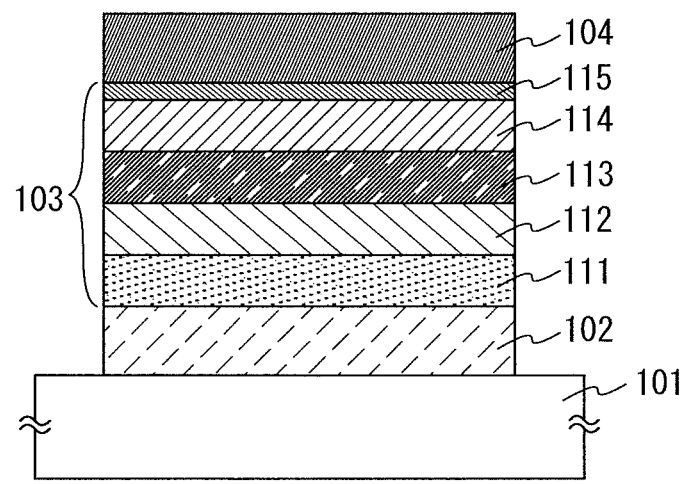
FIGS. 1A and 1B each illustrate a light-emitting element.

Hereinafter, embodiments of the present invention are described with reference to the drawings. Note that the invention is not limited to the following description, and it will be easily understood by those skilled in the art that various changes and modifications can be made without departing from the spirit and scope of the invention. Therefore, the invention should not be construed as being limited to the description in the following embodiments.

(Embodiment 1)

In this embodiment, a fluorene derivative of one embodiment of the present invention is described.

A fluorene derivative of this embodiment is the fluorene derivative represented by General Formula (G1).

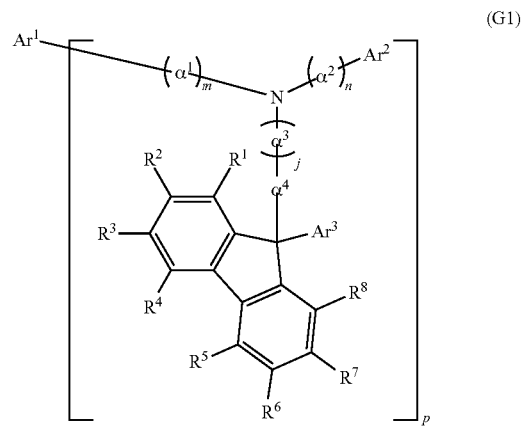

(G1)

In General Formula (G1), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $\alpha^1$ to $\alpha^4$ separately represent a substituted or unsubstituted phenylene group. $Ar^1$ represents a substituted or unsubstituted condensed aromatic hydrocarbon having 14 to 18 carbon atoms forming a ring. $Ar^2$ represents an aryl group having 6 to 13 carbon atoms forming a ring. $Ar^3$ represents an alkyl group having 1 to 6 carbon atoms or a substituted or unsubstituted aryl group having 6 to 12 carbon atoms. Further, j, m, and n separately represent 0 or 1, and p represents 1 or 2.

An alkyl group is preferably used as a substituent in General Formula (G1) for the following reasons. The use of an alkyl group improves solubility in an organic solvent, whereby purification is facilitated and then a more uniform film can be formed in wet process manufacture of an organic EL element. Moreover, the use of an alkyl group makes molecules form a more three-dimensional structure, which leads to improved film properties and more suppression of concentration quenching and excimer formation.

In addition, examples of $Ar^1$ in General Formula (G1) include a substituted or unsubstituted phenanthryl group, a substituted or unsubstituted pyrenyl group, a substituted or unsubstituted triphenylenyl group, a substituted or unsubstituted chrysenyl group, a substituted or unsubstituted anthryl group, a substituted or unsubstituted pentacenyl group, and a substituted or unsubstituted tetracenyl group. Specifically, $Ar^1$ in General Formula (G1) is a substituent represented by any of the following General Formulas (Ar1-1) to (Ar1-4).

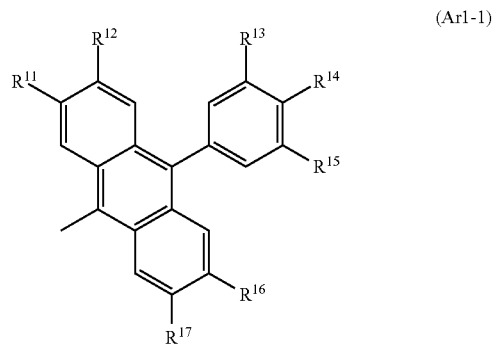

(Ar1-1)

-continued

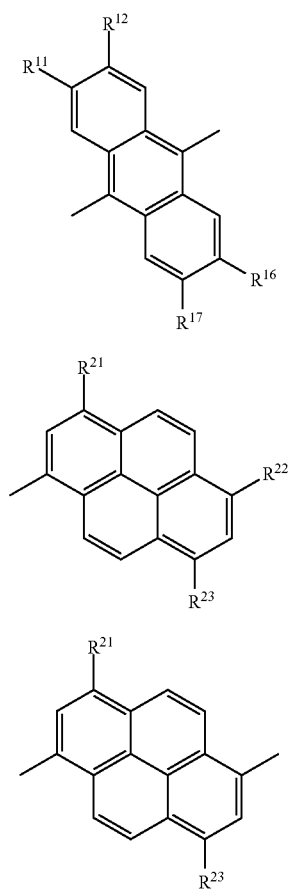

(Ar1-2)

(Ar1-3)

(Ar1-4)

The fluorene derivative of one embodiment of the present invention represented by General Formula (G1) preferably has a substituent represented by any of (Ar1-1) to (Ar1-4) because such a fluorene derivative provides a high yield and high emission efficiency.

In General Formulas (Ar1-1) to (Ar1-4), $R^{11}$ to $R^{17}$ and $R^{21}$ to $R^{23}$ each separately represent a hydrogen atom or an alkyl group having 1 to 6 carbon atoms. As an alkyl group having 1 to 6 carbon atoms, a methyl group, an ethyl group, a propyl group, a pentyl group, a hexyl group, a cyclohexyl group, and the like are specifically given. An alkyl group is preferred as a substituent for the following reasons. The use of an alkyl group improves solubility in an organic solvent, whereby purification is facilitated and then a more uniform film can be formed in wet process manufacture of an organic EL element. Moreover, the alkyl group makes molecules form a more three-dimensional structure, which leads to improved film properties and more suppression of concentration quenching and excimer formation.

In the case where $R^1$ to $R^8$, $\alpha^1$ to $\alpha^4$, $Ar^1$, and $Ar^2$ individually have a substituent, the substituent may be an alkyl group such as a methyl group, an ethyl group, a propyl group, a pentyl group or a hexyl group, or an aryl group such as a phenyl group or a biphenyl group. Such alkyl groups may be connected to each other to form a ring.

In addition, as the fluorene derivative represented by General Formula (G1), the fluorene derivative represented by General Formula (G2) below is preferable.

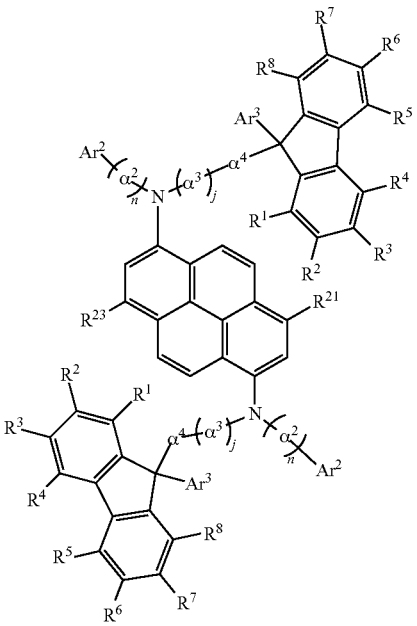

(G2)

The fluorene derivative of one embodiment of the present invention represented by General Formula (G2) shows an emission spectrum with a sharp peak and easily exhibits emission color with high color purity, especially blue with high color purity. In addition, because of the small Stokes shift of this material, when it is added as a light-emitting material to dope a host material in an organic EL element, energy transfer efficiently occurs from the host material and high emission efficiency can be easily obtained.

In General Formula (G2), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $R^{21}$ and $R^{23}$ separately represent a hydrogen atom or an alkyl group having 1 to 6 carbon atoms. Furthermore, $\alpha^2$ to $\alpha^4$ separately represent a substituted or unsubstituted phenylene group. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Furthermore, j and n separately represent 0 or 1.

Specific examples of $Ar^2$ in General Formulas (G1) and (G2) include substituents represented by Structural Formulas (Ar2-1) to (Ar2-6) below.

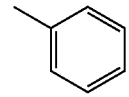

(Ar2-1)

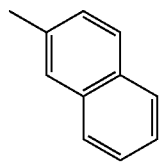

(Ar2-2)

(Ar2-3)
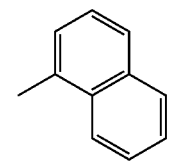

(Ar2-4)
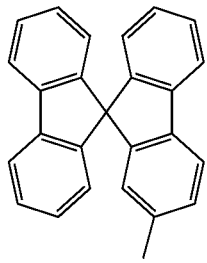

(Ar2-5)
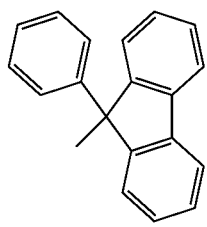

(Ar2-6)
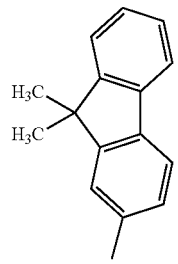

Specific examples of $Ar^3$ in General Formulas (G1) and (G2) include substituents represented by Structural Formulas (Ar3-1) to (Ar3-8) below.

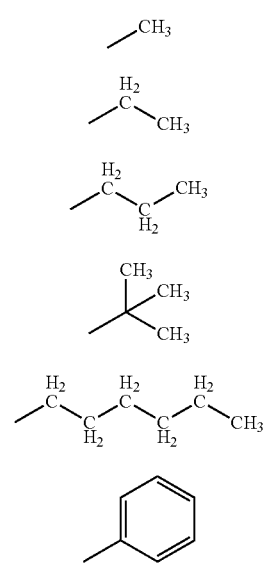

(Ar3-1)
(Ar3-2)
(Ar3-3)
(Ar3-4)
(Ar3-5)
(Ar3-6)

(Ar3-7)
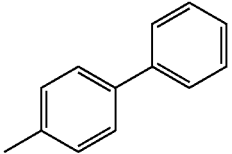

(Ar3-8)
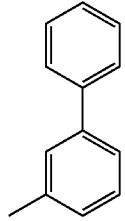

Specific examples of $\alpha^1$ to $\alpha^4$ in General Formulas (G1) and (G2) include substituents represented by Structural Formulas ($\alpha$-1) to ($\alpha$-3) below.

($\alpha$-1)
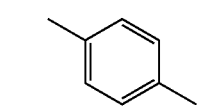

($\alpha$-2)
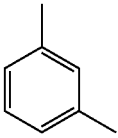

($\alpha$-3)
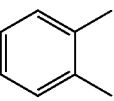

Substituents represented by Structural Formulas (R-1) to (R-9) below are specifically given as $R^1$ to $R^8$ in General Formulas (G1) and (G2) and $R^{11}$ to $R^{17}$ and $R^{21}$ to $R^{23}$ in General Formulas (Ar1-1) to (Ar1-4).

As in Structural Formulas (R-2) to (R-7) below, an alkyl group is preferably used as a substituent for the following reasons. The use of an alkyl group improves solubility in an organic solvent, whereby purification is facilitated and then a more uniform film can be formed in wet process manufacture of an organic EL element. Moreover, the use of an alkyl group makes molecules form a more three-dimensional structure, which leads to improved film properties and more suppression of concentration quenching and excimer formation.

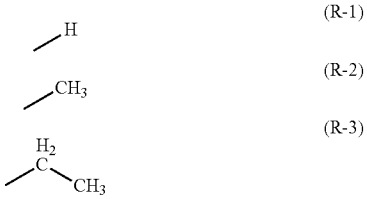

(R-1)
(R-2)
(R-3)

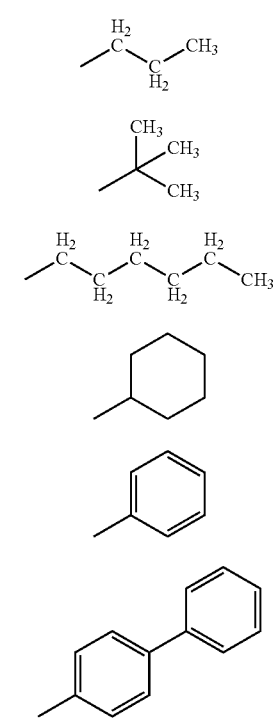

(R-4)
(R-5)
(R-6)
(R-7)
(R-8)
(R-9)

Specific examples of the fluorene derivative represented by General Formula (G1) include, but not limited to, the fluorene derivatives represented by Structural Formulas (100) to (115) and (120) to (127).

As in Structural Formulas (102), (103), (106) to (111), (113), (121), (122), (128), and (131), an alkyl group is preferably used as a substituent for the following reasons. The use of an alkyl group improves solubility in an organic solvent, whereby purification is facilitated and then a more uniform film can be formed in wet process manufacture of an organic EL element. Moreover, the use of an alkyl group makes molecules form a more three-dimensional structure, which leads to improved film properties and more suppression of concentration quenching and excimer formation.

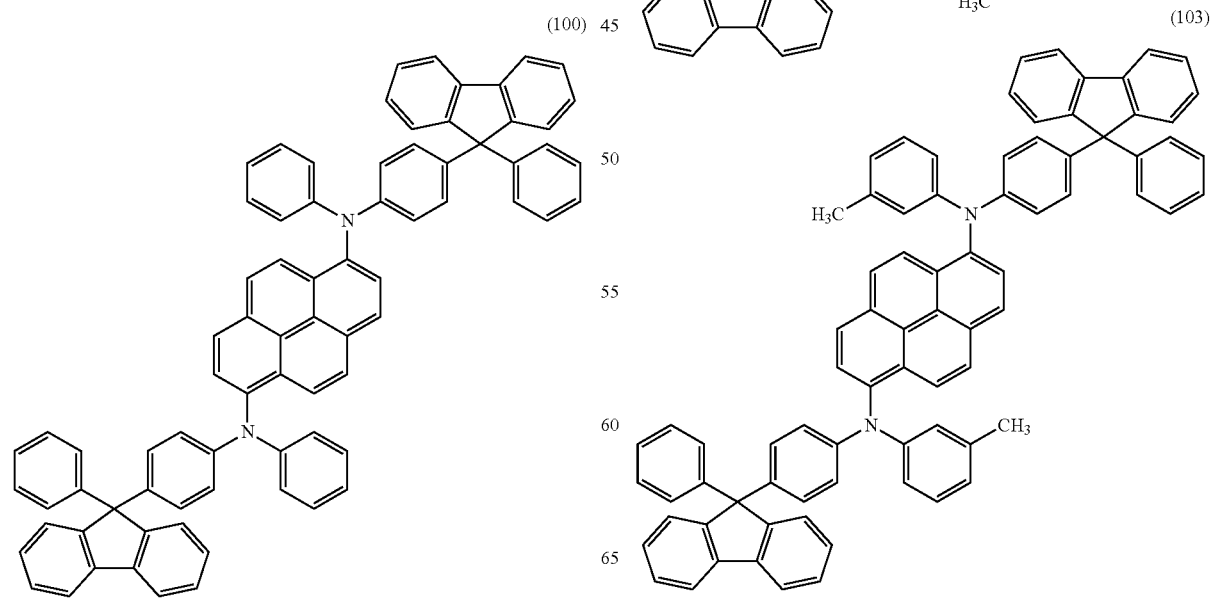

(100)

(101)

(102)

(103)

(104)
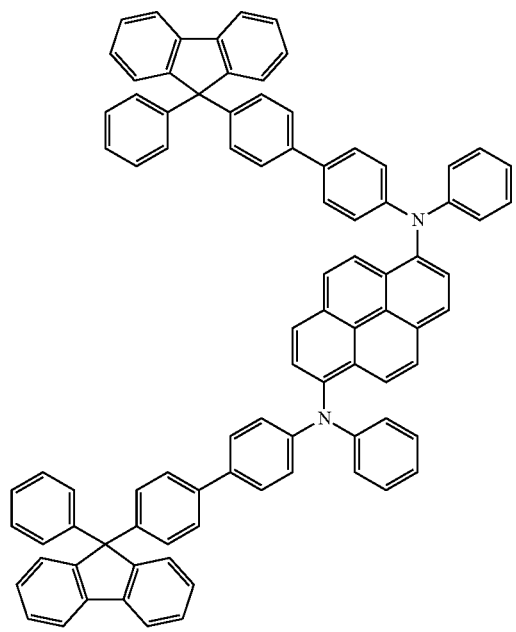
(105)
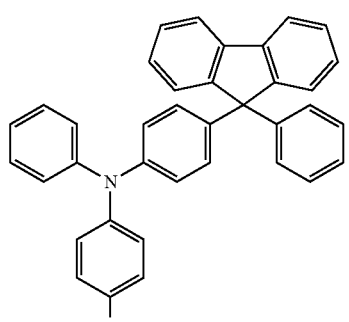
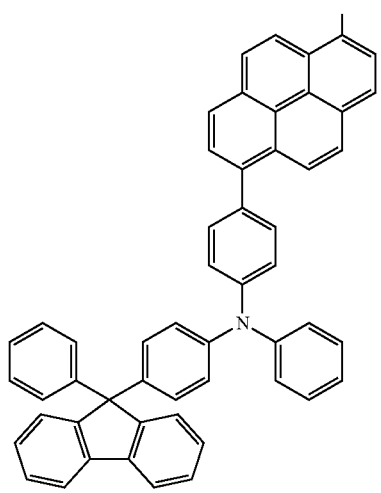
(106)
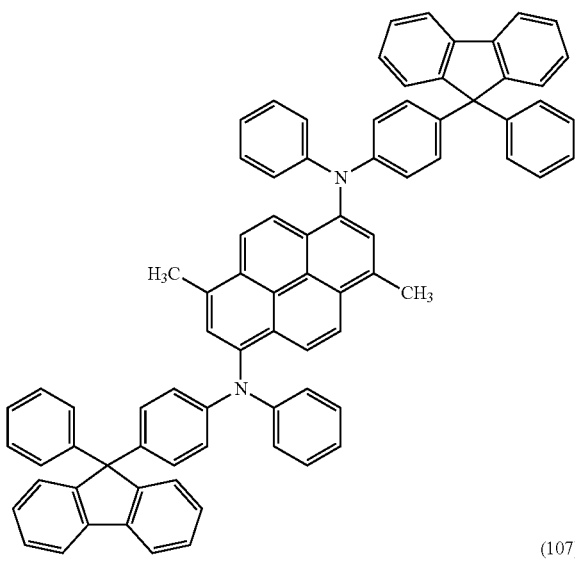
(107)
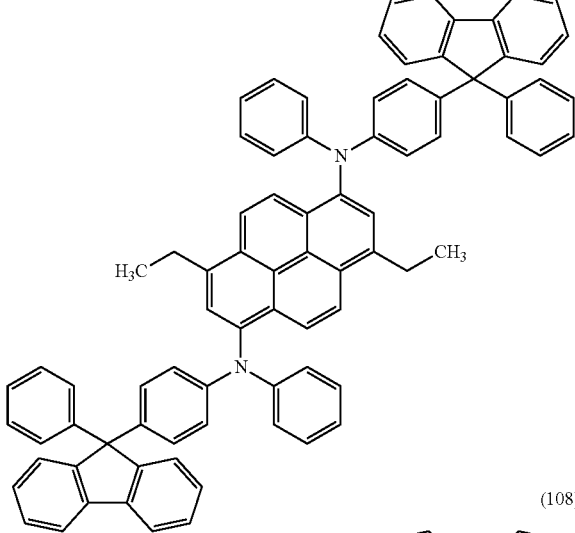
(108)
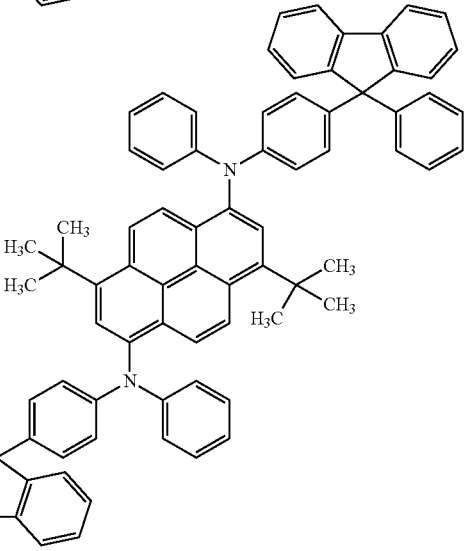

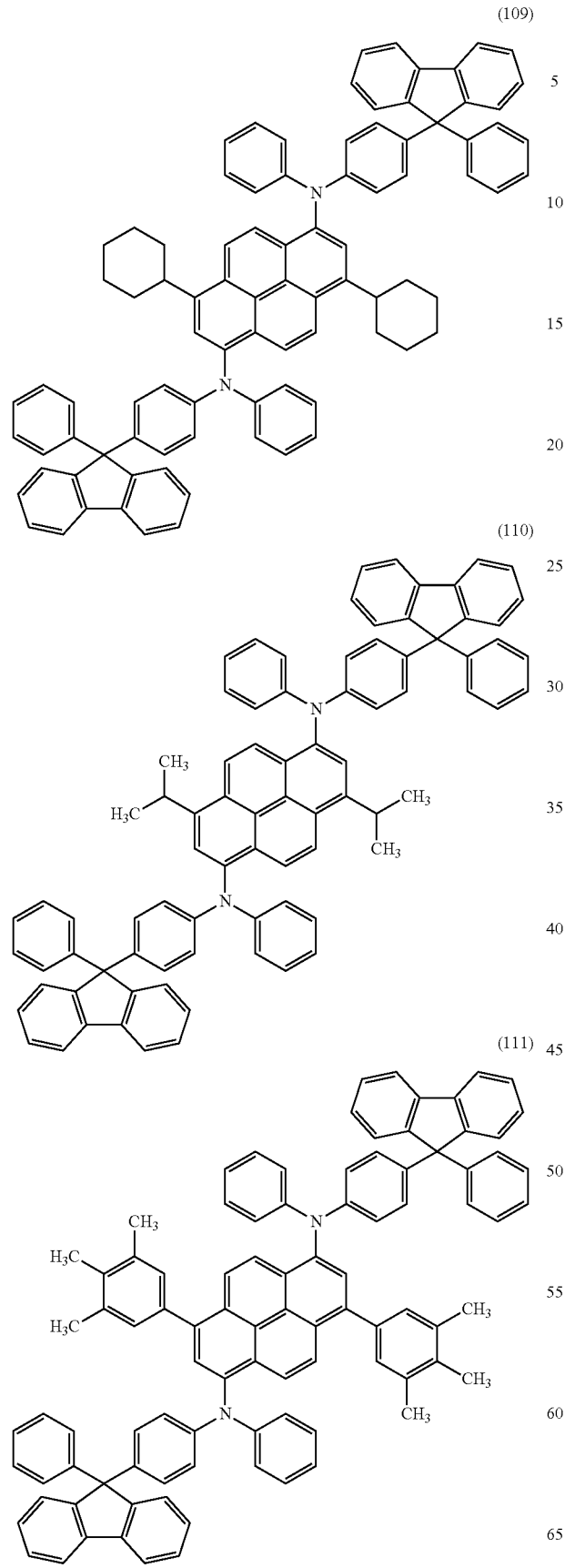
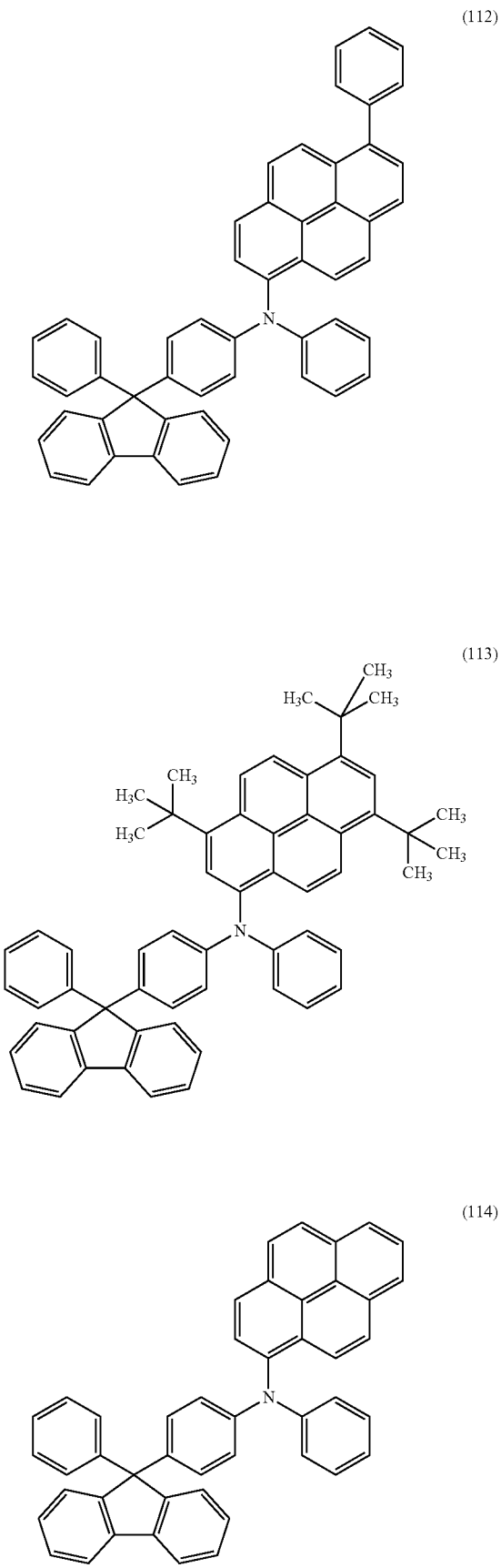

-continued
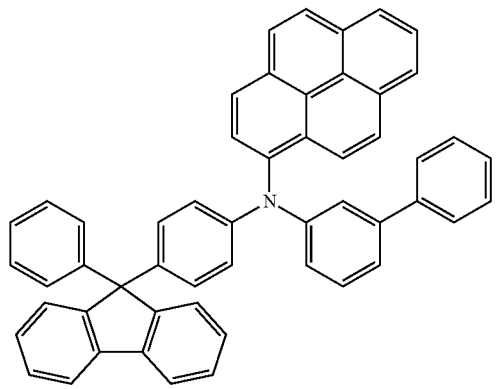
(115)
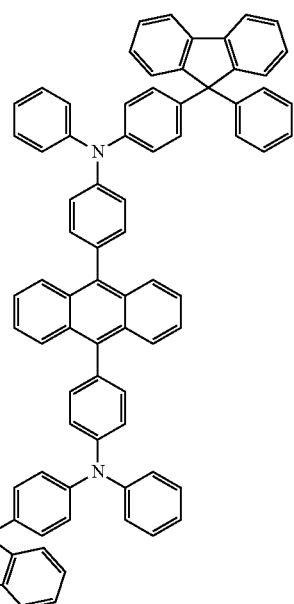
(120)
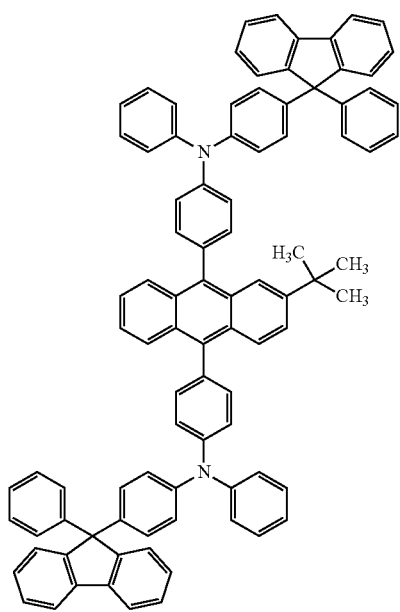
(121)
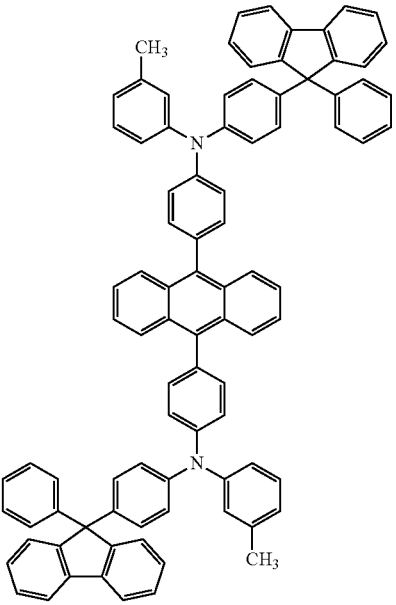
(122)
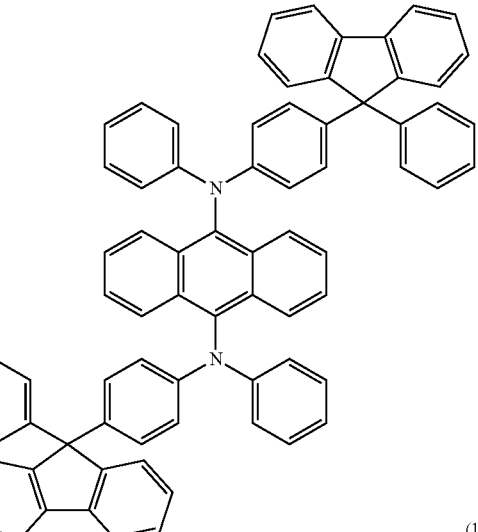
(123)
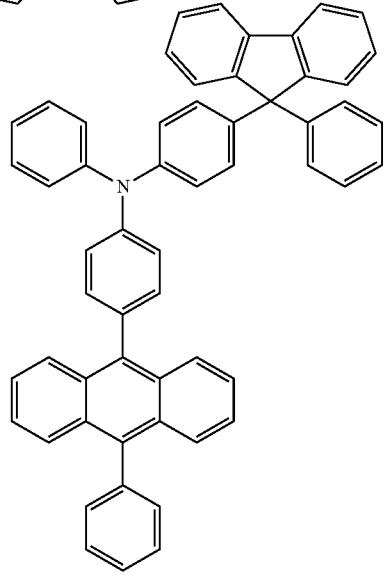
(124)

(125) 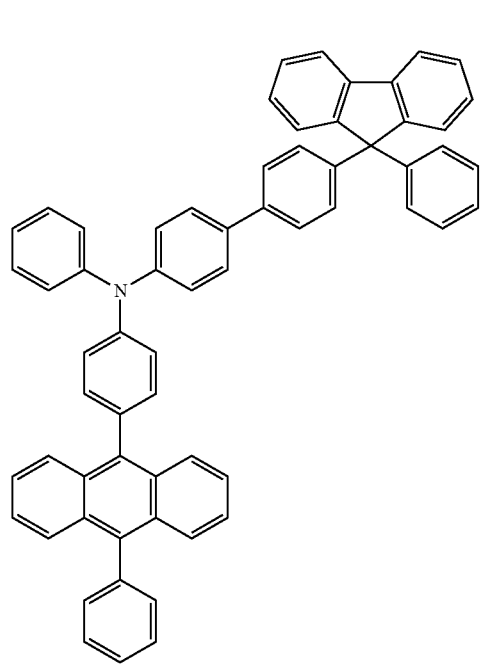
(127) 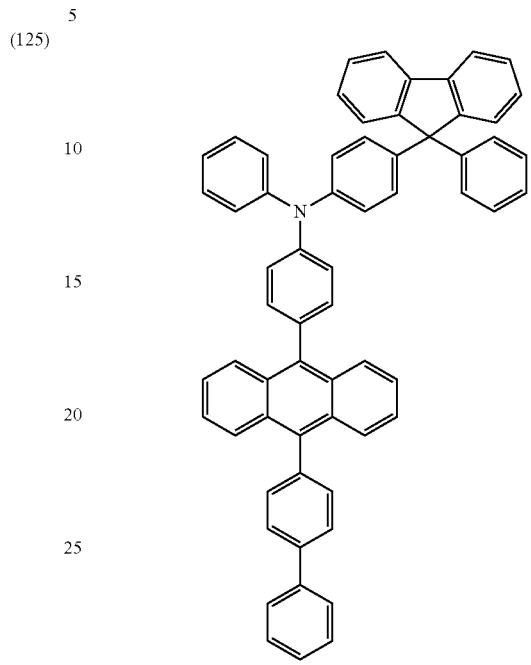
(126) 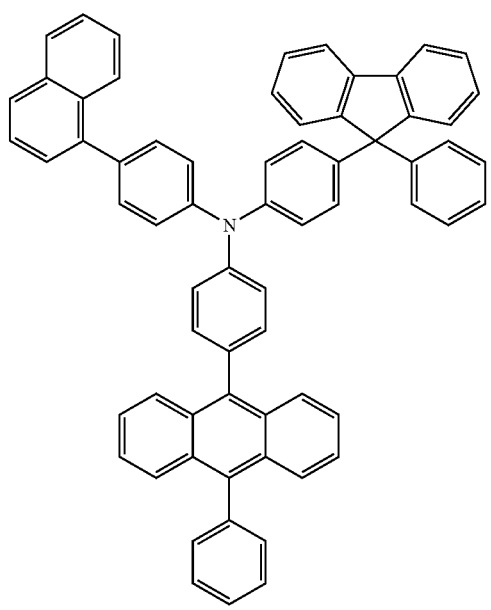
(128) 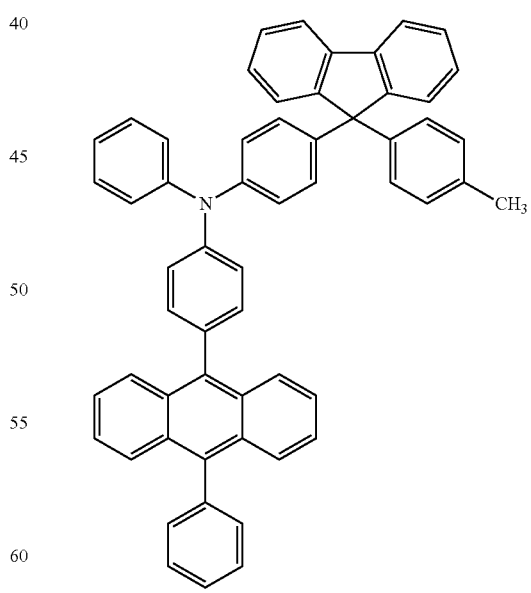

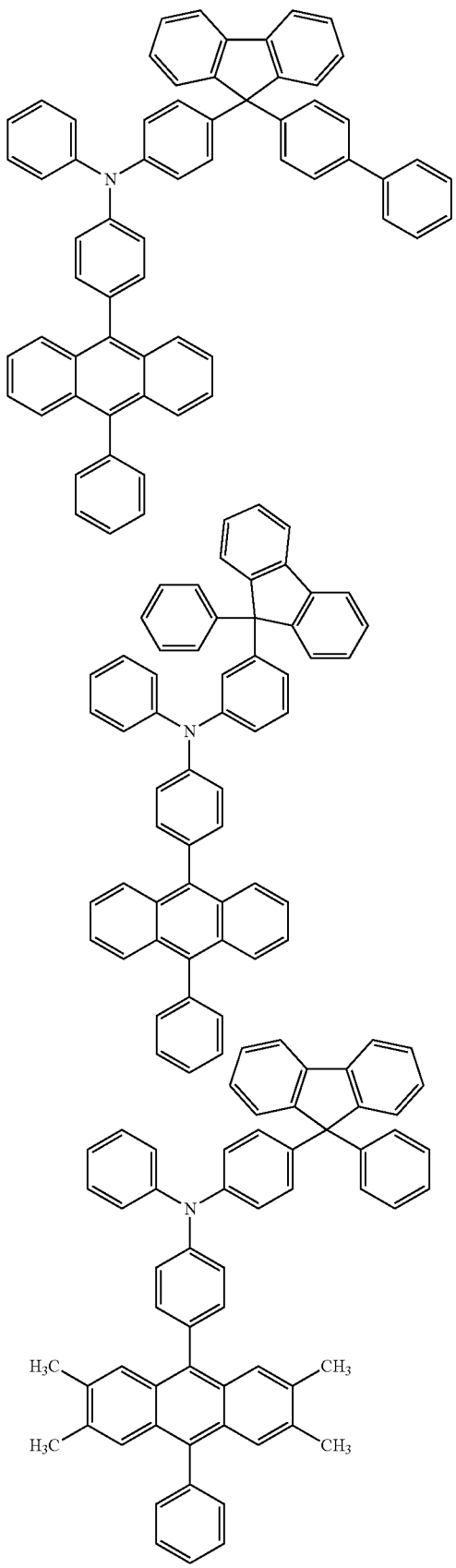

(129)

(130)

(131)

A variety of reactions can be applied to a method for synthesizing a fluorene derivative of this embodiment. For example, the fluorene derivative of this embodiment represented by General Formula (G1) can be synthesized by synthesis reactions described below. Note that the method for synthesizing the fluorene derivative of one embodiment of the present invention is not limited to the following synthesis methods.

<Synthesis Method of Fluorene Derivative Represented by General Formula (G1)>

As shown in Synthesis Scheme (A-1), after a 1-halogenated biphenyl derivative (a1) is lithiated or after a Grignard reagent is prepared from a 1-halogenated biphenyl derivative (a1), a reaction with a benzoyl derivative (a2) is caused, and the resulting substance is dehydrated, whereby a halogenated arylfluorene derivative (a3) can be obtained.

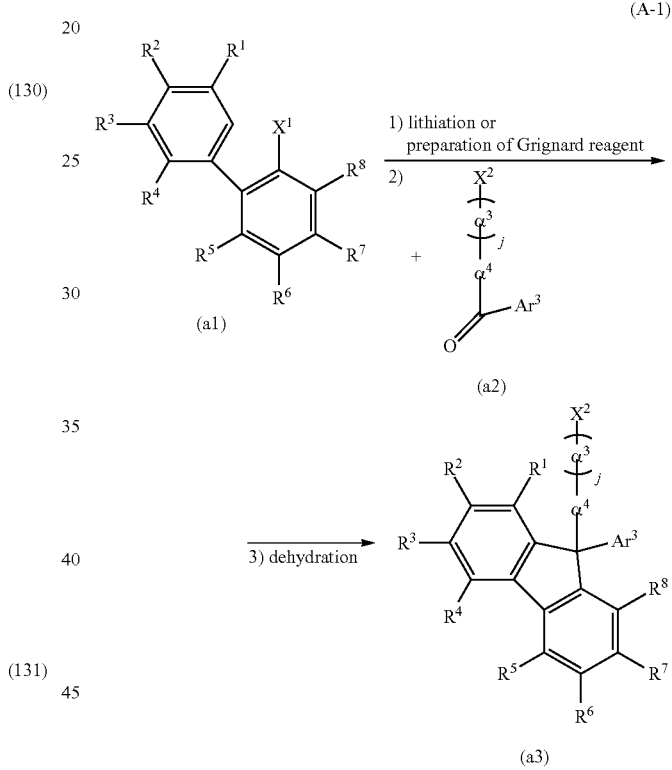

(A-1)

In Synthesis Scheme (A-1), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $\alpha^3$ and $\alpha^4$ separately represent a substituted or unsubstituted phenylene group. $Ar^3$ represents an alkyl group having 1 to 6 carbon atoms or a substituted or unsubstituted aryl group having 6 to 12 carbon atoms. Furthermore, j is 0 or 1. $X^1$ and $X^2$ separately represent a halogen, preferably bromine or iodine, which has high reactivity, more preferably iodine.

As in Synthesis Scheme (A-1), an aryl compound having a halogen group is activated, the resulting substance is reacted with a benzoyl derivative to give a phenol derivative, and acid is added to perform dehydration, whereby a fluorene derivative can be prepared.

Example of the activation includes a lithiation reaction with an alkyl lithium reagent and a reaction preparing a Grignard reagent with activated magnesium. As alkyl lithium, n-butyllithium, tert-butyllithium, methyllithium, and the like can be given. As acid, hydrochloric acid or the like can be used. As a solvent, ethers such as diethyl ether and tetrahydrofuran (THF) can be used.

Next, as shown in Synthesis Scheme (A-2), the halogenated arylfluorene derivative (a3) and an arylamine derivative (a4) are coupled, whereby a diarylamine derivative having a fluorenyl group (a5) can be obtained.

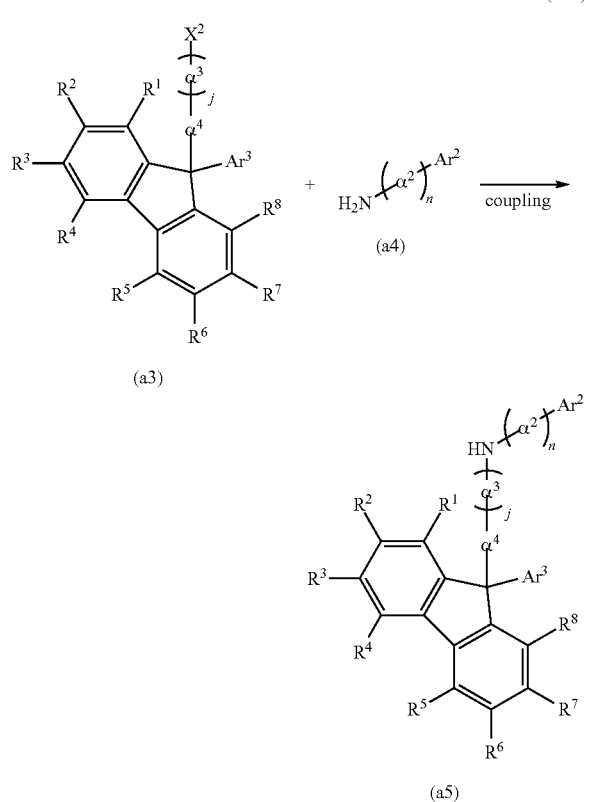

In Synthesis Scheme (A-2), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $\alpha^2$ to $\alpha^4$ separately represent a substituted or unsubstituted phenylene group. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Furthermore, j and n separately represent 0 or 1. $X^2$ represents a halogen, preferably bromine or iodine, which has high reactivity, more preferably iodine.

There are a variety of reaction conditions for a coupling reaction of an aryl compound having a halogen group and an aryl compound having amine (a primary arylamine compound or a secondary arylamine compound) in Synthesis Scheme (A-2). As an example, a synthesis method using a metal catalyst in the presence of a base can be employed.

The case where a Hartwig-Buchwald reaction is performed in Synthesis Scheme (A-2) is shown. A palladium catalyst can be used as the metal catalyst, and a mixture of a palladium complex and a ligand thereof can be used as the palladium catalyst. As examples of the palladium catalyst, bis(dibenzylideneacetone)palladium(0), palladium(II) acetate, and the like can be given. As the ligand, tri(tert-butyl)phosphine, tri(n-hexyl)phosphine, tricyclohexylphosphine, 1,1-bis(diphenylphosphino)ferrocene (abbreviation: DPPF), and the like can be given. As a substance which can be used as the base, an organic base such as sodium tert-butoxide, an inorganic base such as potassium carbonate, and the like can be given. In addition, this reaction is preferably performed in a solution, and toluene, xylene, benzene, and the like can be given as a solvent that can be used in the above reaction. However, the catalyst, ligand, base, and solvent which can be used are not limited thereto. In addition, this reaction is preferably performed under an inert atmosphere of nitrogen, argon, or the like.

The case where an Ullmann reaction is performed in Synthesis Scheme (A-2) is also shown. A copper catalyst can be used as the metal catalyst, and copper iodide (I) and copper acetate (II) can be given as the copper catalyst. As an example of a substance that can be used as the base, an inorganic base such as potassium carbonate can be given. The above reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used in this reaction. However, the catalyst, ligand, base, and solvent which can be used are not limited thereto. In addition, this reaction is preferably performed under an inert atmosphere of nitrogen, argon, or the like.

In the Ullmann reaction, DMPU, xylene, or the like, which has a high boiling point, is preferably used because the substance to be produced can be obtained in a shorter time and a higher yield by setting the reaction temperature to 100° C. or more. In addition, setting the reaction temperature to 150° C. or more is further preferable, in which case DMPU or the like can be used As shown in Synthesis Scheme (A-3), the diarylamine derivative having a fluorenyl group (a5) and a halogenated arene derivative (a6) are coupled, whereby the fluorene derivative of this embodiment represented by General Formula (G1) can be obtained.

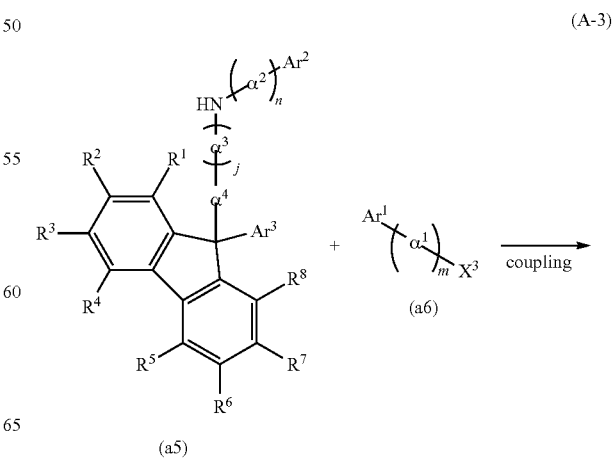

33

-continued

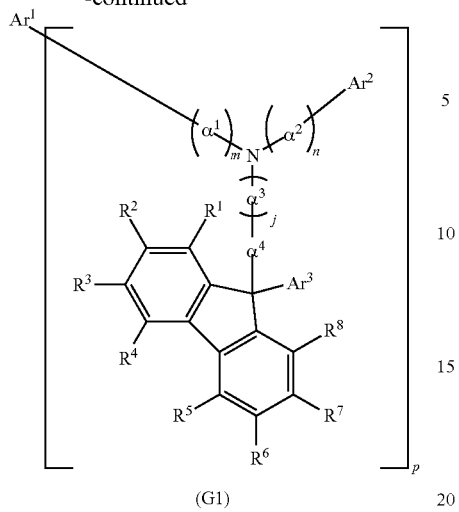

(G1)

In Synthesis Scheme (A-3), $R^1$ to $R^8$ separately represent any of a hydrogen atom, an alkyl group having 1 to 6 carbon atoms, a substituted or unsubstituted phenyl group, or a substituted or unsubstituted biphenyl group. Further, $α^1$ to $α^4$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Further, j, m, and n separately represent 0 or 1, and p represents 1 or 2. $X^3$ represents a halogen, preferably bromine or iodine, which has high reactivity, more preferably iodine.

At this step, in the case where p is 1, one equivalent of the diarylamine derivative having a fluorenyl group (a5) is reacted with the halogenated arene derivative (a6). Alternatively, in the case where p is 2, two equivalents of the diarylamine derivative having a fluorenyl group (a5) are reacted with the halogenated arene derivative (a6).

There are a variety of reaction conditions for a coupling reaction of an aryl compound having a halogen group and an aryl compound having amine (a primary arylamine compound or a secondary arylamine compound) in Synthesis Scheme (A-3). As an example, a synthesis method using a metal catalyst in the presence of a base can be employed.

A Hartwig-Buchwald reaction or an Ullmann reaction can be employed in Synthesis Scheme (A-3) as in Synthesis Scheme (A-2).

As described above, the fluorene derivative of this embodiment can be synthesized.

The fluorene derivative of this embodiment can emit light at short wavelength and provide blue light emission with high color purity.

The fluorene derivative of this embodiment can emit short wavelength light even with a high molecular weight, and thus can be a compound having improved thermophysical properties. Further, molecules have a three-dimensional structure, whereby a film containing this fluorene derivative can be formed to have stable properties (in which crystallization is suppressed).

Further, by using the fluorene derivative of this embodiment to form a light-emitting element, the light-emitting element can have improved properties.

Note that this embodiment can be implemented in combination with any of the other embodiments.

34

(Embodiment 2)

In this embodiment, a fluorene derivative of one embodiment of the present invention is described.

A fluorene derivative of this embodiment is the fluorene derivative represented by General Formula (G3).

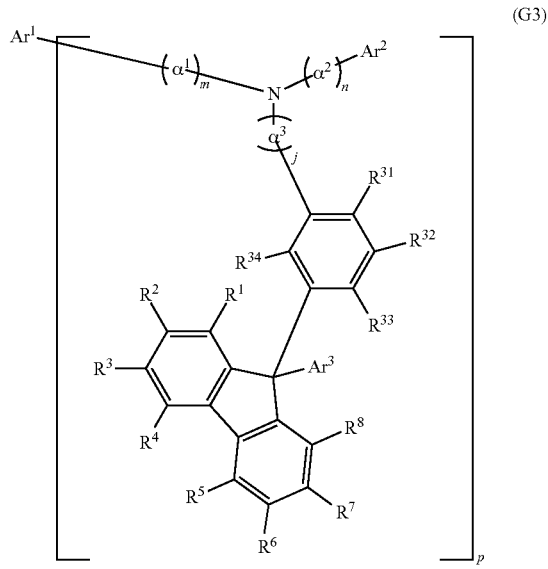

(G3)

In General Formula (G3), $R^1$ to $R^8$ and $R^{31}$ to $R^{34}$ separately represent any of a hydrogen atom, an alkyl group having 1 to 6 carbon atoms, a substituted or unsubstituted phenyl group, or a substituted or unsubstituted biphenyl group. Further, $α^1$ to $α^3$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. $Ar^3$ represents an alkyl group having 1 to 6 carbon atoms or a substituted or unsubstituted aryl group having 6 to 12 carbon atoms. Further, j, m, and n separately represent 0 or 1, and p represents 1 or 2.

A fluorene derivative of this embodiment is the fluorene derivative represented by General Formula (G4) below.

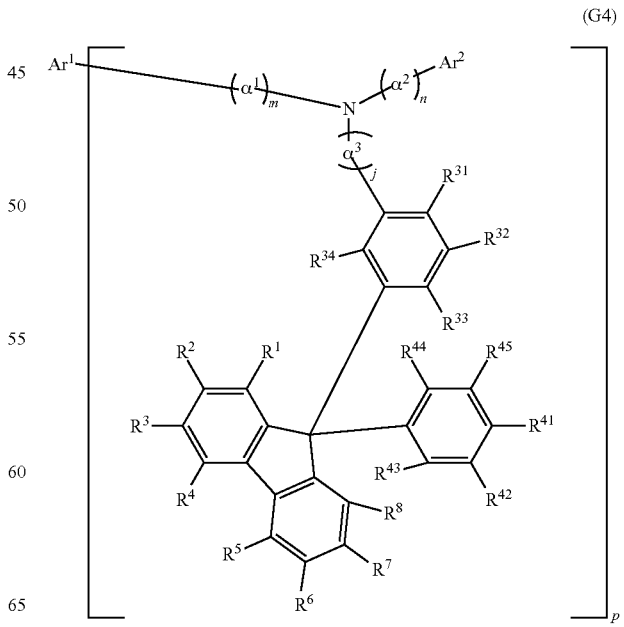

(G4)

In General Formula (G4), $R^1$ to $R^8$, $R^{31}$ to $R^{34}$, and $R^{41}$ to $R^{45}$ separately represent any of a hydrogen atom, an alkyl group having 1 to 6 carbon atoms, a substituted or unsubstituted phenyl group, or a substituted or unsubstituted biphenyl group. Further, $\alpha^1$ to $\alpha^3$ separately represent a substituted or unsubstituted phenylene group. $Ar^1$ represents a substituted or unsubstituted condensed aromatic hydrocarbon having 14 to 18 carbon atoms forming a ring. $Ar^2$ represents a substituted or unsubstituted aryl group having 6 to 13 carbon atoms forming a ring. Further, j, m, and n separately represent 0 or 1, and p represents 1 or 2.

In the fluorene derivatives represented by General Formulas (G3) and (G4), conjugation does not extend because the fluorene skeleton and the amine skeleton are bonded through a sigma bond, and the conjugation is broken because the fluorene skeleton is bonded to the meta position of a benzene ring in the amine skeleton. Therefore, the unit in which the fluorene skeleton is bonded to the meta position of a benzene ring in the amine skeleton is preferred because the emission wavelength of this unit is shorter than that of a unit in which the fluorene skeleton is bonded to the para position of a benzene ring in the amine skeleton. Furthermore, since the fluorene skeleton is bonded to the meta position of a benzene ring in the amine skeleton, molecules can form a more three-dimensional structure. Accordingly, a film containing such a fluorene derivative has improved properties, and concentration quenching and excimer formation can be suppressed more easily.

Note that specific examples of the substituents such as $R^1$ to $R^8$ and $Ar^1$ in the above General Formulas (G3) and (G4) can be found in Embodiment 1 and are not given here. A variety of reactions can be applied to synthesis methods for the above General Formulas (G3) and (G4), details of which can also be found in Embodiment 1.

Specific examples of the fluorene derivative represented by General Formula (G3) include, but not limited to, the fluorene derivatives represented by Structural Formulas (200) to (250).

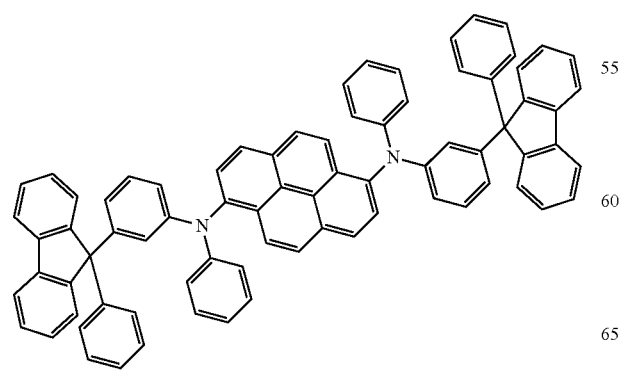

(200)

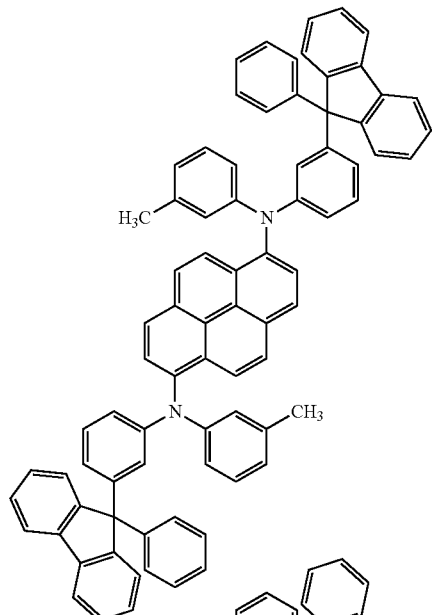

(201)

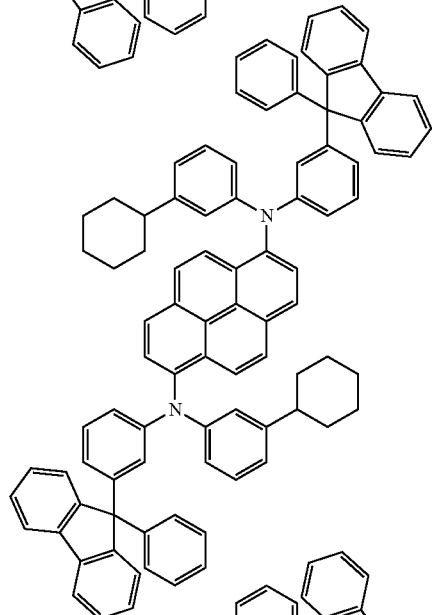

(202)

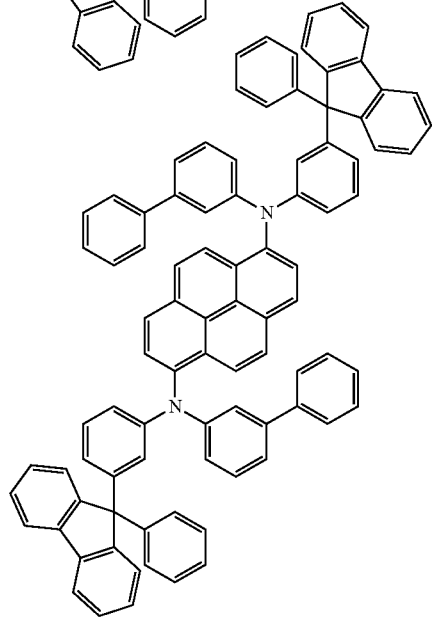

(203)

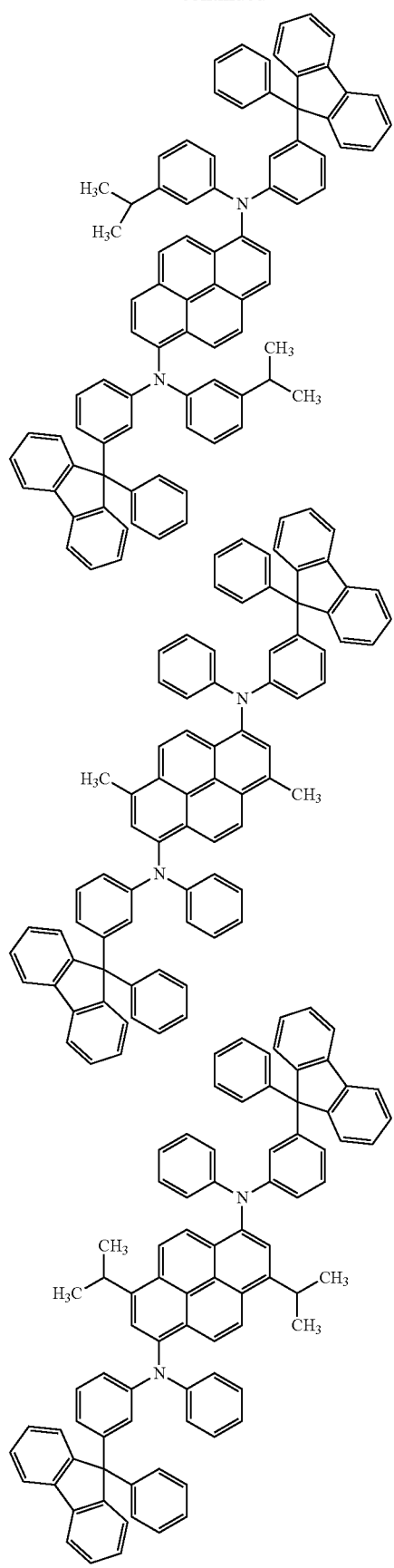
(204)
(205)
(206)
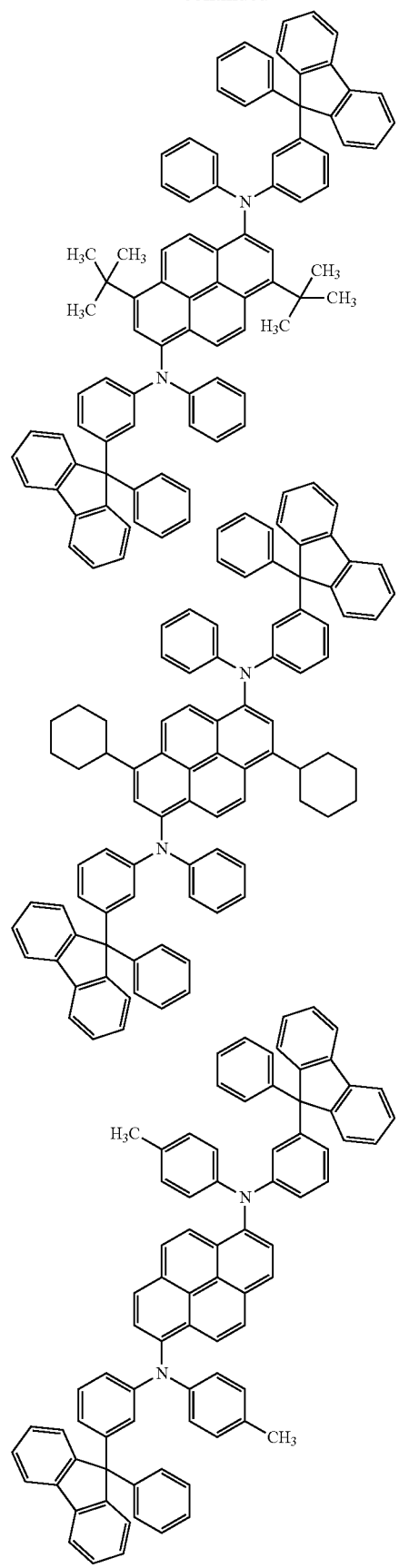
(207)
(208)
(209)

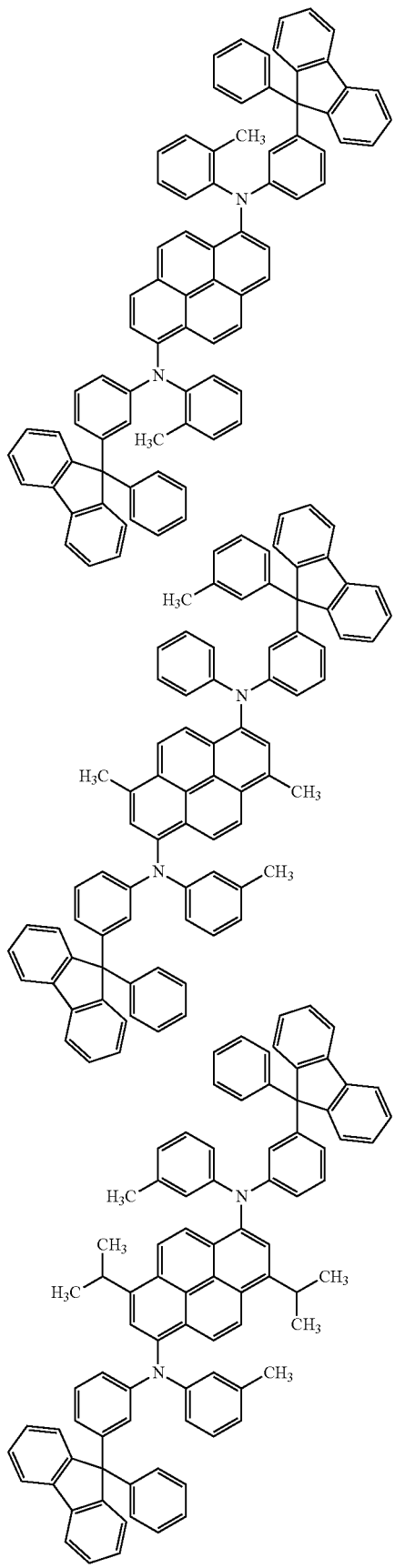
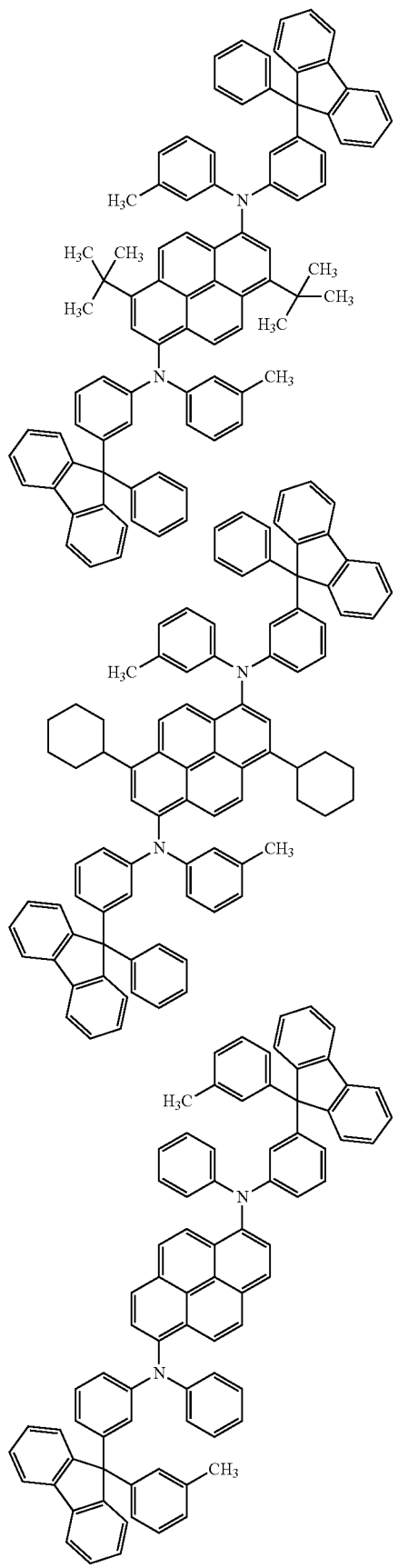

-continued
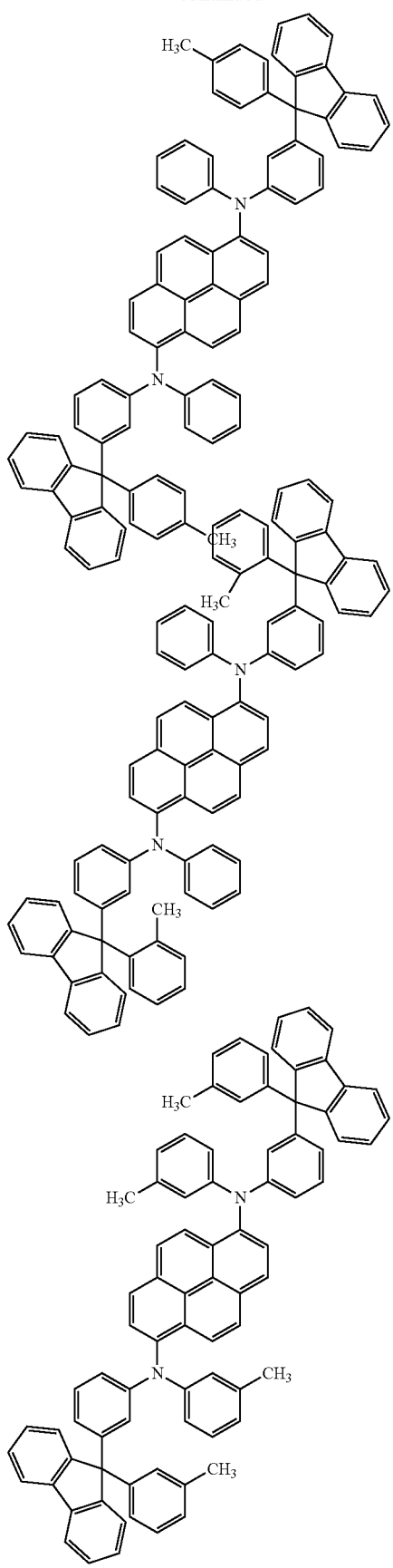
(216)
(217)
(218)
-continued
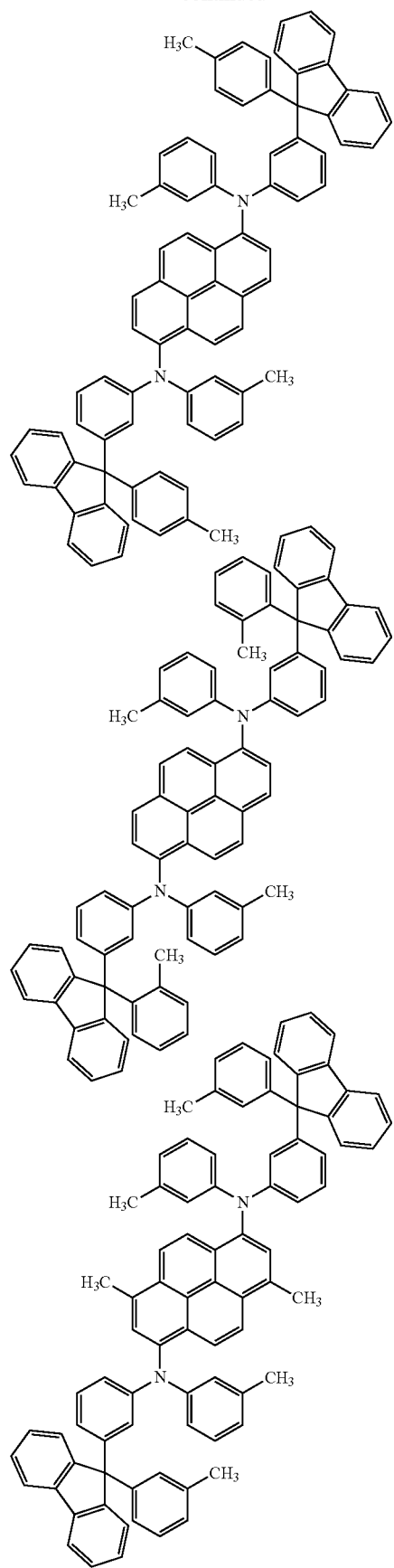
(219)
(220)
(221)

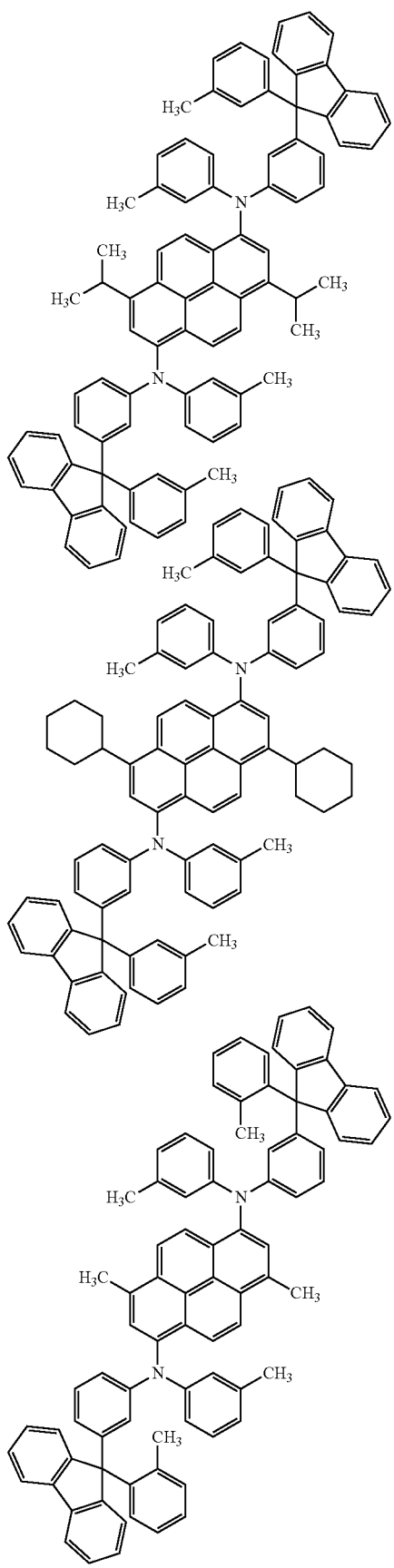
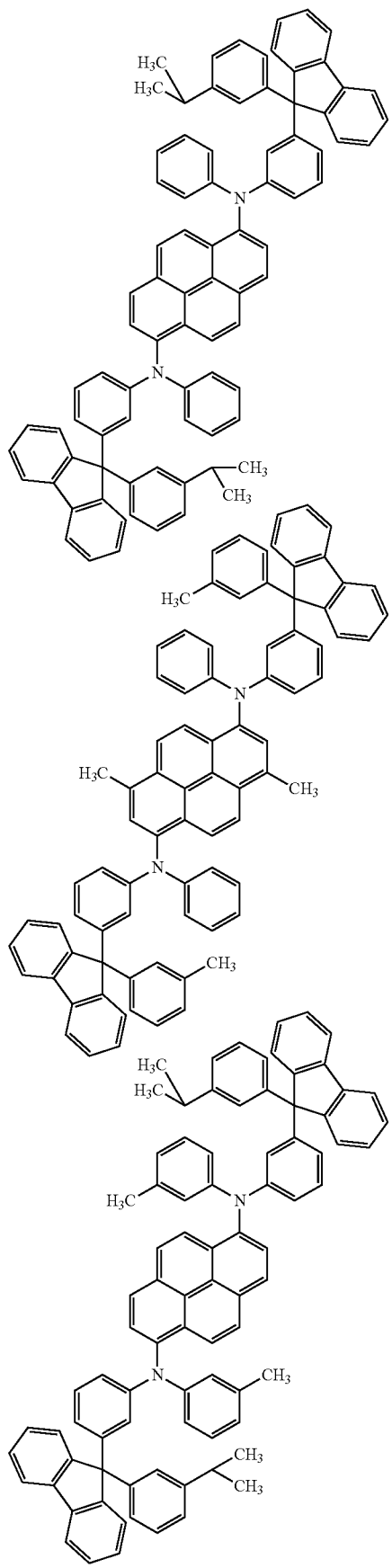

-continued
(228)
(229)
(230)
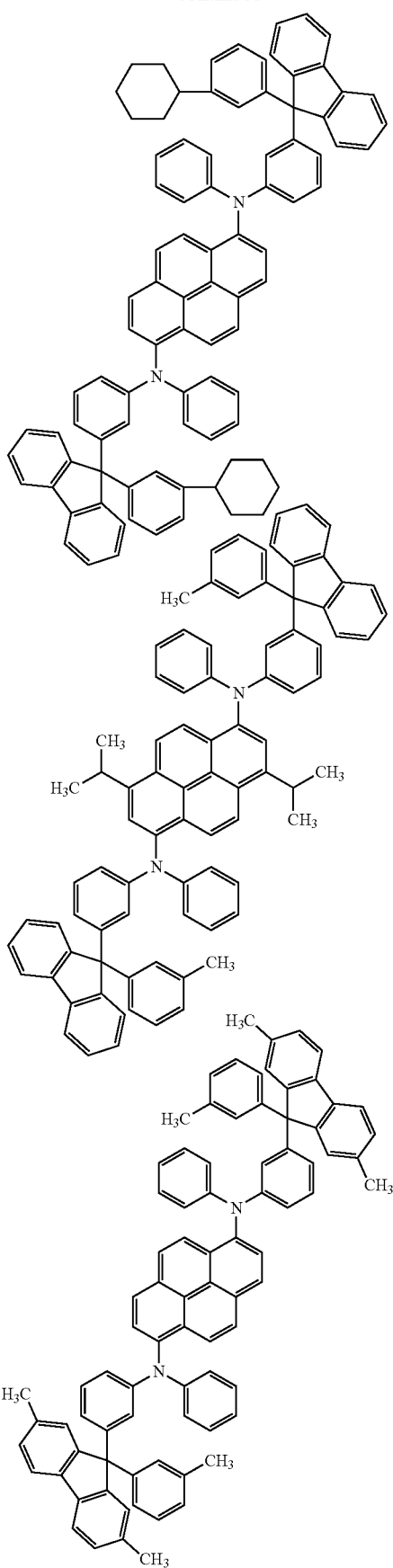
-continued
(231)
(232)
(233)
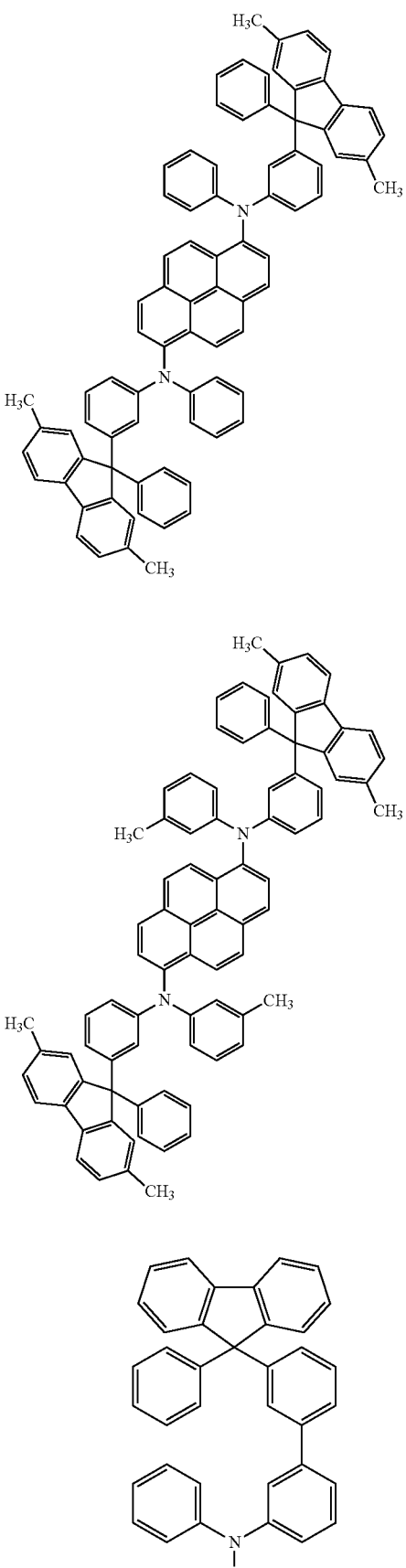

(234)
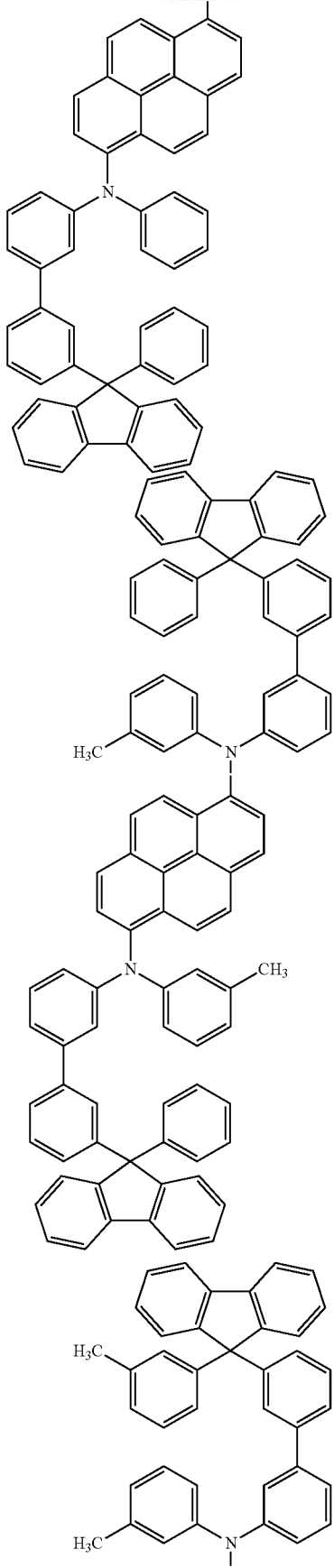
(235)
(236)
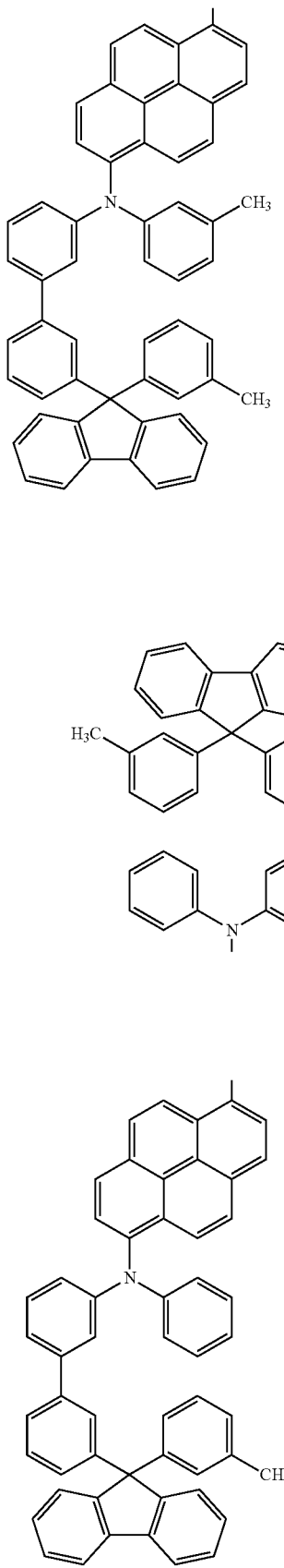

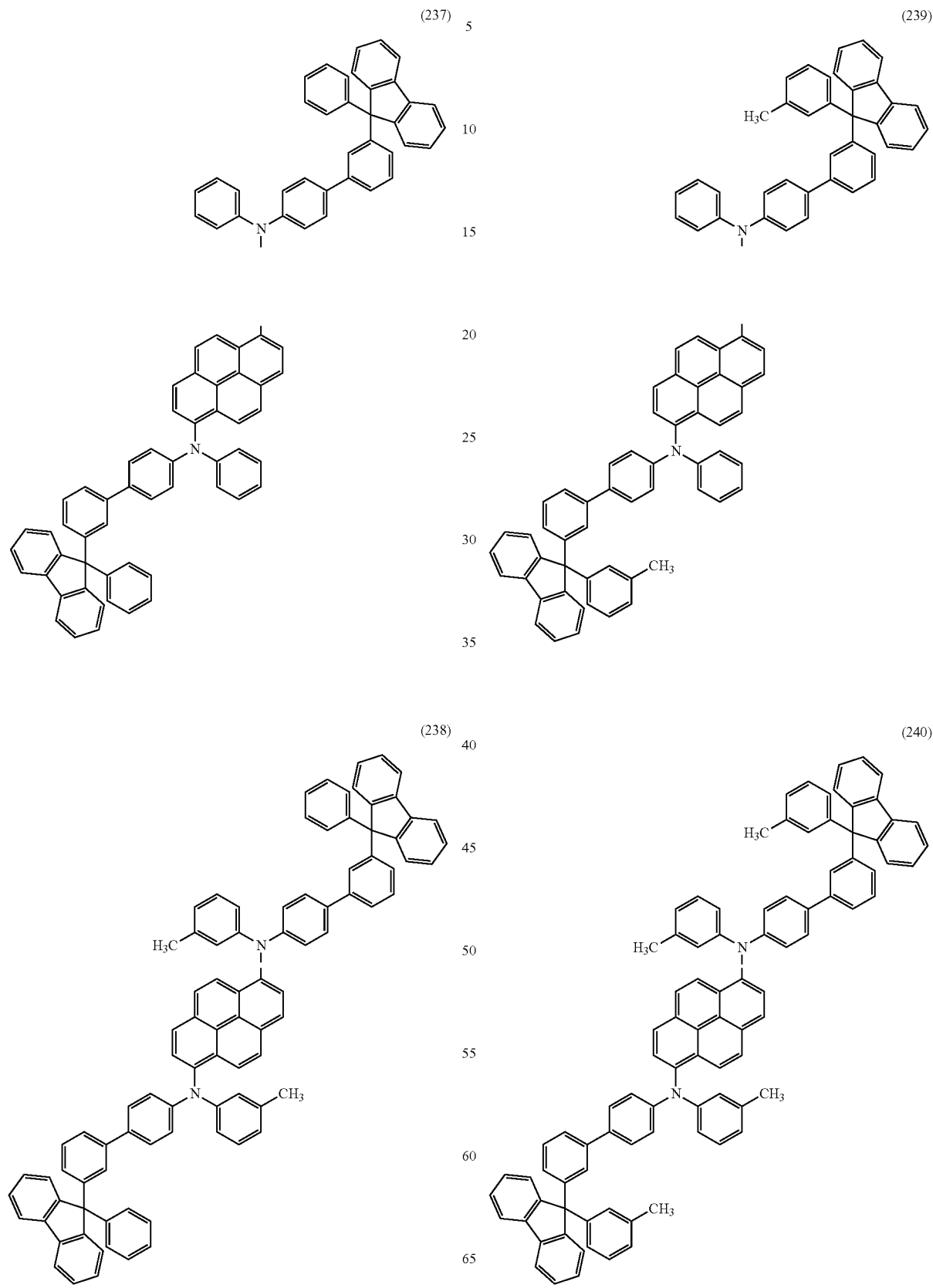

51
-continued
(241)
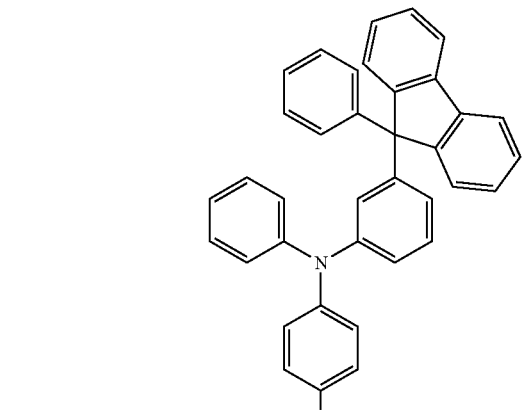
(242)
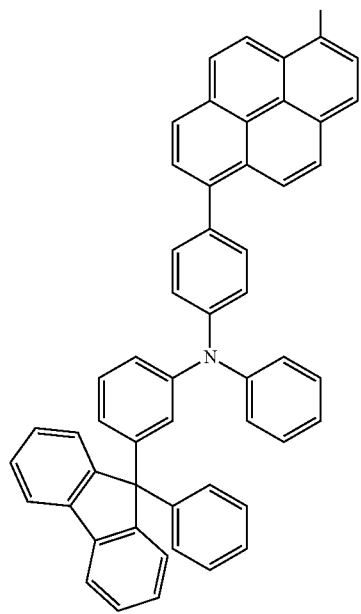
52
-continued
(243)
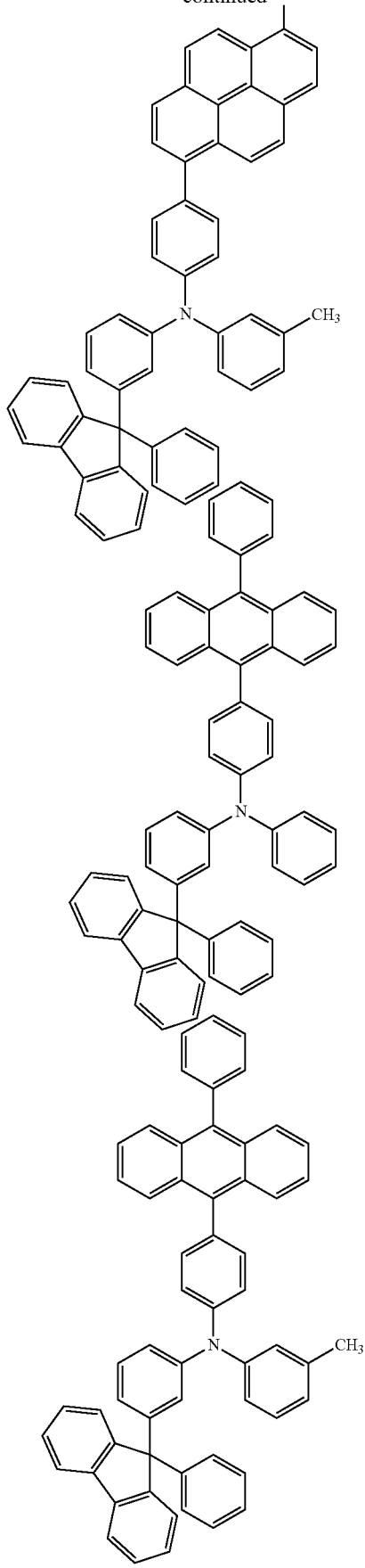
(244)
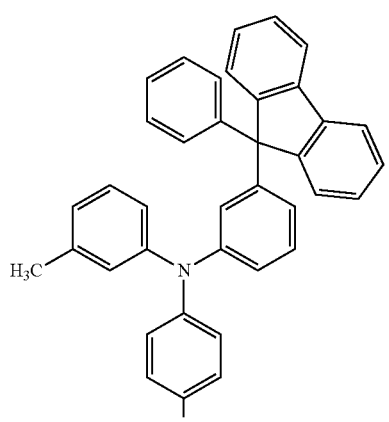

(245)
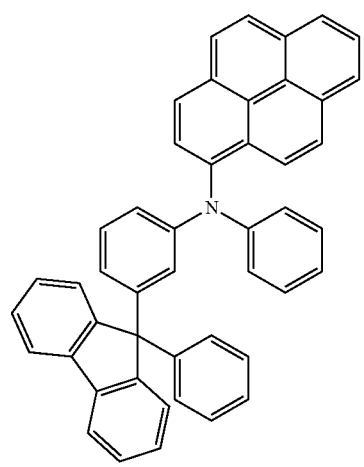
(246)
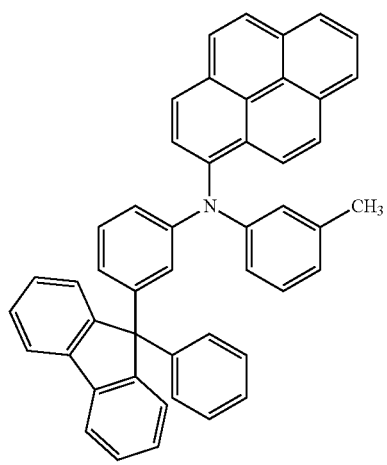
(247)
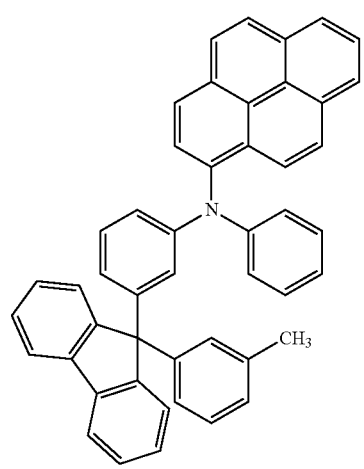
(248)
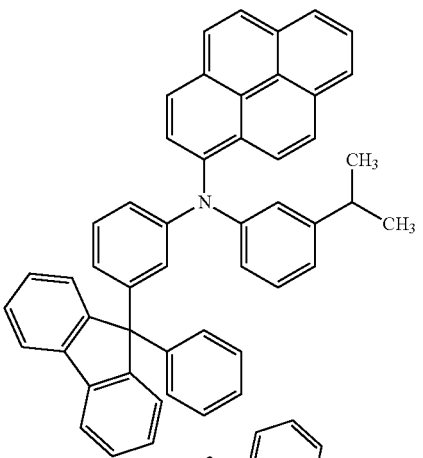
(249)
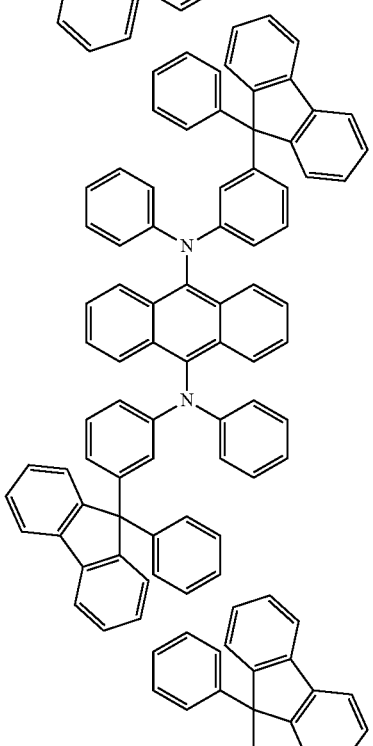
(250)
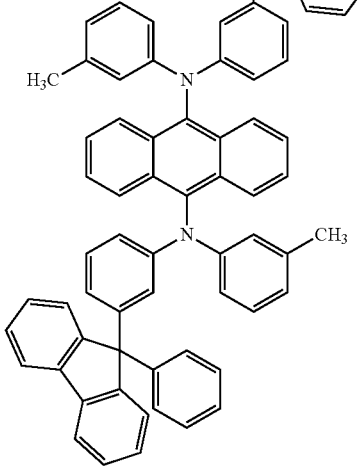
The fluorene derivative of this embodiment can emit light at a short wavelength and provide blue light emission with high color purity. In particular, since conjugation is broken by the bond between the fluorene skeleton and the meta position of a benzene ring in the amine skeleton, the emission wavelength of this fluorene derivative can be shorter than that of a unit in which the fluorene skeleton is bonded to the para position of a benzene ring in the amine skeleton.

The fluorene derivative of this embodiment can emit short wavelength light even with a high molecular weight, and thus can be a compound having improved thermophysical properties. Further, molecules have a more three-dimensional structure because the fluorene skeleton is bonded to the meta position of a benzene ring in the amine skeleton, whereby excimer formation can be suppressed more easily, and a film containing this fluorene derivative can be formed to have stable properties (in which crystallization is suppressed).

The fluorene derivative of this embodiment also provides a high quantum yield and high reliability. Further, in comparison with a material having a structure in which the fluorene skeleton is bonded to the para position of a benzene ring in the amine skeleton, the fluorene derivative of this embodiment achieves improved solubility and reduced sublimation temperature and therefore can be a material that is easy to purify, because of the structure in which the fluorene skeleton is bonded to the meta position of a benzene ring in the amine skeleton. Thus, the fluorene derivative described in this embodiment can be more easily produced on a mass scale, which enables low cost production. Note that, since the fluorene derivative described in this embodiment has a low sublimation temperature, it is possible to increase the deposition rate in the formation of a film containing the fluorene derivative by vacuum evaporation. Thus, the throughput can be improved in forming light-emitting elements by evaporation, leading to a cost reduction of light-emitting elements. Because of its excellent solubility, the fluorene derivative described in this embodiment is effective in forming light-emitting elements by a coating method.

Further, by using the fluorene derivative of this embodiment to form a light-emitting element, the light-emitting element can have improved properties.

Note that this embodiment can be implemented in combination with any of the other embodiments.
(Embodiment 3)

In this embodiment, a light-emitting element formed using the fluorene derivative according to Embodiment 1 or Embodiment 2 is described.

The light-emitting element in this embodiment includes a first electrode which functions as an anode, a second electrode which functions as a cathode, and an EL layer interposed between the first electrode and the second electrode. Note that the light-emitting element in this embodiment can exhibit light emission when a voltage is applied to each electrode so that the potential of the first electrode is higher than that of the second electrode.

In addition, the EL layer of the light-emitting element in this embodiment includes a first layer (hole-injection layer), a second layer (hole-transport layer), a third layer (light-emitting layer), a fourth layer (electron-transport layer), and a fifth layer (electron-injection layer), from the first electrode side.

A structure of the light-emitting element in this embodiment will be described using FIGS. 1A and 1B. A substrate 101 is used as a support of the light-emitting element. For the substrate 101, glass, quartz, plastics, or the like can be used, for example.

The above substrate 101 may remain in a light-emitting device or an electronic device which is a product utilizing the light-emitting element of this embodiment. Alternatively, the substrate 101 may only function as the support of the light-emitting element in its manufacturing process without remaining in an end product.

For a first electrode 102 formed over the substrate 101, a metal, an alloy, an electrically conductive compound, a mixture thereof, or the like which has a high work function (specifically, a work function of 4.0 eV or more) is preferably used. Specific examples are given below: indium tin oxide (ITO), indium tin oxide containing silicon or silicon oxide, indium zinc oxide (IZO), and indium oxide containing tungsten oxide and zinc oxide. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitride of metal materials (for example, titanium nitride), and the like can be given. Note that in this embodiment, since a first layer 111 in an EL layer 103 which is formed in contact with the first electrode 102 includes a composite material which facilitates hole injection regardless of the work function of the first electrode 102, any known material can be used as long as the material can be used as an electrode material (e.g., a metal, an alloy, an electrically conductive compound, a mixture thereof, and an element belonging to Group 1 or Group 2 of the periodic table).

These materials are usually formed by a sputtering method. For example, a film of indium oxide-zinc oxide (IZO) can be formed by a sputtering method using a target in which 1 to 20 wt % zinc oxide is added to indium oxide; and a film of indium oxide containing tungsten oxide and zinc oxide can be formed by a sputtering method using a target in which 0.5 to 5 wt % tungsten oxide and 0.1 to 1 wt % zinc oxide are added to indium oxide. Alternatively, a vacuum evaporation method, a coating method, an inkjet method, a spin coating method, or the like may be used.

Further, in the EL layer 103 formed over the first electrode 102, when a composite material described later is used as a material for the first layer 111 formed in contact with the first electrode 102, any of a variety of metals, alloys, electrically conductive compounds, and a mixture thereof can be used as a substance used for the first electrode 102 regardless of whether the work function is high or low. For example, aluminum (Al), silver (Ag), an alloy containing aluminum (AlSi), or the like can also be used.

Alternatively, it is possible to use any of Group 1 elements and Group 2 elements of the periodic table, that is, alkali metals such as lithium (Li) and cesium (Cs), alkaline earth metals such as magnesium (Mg), calcium (Ca), and strontium (Sr), alloys containing them (e.g., MgAg and AlLi), rare earth metals such as europium (Eu) and ytterbium (Yb), alloys containing them, and the like which are materials with a low work function.

Note that in the case where the first electrode 102 is formed using an alkali metal, an alkaline earth metal, or an alloy thereof, a vacuum evaporation method or a sputtering method can be used. Further alternatively, in the case where a silver paste or the like is used, a coating method, an inkjet method, or the like can be used.

The EL layer 103 formed over the first electrode 102 can be formed using a known material, and either a low molecular compound or a high molecular compound can be used. Note that the substance forming the EL layer 103 is not limited to an organic compound and may partially include an inorganic compound.

The EL layer 103 is formed by stacking an appropriate combination of a hole-injection layer that includes a substance having a high hole-injection property, a hole-transport layer that includes a substance having a high hole-transport property, a light-emitting layer that includes a light-emitting substance, an electron-transport layer that includes a substance having a high electron-transport property, an electron-injection layer that includes a substance having a high electron-injection property, and the like.

Note that the EL layer 103 illustrated in FIG. 1A includes the first layer (hole-injection layer) 111, a second layer (hole-transport layer) 112, a third layer (light-emitting layer) 113, a fourth layer (electron-transport layer) 114, and a fifth layer (electron-injection layer) 115 which are stacked in that order from the first electrode 102 side. Note that the EL layer 103 at least includes a light-emitting layer.

The first layer 111 which is a hole-injection layer is a hole-injection layer that includes a substance having a high hole-injection property. As the substance having a high hole-injection property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used. Alternatively, as a low molecular organic compound, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Further, as examples of low molecular organic compounds, there are aromatic amine compounds such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like. The fluorene derivative described in Embodiment 1 or Embodiment 2 can also be used.

Further alternatively, any of high molecular compounds (e.g., oligomers, dendrimers, or polymers) can be used. For example, there are high molecular compounds such as poly(N-vinylcarbazole) (abbreviation: PVK), poly(4-vinyltriphenylamine) (abbreviation: PVTPA), poly[N-(4-{N'[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Moreover, for the first layer 111, the composite material in which an acceptor substance is mixed into a substance having a high hole-transport property can be used. By using such a substance with a high hole-transport property containing an acceptor substance, a material used to form an electrode may be selected regardless of its work function. In other words, besides a material with a high work function, a material with a low work function may also be used as the first electrode 102. Such a composite material can be formed by co-depositing a substance having a high hole-transport property and a substance having an acceptor property. Note that in this specification, the word "composite" means not only a state in which two materials are simply mixed but also a state in which a plurality of materials are mixed and charges are transferred between the materials.

As the organic compound for the composite material, a variety of compounds such as an aromatic amine compound, a carbazole derivative, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ $cm^2/Vs$ or more is preferably used. However, any substance other than the above substances may also be used as long as it is a substance in which the hole-transport property is higher than the electron-transport property. The organic compounds which can be used for the composite material are specifically shown below.

For example, as the organic compounds that can be used for the composite material, there are aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl-2,3,5,6-tetraphenylbenzene.

Further, there are aromatic hydrocarbon compounds such as 2-tert-butyl-9,10-di(2-naphthyeanthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Furthermore, there are aromatic hydrocarbon compounds such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA). The fluorene derivative described in Embodiment 1 or Embodiment 2 can also be used.

As a substance having an acceptor property, organic compounds such as 7,7,8,8-tetracyano-2,3,5,6-tetrafluoroquinodimethane (abbreviation: $F_4$-TCNQ) and chloranil, and a transition metal oxide can be given. In addition, oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

Note that for the first layer 111, a composite material formed using any of the above-mentioned high molecular compounds such as PVK, PVTPA, PTPDMA, or Poly-TPD and any of the above-mentioned acceptor substances may be used. Note that a composite material, which is formed combining the fluorene derivative described in Embodiment 1 or Embodiment 2 with the above substance having an acceptor property, can also be used for the first layer 111.

The hole-transport layer 112 includes a substance having a high hole-transport property. Examples of the substance having a high hole-transport property include aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and the like. The substances mentioned here are mainly ones that have a hole mobility of $10^{-6}$ cm$^2$/Vs or more. However, substances other than the above described materials may also be used as long as the substances have a higher hole-transport property than an electron-transport property. The fluorene derivative described in Embodiment 1 or 2 can also be used. The layer which includes a substance having a high hole-transport property is not limited to a single layer, and two or more layers containing the aforementioned substances may be stacked.

Alternatively, a high molecular compound such as poly(N-vinylcarbazole) (abbreviation: PVK) or poly(4-vinyltriphenylamine) (abbreviation: PVTPA) can also be used for the hole-transport layer 112.

The third layer 113 is a light-emitting layer which includes a substance having a high light-emitting property. In this embodiment, the third layer 113 includes the fluorene derivative described in Embodiment 1 or 2 as a light-emitting substance.

The third layer 113 may have a structure in which the fluorene derivative described in Embodiment 1 or 2 is included as the main component or dispersed in another substance. Note that in the case where the fluorene derivative described in Embodiment 1 or 2 is dispersed in another substance, the concentration of the fluorene derivative is preferably 20% or less of the total in a weight ratio. Although known substances can be used as a substance in which the fluorene derivative described in Embodiment 1 or 2 is dispersed as a light-emitting substance, it is preferable to use a substance whose lowest unoccupied molecular orbital (LUMO) level is shallower (the absolute value of LUMO is smaller) than that of the light-emitting substance and highest occupied molecular orbital (HOMO) level is deeper (the absolute value of HOMO is larger) than that of the light-emitting substance.

Specifically, a metal complex such as bis[2-(2-benzoxazolyl)phenolato]zinc(II) (abbreviation: ZnPBO), or bis[2-(2-benzothiazolyephenolato]zinc(II) (abbreviation: ZnBTZ) can be used.

In addition, any of the following heterocyclic compounds can be used: 2-(biphenyl-4-yl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(biphenyl-4-yl)-4-phenyl-5-(4-tert-butylphenyl)-1,2,4-triazole (abbreviation: TAZ); 2,2',2"-(1,3,5-benzenetriyl)tris(1-phenyl-1H-benzimidazole) (abbreviation: TPBI); bathophenanthroline (abbreviation: BPhen); bathocuproine (abbreviation: BCP); and the like.

Alternatively, the following condensed aromatic compound can also be used: 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9,9'-bianthryl (abbreviation: BANT), 9,9'-(stilbene-3,3'-diyediphenanthrene (abbreviation: DPNS), 9,9'-(stilbene-4,4'-diyediphenanthrene (abbreviation: DPNS2), 3,3',3"-(benzene-1,3,5-triyetripyrene (abbreviation: TPB3), or the like.

As a substance in which the light-emitting substance is dispersed, plural kinds of substances can be used. For example, in order to suppress crystallization, a substance such as rubrene which suppresses crystallization may be further added. In addition, NPB, Alq, or the like can be further added in order to efficiently transfer energy to the substance having a light-emitting property. With a structure in which a substance having a high light-emitting property is thus dispersed in another substance, crystallization of the third layer 113 can be suppressed. Further, concentration quenching which results from the high concentration of the substance having a high light-emitting property can also be suppressed.

Further, in particular, among the above-described substances, a substance having an electron-transport property is preferably used so that a substance having a light-emitting property is dispersed therein to form the third layer 113. Specifically, it is also possible to use any of the above metal complexes and heterocyclic compounds; CzPA, DNA, and t-BuDNA among the above condensed aromatic compounds; and further macromolecular compounds which will be given later as a substance that can be used for the fourth layer 114.

The light-emitting layer 113 may be a stack of two or more layers. For example, in the case where the light-emitting layer 113 is formed by stacking a first light-emitting layer and a second light-emitting layer in that order from the hole transport layer side, the first light-emitting layer can be formed using a substance having a hole transport property as the host material and the second light-emitting layer can be formed using a substance having an electron transport property as the host material. It is more preferable that a material in which the hole-transport property is higher than the electron-transport property be used for the host material of the first light-emitting layer and a material in which the electron-transport property is higher than the hole-transport property be used for the host material of the second light-emitting layer. With the above structure, a light emission site is formed between the first light-emitting layer and the second light-emitting layer, whereby an element having higher efficiency can be obtained.

When the light-emitting layer having the structure described above is formed using a plurality of materials, the light-emitting layer can be formed using co-evaporation by a vacuum evaporation method; or an inkjet method, a spin coating method, a dip coating method, or the like as a method for mixing a solution.

The fourth layer 114 is an electron-transport layer that includes a substance having a high electron-transport property. For the fourth layer 114, for example, as a low molecular organic compound, a metal complex such as Alq, Almq$_3$, BeBq$_2$, BAlq, Znq, ZnPBO, or ZnBTZ can be used. Alternatively, instead of the metal complex, a heterocyclic compound such as PBD, OXD-7, TAZ, TPBI, BPhen, or BCP can be used. The substances mentioned here are mainly ones that have an electron mobility of $10^{-6}$ cm$^2$/Vs or more. Note that any substance other than the above substances may be used for the electron-transport layer as long as it is a substance in which the electron-transport property is higher than the hole-transport property. Furthermore, the electron transport layer is not limited to a single layer, and two or more layers made of the aforementioned substances may be stacked.

For the fourth layer 114, a high molecular compound can also be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridin-6,6'-diyl)] (abbreviation: PF-BPy), or the like can be used.

The fifth layer 115 is an electron-inject layer that includes a substance having a high electron-inject property. For the fifth layer 115, an alkali metal, an alkaline earth metal, or a compound thereof, such as lithium fluoride (LiF), cesium fluoride (CsF), or calcium fluoride ($CaF_2$), can be used. Alternatively, a layer of an electron-transport substance which contains an alkali metal, an alkaline earth metal, or a compound thereof, specifically, a layer of Alq which contains magnesium (Mg), or the like may be used. Note that in this case, electrons can be more efficiently injected from the second electrode 104.

For the second electrode 104, a metal, an alloy, an electrically conductive compound, a mixture thereof, or the like which has a low work function (specifically, a work function of 3.8 eV or less) can be used. As a specific example of such a cathode material, an element that belongs to Group 1 or 2 of the periodic table, that is, alkali metals such as lithium (Li) and cesium (Cs), alkaline earth metals such as magnesium (Mg), calcium (Ca), and strontium (Sr), alloys containing these (e.g., MgAg and AlLi), rare earth metals such as europium (Eu) and ytterbium (Yb), alloys containing these, and the like can be given.

Note that in the case where the second electrode 104 is formed using an alkali metal, an alkaline earth metal, or an alloy thereof, a vacuum evaporation method or a sputtering method can be used. In the case of using a silver paste or the like, a coating method, an inkjet method, or the like can be used Note that by provision of the fifth layer 115, the second electrode 104 can be formed using any of a variety of conductive materials such as Al, Ag, ITO, and indium oxide-tin oxide containing silicon or silicon oxide regardless of the work functions. A film of such a conductive material can be formed by a sputtering method, an inkjet method, a spin coating method, or the like.

Further, as a formation method of the EL layer 103 in which the first layer (hole-injection layer) 111, the second layer (hole-transport layer) 112, the third layer (light-emitting layer) 113, the fourth layer (electron-transport layer) 114, and the fifth layer (electron-injection layer) 115 are in that order stacked, any of a variety of methods can be employed regardless of whether the method is a dry process or a wet process. For example, a vacuum evaporation method, an inkjet method, a spin coating method, or the like can be used. Note that a different formation method may be employed for each layer.

The second electrode 104 can also be formed by a wet process using a paste of a metal material instead of a dry process such as a sputtering method or a vacuum evaporation method.

The first electrode 102, the first layer (hole-injection layer) 111, the second layer (hole-transport layer) 112, and the third layer (light-emitting layer) 113 allow mainly holes to path therebetween. Therefore, the HOMO levels of the layers (or the work function in the case of metal) are preferably the same or almost the same to reduce the carrier injection barrier between the adjacent layers. Similarly, since the third layer (light-emitting layer) 113, the fourth layer (electron-transport layer) 114, the fifth layer (electron-injection layer) 115, and the second electrode 104 allow mainly electrons to path therebetween, the LUMO levels of the layers (or the work function in the case of metal) are preferably the same or almost the same to reduce the carrier injection barrier between the adjacent layers. A difference in HOMO or LUMO level is preferably less than or equal to 0.2 eV, more preferably less than or equal to 0.1 eV.

Further, it is preferable to confine carriers in the light-emitting layer by increasing a difference in HOMO level between the second layer (hole-transport layer) 112 and the third layer (light-emitting layer) 113 or a difference in LUMO level between the third layer (light-emitting layer) 113 and the fourth layer (electron-transport layer) 114 so that a light-emitting element with higher efficiency can be obtained. Note that in this case, if the barrier is too high, the driving voltage increases to be a burden on the element. Therefore, each of the differences is preferably less than or equal to 0.4 eV, more preferably less than or equal to 0.2 eV.

In the above-described light-emitting element of this embodiment, a current flows due to a potential difference generated between the first electrode 102 and the second electrode 104 and holes and electrons recombine in the EL layer 103, so that light is emitted. Then, this emitted light is extracted out through one or both of the first electrode 102 and the second electrode 104. Accordingly, one of or both the first electrode 102 and the second electrode 104 is/are an electrode having a light-transmitting property.

Figure 2A:
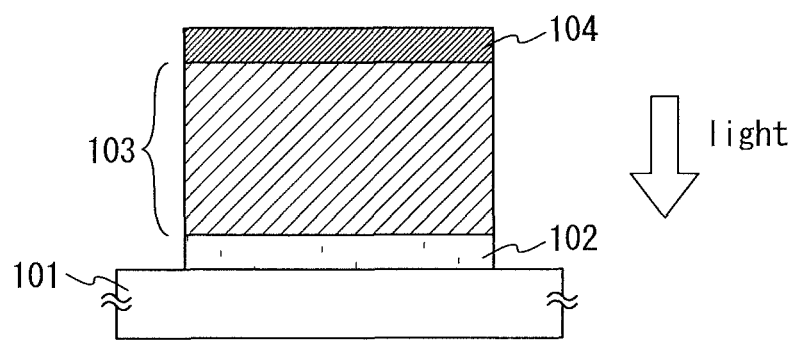
FIGS. 2A to 2C each illustrate a light-emitting element.
Figure 2B:
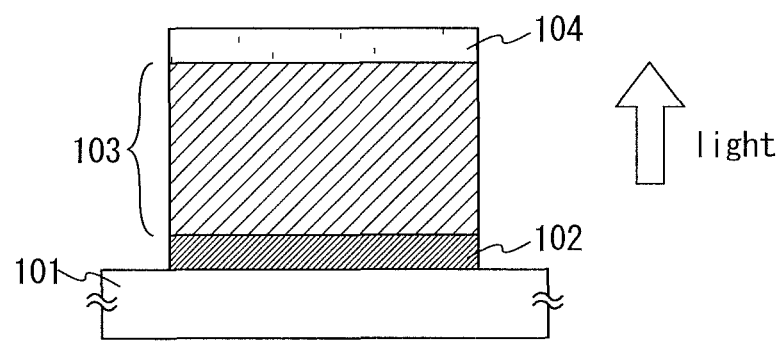
Figure 2C:
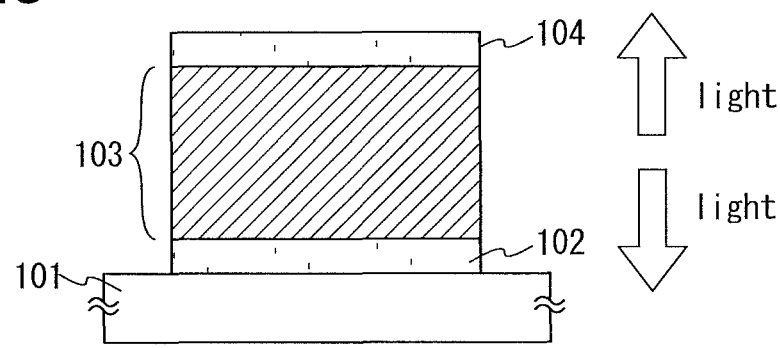

As illustrated in FIG. 2A, when only the first electrode 102 has a light-transmitting property, the emitted light is extracted from a substrate side through the first electrode 102. Alternatively, as illustrated in FIG. 2B, when only the second electrode 104 has a light-transmitting property, the emitted light is extracted from the side opposite to the substrate 101 through the second electrode 104. As illustrated in FIG. 2C, when each of the first electrode 102 and the second electrode 104 has a light-transmitting property, the emitted light is extracted from both the substrate 101 side and the side opposite to the substrate 101 side through the first electrode 102 and the second electrode 104.

The structure of the layers provided between the first electrode 102 and the second electrode 104 is not limited to the aforementioned one. Structures other than the above may be employed as long as at least the second layer 112 which is a hole-transport layer and the third layer 113 which is a light-emitting layer are included.

Figure 1B:
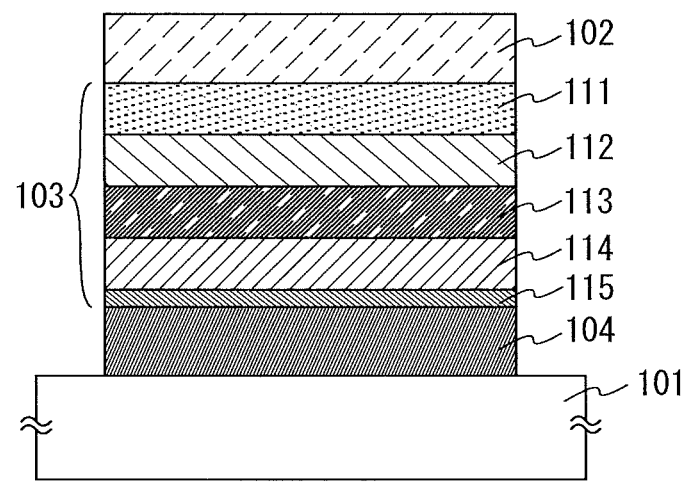

Alternatively, as illustrated in FIG. 1B, a structure may be employed in which the second electrode 104 functioning as a cathode, the EL layer 103, and the first electrode 102 functioning as an anode are stacked in that order over the substrate 101. Note that in the EL layer 103 of this case, the fifth layer 115, the fourth layer 114, the third layer 113, the second layer 112, the first layer 111, and the first electrode 102 are stacked in that order over the second electrode 104.

Note that by use of the light-emitting element of the present invention, a passive matrix light-emitting device or an active matrix light-emitting device in which drive of the light-emitting element is controlled by a thin film transistor (TFT) can be fabricated.

Note that there is no particular limitation on the structure of the TFT in the case of fabricating an active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on the crystallinity of a semiconductor film used for the TFT. An amorphous semiconductor film may be used, or a crystalline semiconductor film may be used.

The light-emitting element described in this embodiment can be made to have improved element efficiency and a long lifetime by including the fluorene derivative described in Embodiment 1 or 2 as a light-emitting substance.

(Embodiment 4)

Figure 3A:
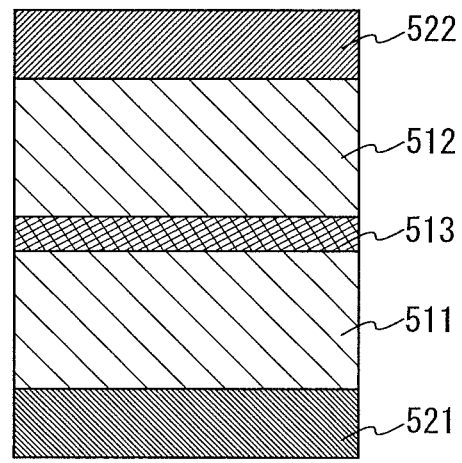
FIGS. 3A and 3B each illustrate a light-emitting element.
Figure 3B:
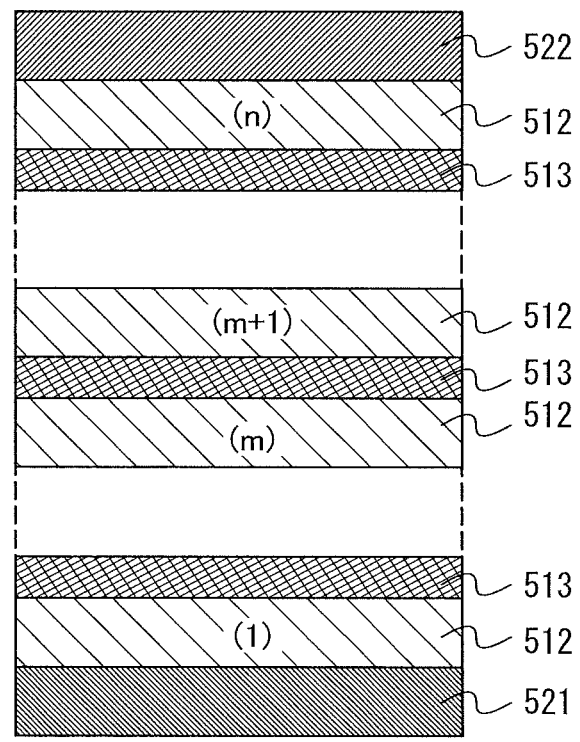

In this embodiment is described a mode of a light-emitting element (also referred to as a stacked-type element) having a plurality of stacked light-emitting units (also referred to as EL layers), with reference to FIGS. 3A and 3B. The light-emitting element is a stacked-type light-emitting element including a plurality of light-emitting units between a first electrode and a second electrode. Each structure of the light-emitting units can be similar to that described in Embodiment 3. In other words, the light-emitting element described in Embodiment 3 is a light-emitting element having one light-emitting unit. In Embodiment 4, a light-emitting element having a plurality of light-emitting units is described.

In FIG. 3A, a first light-emitting unit 511 and a second light-emitting unit 512 are stacked between a first electrode 521 and a second electrode 522. The first electrode 521 and the second electrode 522 can be similar to those in Embodiment 3. The first light-emitting unit 511 and the second light-emitting unit 512 may have the same structure or different structures, and a structure similar to those described in Embodiment 3 can be employed.

A charge-generation layer 513 is a layer which injects electrons into the light-emitting unit on one side and injects holes into the light-emitting unit on the other side when voltage is applied to the first electrode 521 and the second electrode 522, and may have either a single layer structure or a stacked structure of plural layers. As a stacked structure of plural layers, a layer that injects holes and a layer that injects electrons are preferably stacked.

As the layer that injects holes, a semiconductor or an insulator, such as molybdenum oxide, vanadium oxide, rhenium oxide, or ruthenium oxide, can be used. Alternatively, the layer that injects holes may have a structure in which an acceptor substance is added to a substance having a high hole-transport property. The layer which includes a substance having a high hole-transport property and an acceptor substance includes, as an acceptor substance, 7,7,8,8-tetracyano-2,3,5,6-tetrafluoroquinodimethane (abbreviation: $F_4$-TCNQ) or metal oxide such as vanadium oxide, molybdenum oxide, or tungsten oxide. As the substance having a high hole-transport property, a variety of compounds such as an aromatic amine compound, a carbazole derivative, aromatic hydrocarbon, a high-molecular compound, oligomer, dendrimer, polymer, and the like can be used. Note that the fluorene derivative described in Embodiment 1 or Embodiment 2 can also be used in a similar manner. Note that a substance having a hole mobility of $10^{-6}$ cm$^2$/Vs or more is preferably employed as the substance having a high hole-transport property. However, any substance other than the above substances may also be used as long as it is a substance in which the hole-transport property is higher than the electron-transport property. Since the composite material of the substance having a high hole-transport property and the acceptor substance has an excellent carrier-injection property and an excellent carrier-transport property, low-voltage driving and low-current driving can be realized.

As the layer that injects electrons, a semiconductor or an insulator, such as lithium oxide, lithium fluoride, or cesium carbonate, can be used. Alternatively, the electron-injection layer may have a structure in which a donor substance is added to a substance having a high electron-transport property. As the donor substance, an alkali metal, an alkaline earth metal, a rare-earth metal, a metal that belongs to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transport property, the materials described in Embodiment 3 can be used. Note that a substance having a electron-mobility of $10^{-6}$ cm$^2$/Vs or more is preferably employed as the substance having a high electron-transport property. However, any substance other than the above substances may also be used as long as it is a substance in which the electron-transport property is higher than the hole-transport property. Since the composite material of the substance having a high electron-transport property and the donor substance has an excellent carrier-injection property and an excellent carrier-transport property, low-voltage driving and low-current driving can be realized.

Further, the electrode materials described in Embodiment 3 can be used for the charge-generation layer 513. For example, the charge-generation layer 513 may be formed with a combination of a layer which includes a substance having a high hole-transport property and metal oxide and a transparent conductive film. It is preferable that the charge-generation layer be a highly light-transmitting layer in terms of light extraction efficiency.

In any case, the charge-generation layer 513 interposed between the first light-emitting unit 511 and the second light-emitting unit 512 injects electrons into the light-emitting unit on one side and injects holes into the light-emitting unit on the other side when a voltage is applied to the first electrode 521 and the second electrode 522. For example, any structure is acceptable for the charge-generation layer 513 as long as the charge-generation layer 513 injects electrons and holes into the first light-emitting unit 511 and the second light-emitting unit 512, respectively, when a voltage is applied so that the potential of the first electrode is higher than the potential of the second electrode.

In this embodiment, the light-emitting element having two light-emitting units is described; however, one embodiment of the present invention can be similarly applied to a light-emitting element in which three or more light-emitting units are stacked as illustrated in FIG. 3B. By arrangement of a plurality of light-emitting units, which are partitioned by the charge-generation layer between a pair of electrodes, as in the light-emitting element of this embodiment, light emission in a high luminance region can be achieved with current density kept low, thus light-emitting having a long lifetime can be realized. When the light-emitting element is applied for a lighting device as an application example, voltage drop due to resistance of an electrode material can be reduced, thereby achieving homogeneous light emission in a large area. Moreover, a light-emitting device with low power consumption, which can be driven at low voltage, can be achieved.

The light-emitting units emit light having different colors from each other, thereby obtaining light emission of a desired color as the whole light-emitting element. For example, in a light-emitting element having two light-emitting units, the emission colors of the first light-emitting unit and the second light-emitting unit are made complementary, so that the light-emitting element which emits white light as the whole light-emitting element can be obtained. Note that the word "complementary" means color relationship in which an achromatic color is obtained when colors are mixed. That is, white light emission can be obtained by mixture of light obtained from substances emitting the lights of complementary colors. The same can be applied to a light-emitting element which has three light-emitting units. For example, the light-emitting element as a whole can provide white light emission when the emission color of the first light-emitting unit is red, the emission color of the second light-emitting unit is green, and the emission color of the third light-emitting unit is blue.

Note that this embodiment can be combined with any other embodiment as appropriate.

(Embodiment 5)

Figure 4A:
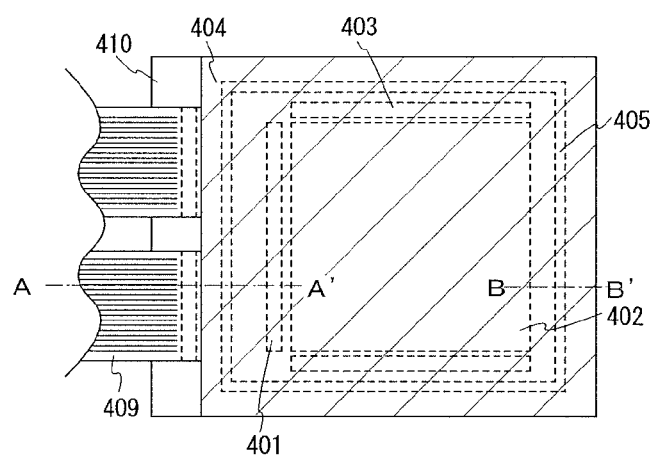
FIGS. 4A and 4B illustrate a light-emitting device.
Figure 4B:
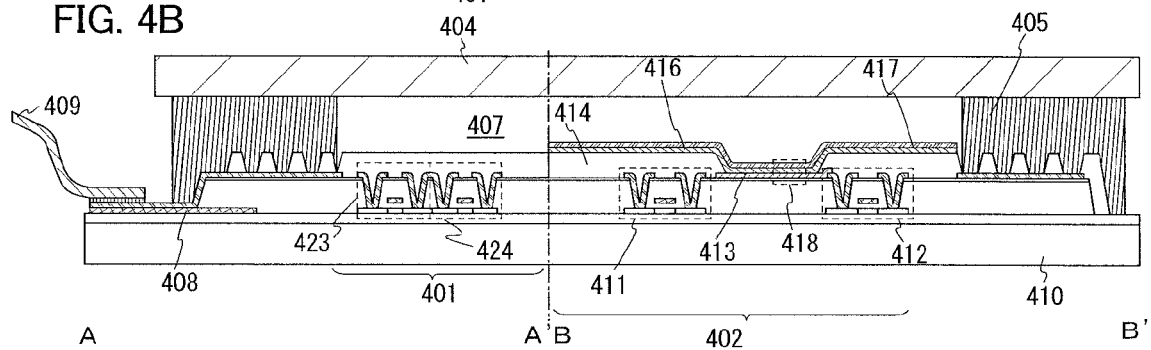

In this embodiment, a light-emitting device having a light-emitting element of Embodiment 3 or 4 in a pixel portion will be described with reference to FIGS. 4A and 4B. FIG. 4A is a top view illustrating a light-emitting device while FIG. 4B is a cross-sectional view taken along lines A-A' and B-B' of FIG. 4A.

In FIG. 4A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Reference numeral 404 denotes a sealing substrate, reference numeral 405 denotes a sealant, and a portion enclosed by the sealant 405 is a space 407.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 4B. The driver circuit portion and the pixel portion are formed over an element substrate 410. In this case, one pixel in the pixel portion 402 and the source side driver circuit 401 which is the driver circuit portion are illustrated. A CMOS circuit, which is a combination of an n-channel TFT 423 with a p-channel TFT 424, is formed as the source side driver circuit 401. Such a driver circuit may be formed using a variety of circuits such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413.

In order to improve the coverage, the insulator 414 is preferably provided such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 µm to 3 µm). Alternatively, the insulator 414 can be formed using either a negative type photosensitive material that becomes insoluble in an etchant by light irradiation or a positive type photosensitive material that becomes soluble in an etchant by light irradiation.

Over the first electrode 413, an EL layer 416 and a second electrode 417 are formed. In this case, the first electrode 413 can be formed using any of a variety of materials such as metals, alloys, and electrically conductive compounds or a mixture thereof. Note that as specific materials, the materials described in Embodiment 3 as a material that can be used for the first electrode can be used.

The EL layer 416 is formed by any of a variety of methods such as an evaporation method using an evaporation mask, an inkjet method, and a spin coating method. The EL layer 416 has any of the structures described in Embodiment 3. Further, as another material included in the EL layer 416, low molecular compounds or high molecular compounds (including oligomers and dendrimers) may be used. As the material for the EL layer, not only an organic compound but also an inorganic compound may be used.

The second electrode 417 can be formed using any of a variety of metals, alloys, and electrically conductive compounds, or a mixture thereof. Among such materials, a metal, an alloy, an electrically conductive compound, a mixture thereof, or the like having a low work function (a work function of 3.8 eV or less) is preferably used when the second electrode 417 is used as a cathode. As an example, an element belonging to Group 1 or Group 2 in the periodic table, i.e., an alkali metal such as lithium (Li) or cesium (Cs), an alkaline earth metal such as magnesium (Mg), calcium (Ca), or strontium (Sr), an alloy containing any of these (e.g., MgAg and AlLi) and the like can be given.

Note that when light generated in the EL layer 416 is transmitted through the second electrode 417, the second electrode 417 can be formed using a stack of a thin metal film with a small thickness and a transparent conductive film (indium oxide-tin oxide (ITO), indium oxide-tin oxide containing silicon or silicon oxide, indium oxide-zinc oxide (IZO), indium oxide containing tungsten oxide and zinc oxide, or the like).

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with a filler such as an inert gas (e.g., nitrogen or argon) or the sealant 405.

Note that as the sealant 405, an epoxy-based resin is preferably used. A material used for these is desirably a material which does not transmit moisture or oxygen as possible. As a material for the sealing substrate 404, a glass substrate, a quartz substrate, or a plastic substrate including fiberglass-reinforced plastics (FRP), polyvinyl fluoride (PVF), polyester, acrylic, or the like can be used.

As described above, the active matrix light-emitting device having the light-emitting element of Embodiment 3 or 4 can be obtained.

Figure 5A:
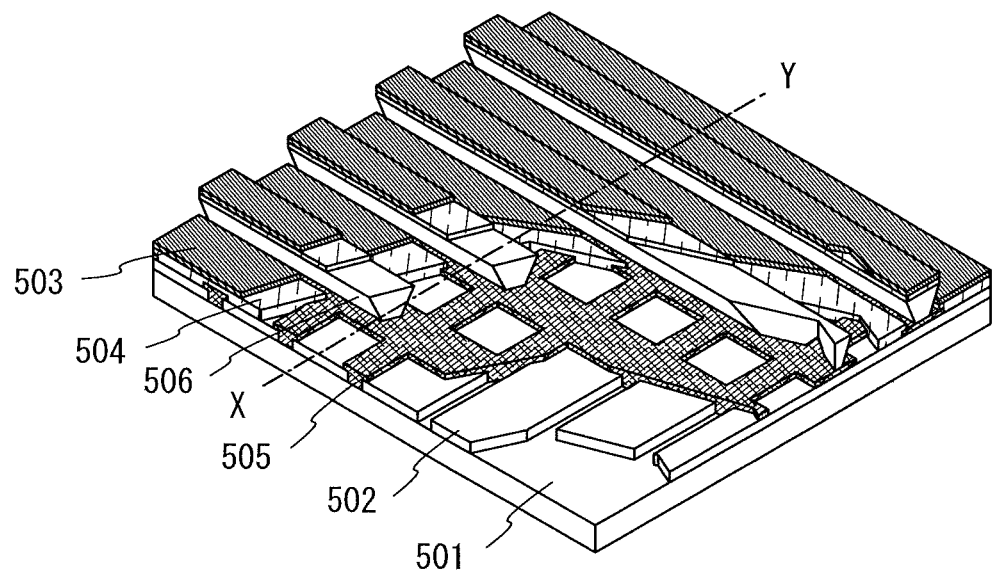
FIGS. 5A and 5B illustrate a light-emitting device.
Figure 5B:
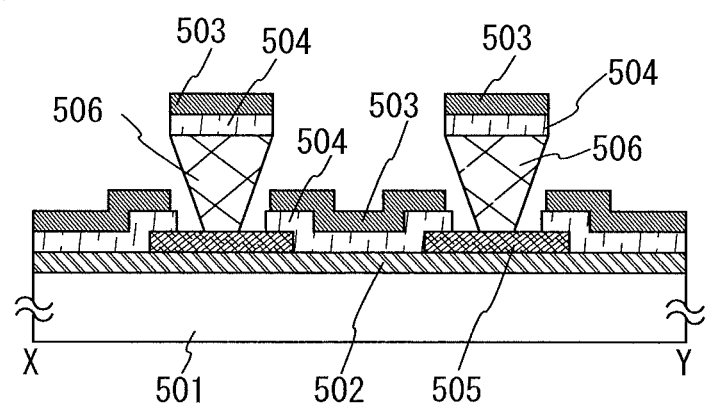

Further, the light-emitting element of Embodiment 3 or 4 can be used for a passive matrix light-emitting device instead of the above active matrix light-emitting device. FIGS. 5A and 5B illustrate a perspective view and a cross-sectional view of a passive matrix light-emitting device using the light-emitting element described in the above embodiment. FIG. 5A is a perspective view of the light-emitting device, and FIG. 5B is a cross-sectional view taken along line X-Y of FIG. 5A.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are aslope so that a distance between both sidewalls is gradually narrowed toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). By provision of the partition layer 506 in such a manner, a defect of the light-emitting element due to static electricity or the like can be prevented.

Accordingly, the passive matrix light-emitting device having the light-emitting element of Embodiment 3 or 4 can be obtained.

Note that any of the light-emitting devices described in this embodiment (the active matrix light-emitting device and the passive matrix light-emitting device) are formed using the light-emitting element described in the above embodiment, which has high emission efficiency and a long lifetime, and accordingly a light-emitting device with low power consumption and high reliability can be obtained.

Note that in this embodiment, an appropriate combination of the structures described in any other embodiment can be used.

(Embodiment 6)

In this embodiment, electronic devices and lighting devices including the light-emitting device described in Embodiment 5 are described. Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic book readers), image reproducing devices in which a recording medium is provided (specifically, devices that are capable of reproducing recording media such as digital versatile discs (DVDs) and provided with a display device that can display an image), and the like. Specific examples of these electronic devices are shown in FIGS. 6A to 6D.

Figure 6A:
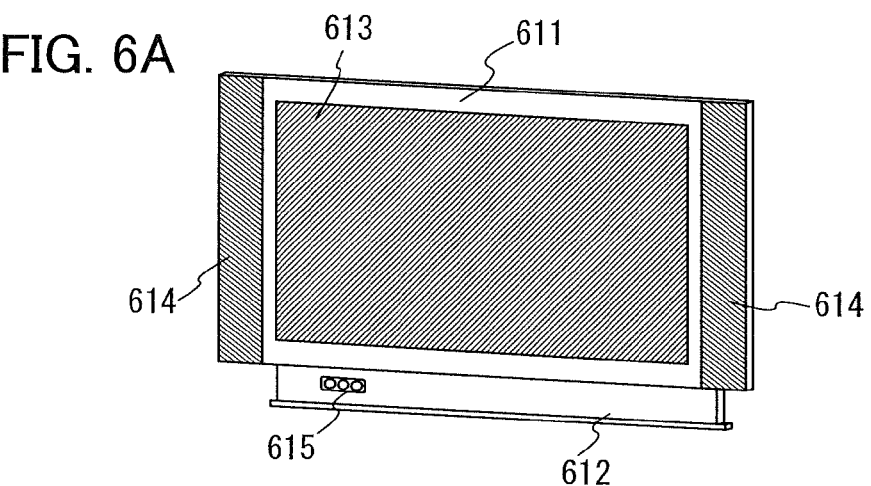
FIGS. 6A to 6D illustrate electronic devices.

FIG. 6A illustrates a television set according to one embodiment of the present invention, which includes a housing 611, a supporting base 612, a display portion 613, speaker portions 614, video input terminals 615, and the like. In this television set, the light-emitting device of the present invention can be applied to the display portion 613. Since the light-emitting device of the present invention has the feature of high emission efficiency, a television set with low power consumption can be obtained by application of the light-emitting device of the present invention.

Figure 6B:
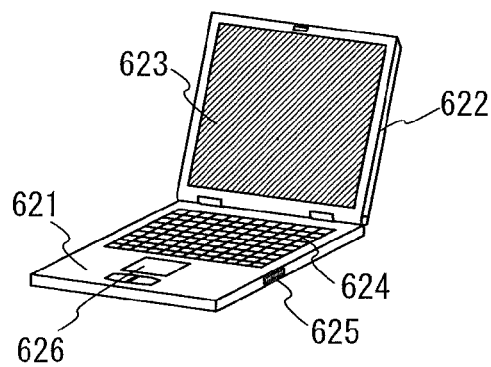

FIG. 6B illustrates a computer according to one embodiment of the present invention, which includes a main body 621, a housing 622, a display portion 623, a keyboard 624, an external connection port 625, a pointing device 626, and the like. In this computer, the light-emitting device of the present invention can be applied to the display portion 623. Since the light-emitting device of the present invention has the feature of high emission efficiency, a computer with low power consumption can be obtained by application of the light-emitting device of the present invention.

Figure 6C:
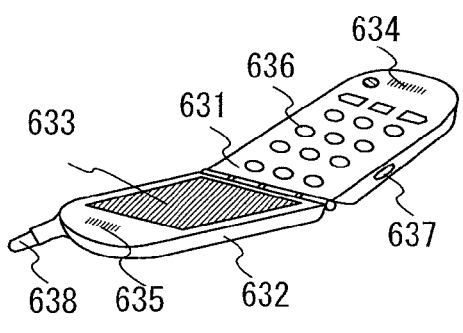

FIG. 6C shows a cellular phone according to one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. Since the light-emitting device of the present invention has the feature of high emission efficiency, a cellular phone having reduced power consumption can be obtained by application of the light-emitting device of the present invention.

Figure 6D:
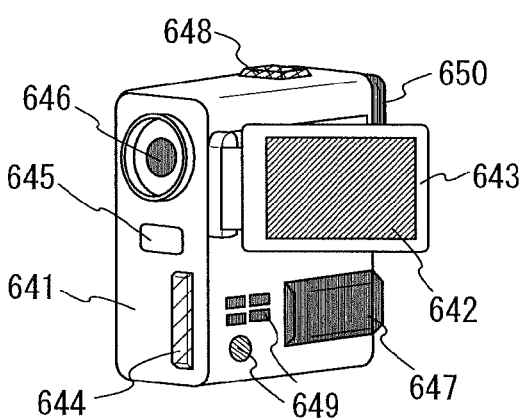

FIG. 6D shows a camera according to one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of the present invention can be applied to the display portion 642. Since the light-emitting device of the present invention has the feature of high emission efficiency, a camera having reduced power consumption can be obtained by application of the light-emitting device of the present invention.

As thus described, application range of the light-emitting device of one embodiment of the present invention is quite wide, and this light-emitting device can be applied to electronic devices of a variety of fields. With use of the light-emitting device of the present invention, an electronic device having reduced power consumption can be obtained.

Figure 7:
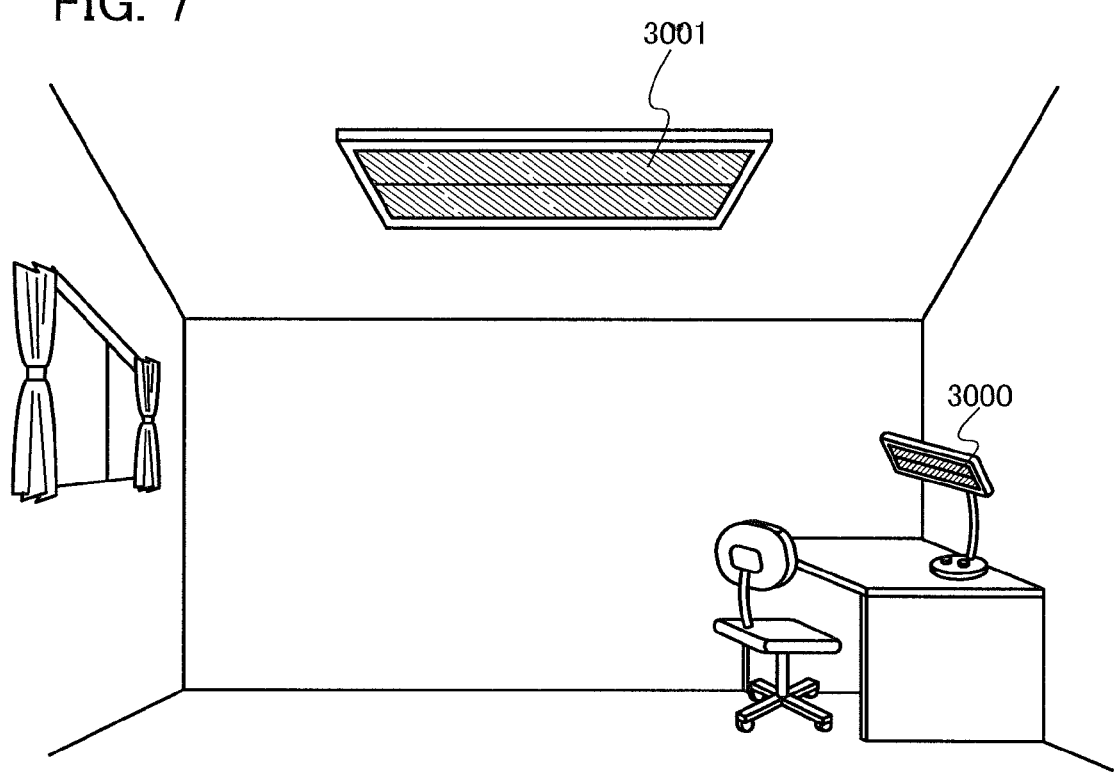
FIG. 7 illustrates a lighting device.

Moreover, the light-emitting device of one embodiment of the present invention can be used as a lighting device. FIG. 7 is an example in which the light-emitting device formed in accordance with the above embodiment is used as an indoor lighting device 3001. Since the light-emitting device described in the above embodiment can be increased in area, the light-emitting device can be used as a lighting device having a large area. The light-emitting device described in the above embodiment can also be used as a desk lamp 3000. Note that the lighting device includes in its category, a ceiling light, a wall light, a lightning for an inside of a car, an emergency exit light, and the like. Since the light-emitting device fabricated in accordance with the above embodiment has a long-lifetime light-emitting element, the light-emitting device can be used as a long-lifetime lighting device.

Note that the structure described of this embodiment can be implemented in combination with any of the structures described in other embodiments as appropriate.

EXAMPLE 1

In this example, 4-(10-phenyl-9-anthryl)-4'-(9-phenyl-9H-fluoren-9-yl)triphenylamine (abbreviation: FLPAPA) represented by Structural Formula (124) in Embodiment 1 was produced.

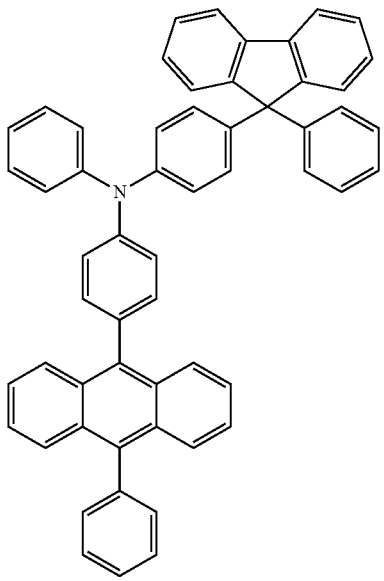

(124)

Step 1: Synthesis method of 9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dripped into this mixture, the mixture was stirred and heated under reflux for 2.5 hours. Accordingly, a Grignard reagent was prepared.

In a 500-mL three-neck flask were put 10 g (40 mmol) of 4-bromobenzophenone and 100 mL of diethyl ether. After the Grignard reagent prepared as above was slowly dripped into this mixture, the mixture was heated and stirred under reflux for 9 hours.

After the reaction, this mixture was filtered to give a residue. The obtained residue was dissolved in 150 mL of ethyl acetate, and a hydrochloric acid solution (1 mol/L) was added thereto. The mixture was stirred for 2 hours. The organic layer of this solution was washed with water. Then, magnesium sulfate was added thereto so as to adsorb moisture. This suspension was filtered and the obtained filtrate was concentrated to give a candy-like substance.

In a 500-mL recovery flask were put this candy-like substance, 50 mL of glacial acetic acid and 1.0 mL of hydrochloric acid. The mixture was heated and stirred under a nitrogen atmosphere at 130° C. for 1.5 hours to be reacted.

After the reaction, this reaction mixture solution was filtered to give a residue. The obtained residue was washed with water, aqueous sodium hydroxide, water, and methanol in this order, and then was dried, whereby 11 g of a white powder was obtained in 69% yield, which was the substance to be produced. The synthesis scheme of the above Step 1 is shown in the following (E1-1).

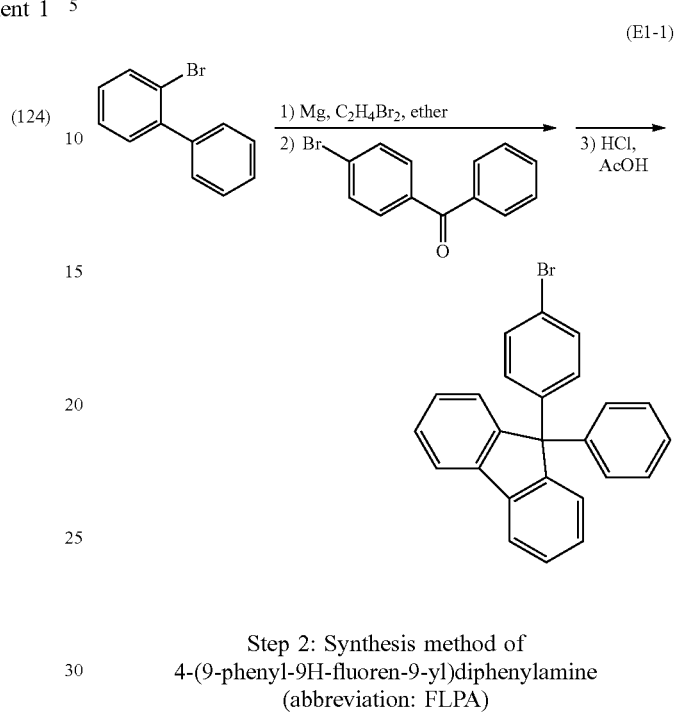

(E1-1)

Step 2: Synthesis method of 4-(9-phenyl-9H-fluoren-9-yl)diphenylamine (abbreviation: FLPA)

In a 200 mL three-neck flask were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide. The air in the flask was replaced with nitrogen. To this mixture were added 147.0 mL of toluene and 0.4 mL of a 10% hexane solution of tri(tert-butyl)phosphine. The temperature of this mixture was set to 60° C., and 66.1 mg (0.1 mmol) of bis(dibenzylideneacetone)palladium(0) was added to the mixture, followed by stirring for 3.5 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (the developing solvent has a 2:1 ratio of hexane to toluene). The obtained fractions were concentrated to give 6.0 g of a white solid in a yield of 99%, which was the substance to be produced. The synthesis scheme of this Step 2 is shown in (E1-2) given below.

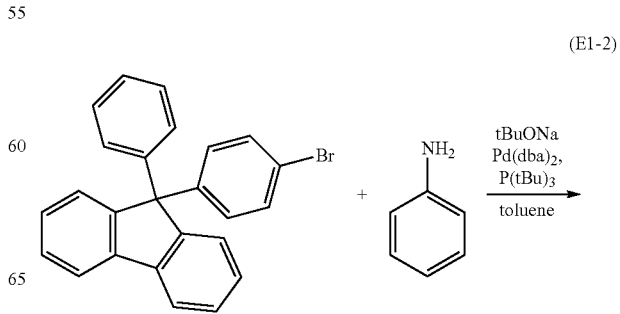

(E1-2)

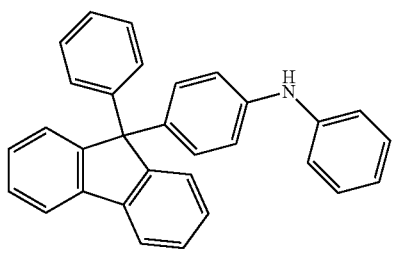
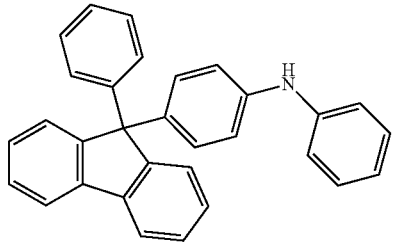

Step 3: Synthesis method of 4-(10-phenyl-9-anthryl)-4'-(9-phenyl-9H-fluoren-9-yl)triphenylamine (abbreviation: FLPAPA)

In a 50 mL three-neck flask were put 0.8 g (2.0 mmol) of 9-(4-bromophenyl)-10-phenylanthracene, 0.8 g (2.0 mmol) of 4-(9-phenyl-9H-fluoren-9-yl)diphenylamine, and 0.6 g (6.1 mmol) of sodium tert-butoxide. The air in the flask was replaced with nitrogen. To this mixture were added 15.0 mL of toluene and 0.2 mL of a 10% hexane solution of tri(tert-butyl)phosphine. The temperature of this mixture was set to 60° C., and 28.6 mg (0.05 mmol) of bis(dibenzylideneacetone)palladium(0) was added to the mixture, followed by stirring for 3.0 hours. After the stirring, the mixture was suction-filtered through Florisil, Celite, and alumina to give a filtrate. The filtrate was concentrated to give a solid, which was then purified by silica gel column chromatography (the developing solvent has a 2:1 ratio of hexane to toluene). The obtained fractions were concentrated to give a yellow solid. Recrystallization of the solid from a mixed solvent of chloroform and hexane gave 1.3 g of a pale yellow powdered solid in 86% yield, which was the substance to be produced.

By a train sublimation method, 1.2 g of the obtained yellow solid was purified. In the purification, the pale yellow solid was heated at 340° C. under a pressure of 2.7 Pa with a flow rate of argon gas of 5.0 mL/min. After the purification, 1.1 g of the substance to be produced was obtained in 88% yield. The synthesis scheme of Step 3 is shown by the following (E1-3).

(E1-3)

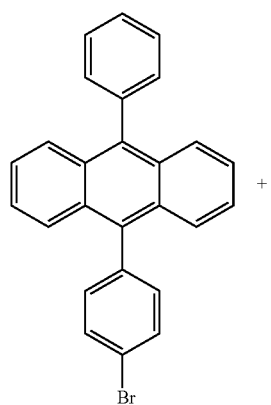
+

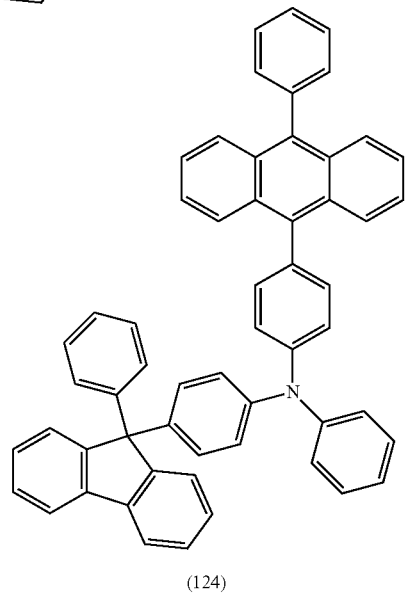

(124)

A nuclear magnetic resonance (NMR) method and a mass spectrometry identified this compound as 4-(10-phenyl-9-anthryl)-4'-(9-phenyl-9H-fluoren-9-yl)triphenylamine (abbreviation: FLPAPA), which was the substance to be produced.

$^1$H NMR data of the obtained compound are: $^1$H NMR (CDCl$_3$, 300 MHz): δ=7.03-7.40 (m, 26H), 7.46-7.49 (m, 4H), 7.54-7.63 (m, 3H), 7.66-7.70 (m, 2H), 7.77-7.81 (m, 4H).

Figure 8A:
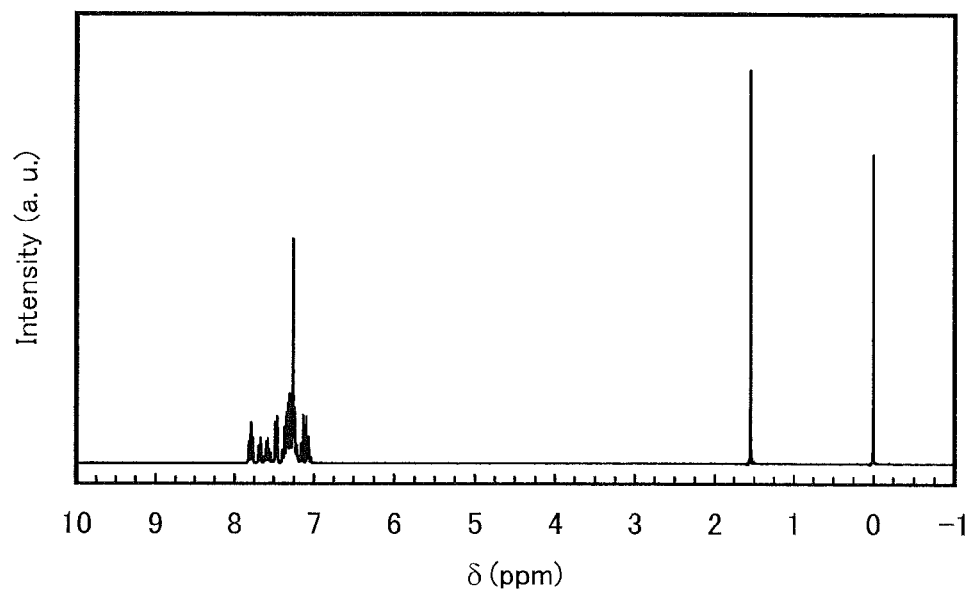
FIGS. 8A and 8B show $^1$H NMR charts of FLPAPA.
Figure 8B:
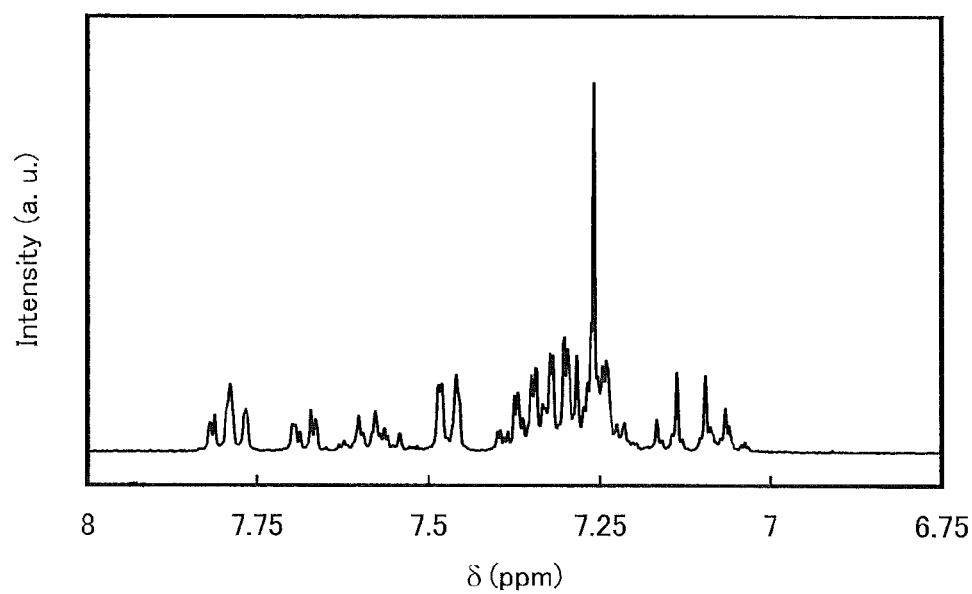

FIGS. 8A and 8B show the $^1$H NMR charts. Note that FIG. 8B is a chart showing an enlarged part of FIG. 8A in the range of 6.75 to 8.0 ppm.

The measurement result of the mass spectrometry of the obtained compound is: MS (ESI-MS): m/z=738 (M+H)$^+$; C$_{57}$H$_{39}$N$_2$ (737.31).

Figure 9A:
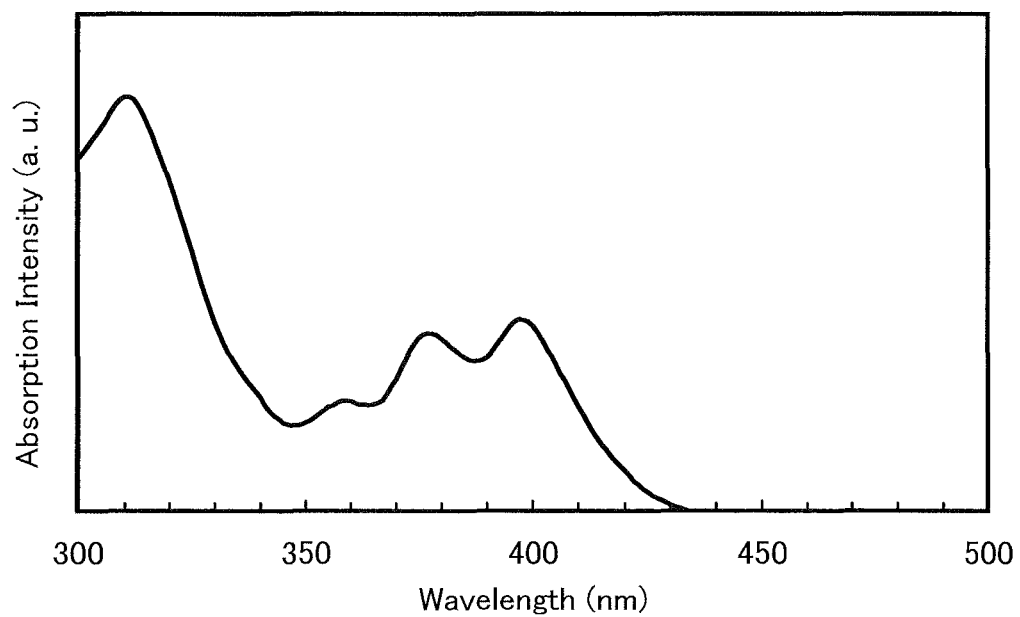
FIGS. 9A and 9B show an absorption spectrum and an emission spectrum of a toluene solution of FLPAPA.
Figure 9B:
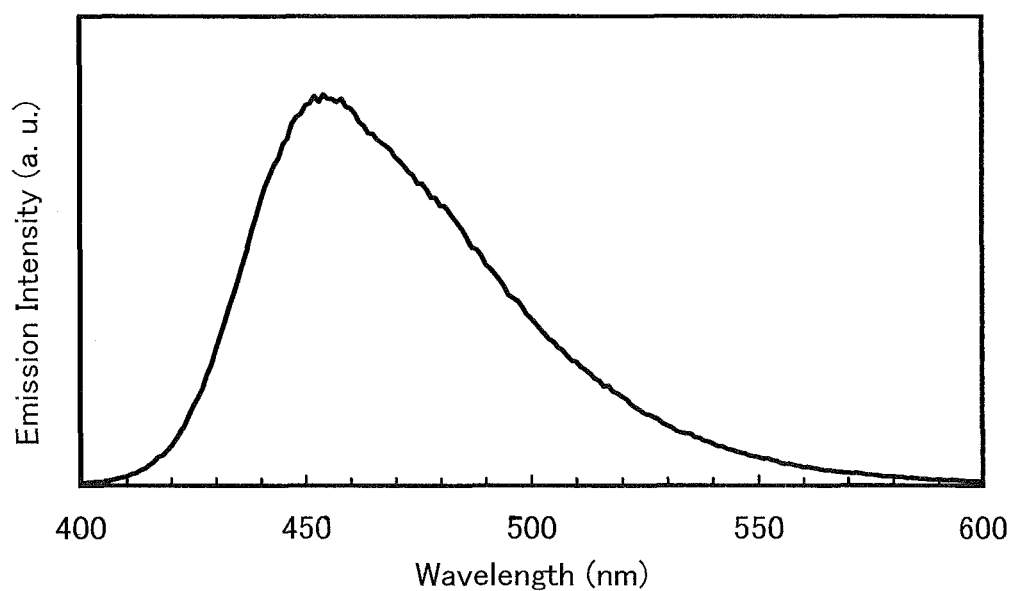
Figure 10A:
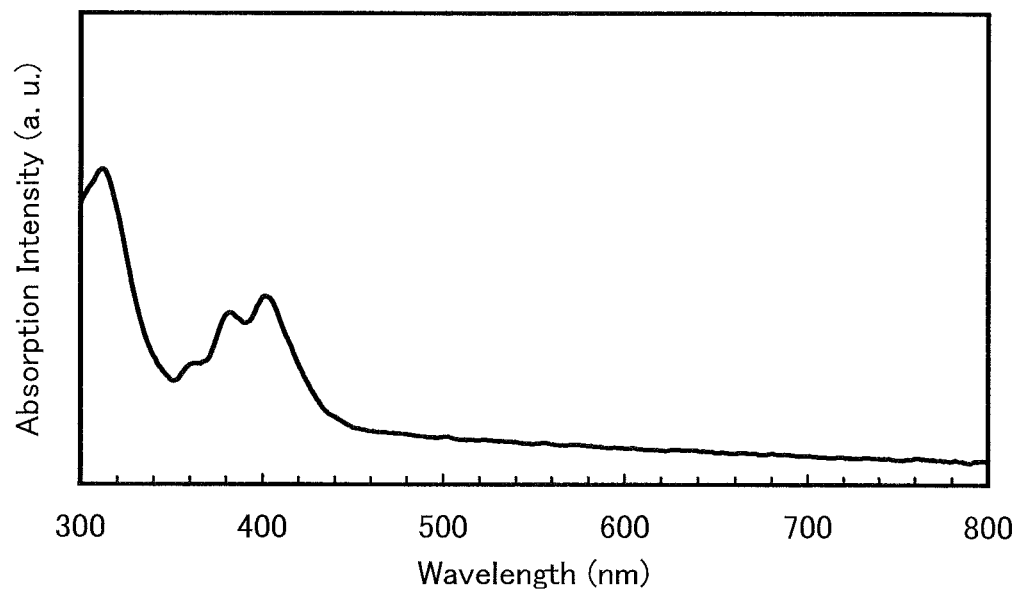
FIGS. 10A and 10B show an absorption spectrum and an emission spectrum of a thin film of FLPAPA.
Figure 10B:
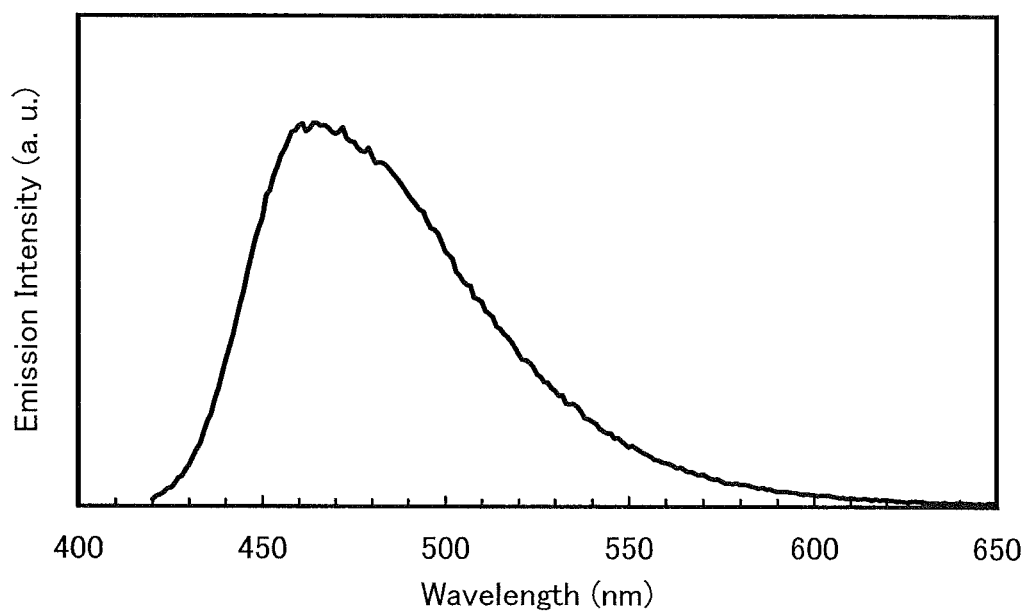

Further, FIG. 9A shows an absorption spectrum of a toluene solution of FLPAPA, and FIG. 9B shows an emission spectrum thereof. FIG. 10A shows an absorption spectrum of a thin film of FLPAPA, and FIG. 10B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell while the thin film was obtained by evaporation onto a quartz substrate. FIG. 9A show the absorption spectrum of the solution which was obtained by subtracting the absorption spectra of quartz and toluene, and FIG. 10A shows the absorption spectrum of the thin film which was obtained by subtracting the absorption spectrum of a quartz substrate. In FIGS. 9A and B and FIGS. 10A and 10B, the horizontal axis represents wavelength (nm) and the vertical axis represents intensity (arbitrary unit). In the case of the toluene solution, absorption was observed at around 397 nm, and the maximum emission wavelength was 454 nm (excitation wavelength: 397 nm). In the case of the thin film, absorption was observed at around 312 nm, 382 nm, and 401 nm, and the maximum emission wavelength was 465 nm (excitation wavelength: 404 nm).

These results indicate that the emission spectrum of the toluene solution of FLPAPA shows a very sharp peak with a half-width of 60 nm. The Stokes shift of the toluene solution is found to be as small as 57 nm.

The HOMO level and the LUMO level of the thin film of FLPAPA were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of FLPAPA which is shown in FIG. 10B, was regarded as an optical energy gap and added to the value of the HOMO level. As a result, the HOMO level and LUMO level of FLPAPA were found to be −5.54 eV and −2.65 eV, respectively, and the energy gap was found to be 2.89 eV.

Next, the oxidation-reduction characteristics were examined by cyclic voltammetry (CV). Note that an electrochemical analyzer (ALS model 600A or 600C, manufactured by BAS Inc.) was used for the measurement. The method of the measurement is detailed below.

(Calculation of Potential Energy of Reference Electrode with Respect to Vacuum Level)

First, the potential energy (eV) of the reference electrode (an Ag/Ag$^+$ electrode) used in Example 1 with respect to the vacuum level was calculated. In other words, the Fermi level of the Ag/Ag$^+$ electrode was calculated. It is known that the oxidation-reduction potential of ferrocene in methanol is +0.610 [V vs. SHE] with respect to the normal hydrogen electrode (Reference: Christian R. Goldsmith et al., J. Am. Chem. Soc., Vol. 124, No. 1, 83-96, 2002). On the other hand, using the reference electrode used in this example, the oxidation-reduction potential of ferrocene in methanol was calculated to be +0.11 [V vs. Ag/Ag$^+$]. Therefore, it was found that the potential energy of the reference electrode used in this example was lower than that of the standard hydrogen electrode by 0.50 [eV].

Note that it is known that the potential energy of the normal hydrogen electrode from the vacuum level is −4.44 eV (Reference: Toshihiro Ohnishi and Tamami Koyama, High molecular EL material, Kyoritsu shuppan, pp. 64-67). Accordingly, the potential energy of the reference electrode used in this example with respect to the vacuum level can be calculated to be −4.44−0.50=−4.94 [eV].

(CV Measurement of Produced Substance)

As for a solution used for the CV measurement, dehydrated dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. Note that the measurement was conducted at room temperature (20° C. to 25° C.). In addition, the scan rate at the CV measurement was set to 0.1 V/sec in all the measurement.

This solution was used to carry out the CV measurement of the substance produced. The potential of the working electrode with respect to the reference electrode was scanned from −0.10 V to 1.50 V and then from 1.50 V to −0.10 V, whereby a distinct peak indicating oxidation was observed. The shape of the peak did not greatly change even after 100 scan cycles. This indicates that FLPAPA has properties effective against repetition of redox reactions between an oxidized state and a neutral state.

In this CV measurement, the oxidation peak potential (from the neutral state to the oxidation state) $E_{pa}$ was 0.67 V. In addition, the reduction peak potential (from the oxidation side to the neutral state) $E_{pc}$ was 0.53 V. Therefore, the half-wave potential (potential intermediate between $E_{pa}$ and $E_{pc}$, $(E_{pa}+E_{pc})/2$ [V]) can be calculated to be 0.60 V. This shows that FLPAPA is oxidized by an electrical energy of 0.60 [V vs. Ag/Ag$^+$]. Here, since the potential energy of the reference electrode, which was used above, with respect to the vacuum level was −4.94 [eV] as described above, the HOMO level of FLPAPA was calculated as follows: −4.94−0.60=−5.54 [eV].

Thermogravimetry-differential thermal analysis (TG-DTA) of obtained FLPAPA was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 420° C., which is indicative of high heat resistance.

EXAMPLE 2

This example will show Synthesis Examples 1 and 2 in which N,N'-bis[4-(9-phenyl-9H-fluoren-9-yl)phenyl]-N,N'-diphenyl-pyrene-1,6-diamine (abbreviation: 1,6FLPAPrn) represented by Structural Formula (100) in Embodiment 1 was produced.

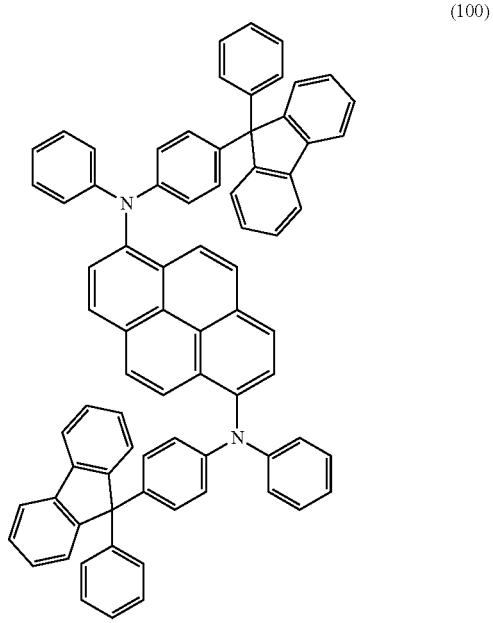 [SMILES: c1ccc(N(c2ccc(C3(c4ccccc4)c4ccccc4-c4ccccc43)cc2)c2ccc3ccc4c(N(c5ccccc5)c5ccc(C6(c7ccccc7)c7ccccc7-c7ccccc76)cc5)ccc5ccc2c3c54)cc1]

(100)

SYNTHESIS EXAMPLE 1

First, Synthesis Example 1 will be described.

In a 50 mL three-neck flask were put 0.4 g (1.2 mmol) of 1,6-dibromopyrene, 1.0 g (2.4 mmol) of 4-(9-phenyl-9H-fluoren-9-yl)diphenylamine (abbreviation: FLPA) obtained in Step 2 of Example 1 and 0.3 g (3.6 mmol) of sodium tert-butoxide. The air in the flask was replaced with nitrogen. To this mixture were added 11.5 mL of toluene and 0.20 mL of a 10% hexane solution of tri(tert-butyl)phosphine. The temperature of this mixture was set to 70° C., and 31.1 mg (0.05 mmol) of bis(dibenzylideneacetone)palladium(0) was added to the mixture, followed by stirring for 4.0 hours. After the stirring, the mixture was suction-filtered through Florisil, Celite, and alumina to give a filtrate. The filtrate was concentrated to give a solid, which was then purified by silica gel column chromatography (the developing solvent was chloroform). The obtained fractions were concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, whereby 0.8 g of a pale yellow powdered solid was obtained in 68% yield, which was the substance to be produced.

By a train sublimation method, 0.8 g of the obtained yellow solid was purified. Under a pressure of 2.7 Pa with a flow rate of argon at 5.0 mL/min, the sublimation purification was carried out at 360° C. After the purification, 0.4 g of the substance to be produced was obtained in a yield of 56%. The synthesis scheme of this Synthesis Example 1 is shown by the following (E2-A).

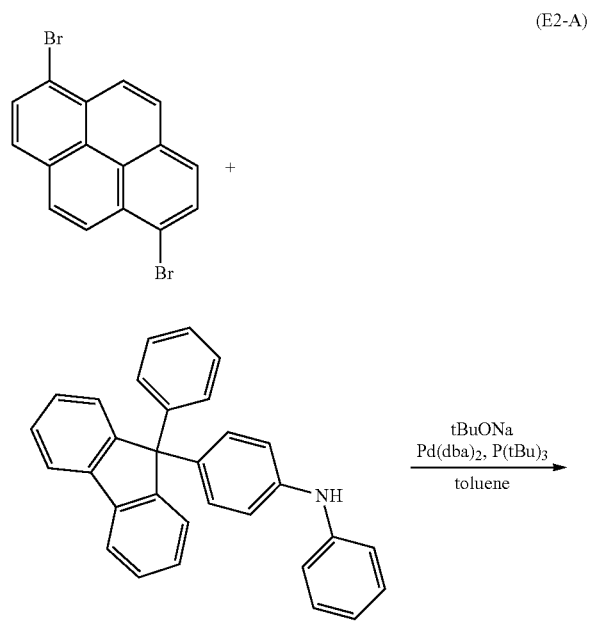

(E2-A)

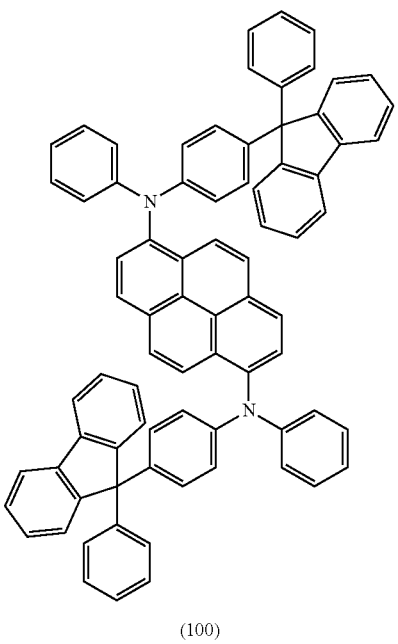

(100)

SYNTHESIS EXAMPLE 2

Next, Synthesis Example 2 shows a synthesis method of 1,6FLPAPrn, which is different from that in Synthesis Example 1.

In a 300 mL three-neck flask were put 3.0 g (8.3 mmol) of 1,6-dibromopyrene and 6.8 g (17 mmol) of 4-(9-phenyl-9H-fluoren-9-yl)diphenylamine (abbreviation: FLPA) obtained in Step 2 of Example 1. The air in the flask was replaced with nitrogen. To this mixture were added 100 mL of toluene, 0.10 mL of a 10 wt % hexane solution of tri(tert-butyl)phosphine, and 2.4 g (25 mmol) of sodium tert-butoxide. This mixture was degassed while being stirred under reduced pressure. This mixture was heated at 80° C., and after whether the material was dissolved was confirmed, 48 mg (0.083 mmol) of bis(dibenzylideneacetone)palladium (0) was added. This mixture was stirred at 80° C. for 1.5 hours. After the stirring, the precipitated yellow solid was collected through suction filtration without cooling the mixture. The obtained solid was suspended in 3 L of toluene and heated at 110° C. This suspension was suction-filtered through alumina, Celite, and Florisil while the temperature of the suspension was kept at 110° C. Further, the suspension was processed with 200 mL of toluene which had been heated to 110° C. The resulting filtrate was concentrated to about 300 mL, which was then recrystallized. Accordingly, 5.7 g of a substance was obtained in 67% yield, which was the substance to be produced.

By a train sublimation method, 3.56 g of the obtained yellow solid was purified. Under a pressure of 5.0 Pa with a flow rate of argon at 5.0 mL/min, the sublimation purification was carried out at 353° C. After the purification, 2.54 g of a yellow solid was obtained in a yield of 71%, which was the substance to be produced. The synthesis scheme of this Synthesis Example 2 is shown by the following (E2-B).

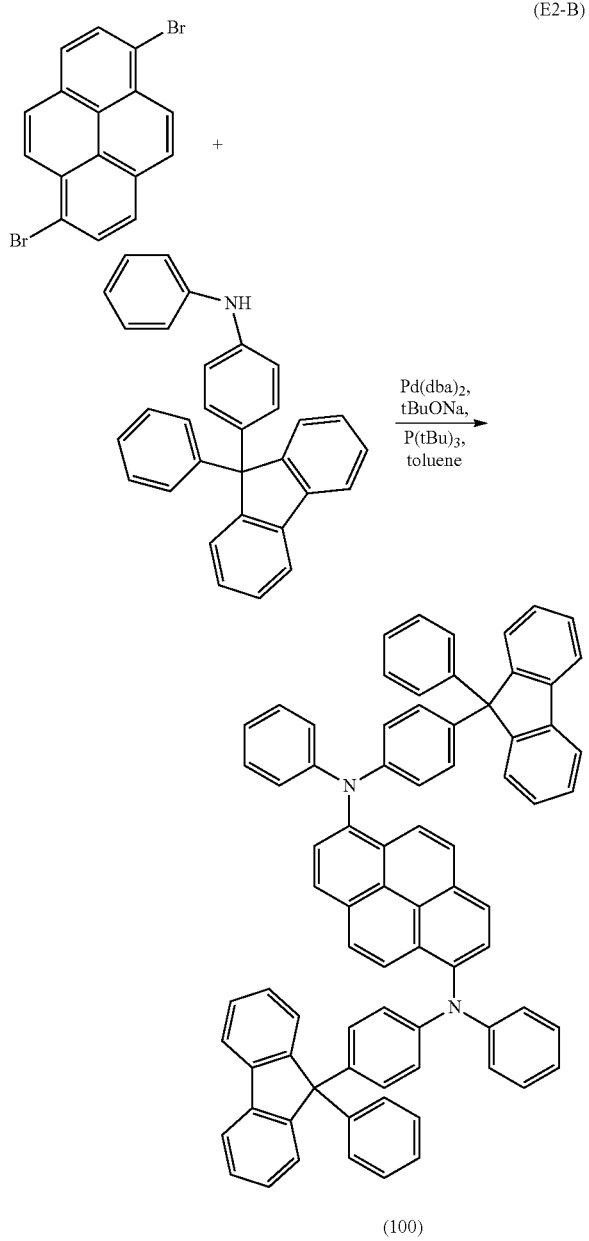

A nuclear magnetic resonance (NMR) method and a mass spectrometry identified the compound, which was obtained through Synthesis Example 1 and 2, as N,N'-bis[4-(9-phenyl-9H-fluoren-9-yl)phenyl]-N,N'-diphenyl-pyrene-1,6-diamine (abbreviation: 1,6FLPAPrn), which was the substance to be produced.

$^1$H NMR data of the compound obtained through Synthesis Examples 1 and 2 are: $^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H).

Figure 11A:
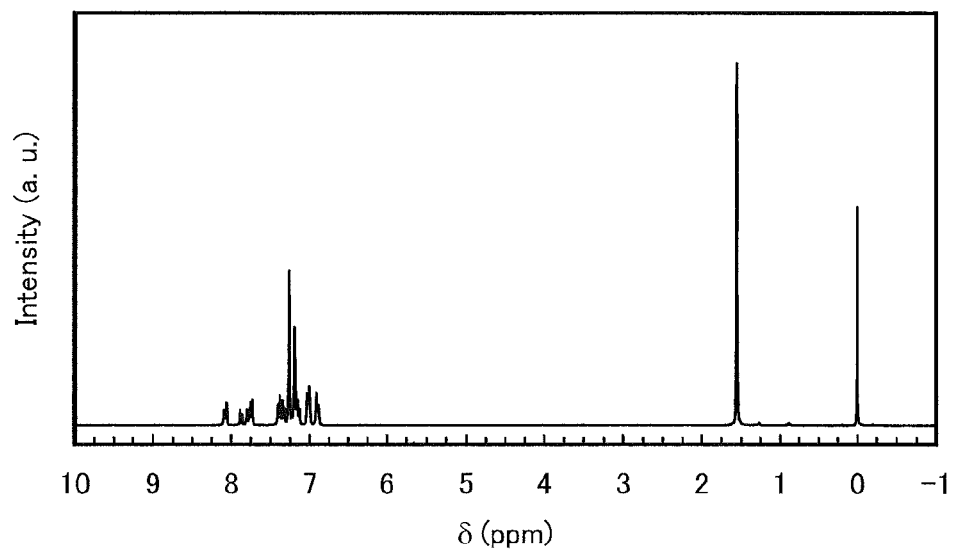
FIGS. 11A and 11B show $^1$H NMR charts of 1,6FLPAPrn.
Figure 11B:
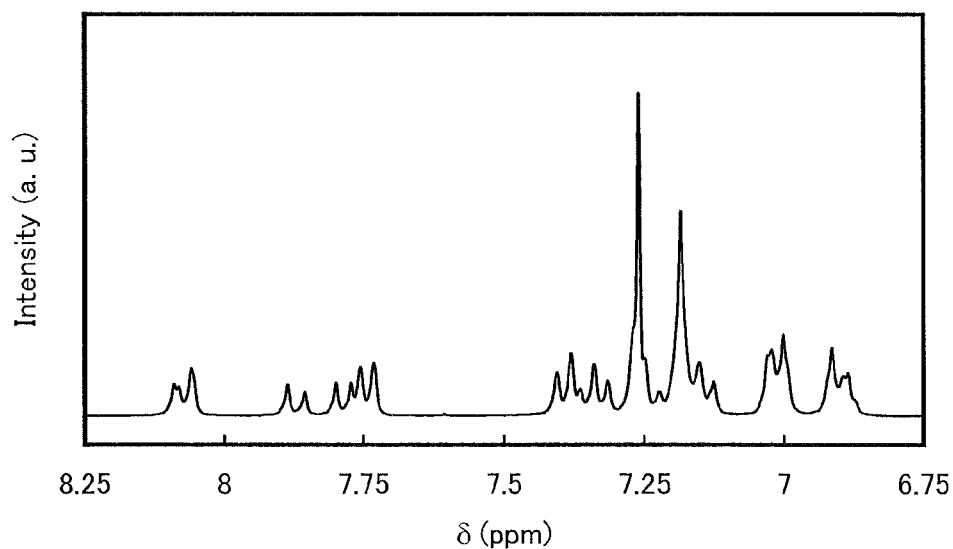

FIGS. 11A and 11B show the $^1$H NMR charts. Note that FIG. 11B is a chart showing an enlarged part of FIG. 11A in the range of 6.75 to 8.25 ppm.

The measurement result of the compound, which was obtained through Synthesis Examples 1 and 2, by the mass spectrometry is MS (ESI-MS): m/z=1017 (M+H)$^+$; C$_{78}$H$_{52}$N$_2$ (1016.41).

Figure 12A:
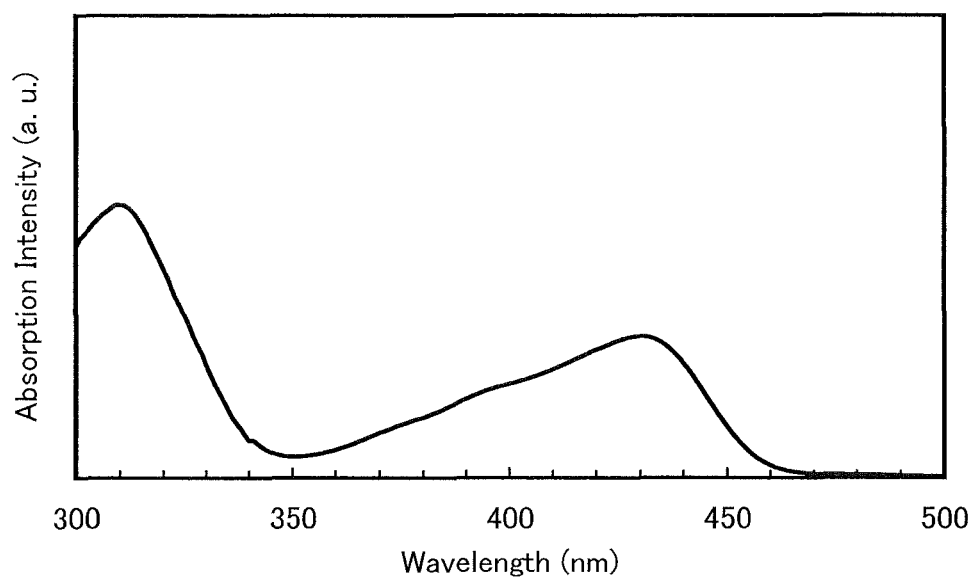
FIGS. 12A and 12B show an absorption spectrum and an emission spectrum of a toluene solution of 1,6FLPAPrn.
Figure 12B:
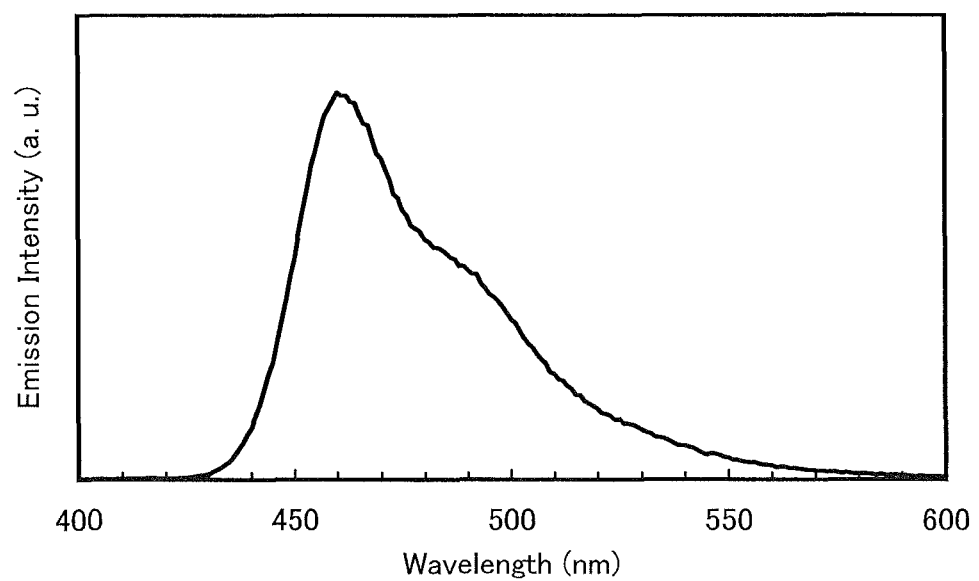
Figure 13A:
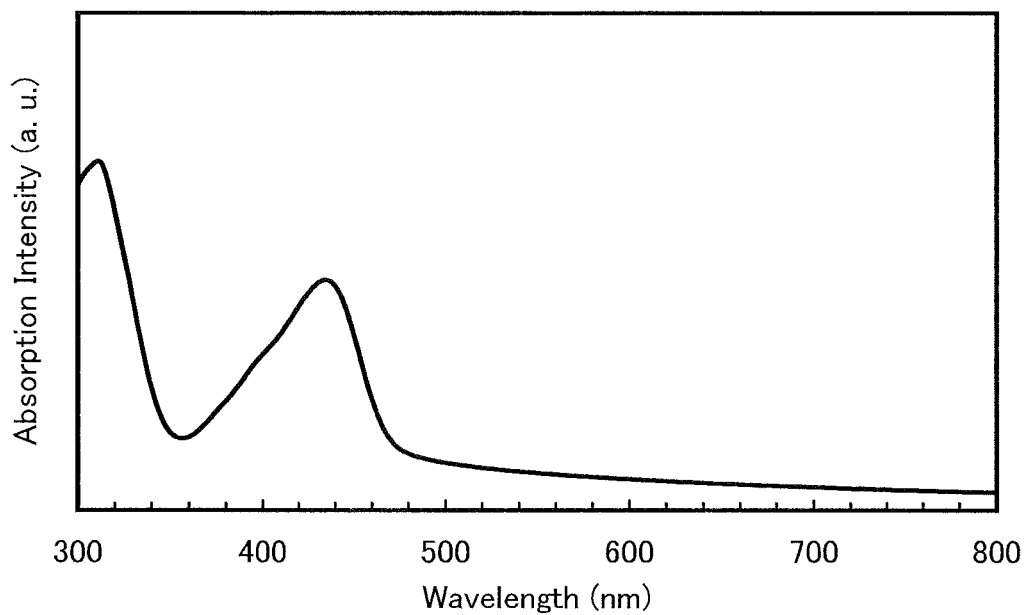
FIGS. 13A and 13B show an absorption spectrum and an emission spectrum of a thin film of 1,6FLPAPrn.
Figure 13B:
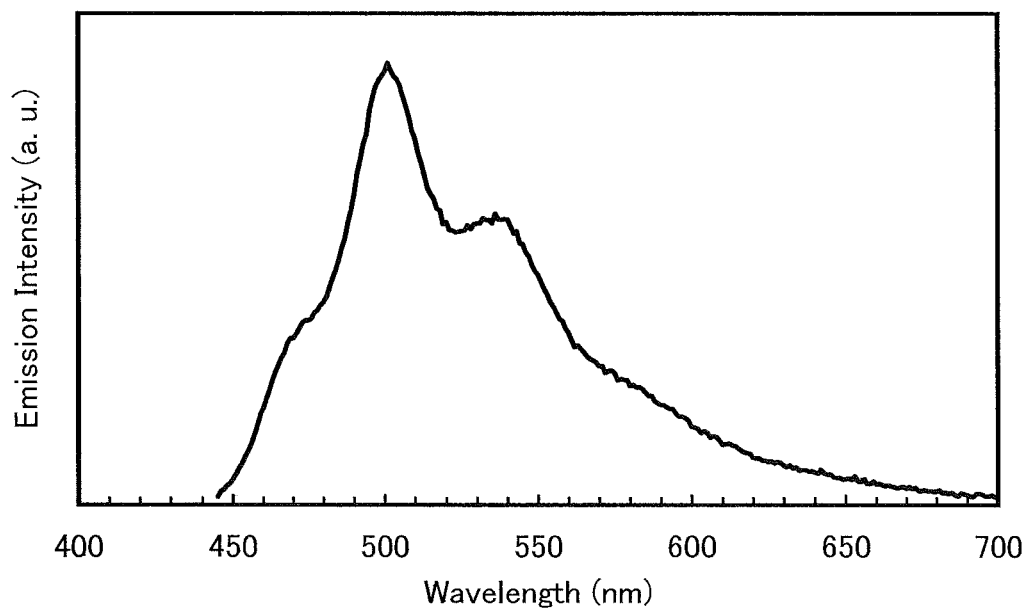

Further, FIG. 12A shows an absorption spectrum of a toluene solution of 1,6FLPAPrn, and FIG. 12B shows an emission spectrum thereof. FIG. 13A shows an absorption spectrum of a thin film of 1,6FLPAPrn, and FIG. 13B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 12A show the absorption spectrum of the solution which was obtained by subtracting the absorption spectra of quartz and toluene, and FIG. 13A shows the absorption spectrum of the thin film which was obtained by subtracting the absorption spectrum of a quartz substrate. In FIGS. 12A and 12B and FIGS. 13A and 13B, the horizontal axis represents wavelength (nm) and the vertical axis represents intensity (arbitrary unit). In the case of the toluene solution, absorption was observed at around 311 nm and 431 nm, and the maximum emission wavelength was 461 nm (excitation wavelength: 370 nm). In the case of the thin film, absorption was observed at around 238 nm, 268 nm, 311 nm, and 435 nm, and the maximum emission wavelength was 501 nm (excitation wavelength: 430 nm).

These results indicate that the emission spectrum of the toluene solution of 1,6FLPAPrn shows a very sharp peak with a half-width of 45 nm The Stokes shift of the toluene solution is found to be 30 nm, which is a very small value.

The HOMO level and the LUMO level of the thin film of 1,6FLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6FLPAPrn which is shown in FIG. 13B, was regarded as an optical energy gap and added to the value of the HOMO level. As a result, the HOMO level and LUMO level of 1,6FLPAPrn were found to be −5.40 eV and −2.73 eV, respectively, and the energy gap was found to be 2.67 eV.

The oxidation-reduction characteristics of were examined by cyclic voltammetry (CV). Note that an electrochemical analyzer (ALS model 600A or 600C, manufactured by BAS Inc.) was used for the measurement. Since the measurement method is similar to that of Example 1, the description is omitted.

In the CV measurement of this example, the potential of the working electrode with respect to the reference electrode was scanned from −0.10 V to 0.6 V and then from 0.6 V to −0.10 V, whereby a distinct peak indicating oxidation was observed. The shape of the peak did not greatly change even after 100 scan cycles. This indicates that 1,6FLPAPrn has good properties effective against repetition of redox reactions between an oxidized state and a neutral state.

In this CV measurement, the oxidation peak potential (from the neutral state to the oxidation state) $E_{pa}$ was 0.51 V. In addition, the reduction peak potential (from the oxidation side to the neutral state) $E_{pc}$ was 0.41 V. Therefore, the half-wave potential (potential intermediate between $E_{pa}$ and $E_{pc}$, $(E_{pa}+E_{pc})/2$ [V]) can be calculated to be 0.46 V. This shows that 1,6FLPAPrn is oxidized by an electrical energy of 0.46 [V vs. Ag/Ag$^+$]. Here, since the potential energy of the reference electrode, which was used above, with respect to the vacuum level is −4.94 [eV] as described above, the HOMO level of 1,6FLPAPrn was calculated as follows: −4.94−0.46=−5.40 [eV].

Thermogravimetry-differential thermal analysis (TG-DTA) of obtained 1,6FLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high thermal stability. The measurement was carried out under a pressure of $9.3\times10^{-4}$ Pa at a temperature rising rate of 10° C./min. The relationship between weight and temperature (thermogravimetry) shows that the 5% weight loss temperature is 365° C., which is indicative of a good sublimation property. Thus, the fluorene derivative (1,6FLPAPrn) of one embodiment of the present invention is found to be a material having a low sublimation temperature and a good sublimation property despite its high molecular weight.

EXAMPLE 3

In this example, N,N'-bis[4-(9-phenyl-9H-fluoren-9-yl)phenyl]-N,N'-bis(4-tert-butylphenyl)-pyrene-1,6-diamine (abbreviation: 1,6tBu-FLPAPrn) represented by Structural Formula (102) in Embodiment 1 was produced.

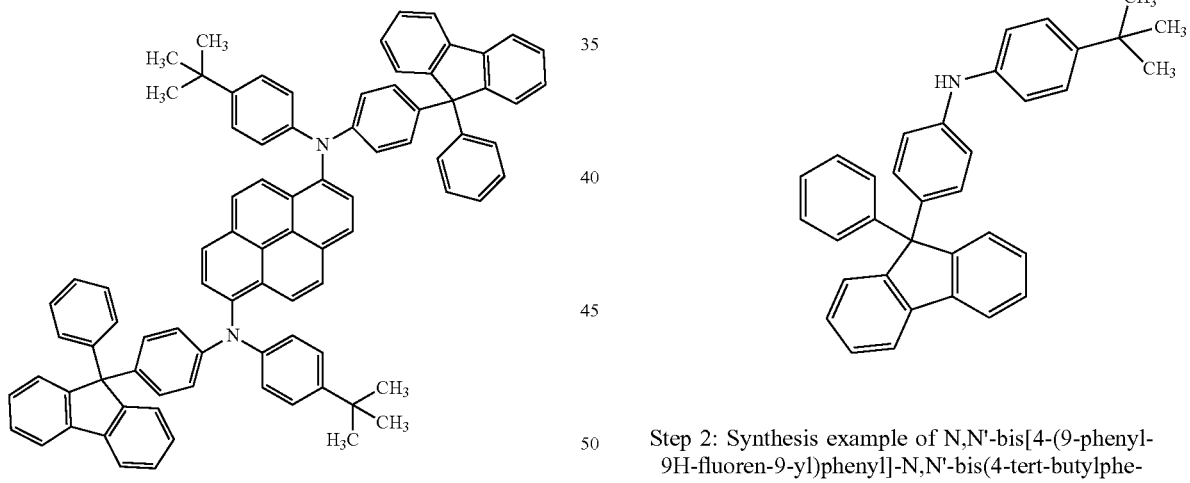

Step 1: Synthesis example of 4-tert-butylphenyl-4-(9-phenyl-9H-fluoren-9-yl)phenylamine (abbreviation: tBu-FLPA)

In a 100 mL three-neck flask were put 2.6 g (6.4 mmol) of 9-(4-bromophenyl)-9-phenylfluorene in Step 1 of Example 1 and 1.9 g (19.8 mmol) of sodium tert-butoxide. The air in the flask was replaced with nitrogen. To this mixture were added 32.0 mL of toluene, 2.5 mL (15.9 mmol) of 4-tert-butylaniline, and 0.30 mL of a 10% hexane solution of tri(tert-butyl)phosphine. The temperature of this mixture was set to 60° C., and 41.9 mg (0.07 mmol) of bis(dibenzylideneacetone)palladium(0) was added to the mixture. The temperature of the mixture was raised to 80° C., followed by stirring for 4.0 hours. After the stirring, the mixture was suction-filtered through Florisil, Celite, and alumina to give a filtrate. The filtrate was concentrated to give a solid, which was then purified by silica gel column chromatography (the developing solvent has a 3:4 ratio of hexane to toluene). The obtained fractions were concentrated to give a while solid. Recrystallization of the obtained white solid from a mixed solvent of toluene and hexane gave 2.3 g of tBu-FLPA in 76% yield, which was the substance to be produced. The synthesis scheme of this Step 1 is shown in the following (E3-1).

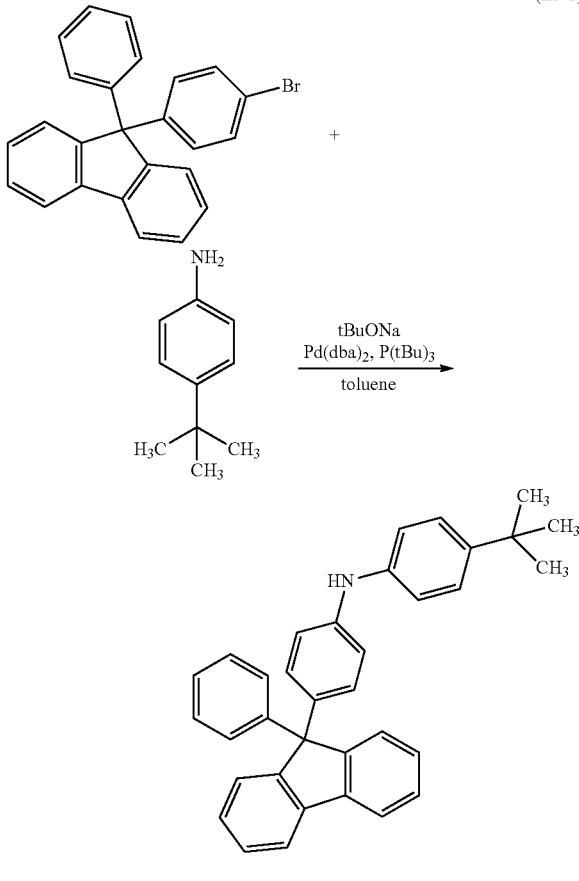

Step 2: Synthesis example of N,N'-bis[4-(9-phenyl-9H-fluoren-9-yl)phenyl]-N,N'-bis(4-tert-butylphenyl)-pyrene-1,6-diamine (abbreviation: 1,6tBu-FLPAPrn)

In a 100 mL three-neck flask were put 0.5 g (1.3 mmol) of 1,6-dibromopyrene, 1.2 g (2.7 mmol) of tBu-FLPA, and 0.4 g (4.0 mmol) of sodium tert-butoxide. The air in the flask was replaced with nitrogen. To this mixture were added 25.0 mL of toluene and 0.20 mL of a 10% hexane solution of tri(tert-butyl)phosphine. The temperature of this mixture was set to 80° C., and 41.6 mg (0.07 mmol) of bis(dibenzylideneacetone)palladium(0) was added to the mixture, followed by stirring for 3.5 hours. After the stirring, the mixture was suction-filtered through Florisil, Celite, and alumina to give a filtrate. The filtrate was concentrated to give a solid, which was then purified by silica gel column chromatography (the developing solvent has a 3:2 ratio of hexane to toluene). The obtained fractions were concentrated to give a yellow solid, which was the substance to be produced. Recrystallization of the solid from a mixed solvent of toluene and hexane gave 1.3 g of a yellow solid in 86% yield, which was the substance to be produced.

Because the substance produced (1,6tBu-FLPAPrn) has a structure in which a tert-butyl group which is an alkyl group is bonded to a benzene ring in an amine skeleton, 1,6tBu-FLPAPrn has higher solubility in an organic solvent such as toluene or chloroform than 1,6FLPAPrn obtained in Example 2. Such improvement of the solubility in a solvent facilitates purification of the fluorene derivative (1,6tBu-FLPAPrn) of this example, demonstrating the easiness of its synthesis.

By a train sublimation method, 0.9 g of the obtained yellow solid was purified. In the purification, the yellow solid was heated at 371° C. under a pressure of 2.7 Pa with a flow rate of argon gas of 5.0 mL/min. After the purification, 0.8 g of the substance to be produced was obtained in a yield of 90%. The synthesis scheme of this Step 2 is shown by the following (E3-2).

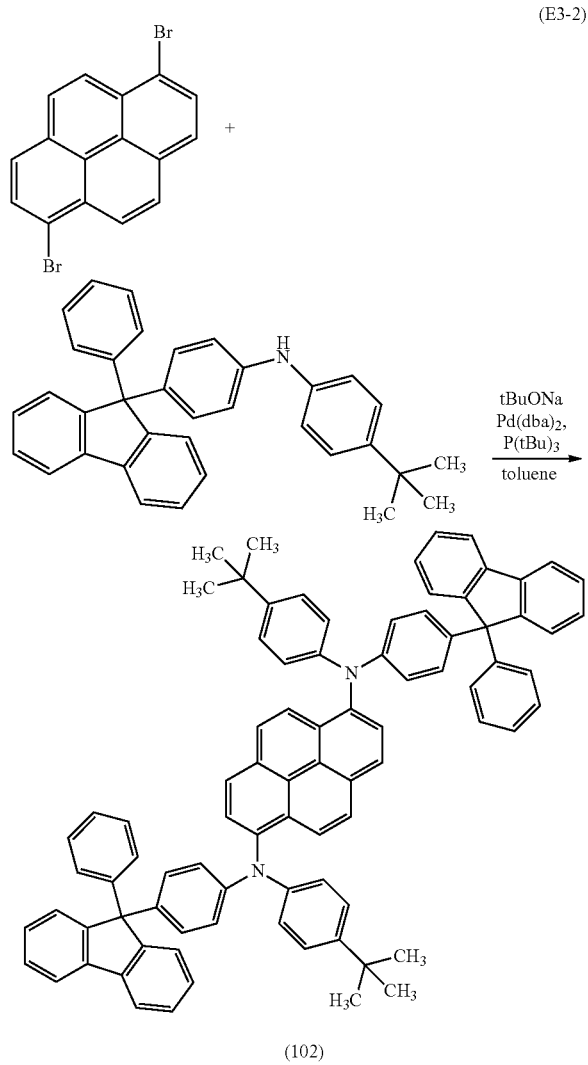

A nuclear magnetic resonance (NMR) method and a mass spectrometry identified this compound as N,N'-bis[4-(9-phenyl-9H-fluoren-9-yl)phenyl]-N,N'-bis(4-tert-butylphenyl)-pyrene-1,6-diamine (abbreviation: 1,6tBu-FLPAPrn), which was the substance to be produced.

$^1$H NMR data of the obtained compound are: $^1$H NMR (CDCl$_3$, 300 MHz): δ=1.25 (s, 18H), 6.84-6.87 (m, 4H), 6.95-7.00 (m, 8H), 7.15-7.36 (m, 22H), 7.39 (d, J=7.2 Hz, 4H), 7.74 (d, J=7.2 Hz, 4H), 7.79 (d, J=8.4 Hz, 2H), 7.87 (d, J=9.3 Hz, 2H), 8.06 (d, J=8.4 Hz, 2H), 8.09 (d, J=9.3 Hz, 2H).

Figure 14A:
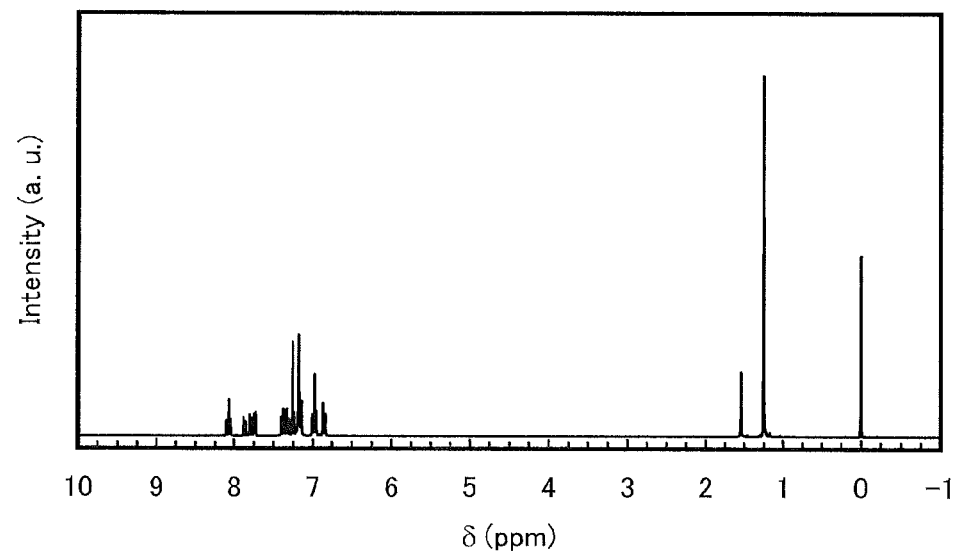
FIGS. 14A and 14B show $^1$H NMR charts of 1,6tBu-FLPAPrn.
Figure 14B:
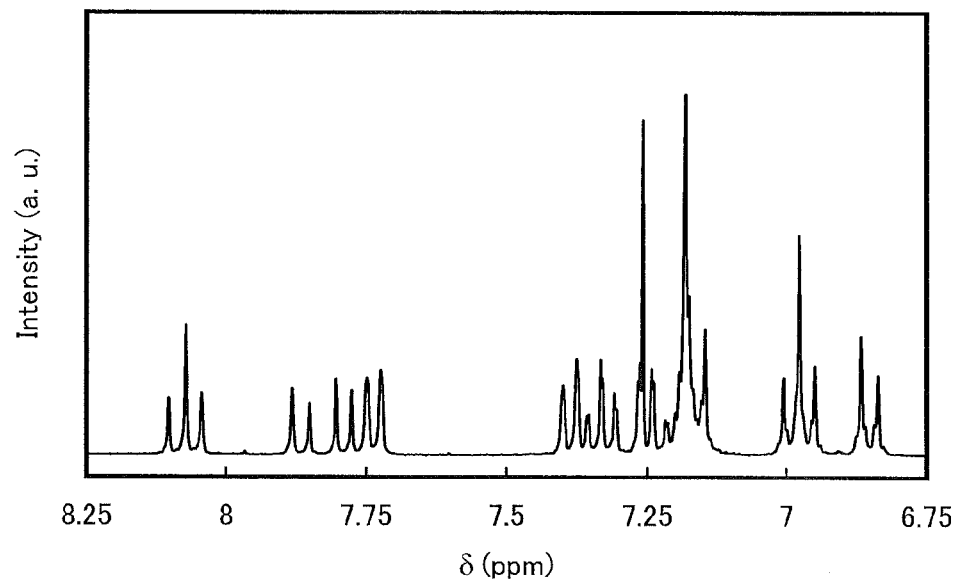

FIGS. 14A and 14B show the $^1$H NMR charts. Note that FIG. 14B is a chart showing an enlarged part of FIG. 14A in the range of 6.75 to 8.25 ppm.

The measurement result of the mass spectrometry of the obtained compound is: MS (ESI-MS): m/z=1130 (M+H)$^+$; C$_{86}$H$_{68}$N$_2$ (1128.54).

Figure 15A:
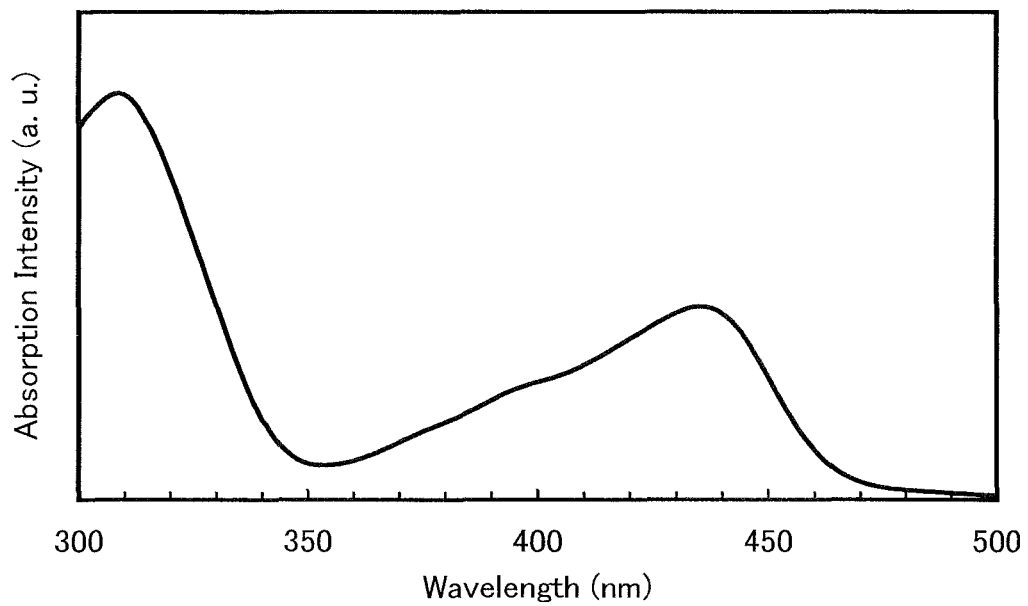
FIGS. 15A and 15B show an absorption spectrum and an emission spectrum of a toluene solution of 1,6tBu-FLPAPrn.
Figure 15B:
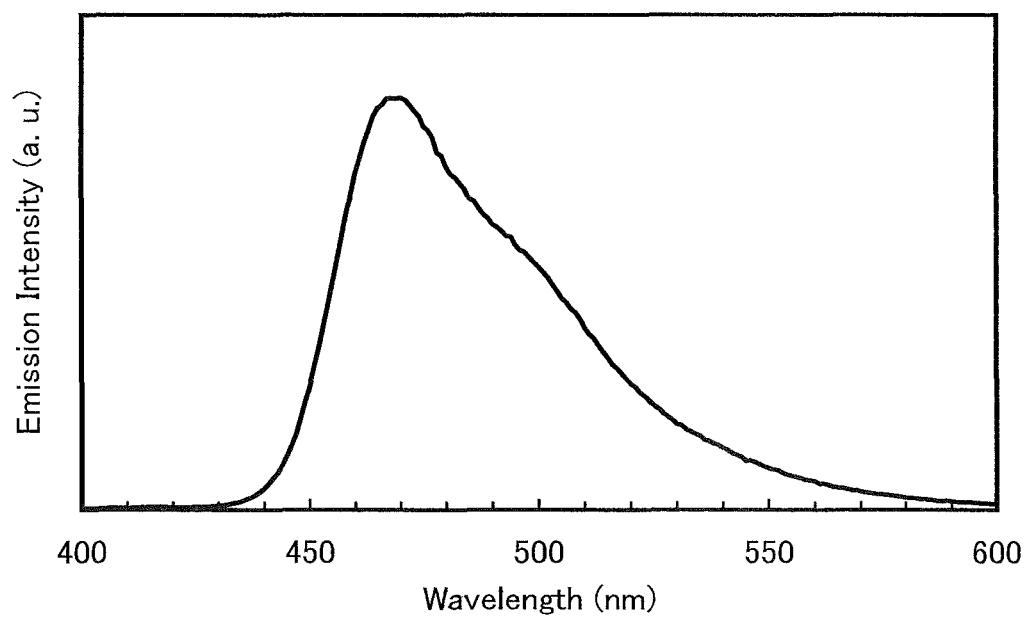
Figure 16A:
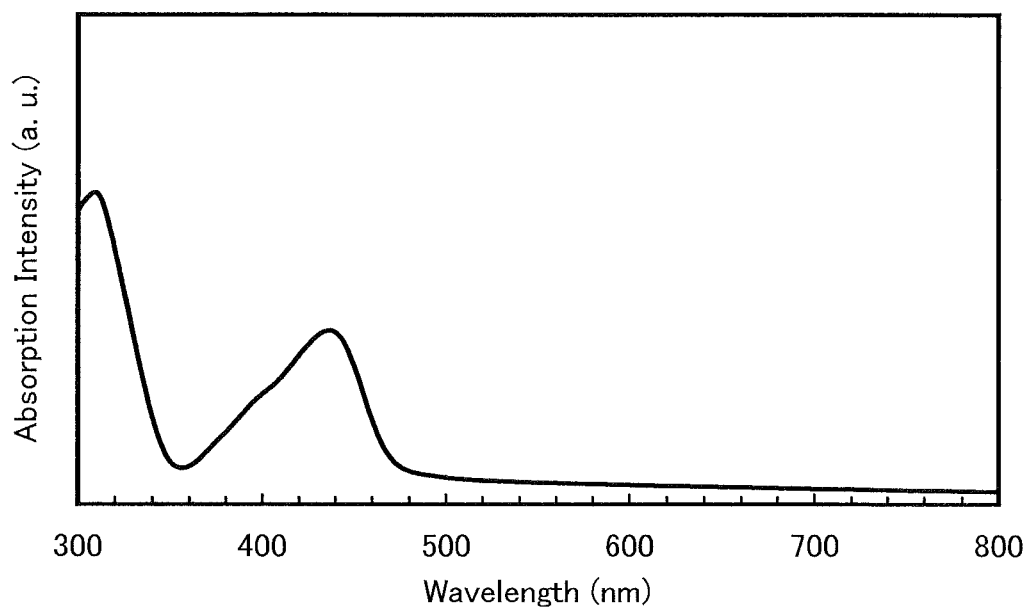
FIGS. 16A and 16B show an absorption spectrum and an emission spectrum of a thin film of 1,6tBu-FLPAPrn.
Figure 16B:
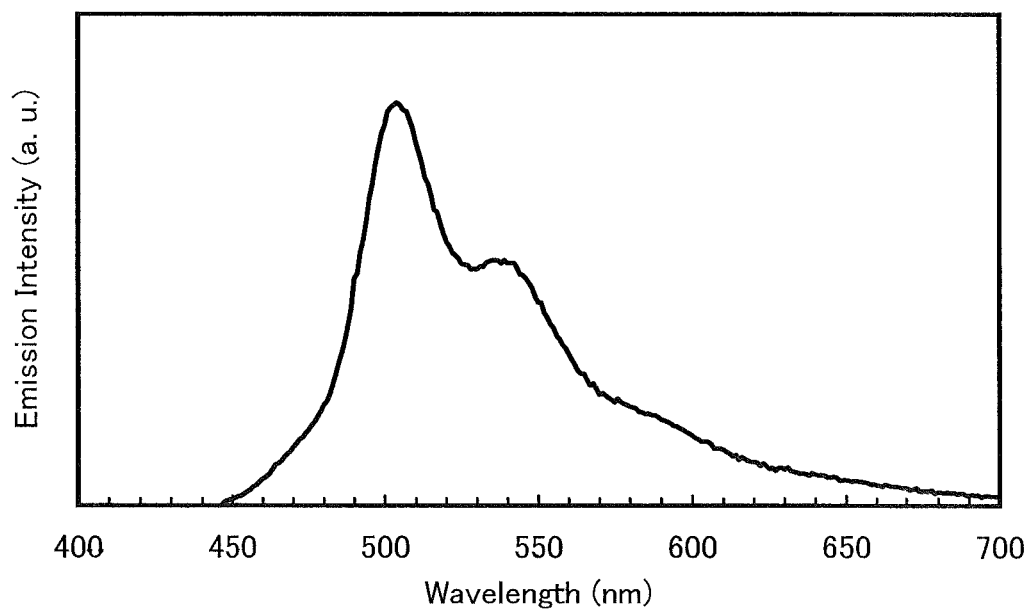

Further, FIG. 15A shows an absorption spectrum of a toluene solution of 1,6tBu-FLPAPrn, and FIG. 15B shows an emission spectrum thereof. FIG. 16A shows an absorption spectrum of a thin film of 1,6tBu-FLPAPrn, and FIG. 16B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 15A show the absorption spectrum of the solution which was obtained by subtracting the absorption spectra of quartz and toluene, and FIG. 16A shows the absorption spectrum of the thin film which was obtained by subtracting the absorption spectrum of a quartz substrate. In FIGS. 15A and 15B and FIGS. 16A and 16B, the horizontal axis represents wavelength (nm) and the vertical axis represents intensity (arbitrary unit). In the case of the toluene solution, absorption was observed at around 437 nm, and the maximum emission wavelength was 470 nm (excitation wavelength: 370 nm). In the case of the thin film, absorption was observed at around 437 nm, and the maximum emission wavelength was 504 nm (excitation wavelength: 432 nm).

These results indicate that the emission spectrum of the toluene solution of 1,6tBu-FLPAPrn shows a very sharp peak with a half-width of 53 nm. The Stokes shift of the toluene solution is found to be 33 nm, which is a very small value.

The oxidation-reduction characteristics of were examined by cyclic voltammetry (CV). Note that an electrochemical analyzer (ALS model 600A or 600C, manufactured by BAS Inc.) was used for the measurement. Since the measurement method is similar to that of Example 1, the description is omitted.

In the CV measurement of this example, the potential of the working electrode with respect to the reference electrode was scanned from −0.10 V to 0.57 V and then from 0.57 V to −0.10 V, whereby a distinct peak indicating oxidation was observed. The shape of the peak did not greatly change even after 100 scan cycles. This indicates that 1,6tBu-FLPAPrn has good properties effective against repetition of redox reactions between an oxidized state and a neutral state.

In this CV measurement, the oxidation peak potential (from the neutral state to the oxidation state) $E_{pa}$ was 0.50 V. In addition, the reduction peak potential (from the oxidation side to the neutral state) $E_{pc}$ was 0.38 V. Therefore, the half-wave potential (potential intermediate between $E_{pa}$ and $E_{pc}$, $(E_{pa}+E_{pc})/2$ [V]) can be calculated to be 0.44 V. This shows that 1,6tBu-FLPAPrn is oxidized by an electrical energy of 0.44 [V vs. Ag/Ag+]. Here, since the potential energy of the reference electrode, which was used above, with respect to the vacuum level is −4.94 [eV] as described above, the HOMO level of 1,6tBu-FLPAPrn was calculated as follows: −4.94−0.44=−5.38 [eV].

The HOMO level and the LUMO level of the thin film of 1,6tBu-FLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6tBu-FLPAPrn which is shown in FIG. 16B, was regarded as an optical energy gap and added to the value of the HOMO level. As a result, the HOMO level and LUMO level of 1,6tBu-FLPAPrn were found to be −5.28 eV and −2.61 eV, respectively, and the energy gap was found to be 2.67 eV.

Thermogravimetry-differential thermal analysis (TG-DTA) of obtained 1,6tBu-FLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

EXAMPLE 4

This example will show a method for manufacturing a light-emitting element using the fluorene derivative described in Embodiment 1 as a light-emitting material and measurement results of its element characteristics, as well as measurement results of those of a reference light-emitting element. Specifically, this example will show the light-emitting element formed using 4-(10-phenyl-9-anthryl)-4'-(9-phenyl-9H-fluoren-9-yl)triphenylamine (abbreviation: FLPAPA) represented by Structural Formula (124) which is described in Example 1.

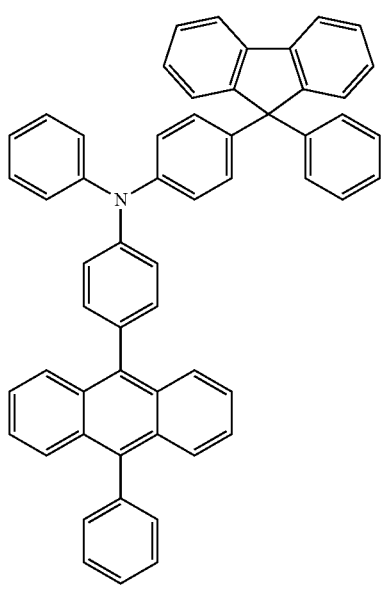

(124)

Figure 17A:
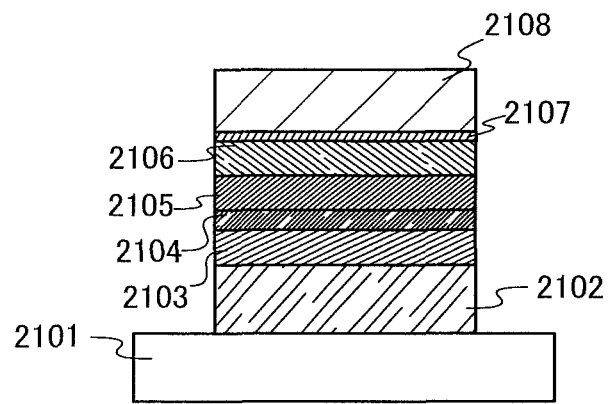
FIGS. 17A and 17B illustrate light-emitting elements of Examples.

Fabrication methods of Light-emitting Element 1 and Reference Light-emitting Element 1 will now be described referring to FIG. 17A. In addition, structural formulas of the organic compounds used in this example are shown below.

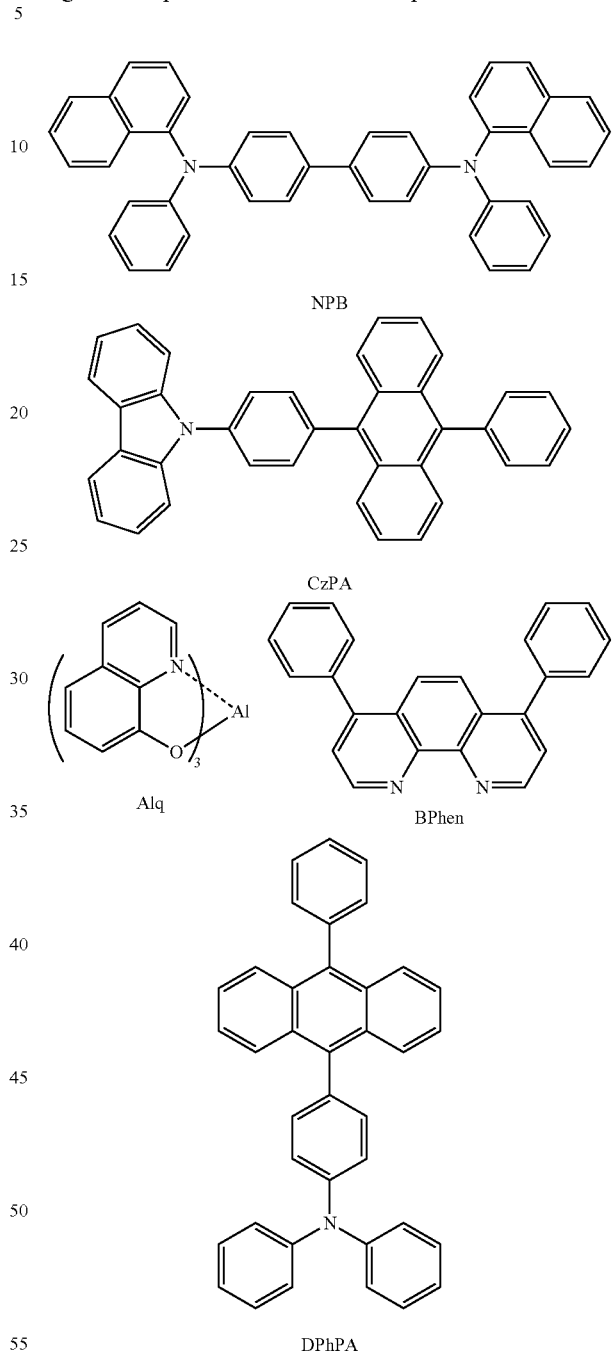

(Light-Emitting Element 1)

First, indium oxide-tin oxide containing silicon oxide was deposited by a sputtering method on a substrate 2101 which is a glass substrate, whereby an anode 2102 was formed. Its thickness was 110 nm and the electrode area was 2 mm×2 mm.

Next, an EL layer having a stack of plural layers was formed over the anode 2102. In this example, the EL layer includes a hole-injection layer 2103, a hole-transport layer 2104, a light-emitting layer 2105, an electron-transport layer 2106, and an electron-injection layer 2107, which are sequentially stacked.

Next, the substrate 2101 was fixed to a substrate holder in a vacuum evaporation apparatus so that a surface of the substrate 2101 on which the anode 2102 was formed faced downward. The pressure in the vacuum evaporation apparatus was reduced to about $10^{-4}$ Pa. Then, on the anode 2102, 4,4'-bis[N-(1-naphthyl)-N-phenylamino]biphenyl (abbreviation: NPB) and molybdenum(VI) oxide were co-evaporated to form the hole-injection layer 2103. Its thickness was 50 nm, and the evaporation rate was controlled so that the weight ratio of NPB to molybdenum(VI) oxide was 4:1 (=NPB:molybdenum(VI) oxide). Note that the co-evaporation method refers to an evaporation method in which evaporation is carried out from a plurality of evaporation sources at the same time in one treatment chamber.

Next, a 10-nm-thick film of a hole-transport material was formed on the hole-injection layer 2103 by an evaporation method using resistance heating, whereby the hole-transport layer 2104 was formed. Note that NPB was used for the hole-transport layer 2104.

Next, the light-emitting layer 2105 was formed on the hole-transport layer 2104 by an evaporation method using resistance heating. As the light-emitting layer 2105, a 30-nm-thick film was formed by co-evaporation of 9-[4-(10-phenyl-9-anthryl)phenyl]-9H-carbazole (abbreviation: CzPA) and 4-(10-phenyl-9-anthryl)-4'-(9-phenyl-9H-fluoren-9-yl)triphenylamine (abbreviation: FLPAPA). Here, the evaporation rate was controlled so that the weight ratio of CzPA to FLPAPA was 1:0.1 (=CzPA:FLPAPA).

Furthermore, on the light-emitting layer 2105, a 10-nm-thick film of tris(8-quinolinolato)aluminum (abbreviation: Alq) and, thereon, a 15-nm-thick film of bathophenanthroline (abbreviation: BPhen) were deposited, whereby the electron-transport layer 2106 was formed. The electron-transport layer 2106 was formed by an evaporation method using resistance heating.

Next, lithium fluoride (LiF) was deposited to a thickness of 1 nm on the electron-transport layer 2106, whereby the electron-injection layer 2107 was formed.

Lastly, a 200-nm-thick film of aluminum was formed by an evaporation method using resistance heating to form the cathode 2108. Thus, Light-emitting Element 1 of this example was fabricated.

(Reference Light-Emitting Element 1)

Reference Light-emitting Element 1 was manufactured in the same way as Light-emitting Element 1 except for the light-emitting layer 2105 and the electron-transport layer 2106. For Reference Light-emitting Element 1, the light-emitting layer 2105 was formed to a thickness of 30 nm by co-evaporation of 9-[4-(10-phenyl-9-anthryl)phenyl]-9H-carbazole (abbreviation: CzPA) and 4-(10-phenyl-9-anthryl) triphenylamine (abbreviation: DPhPA). Here, the evaporation rate was controlled such that the weight ratio of CzPA to DPhPA was 1:0.1 (=CzPA:DPhPA).

Furthermore, on the light-emitting layer 2105, a 10-nm-thick film of tris(8-quinolinolato)aluminum (abbreviation: Alq) and, thereon, a 20-nm-thick film of bathophenanthroline (abbreviation: BPhen) were deposited, whereby the electron-transport layer 2106 was formed. The electron-transport layer 2106 was formed by an evaporation method using resistance heating.

Thus, Reference Light-emitting Element 1 of this example was fabricated.

Table 1 shows element structures of Light-emitting Element 1 and Reference Light-emitting Element 1 manufactured in this example. In Table 1, all the mixture ratios are weight ratios.

TABLE 1

| | Light-Emitting Element 1 | Reference Light-Emitting Element 1 |
|---|---|---|
| Anode 2102 | ITSO 110 nm | ITSO 110 nm |
| Hole-injection layer 2103 | NPB:MoOx (=4:1) 50 nm | NPB:MoOx (=4:1) 50 nm |
| Hole-transport layer 2104 | NPB 10 nm | NPB 10 nm |
| Light-emitting layer 2105 | CzPA:FLPAPA (=1:0.1) 30 nm | CzPA:DPhPA (=1:0.1) 30 nm |
| Electron-transport layer 2106 | Alq 10 nm Bphen 15 nm | Alq 10 nm Bphen 20 nm |
| Electron-injection layer 2107 | LiF 1 nm | LiF 1 nm |
| Cathode 2108 | Al 200 nm | Al 200 nm |

All the mixture ratios are weight ratios.

Light-emitting Element 1 and Reference Light-emitting Element 1 thus obtained were sealed in a glove box containing a nitrogen atmosphere so as not to be exposed to air. Then, operation characteristics of the elements were measured. Note that the measurement was carried out at room temperature (in the atmosphere kept at 25° C.).

Figure 18:
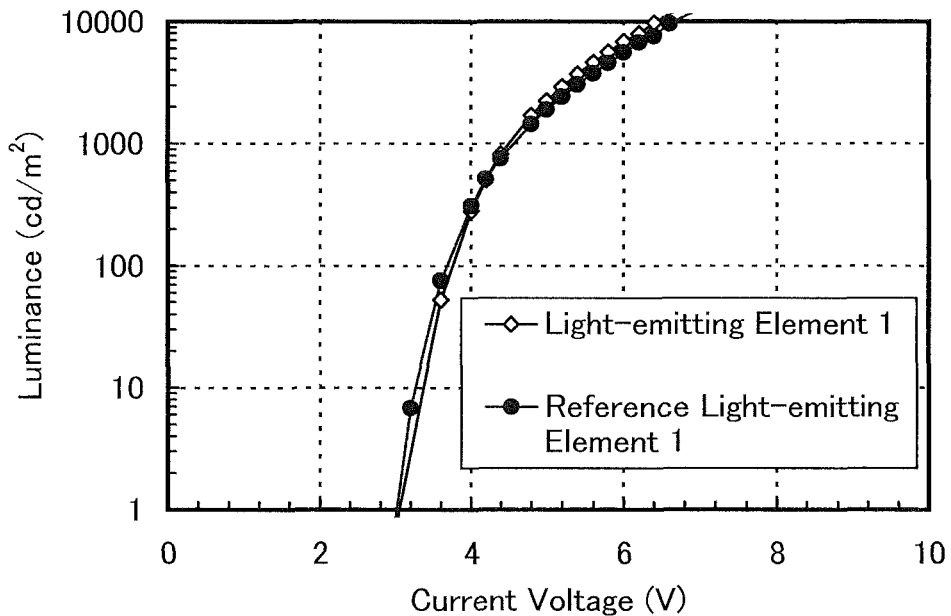
FIG. 18 shows characteristics of Light-emitting Element 1 and Reference Light-emitting Element 1.
Figure 19:
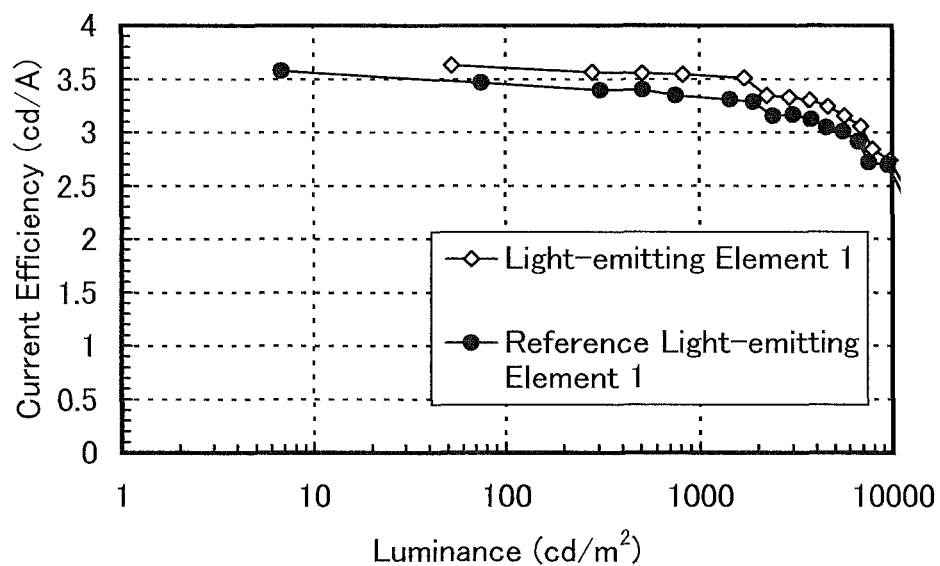
FIG. 19 shows characteristics of Light-emitting Element 1 and Reference Light-emitting Element 1.

FIG. 18 shows voltage vs. luminance characteristics of Light-emitting Element 1 and Reference Light-emitting Element 1, and FIG. 19 shows luminance vs. current efficiency characteristics. In FIG. 18, the vertical axis represents luminance (cd/m$^2$) and the horizontal axis represents current voltage (V). In FIG. 19, the vertical axis represents current efficiency (cd/A) and the horizontal axis represents luminance (cd/m$^2$). Further, Table 2 shows the chromaticity of the light-emitting elements at around 1000 cd/m$^2$.

TABLE 2

| | Chromaticity coordinates (x, y) |
|---|---|
| Light-Emitting Element 1 | (0.15, 0.15) |
| Reference Light-Emitting Element 1 | (0.16, 0.15) |

Figure 20:
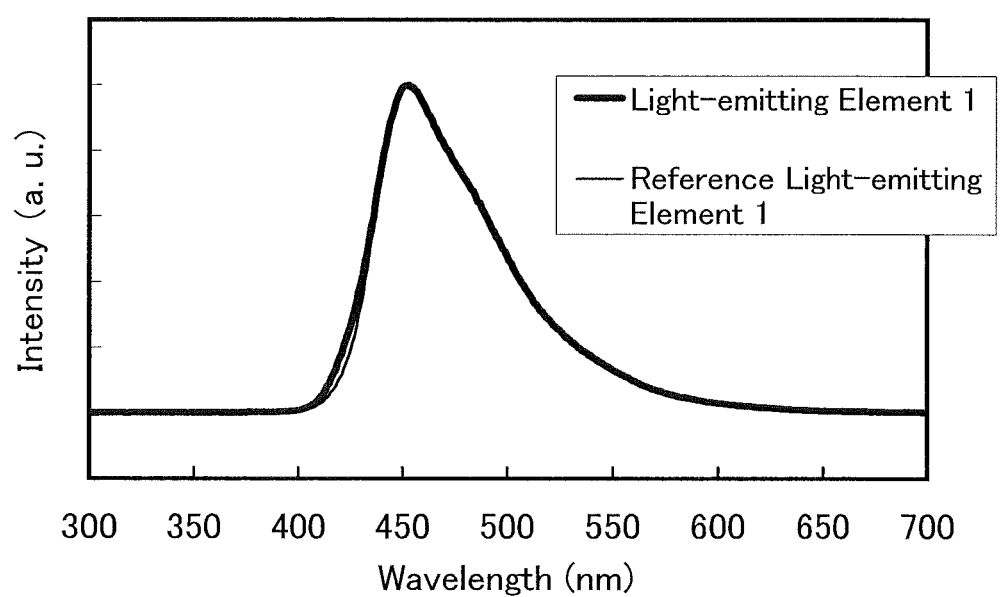
FIG. 20 shows characteristics of Light-emitting Element 1 and Reference Light-emitting Element 1.

FIG. 20 shows emission spectra of Light-emitting Element 1 and Reference Light-emitting Element 1.

As apparent from FIG. 20 and Table 2, both Light-emitting Element 1 of this example and Reference Light-emitting Element 1 exhibit good blue emission. In addition, FIG. 19 reveals that Light-emitting Element 1 of this example has higher emission efficiency than that of Reference Light-emitting Element 1.

Fabricated Light-emitting Element 1 and Reference Light-emitting Element 1 underwent reliability tests. In the reliability tests, the initial luminance was set at 1000 cd/m$^2$, these elements were operated at a constant current density, and the luminance was measured at regular intervals.

Figure 21:
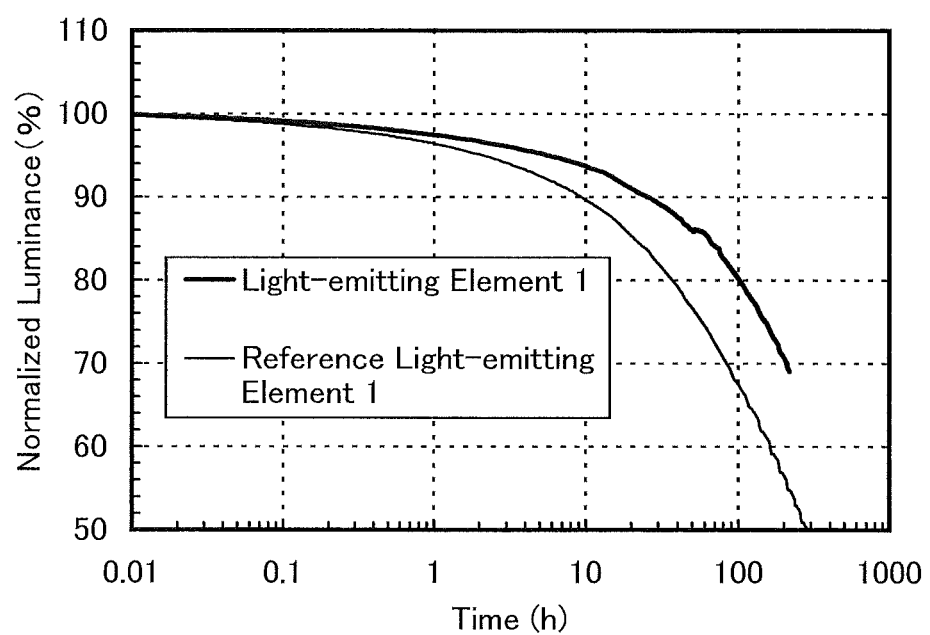
FIG. 21 shows characteristics of Light-emitting Element 1 and Reference Light-emitting Element 1.

Results of the reliability tests are shown in FIG. 21. In FIG. 21, the horizontal axis represents current flow time (hour), and the vertical axis represents the proportion of luminance at each time in the initial luminance, i.e., normalized luminance (%).

As shown in FIG. 21, the luminance of Light-emitting Element 1 does not deteriorate over time so much as Reference Light-emitting Element 1, indicating that Light-emitting Element 1 has a long lifetime. Light-emitting Element 1 kept 69% of the initial luminance after driving for 220 hours, which is also indicative of its long lifetime.

As described above, it is found that Light-emitting Element 1 of this example can be a light-emitting element that achieves a long lifetime, high reliability, high color purity, and high emission efficiency.

EXAMPLE 5

This example will show a method for manufacturing a light-emitting element that uses the fluorene derivative described in Embodiment 1 as a light-emitting material and differs in structure from the elements of Example 4, and measurement results of its element characteristics as well as measurement results of those of reference light-emitting elements. Specifically, this example will show the light-emitting element formed using N,N'-bis[4-(9-phenyl-9H-fluoren-9-yl)phenyl]-N,N'-diphenyl-pyrene-1,6-diamine (abbreviation: 1,6FLPAPrn) represented by Structural Formula (100) which is described in Example 2.

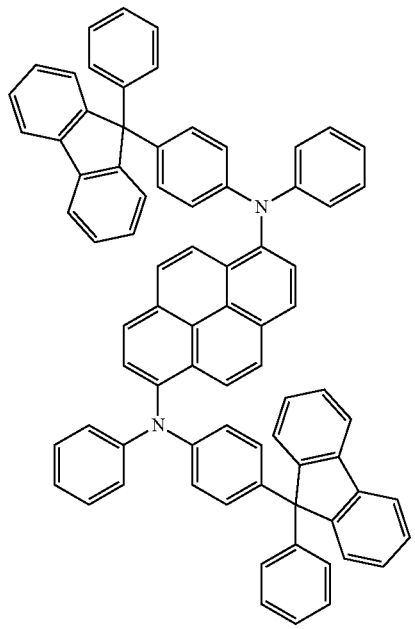

(100)

Fabrication methods of Light-emitting Element 2 and Reference Light-emitting Elements 2A and 2B will be now described. In addition, structural formulas of the organic compounds used in this example are shown below. Note that the organic compounds whose molecular structures are already shown in the above examples are not detailed here. The structure of the elements, which is the same as that in Example 4, can be found in FIG. 17A.

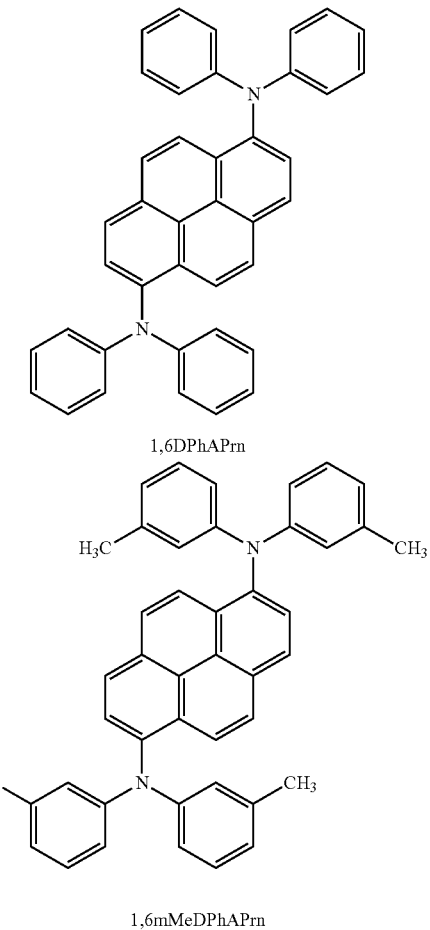

1,6DPhAPrn 1,6mMeDPhAPrn

Light-emitting Element 2 of this example and Reference Light-emitting Elements 2A and 2B were manufactured in the same way as Light-emitting Element 1 of Example 4 except for the light-emitting layer 2105.

(Light-Emitting Element 2)

For Light-emitting Elements 2, the light-emitting layer 2105 was formed to a thickness of 30 nm by co-evaporation of 9-[4-(10-phenyl-9-anthryl)phenyl]-9H-carbazole (abbreviation: CzPA) and N,N'-bis[4-(9-phenyl-9H-fluoren-9-yl)phenyl]-N,N'-diphenyl-pyrene-1,6-diamine (abbreviation: 1,6FLPAPrn). Here, the evaporation rate was controlled such that the weight ratio of CzPA to 1,6FLPAPm was 1:0.05 (=CzPA:1,6FLPAPrn).

(Reference Light-Emitting Element 2A)

For Reference Light-emitting Elements 2A, the light-emitting layer 2105 was formed to a thickness of 30 nm by co-evaporation of 9-[4-(10-phenyl-9-anthryl)phenyl]-9H-carbazole (abbreviation: CzPA) and N,N,N',N'-tetraphenylpyrene-1,6-diamine (abbreviation: 1,6DPhAPrn). Here, the evaporation rate was controlled such that the weight ratio of CzPA to 1,6DPhAPrn was 1:0.05 (=CzPA:1,6DPhAPrn).

(Reference Light-Emitting Element 2B)

For Reference Light-emitting Elements 2B, the light-emitting layer 2105 was formed to a thickness of 30 nm by co-evaporation of 9-[4-(10-phenyl-9-anthryl)phenyl]-9H-carbazole (abbreviation: CzPA) and N,N,N',N'-tetra(3-methylphenyl)pyrene-1,6-diamine (abbreviation: 1,6mMeDPhAPrn). Here, the evaporation rate was controlled such that the weight ratio of CzPA to 1,6mMeDPhAPrn was 1:0.05 (=CzPA:1,6mMeDPhAPrn).

Table 3 shows element structures of Light-emitting Element 2 and Reference Light-emitting Elements 2A and 2B manufactured in this example. In Table 3, all the mixture ratios are weight ratios.

TABLE 3

|  | Light-Emitting Element 2 | Reference Light-Emitting Element 2A | Reference Light-Emitting Element 2B |
| --- | --- | --- | --- |
| Anode 2102 | ITSO 110 nm | ITSO 110 nm | ITSO 110 nm |
| Hole-injection layer 2103 | NPB:MoOx (=4:1) 50 nm | NPB:MoOx (=4:1) 50 nm | NPB:MoOx (=4:1) 50 nm |
| Hole-transport layer 2104 | NPB 10 nm | NPB 10 nm | NPB 10 nm |
| Light-emitting layer 2105 | CzPA:1,6FLPAPrn (=1:0.05) 30 nm | CzPA:1,6DPhAPrn (=1:0.05) 30 nm | CzPA:1,6mMeDPhAPrn (=1:0.05) 30 nm |
| Electron-transport layer 2106 | Alq 10 nm Bphen 15 nm | Alq 10 nm Bphen 15 nm | Alq 10 nm Bphen 15 nm |
| Electron-injection layer 2107 | LiF 1 nm | LiF 1 nm | LiF 1 nm |
| Cathode 2108 | Al 200 nm | Al 200 nm | Al 200 nm |

All the mixture ratios are weight ratios.

Light-emitting Element 2 and Reference Light-emitting Elements 2A and 2B thus obtained were sealed in a glove box having a nitrogen atmosphere without being exposed to the air. Then, the operating characteristics of Light-emitting Element 2 and Reference Light-emitting Element 2A and 2B were measured. Note that the measurement was carried out at room temperature (in an atmosphere kept at 25° C.).

Figure 22:
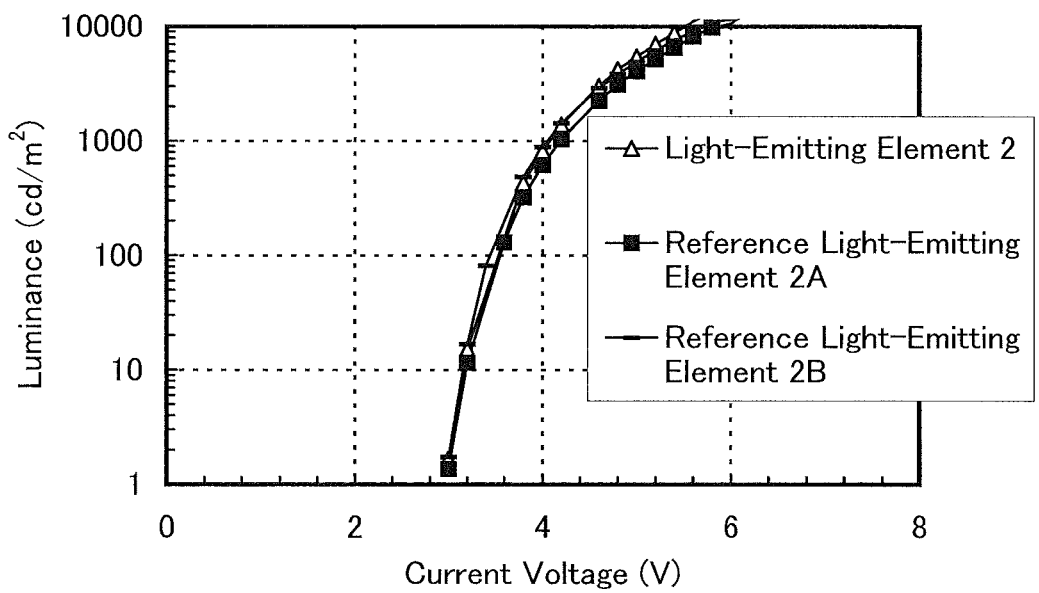
FIG. 22 shows characteristics of Light-emitting Element 2 and Reference Light-emitting Elements 2A and 2B.
Figure 23:
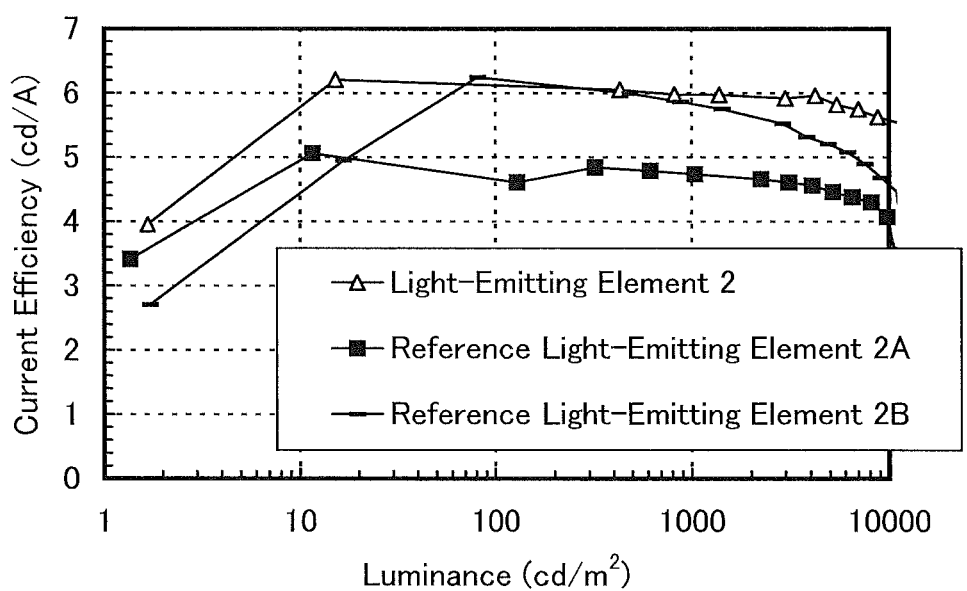
FIG. 23 shows characteristics of Light-emitting Element 2 and Reference Light-emitting Elements 2A and 2B.
Figure 24:
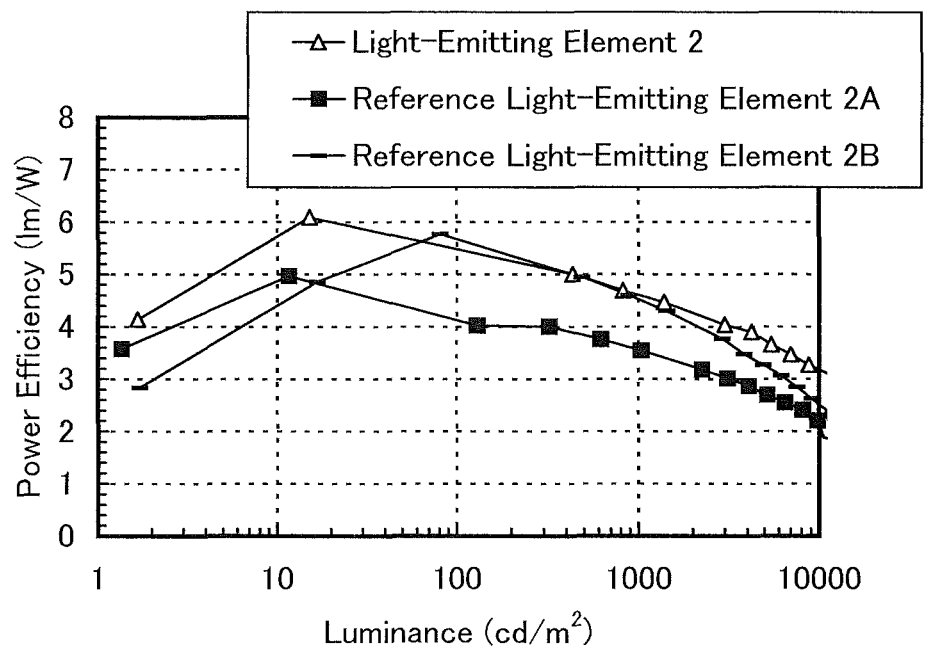
FIG. 24 shows characteristics of Light-emitting Element 2 and Reference Light-emitting Elements 2A and 2B.
Figure 25:
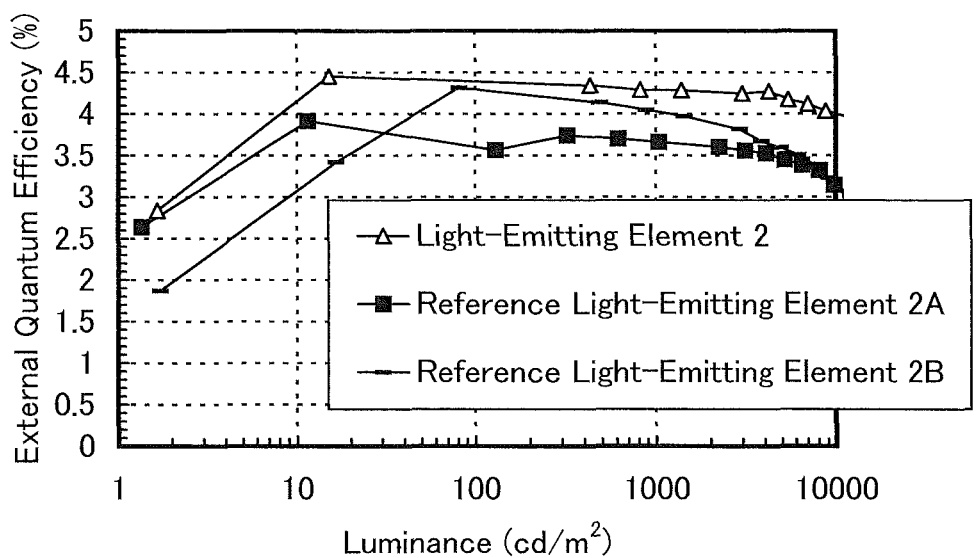
FIG. 25 shows characteristics of Light-emitting Element 2 and Reference Light-emitting Elements 2A and 2B.

FIG. 22 shows voltage vs. luminance characteristics of Light-emitting Element 2 and Reference Light-emitting Elements 2A and 2B, FIG. 23 shows luminance vs. current efficiency characteristics, FIG. 24 shows luminance vs. power efficiency characteristics, and FIG. 25 shows luminance vs. external quantum efficiency characteristics. In FIG. 22, the vertical axis represents luminance ($cd/m^2$) and the horizontal axis represents current voltage (V). In FIG. 23, the vertical axis represents current efficiency (cd/A) and the horizontal axis represents luminance ($cd/m^2$). In FIG. 24, the vertical axis represents power efficiency (lm/W) and the horizontal axis represents luminance ($cd/m^2$). In FIG. 25, the vertical axis represents external quantum efficiency (%) and the horizontal axis represents luminance ($cd/m^2$). Further, Table 4 shows the chromaticity of the light-emitting elements at around 1000 $cd/m^2$.

TABLE 4

|  | Chromaticity coordinates (x, y) |
| --- | --- |
| Light-Emitting Element 2 | (0.15, 0.20) |
| Reference Light-Emitting Element 2A | (0.15, 0.17) |
| Reference Light-Emitting Element 2B | (0.15, 0.21) |

Figure 26:
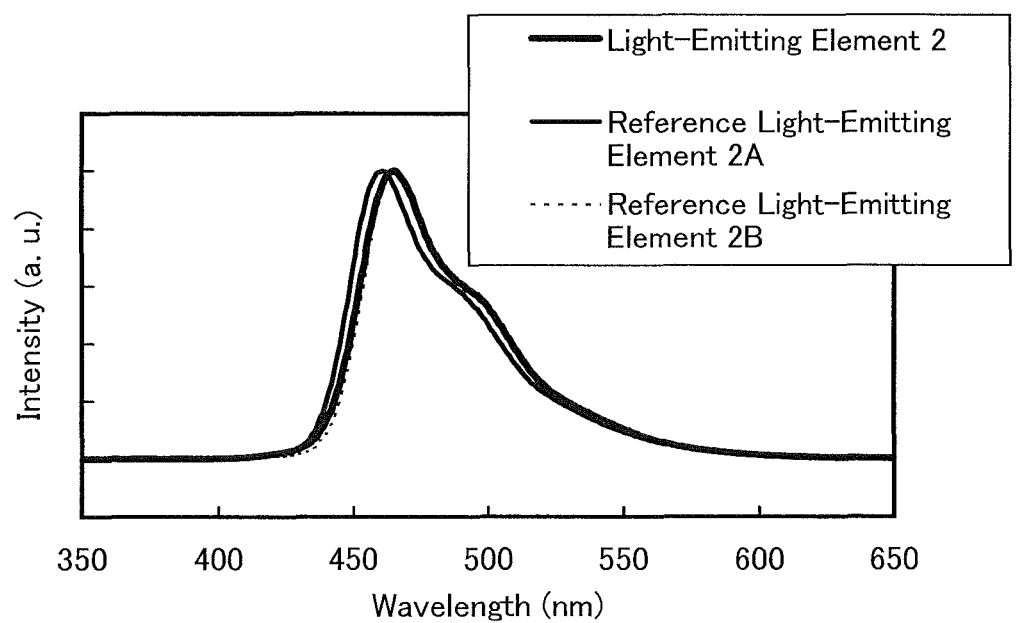
FIG. 26 shows characteristics of Light-emitting Element 2 and Reference Light-emitting Elements 2A and 2B.

FIG. 26 shows emission spectra of Light-emitting Element 2 and Reference Light-emitting Elements 2A and 2B.

FIG. 26 and Table 4 show that Light-emitting Element 2 of this example exhibits the same degree of blue emission as Reference Light-emitting Element 2B. In addition, as apparent from FIG. 23, FIG. 24, and FIG. 25, the emission efficiency of Light-emitting Element 2 of this example is the same as that of Reference Light-emitting Element 2A and higher than that of Reference Light-emitting Element 2B.

Figure 27:
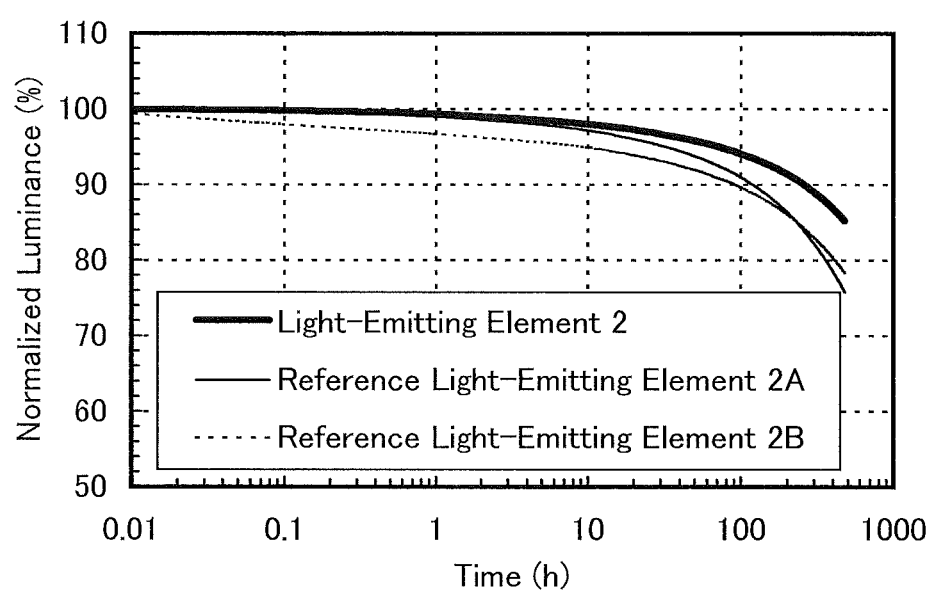
FIG. 27 shows characteristics of Light-emitting Element 2 and Reference Light-emitting Elements 2A and 2B.

Fabricated Light-emitting Element 2 and Reference Light-emitting Elements 2A and 2B underwent reliability tests. In the reliability tests, the initial luminance was set at 1000 $cd/m^2$, these elements were operated at a constant current density, and the luminance was measured at regular intervals. Results of the reliability tests are shown in FIG. 27. In FIG. 27, the horizontal axis represents current flow time (hour), and the vertical axis represents the proportion of luminance at each time in the initial luminance, i.e., normalized luminance (%).

As shown in FIG. 27, the luminance of Light-emitting Element 2 does not deteriorate over time so much as Reference Light-emitting Elements 2A and 2B, indicating that Light-emitting Element 2 has a long lifetime. Light-emitting Element 2 kept 85% of the initial luminance after driving for 480 hours, which is also indicative of its long lifetime.

As described above, it is found that Light-emitting Element 2 of this example can be a light-emitting element that achieves a long lifetime, high reliability, high color purity, and high emission efficiency.

EXAMPLE 6

In this example, as to a light-emitting element which differs in structure from the elements of Example 5 and includes N,N'-bis[4-(9-phenyl-9H-fluoren-9-yl)phenyl]-N,N'-diphenyl-pyrene-1,6-diamine (abbreviation: 1,6FLPA-Prn) represented by Structural Formula (100) described in Example 2, its manufacturing method and measurement results of element characteristics of this element as well as measurement results of reference light-emitting elements will be described.

Fabrication methods of Light-emitting Element 3 and Reference Light-emitting Elements 3A and 3B will be now described. In addition, structural formulas of the organic compounds used in this example are shown below. Note that the organic compounds whose molecular structures are already shown in the above examples are not detailed here.

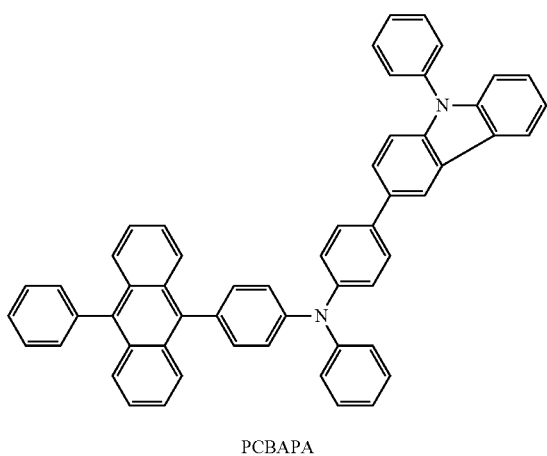 [SMILES: c1ccc(-c2c3ccccc3c(-c3ccc(N(c4ccccc4)c4ccc(-c5ccc6c(c5)c5ccccc5n6-c5ccccc5)cc4)cc3)c3ccccc23)cc1]

PCBAPA

Figure 17B:
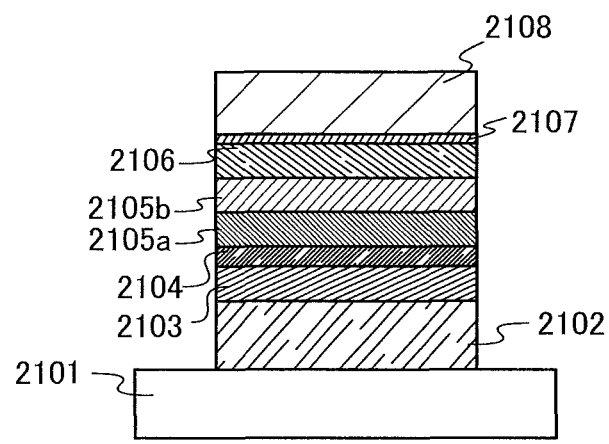

FIG. 17B illustrates the element structure of Light-emitting Element 3 of this example and Reference Light-emitting Elements 3A and 3B. Light-emitting Element 3 of this example and Reference Light-emitting Elements 3A and 3B have an EL layer between the anode 2102 and the cathode 2108. The EL layer includes the hole-injection layer 2103, the hole-transport layer 2104, a first light-emitting layer 2105a, a second light-emitting layer 2105b, the electron-transport layer 2106, and the electron-injection layer 2107, which are sequentially stacked over the anode 2102.

In Light-emitting Element 3 of this example and Reference Light-emitting Elements 3A and 3B, the anode 2102, the hole-injection layer 2103, the hole-transport layer 2104, the electron-transport layer 2106, the electron-injection layer 2107, and the cathode 2108 were formed in the same way as Light-emitting Element 1 of Example 4.

(Light-Emitting Element 3)

For Light-emitting Element 3, the first light-emitting layer 2105a was formed to a thickness of 25 nm by evaporation of 4-(10-phenyl-9-anthryl)-4'-(9-phenyl-9H-carbazol-3-yl)triphenylamine (abbreviation: PCBAPA).

Next, the second light-emitting layer 2105b was formed over the first light-emitting layer 2105a. The second light-emitting layer 2105b was formed to a thickness of 30 nm by co-evaporation of 9-[4-(10-phenyl-9-anthryl)phenyl]-9H-carbazole (abbreviation: CzPA) and N,N'-bis[4-(9-phenyl-9H-fluoren-9-yl)phenyl]-N,N'-diphenyl-pyrene-1,6-diamine (abbreviation: 1,6FLPAPrn). Here, the evaporation rate was controlled such that the weight ratio of CzPA to 1,6FLPAPm was 1:0.05 (=CzPA:1,6FLPAPrn).

(Reference Light-Emitting Element 3A)

For Reference Light-emitting Elements 3A, the first light-emitting layer 2105a was formed as in Light-emitting Element 3. The second light-emitting layer 2105b was formed to a thickness of 30 nm by co-evaporation of 9-[4-(10-phenyl-9-anthryl)phenyl]-9H-carbazole (abbreviation: CzPA) and N,N,N',N'-tetraphenylpyrene-1,6-diamine (abbreviation: 1,6DPhAPrn). Here, the evaporation rate was controlled such that the weight ratio of CzPA to 1.6DPhAPrn was 1:0.05 (=CzPA:1,6DPhAPrn).

(Reference Light-Emitting Element 3B)

For Reference Light-emitting Elements 3B, the first light-emitting layer 2105a was formed as in Light-emitting Element 3. The second light-emitting layer 2105b was formed to a thickness of 30 nm by co-evaporation of 9-[4-(10-phenyl-9-anthryl)phenyl]-9H-carbazole (abbreviation: CzPA) and N,N,N',N'-tetra(3-methylphenyl)pyrene-1,6-diamine (abbreviation: 1,6mMeDPhAPrn). Here, the evaporation rate was controlled such that the weight ratio of CzPA to 1,6mMeDPhAPrn was 1:0.05 (=CzPA:1,6mMeDPhAPrn).

Table 5 shows element structures of Light-emitting Element 3 and Reference Light-emitting Elements 3A and 3B manufactured in this example. In Table 5, all the mixture ratios are weight ratios.

TABLE 5

| | Light-Emitting Element 3 | Reference Light-Emitting Element 3A | Reference Light-Emitting Element 3B |
| --- | --- | --- | --- |
| Anode 2102 | ITSO 110 nm | ITSO 110 nm | ITSO 110 nm |
| Hole-injection layer 2103 | NPB:MoOx (=4:1) 50 nm | NPB:MoOx (=4:1) 50 nm | NPB:MoOx (=4:1) 50 nm |
| Hole-transport layer 2104 | NPB 10 nm | NPB 10 nm | NPB 10 nm |
| First Light-emitting layer 2105a | PCBAPA 25 nm | PCBAPA 25 nm | PCBAPA 25 nm |
| Second Light-emitting layer 2105b | CzPA:1,6FLPAPrn (=1:0.05) 30 nm | CzPA:1,6DPhAPrn (=1:0.05) 30 nm | CzPA:1,6mMeDPhAPrn (=1:0.05) 30 nm |
| Electron-transport layer 2106 | Alq 10 nm | Alq 10 nm | Alq 10 nm |
| | Bphen 15 nm | Bphen 15 nm | Bphen 15 nm |
| Electron-injection layer 2107 | LiF 1 nm | LiF 1 nm | LiF 1 nm |
| Cathode 2108 | Al 200 nm | Al 200 nm | Al 200 nm |

All the mixture ratios are weight ratios.

Light-emitting Element 3 and Reference Light-emitting Elements 3A and 3B thus obtained were sealed in a glove box having a nitrogen atmosphere without being exposed to the air. Then, the operating characteristics of the elements were measured. Note that the measurement was carried out at room temperature (in an atmosphere kept at 25° C.).

Figure 28:
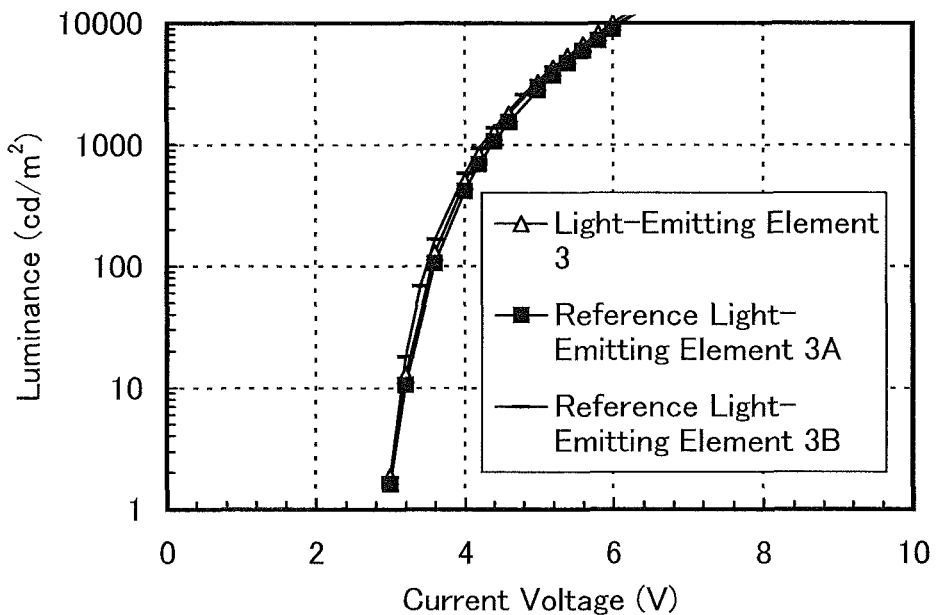
FIG. 28 shows characteristics of Light-emitting Element 3 and Reference Light-emitting Elements 3A and 3B.
Figure 29:
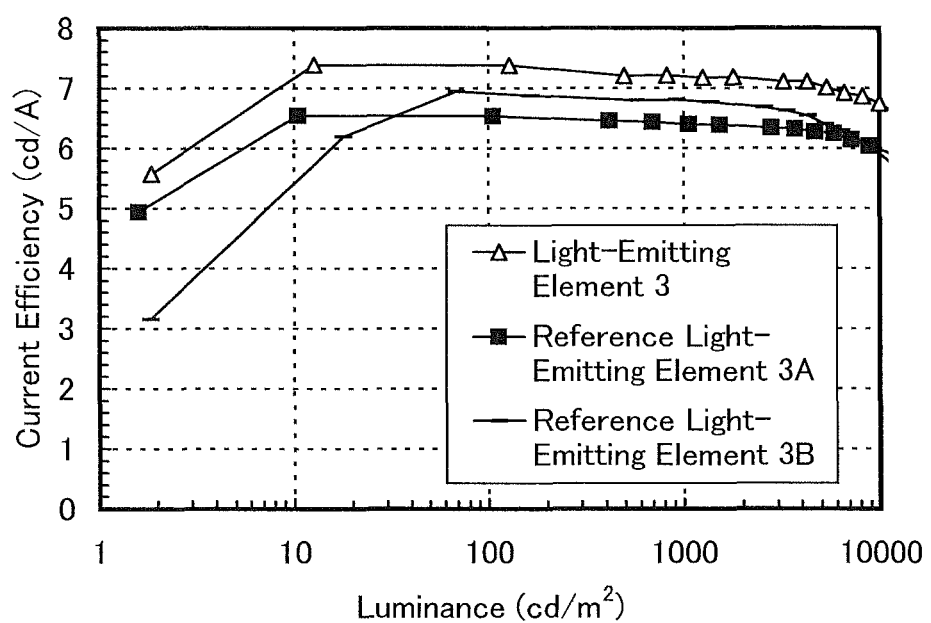
FIG. 29 shows characteristics of Light-emitting Element 3 and Reference Light-emitting Elements 3A and 3B.
Figure 30:
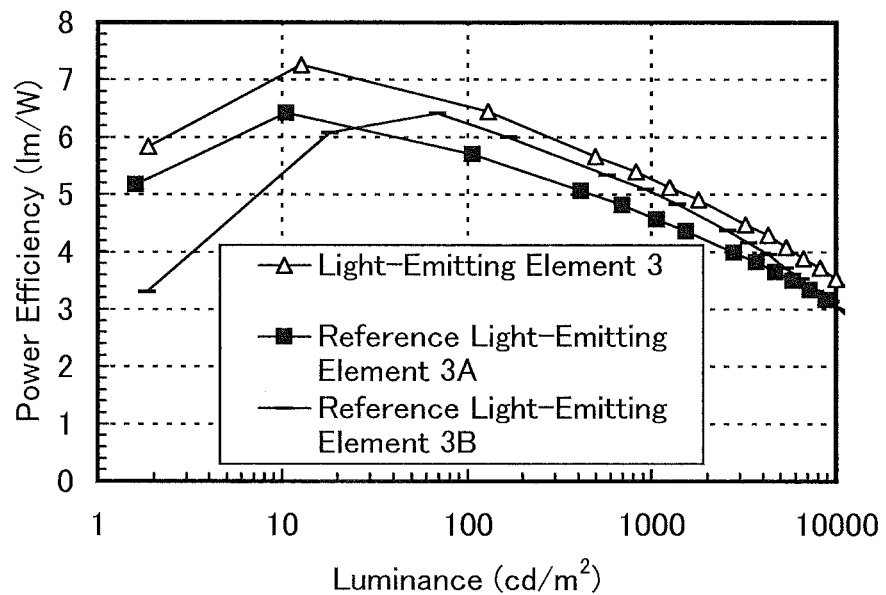
FIG. 30 shows characteristics of Light-emitting Element 3 and Reference Light-emitting Elements 3A and 3B.
Figure 31:
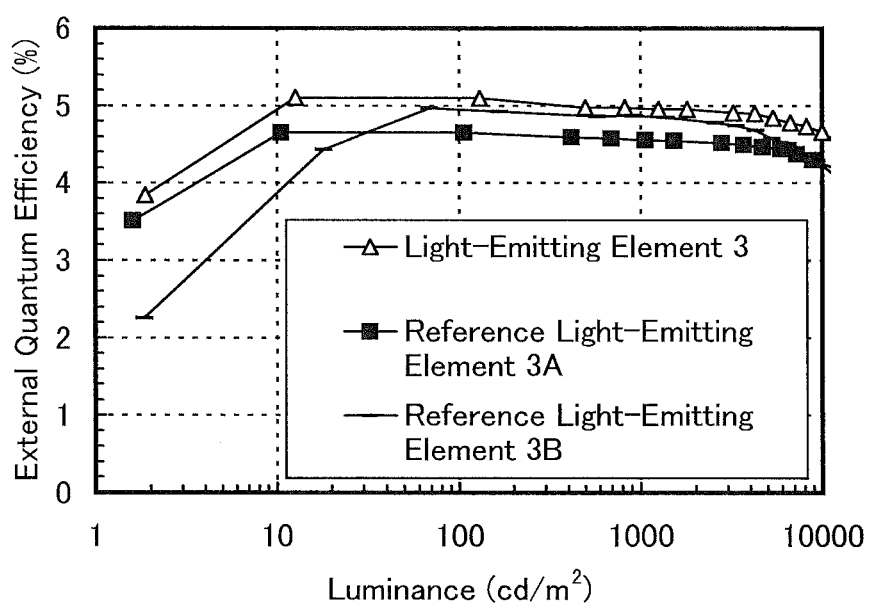
FIG. 31 shows characteristics of Light-emitting Element 3 and Reference Light-emitting Elements 3A and 3B.

FIG. 28 shows voltage vs. luminance characteristics of Light-emitting Element 3 and Reference Light-emitting Elements 3A and 3B, FIG. 29 shows luminance vs. current efficiency characteristics thereof, FIG. 30 shows luminance vs. power efficiency characteristics, and FIG. 31 shows luminance vs. external quantum efficiency characteristics. In FIG. 28, the vertical axis represents luminance (cd/m$^2$) and the horizontal axis represents current voltage (V). In FIG. 29, the vertical axis represents current efficiency (cd/A) and the horizontal axis represents luminance (cd/m$^2$). In FIG. 30, the vertical axis represents power efficiency (lm/W) and the horizontal axis represents luminance (cd/m$^2$). In FIG. 31, the vertical axis represents external quantum efficiency (%) and the horizontal axis represents luminance (cd/m²). Further, Table 6 shows the chromaticity of the light-emitting elements at around 1000 cd/m².

TABLE 6

|  | Chromaticity coordinates (x, y) |
| --- | --- |
| Light-Emitting Element 3 | (0.15, 0.21) |
| Reference Light-Emitting Element 3A | (0.15, 0.20) |
| Reference Light-Emitting Element 3B | (0.15, 0.20) |

Figure 32:
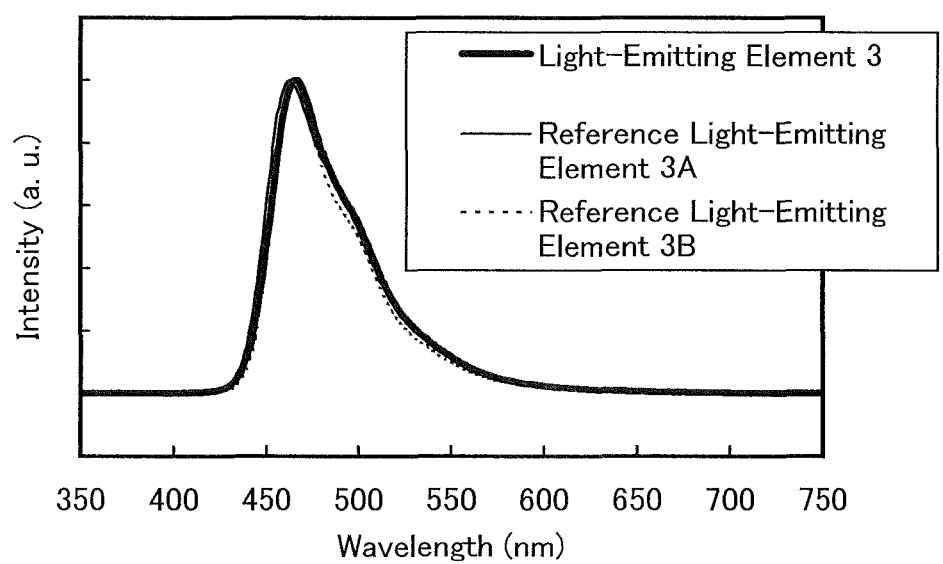
FIG. 32 shows characteristics of Light-emitting Element 3 and Reference Light-emitting Elements 3A and 3B.

FIG. 32 shows emission spectra of Light-emitting Element 3 and Reference Light-emitting Elements 3A and 3B.

FIG. 32 and Table 6 show that Light-emitting Element 3 of this example exhibits the same degree of blue emission as Reference Light-emitting Element 3B. In addition, as apparent from FIG. 29, FIG. 30, and FIG. 31, the emission efficiency of Light-emitting Element 3 of this example is the same as that of Reference Light-emitting Element 3A and higher than that of Reference Light-emitting Element 3B.

Figure 33:
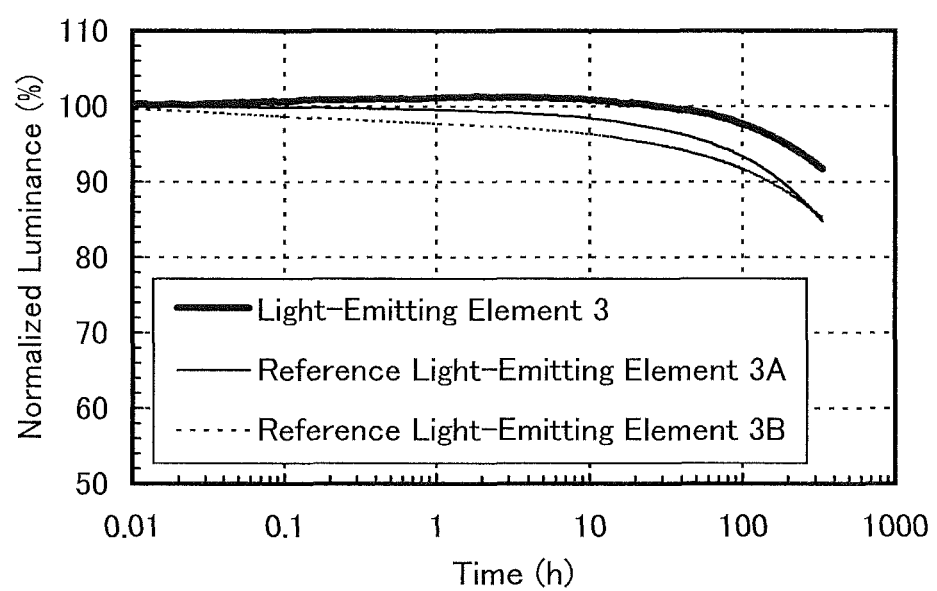
FIG. 33 shows characteristics of Light-emitting Element 3 and Reference Light-emitting Elements 3A and 3B.

Fabricated Light-emitting Element 3 and Reference Light-emitting Elements 3A and 3B underwent reliability tests. In the reliability tests, the initial luminance was set at 1000 cd/m², these elements were operated at a constant current density, and the luminance was measured at regular intervals. Results of the reliability tests are shown in FIG. 33. In FIG. 33, the horizontal axis represents current flow time (hour), and the vertical axis represents the proportion of luminance at each time in the initial luminance, i.e., normalized luminance (%).

As shown in FIG. 33, the luminance of Light-emitting Element 3 does not deteriorate over time so much as Reference Light-emitting Elements 3A and 3B, indicating that Light-emitting Element 3 has a long lifetime. Light-emitting Element 3 kept 92% of the initial luminance after driving for 330 hours, which is also indicative of its long lifetime.

As described above, it is found that Light-emitting Element 3 of this example can be a light-emitting element that achieves a long lifetime, high reliability, high color purity, and high emission efficiency.

EXAMPLE 7

In this example, N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn) represented by Structural Formula (109) in Embodiment 1 was produced.

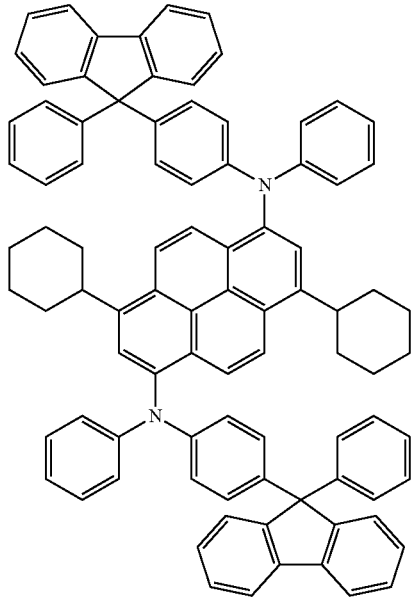

(109)

In a 50 mL three-neck flask were put 0.6 g (1.2 mmol) of 1,6-dibromo-3,8-dicyclohexylpyrene, 1.0 g (2.5 mmol) of 4-(9-phenyl-9H-fluoren-9-yl)diphenylamine, and 0.4 g (4.0 mmol) of sodium tert-butoxide. The air in the flask was replaced with nitrogen. To this mixture were added 12.2 mL of toluene and 0.20 mL of a 10% hexane solution of tri(tert-butyl)phosphine. The temperature of this mixture was set to 60° C., and 18.4 mg (0.03 mmol) of bis(dibenzylideneacetone)palladium(0) was added to the mixture. The temperature of the mixture was raised to 80° C., followed by stirring for 0.5 hours. After the stirring, 12.0 mL of toluene was added to the mixture, which was stirred for 1.5 hours. After the stirring, 900 mL of toluene was added to the mixture, and the mixture was suction-filtered through Florisil, Celite, and alumina to give a filtrate. The filtrate was concentrated to give a solid. To the obtained solid was added 150 mL of toluene, and the mixture was heated. Suction filtration of the mixture gave a yellow solid. The obtained yellow solid was washed with toluene, whereby 0.4 g of a yellow solid was obtained in 30% yield, which was the substance to be produced.

Because the substance produced (ch-1,6FLPAPrn) has a structure in which a cyclohexyl group which is an alkyl group is bonded to a pyrene skeleton, ch-1,6FLPAPm has higher solubility in an organic solvent such as toluene than 1,6FLPAPrn obtained in Example 2. Such improvement of the solubility in a solvent facilitates purification of the fluorene derivative of this example (ch-1,6FLPAPrn), demonstrating the easiness of its synthesis.

By a train sublimation method, 0.4 g of the obtained yellow solid was purified. In the purification, the yellow solid was heated at 360° C. under a pressure of 2.3 Pa with a flow rate of argon gas of 6.0 mL/min. After the purification, 0.2 g of a yellow solid was obtained in a yield of 38%, which was the substance to be produced. The synthesis scheme is shown by the following (E7).

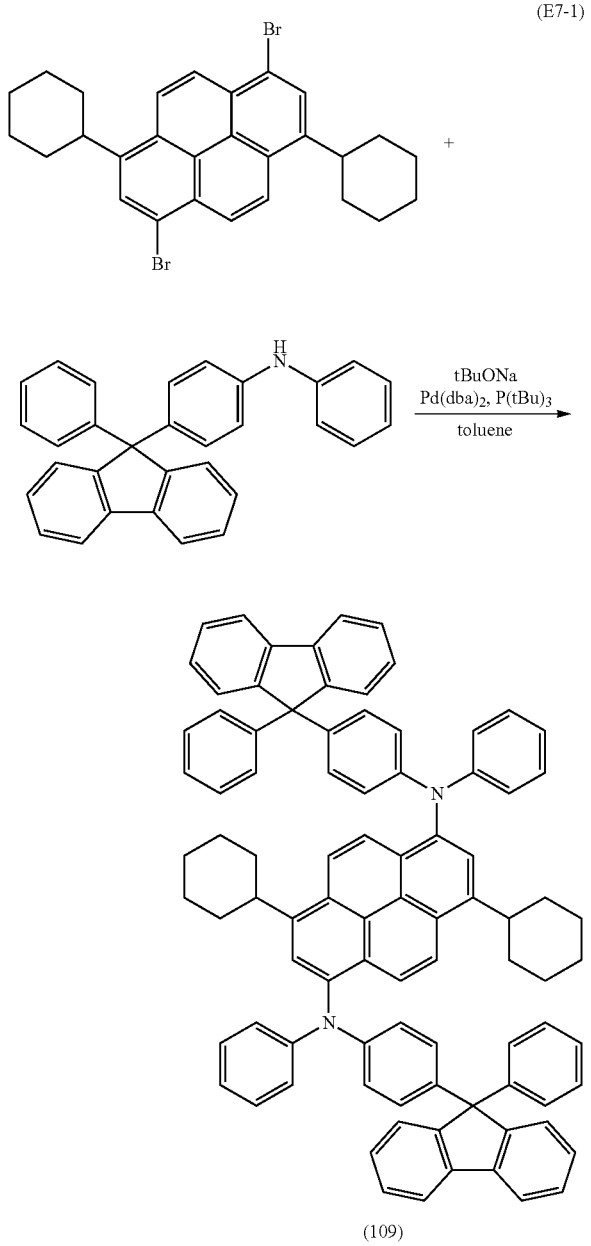

A nuclear magnetic resonance (NMR) method and a mass spectrometry identified this compound as N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn), which was the substance to be produced.

$^1$H NMR data of the obtained compound are: $^1$H NMR (CDCl$_3$, 300 MHz): δ=1.31-1.51 (m, 10H), 1.78-1.87 (m, 10H), 3.44-3.53 (m, 2H), 6.85-7.41 (m, 40H), 7.73-7.76 (m, 6H), 8.07-8.16 (m, 4H).

Figure 34A:
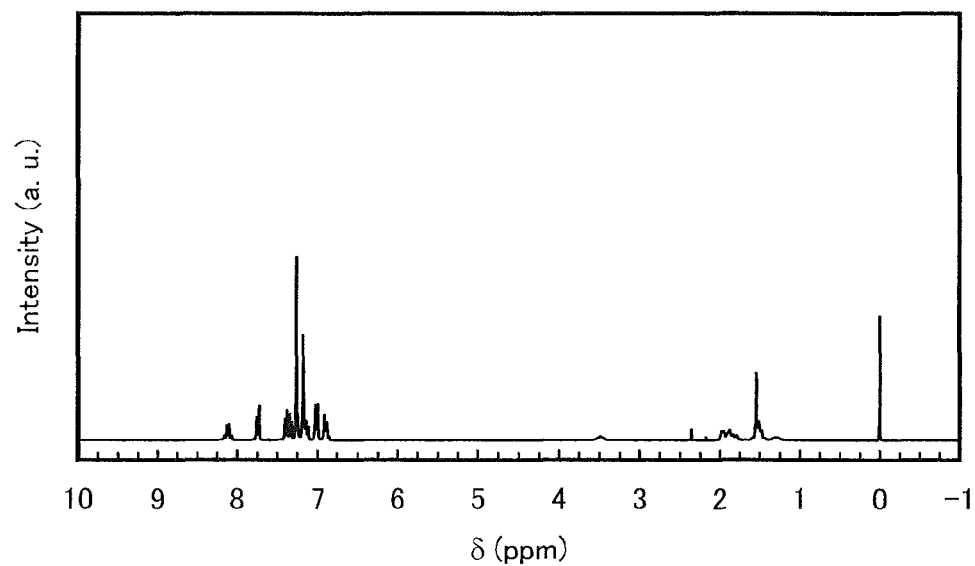
FIGS. 34A and 34B show $^1$H NMR charts of ch-1,6FLPAPrn.
Figure 34B:
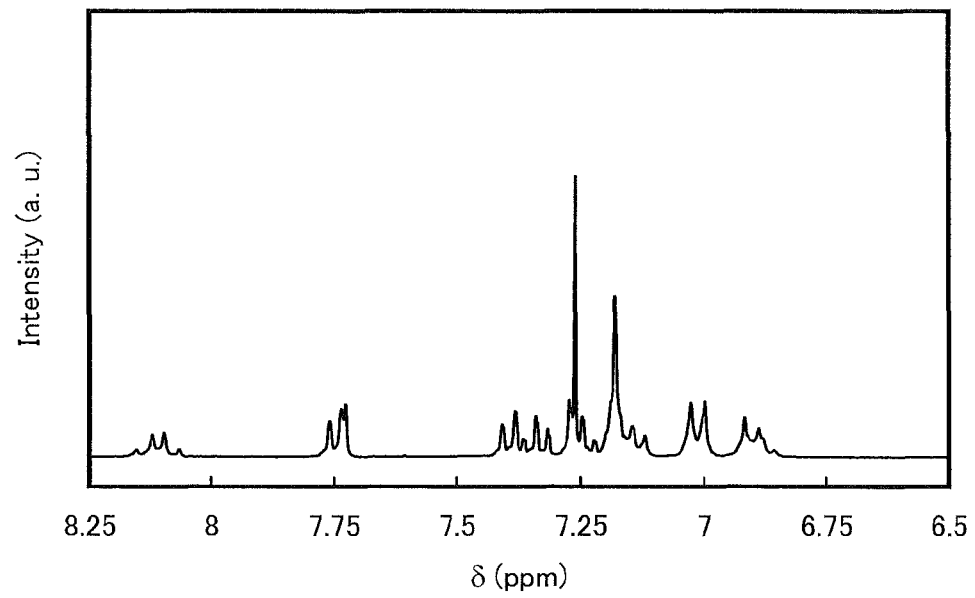

FIGS. 34A and 34B show the $^1$H NMR charts. Note that FIG. 14B is a chart showing an enlarged part of FIG. 14A in the range of 6.5 to 8.25 ppm.

The measurement result of the mass spectrometry of the obtained compound is: MS (ESI-MS): m/z=1181 (M+H)$^+$; C$_{90}$H$_{72}$N$_2$ (1180.57).

Figure 35A:
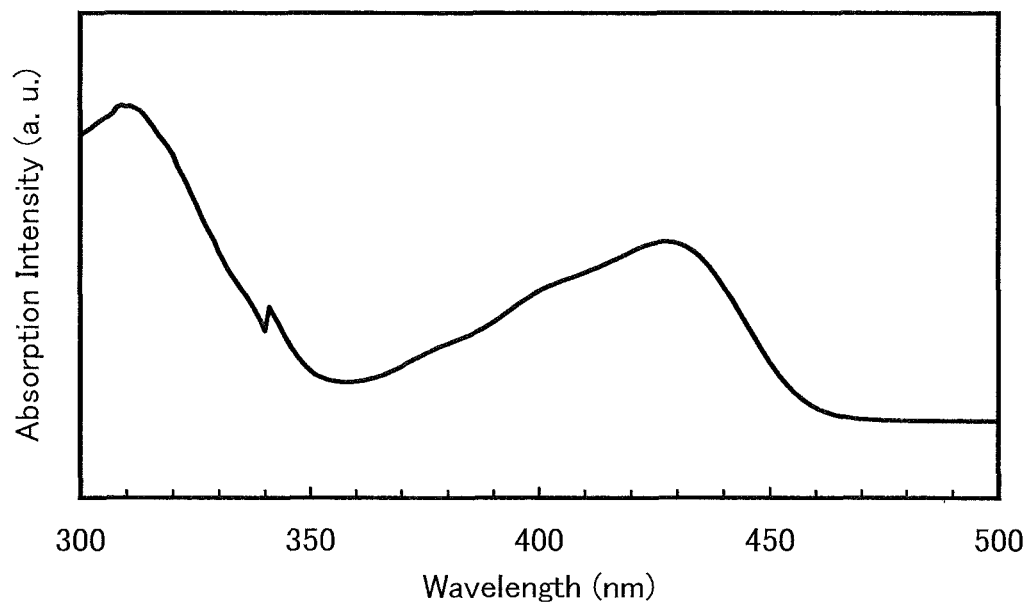
FIGS. 35A and 35B show an absorption spectrum and an emission spectrum of a toluene solution of ch-1,6FLPAPrn.
Figure 35B:
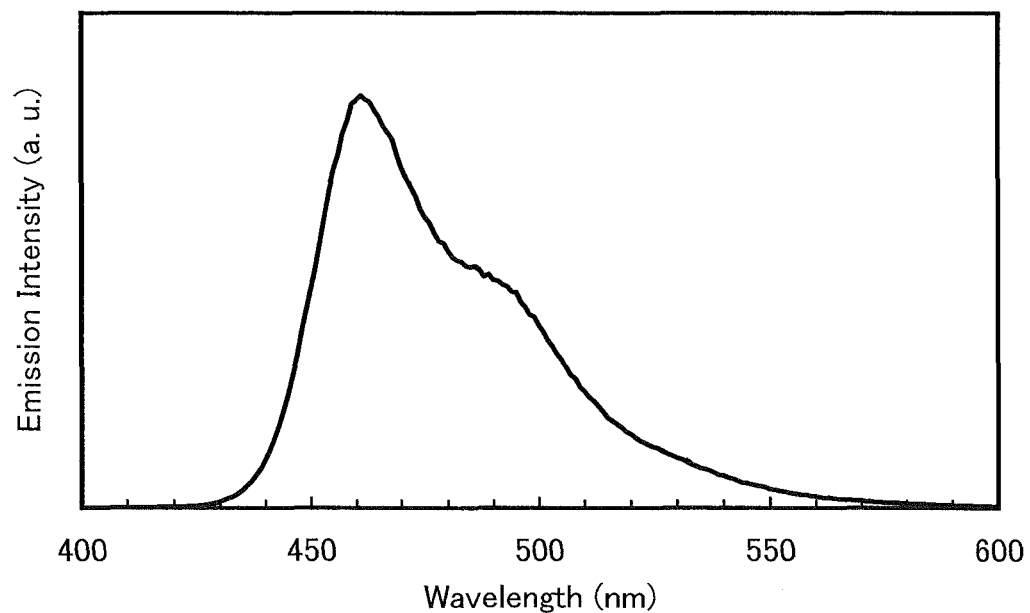
Figure 36A:
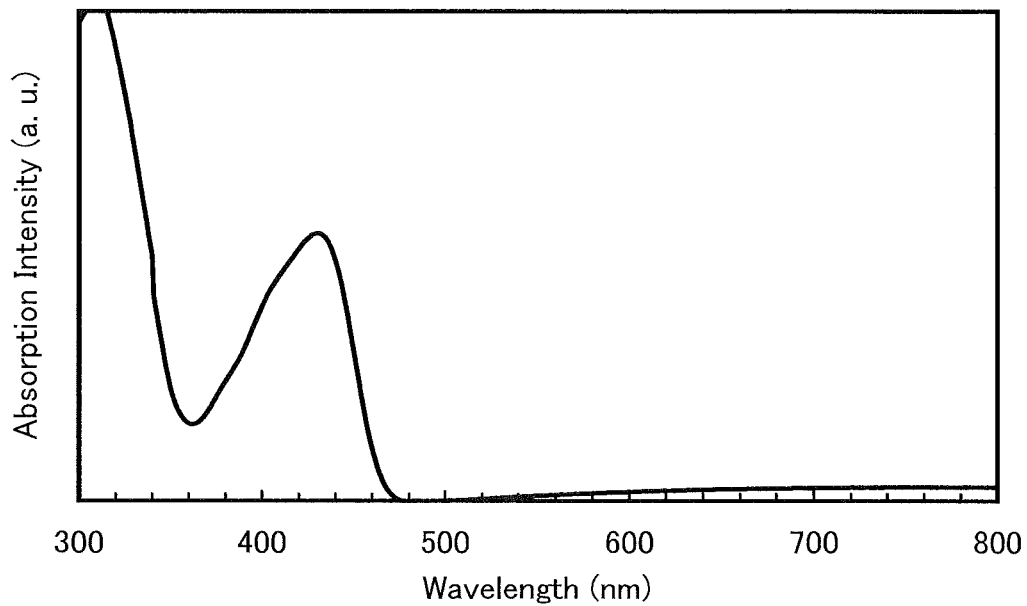
FIGS. 36A and 36B show an absorption spectrum and an emission spectrum of a thin film of ch-1,6FLPAPrn.
Figure 36B:
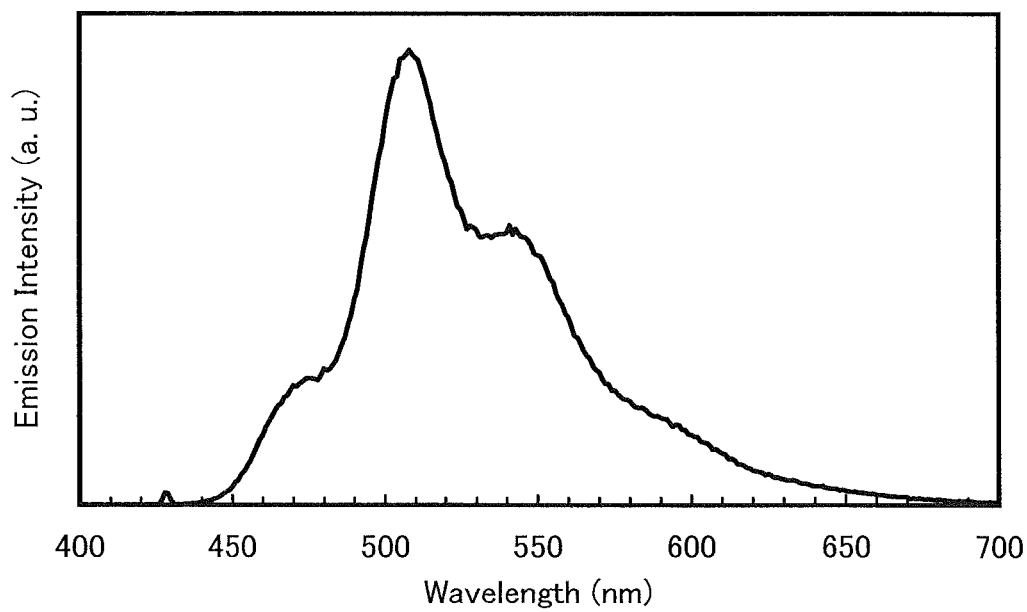

Further, FIG. 35A shows an absorption spectrum of a toluene solution of ch-1,6FLPAPrn, and FIG. 35B shows an emission spectrum thereof. FIG. 36A shows an absorption spectrum of a thin film of ch-1,6FLPAPrn, and FIG. 36B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 35A show the absorption spectrum of the solution which was obtained by subtracting the absorption spectra of quartz and toluene, and FIG. 36A shows the absorption spectrum of the thin film which was obtained by subtracting the absorption spectrum of a quartz substrate. In FIGS. 35A and 35B and FIGS. 36A and 36B, the horizontal axis represents wavelength (nm) and the vertical axis represents intensity (arbitrary unit). In the case of the toluene solution, absorption was observed at around 428 nm, and the maximum emission wavelength was 461 nm (excitation wavelength: 370 nm). In the case of the thin film, absorption was observed at around 430 nm, and the maximum emission wavelength was 508 nm (excitation wavelength: 428 nm).

The HOMO level and the LUMO level of the thin film of ch-1,6FLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of ch-1,6FLPAPrn which is shown in FIG. 36B, was regarded as an optical energy gap and added to the value of the HOMO level. As a result, the HOMO level and LUMO level of ch-1,6FLPAPrn were found to be −5.41 eV and −2.68 eV, respectively, and the energy gap was found to be 2.73 eV.

Thermogravimetry-differential thermal analysis (TG-DTA) of obtained ch-1,6FLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 492° C. or more, which is indicative of high heat resistance.

EXAMPLE 8

In this example, N,N'-bis(3-methylphenyl)-N,N'-bis[4-(9-phenyl-9H-fluoren-9-yl)phenyl]-pyrene-1,6-diamine (abbreviation: 1,6mMeFLPAPrn) represented by Structural Formula (103) in Embodiment 1 was produced.

(103)

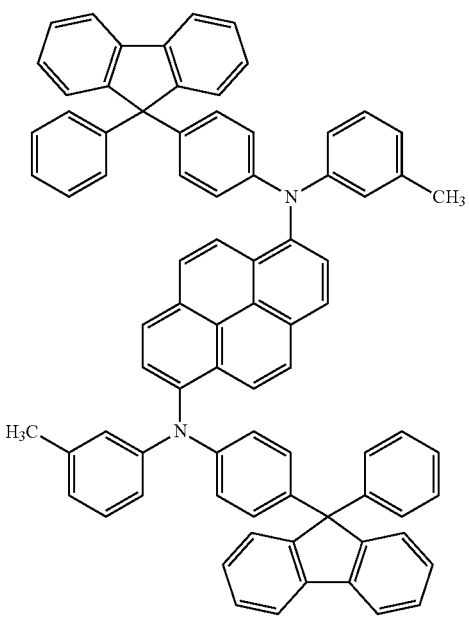

Step 1: Synthesis method of 3-methylphenyl-4-(9-phenyl-9H-fluoren-9-yl)phenylamine (abbreviation: mMeFLPA)

In a 200 mL three-neck flask were put 4.7 g (11.8 mmol) of 9-(4-bromophenyl)-9-phenylfluorene and 3.4 g (35.4 mmol) of sodium tert-butoxide. The air in the flask was replaced with nitrogen. To this mixture were added 60.0 mL of toluene, 1.3 mL (12.0 mmol) of m-toluidine, and 0.2 mL of a 10% hexane solution of tri(tert-butyl)phosphine. The temperature of this mixture was set to 60° C., and 36.7 mg (0.1 mmol) of bis(dibenzylideneacetone)palladium(0) was added to the mixture. The temperature of this mixture was raised to 80° C., followed by stirring for 2.0 hours. After the stirring, the mixture was suction-filtered through Florisil, Celite, and alumina to give a filtrate. The filtrate was concentrated to give a solid, which was then purified by silica gel column chromatography (the developing solvent has a 1:1 ratio of hexane to toluene). Accordingly, 4.7 g of a white solid was obtained in 93% yield, which was the substance to be produced. The synthesis scheme of this Step 1 is shown in the following (E8-1).

-continued

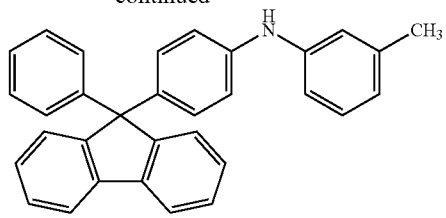

Step 2: Synthesis method of N,N'-bis(3-methylphenyl)-N,N'-bis[4-(9-phenyl-9H-fluoren-9-yl)phenyl]-pyrene-1,6-diamine (abbreviation: 1,6mMeFLPA-Prn)

In a 100 mL three-neck flask were put 0.6 g (1.7 mmol) of 1,6-dibromopyrene, 1.1 g (3.4 mmol) of 3-methylphenyl-4-(9-phenyl-9H-fluoren-9-yl)phenylamine, and 0.5 g (5.1 mmol) of sodium tert-butoxide. The air in the flask was replaced with nitrogen. To this mixture were added 17.0 mL of toluene and 0.2 mL of a 10% hexane solution of tri(tert-butyl)phosphine. The temperature of this mixture was set to 75° C., and 32.5 mg (0.1 mmol) of bis(dibenzylideneacetone)palladium(0) was added to the mixture. The temperature of this mixture was raised to 80° C., followed by stirring for 2.0 hours. After the stirring, toluene was added to the mixture, and the mixture was heated and suction-filtered through Florisil, Celite, and alumina to give a filtrate. The filtrate was concentrated to give a solid, which was then purified by silica gel column chromatography (the developing solvent has a 5:4 ratio of hexane to toluene) to give a yellow solid, which was the substance to be produced. Recrystallization of the obtained yellow solid from a mixed solution of toluene and hexane gave 1.2 g of a yellow solid in 72% yield, which was the substance to be produced.

Because the substance produced (1,6mMeFLPAPrn) has a structure in which a methyl group which is an alkyl group is bonded to a benzene ring in an amine skeleton, 1,6mMeFLPAPrn has higher solubility in an organic solvent such as toluene than 1,6FLPAPrn obtained in Example 2. Such improvement of the solubility in a solvent facilitates purification of the fluorene derivative of this example (1,6mMeFLPAPrn), demonstrating the easiness of its synthesis.

By a train sublimation method, 0.6 g of the obtained yellow solid was purified. In the purification, the yellow solid was heated at 347° C. under a pressure of 2.4 Pa with a flow rate of argon gas of 6.0 mL/min. After the purification, 0.5 g of a yellow solid was obtained in a yield of 85%, which was the substance to be produced. The synthesis scheme of Step 2 is shown by the following (E8-2).

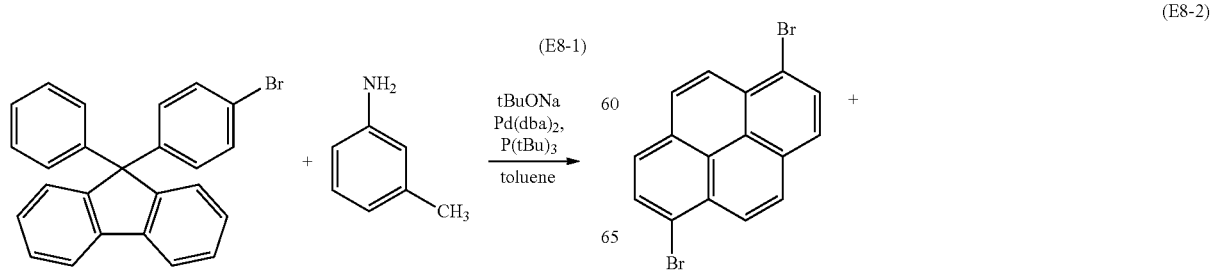

-continued

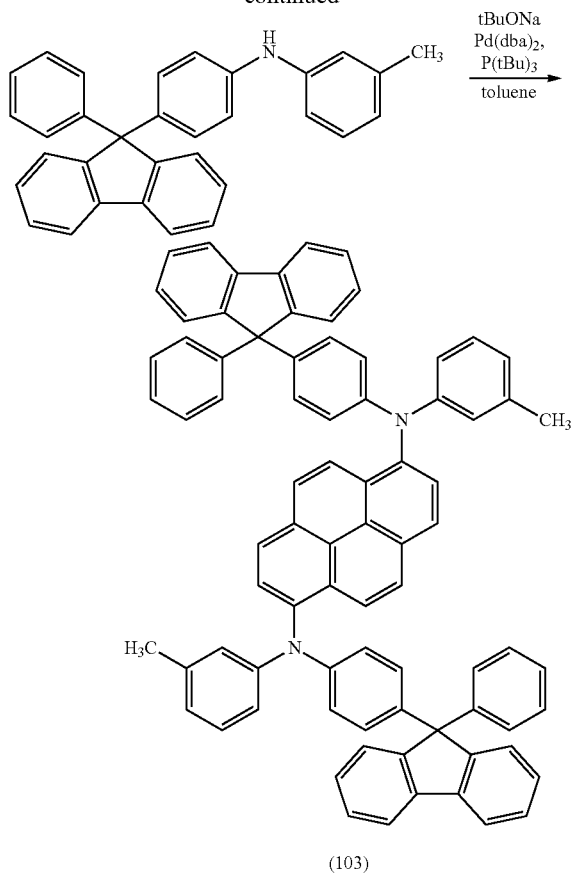

(103)

A nuclear magnetic resonance (NMR) method identified this compound as N,N'-bis(3-methylphenyl)-N,N'-bis[4-(9-phenyl-9H-fluoren-9-yl)phenyl]-pyrene-1,6-diamine (abbreviation: 1,6mMeFLPAPrn), which was the substance to be produced.

$^1$H NMR data of the obtained compound are: $^1$H NMR (CDCl$_3$, 300 MHz): δ=2.17 (s, 6H), 6.73 (d, J=7.2 Hz, 2H), 6.83-6.91 (m, 8H), 6.98-7.08 (m, 6H), 7.12-7.41 (m, 22H), 7.73-7.79 (m, 6H), 7.88 (d, J=9.3 Hz, 2H), 8.05-8.10 (m, 4H).

Figure 37A:
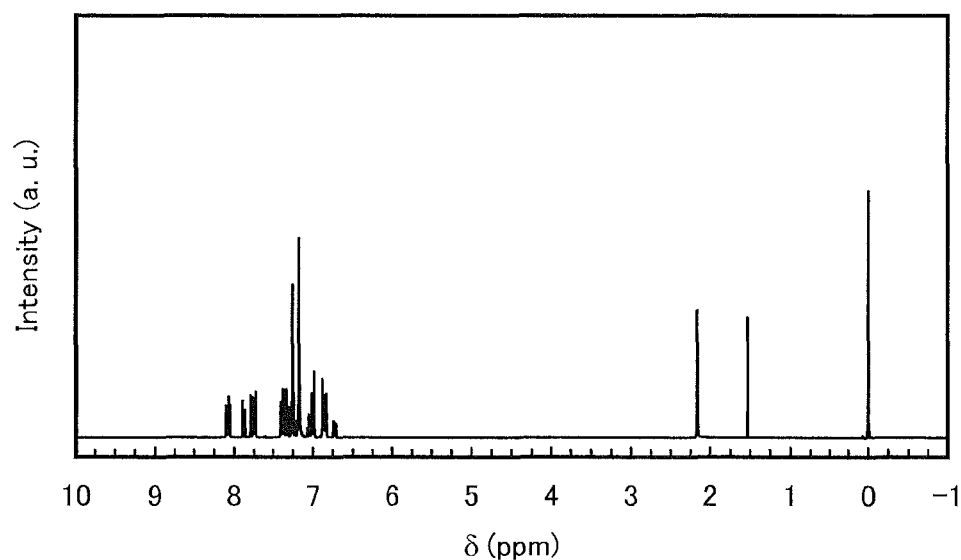
FIGS. 37A and 37B show $^1$H NMR charts of 1,6mMeFLPAPrn.
Figure 37B:
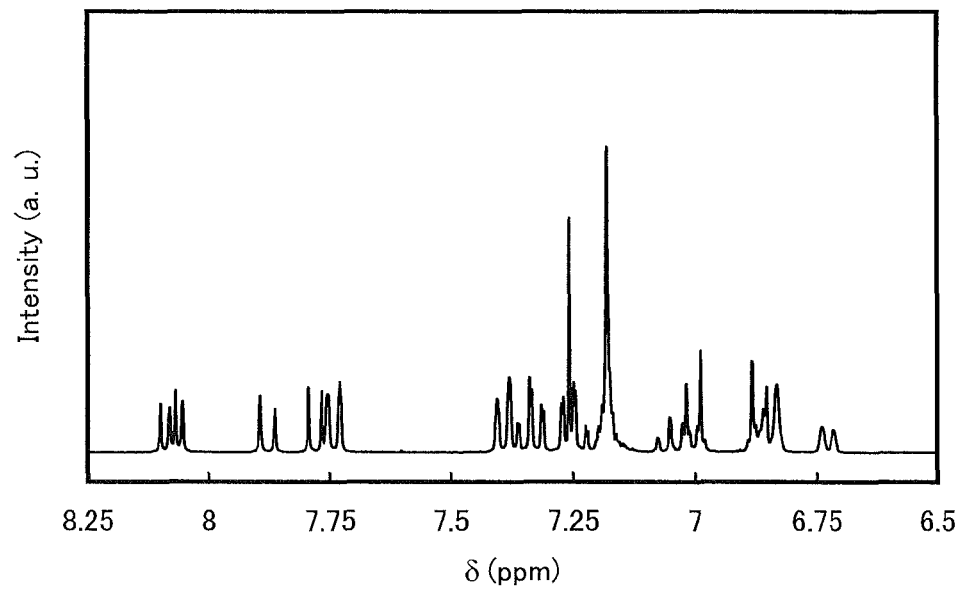

FIGS. 37A and 37B show the $^1$H NMR charts. Note that FIG. 37B is a chart showing an enlarged part of FIG. 37A in the range of 6.5 to 8.25 ppm.

Figure 38A:
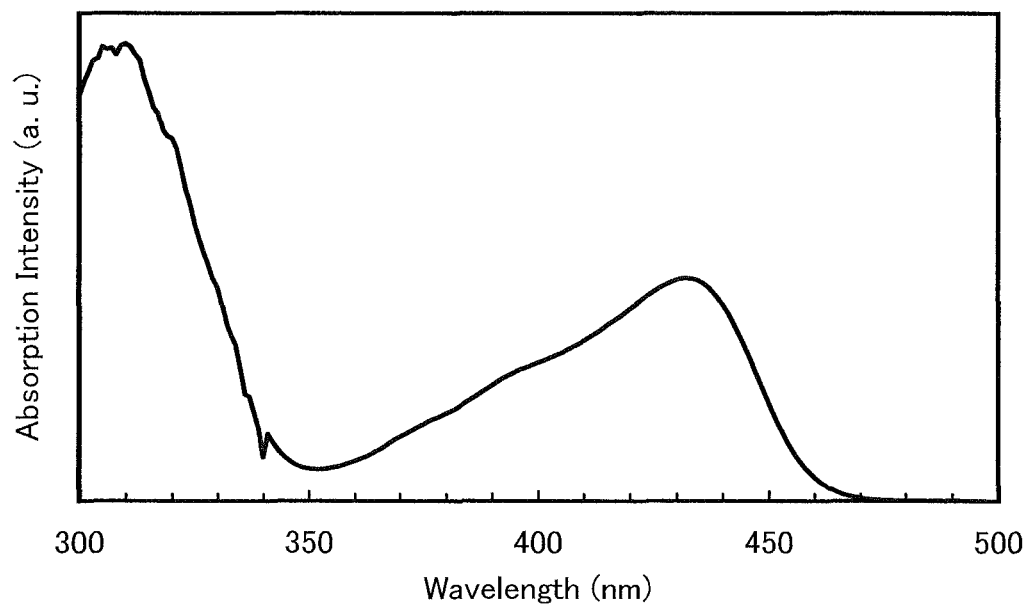
FIGS. 38A and 38B show an absorption spectrum and an emission spectrum of a toluene solution of 1,6mMeFLPAPrn.
Figure 38B:
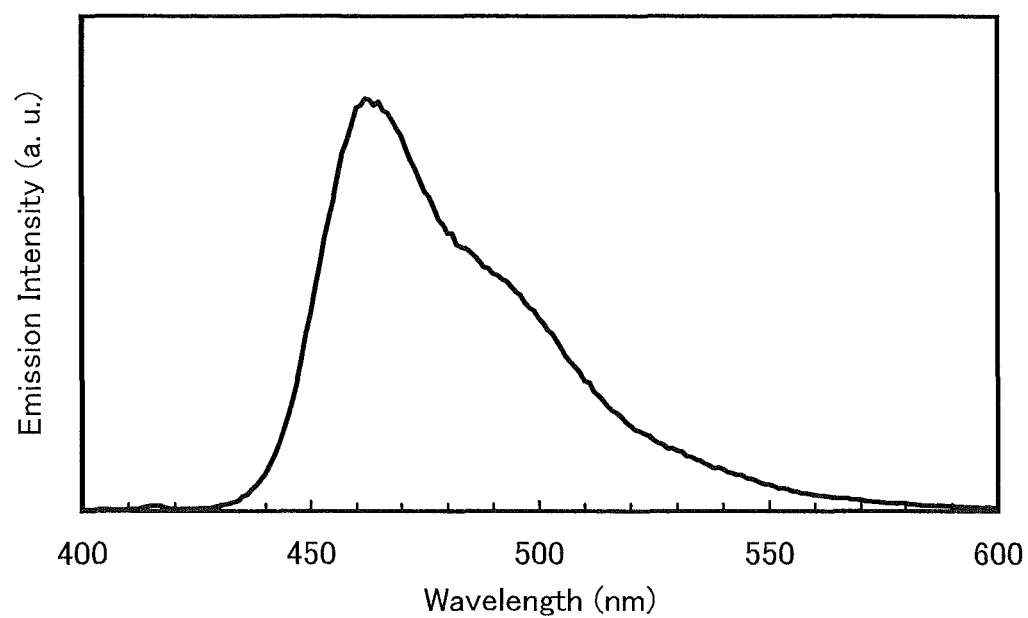
Figure 39A:
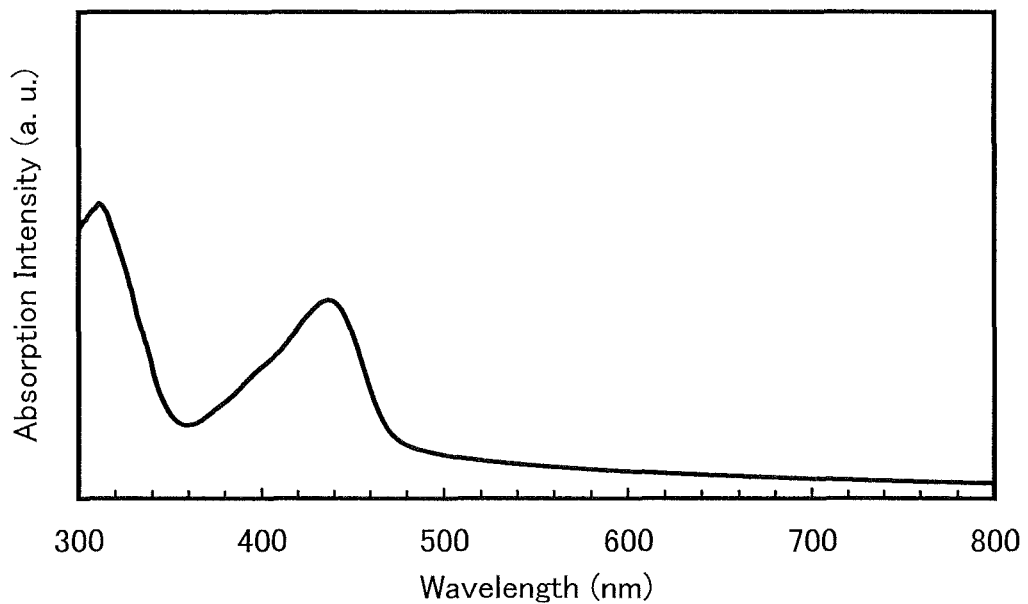
FIGS. 39A and 39B show an absorption spectrum and an emission spectrum of a thin film of 1,6mMeFLPAPrn.
Figure 39B:
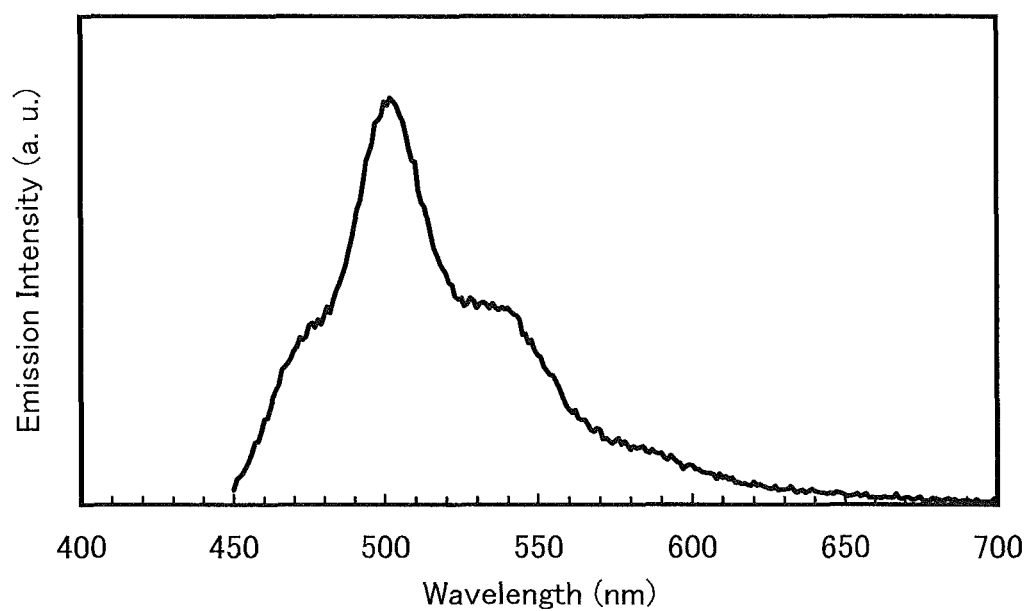

Further, FIG. 38A shows an absorption spectrum of a toluene solution of 1,6mMeFLPAPrn, and FIG. 38B shows an emission spectrum thereof. FIG. 39A shows an absorption spectrum of a thin film of 1,6mMeFLPAPrn, and FIG. 39B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 38A show the absorption spectrum of the solution which was obtained by subtracting the absorption spectra of quartz and toluene, and FIG. 39A shows the absorption spectrum of the thin film which was obtained by subtracting the absorption spectrum of a quartz substrate. In FIGS. 38A and 38B and FIGS. 39A and 39B, the horizontal axis represents wavelength (nm) and the vertical axis represents intensity (arbitrary unit). In the case of the toluene solution, absorption was observed at around 433 nm, and the maximum emission wavelength was 463 nm (excitation wavelength: 370 nm). In the case of the thin film, absorption was observed at around 437 nm, and the maximum emission wavelength was 502 nm (excitation wavelength: 435 nm).

The HOMO level and the LUMO level of the thin film of 1,6mMeFLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mMeFLPAPrn which is shown in FIG. 39B, was regarded as an optical energy gap and added to the value of the HOMO level. As a result, the HOMO level and LUMO level of 1,6mMeFLPAPrn were found to be −5.41 eV and −2.75 eV, respectively, and the energy gap was found to be 2.66 eV.

Thermogravimetry-differential thermal analysis (TG-DTA) of obtained 1,6mMeFLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

EXAMPLE 9

In this example, N,N'-bis(3,5-dimethylphenyl)-N,N'-bis[4-(9-phenyl-9H-fluoren-9-yl)phenyl]-pyrene-1,6-diamine (abbreviation: 1,6DMeFLPAPrn) represented by Structural Formula (117) in Embodiment 1 was produced.

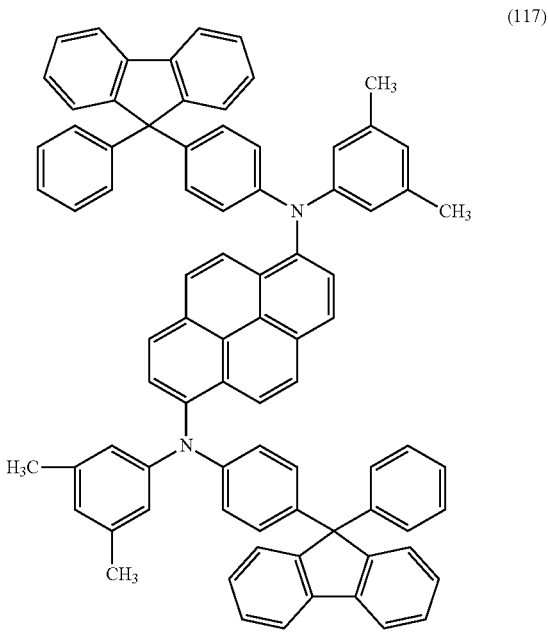

(117)

Step 1: Synthesis method of 3,5-dimethylphenyl-4-(9-phenyl-9H-fluoren-9-yl)phenylamine (abbreviation: DMeFLPA)

In a 200 mL three-neck flask were put 3.6 g (9.1 mmol) of 9-(4-bromophenyl)-9-phenylfluorene and 2.7 g (27.7 mmol) of sodium tert-butoxide. The air in the flask was replaced with nitrogen. To this mixture were added 46.0 mL of toluene and 1.2 mL (9.6 mmol) of 3,5-dimethylaniline. The temperature of this mixture was set to 60° C., and 53.2 mg (0.1 mmol) of bis(dibenzylideneacetone)palladium(0) was added to the mixture. The temperature of the mixture was raised to 80° C., followed by stirring for 0.5 hours. Then, 0.30 mL of a 10% hexane solution of tri(tert-butyl) phosphine was added to the mixture, which was then stirred for 4.5 hours. After the stirring, the mixture was suction-filtered through Florisil, Celite, and alumina to give a filtrate. The filtrate was concentrated to give a solid, which was then purified by silica gel column chromatography (the developing solvent has a 1:1 ratio of hexane to toluene) to give a while solid. Recrystallization of the obtained white solid from toluene and hexane gave 3.7 g of a white solid in 92% yield, which was the substance to be produced. The synthesis scheme of this Step 1 is shown in the following (E9-1).

Step 2: Synthesis method of N,N'-bis(3,5-dimethylphenyl)-N,N'-bis[4-(9-phenyl-9H-fluoren-9-yl)phenyl]-pyrene-1,6-diamine (abbreviation: 1,6DMeFLPAPrn)

In a 200 mL three-neck flask were put 0.6 g (1.7 mmol) of 1,6-dibromopyrene, 1.5 g (3.4 mmol) of 3,5-dimethylphenyl-4-(9-phenyl-9H-fluoren-9-yl)phenylamine, and 0.5 g (5.1 mmol) of sodium tert-butoxide. The air in the flask was replaced with nitrogen. To this mixture were added 17.0 mL of toluene and 0.2 mL of a 10% hexane solution of tri(tert-butyl)phosphine. The temperature of this mixture was set to 80° C., and 37.0 mg (0.1 mmol) of bis(dibenzylideneacetone)palladium(0) was added to the mixture. The temperature of the mixture was raised to 85° C., followed by stirring for 2.0 hours. After the stirring, the mixture was suction-filtered through Florisil, Celite, and alumina to give a filtrate. The filtrate was concentrated to give a solid. To the obtained solid was added 70 mL of toluene, and the mixture was suction-filtered. Then, recrystallization of the solid from a mixed solvent of toluene and hexane gave 1.0 g of a yellow solid in 56% yield, which was the substance to be produced.

Because the substance produced (1,6DMeFLPAPrn) has a structure in which a methyl group which is an alkyl group is bonded to a benzene ring in an amine skeleton, 1,6DMeFLPAPrn has higher solubility in an organic solvent such as toluene than 1,6FLPAPrn obtained in Example 2. Such improvement of the solubility in a solvent facilitates purification of the fluorene derivative of this example (1,6DMeFLPAPrn), demonstrating the easiness of its synthesis.

By a train sublimation method, 1.0 g of the obtained yellow solid was purified. In the purification, the yellow solid was heated at 360° C. under a pressure of 2.3 Pa with a flow rate of argon gas of 5.0 mL/min. After the purification, 0.9 g of a yellow solid was obtained in a yield of 91%, which was the substance to be produced. The synthesis scheme of Step 2 is shown by the following (E9-2).

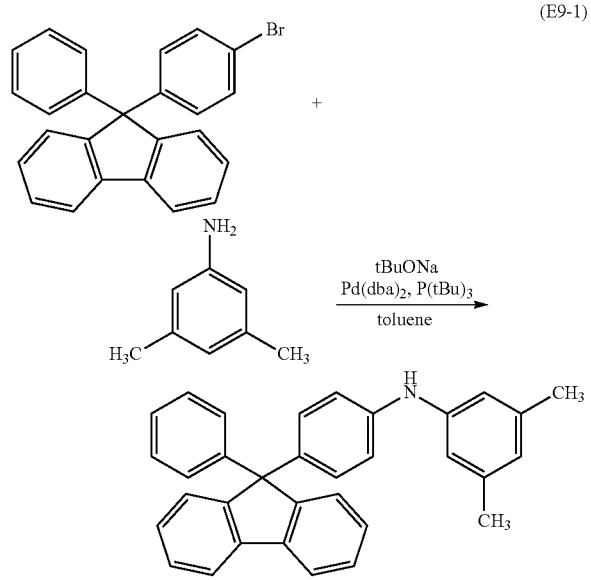

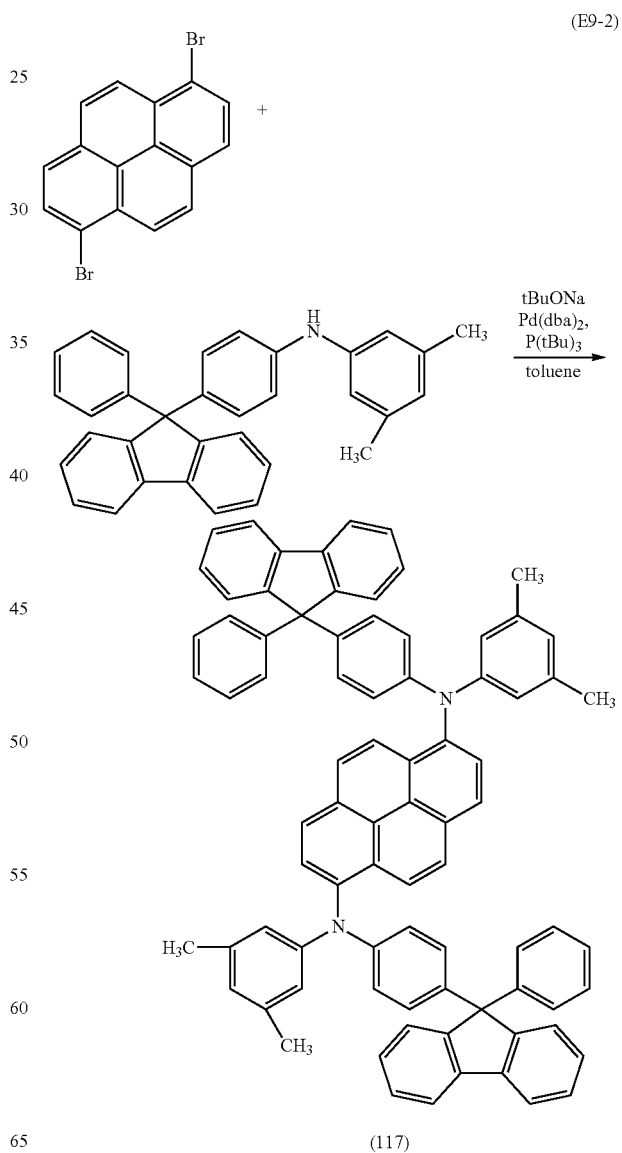

A nuclear magnetic resonance (NMR) method identified this compound as N,N'-bis(3,5-dimethylphenyl)-N,N'-bis[4-(9-phenyl-9H-fluoren-9-yl)phenyl]-pyrene-1,6-diamine (abbreviation: 1,6DMeFLPAPrn), which was the substance to be produced.

$^1$H NMR data of the obtained compound are: NMR (CDCl$_3$, 300 MHz): δ=2.14 (s, 12H), 6.57 (s, 2H), 6.67 (s, 4H), 6.84 (d, J=8.7 Hz, 4H), 6.99 (d, J=8.7 Hz, 4H), 7.19-7.41 (m, 22H), 7.73-7.79 (m, 6H), 7.89 (d, J=9.3 Hz, 2H), 8.06-8.11 (m, 4H).

Figure 40A:
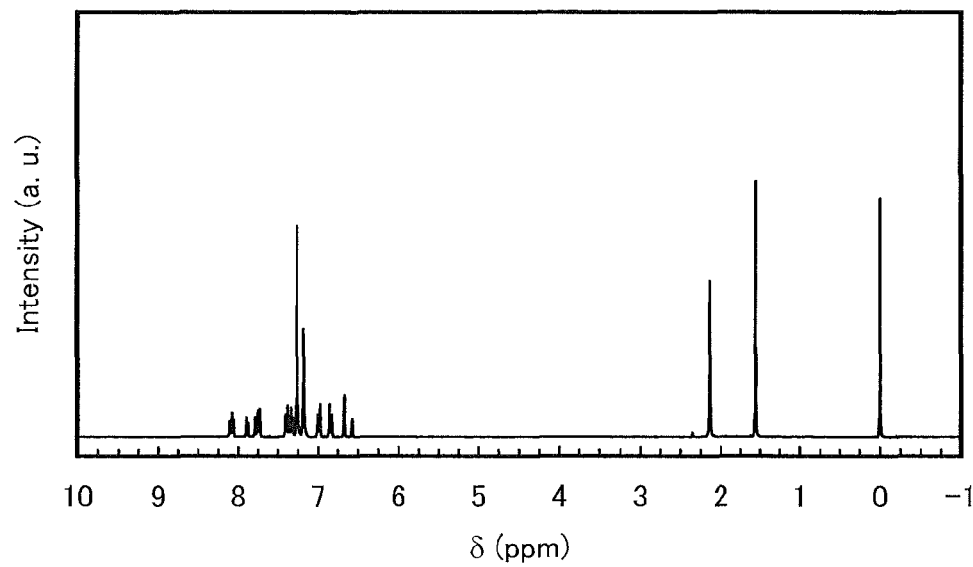
FIGS. 40A and 40B show $^1$H NMR charts of 1,6DMeFLPAPrn.
Figure 40B:
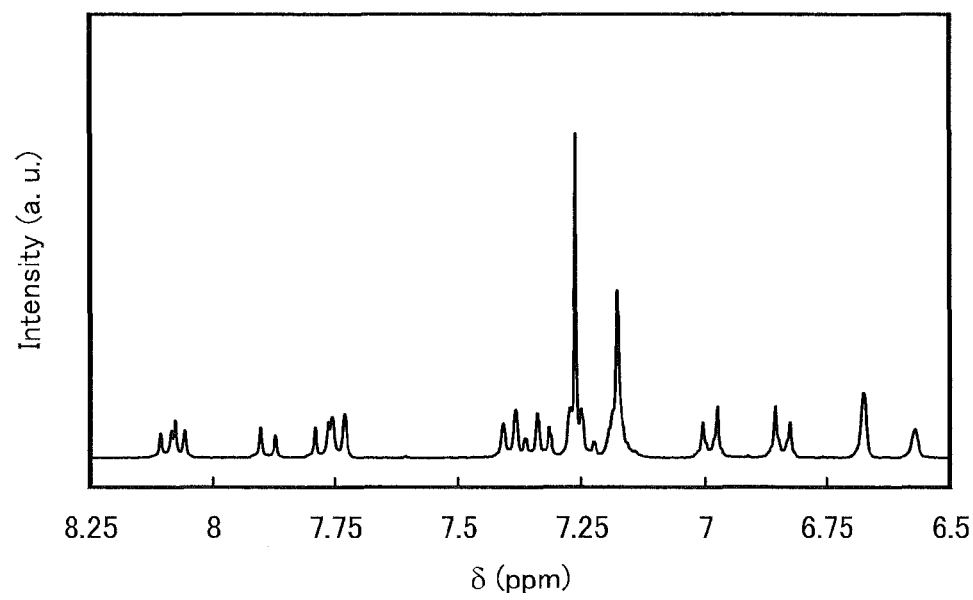

FIGS. 40A and 40B show the $^1$H NMR charts. Note that FIG. 40B is a chart showing an enlarged part of FIG. 40A in the range of 6.5 to 8.25 ppm.

Figure 41A:
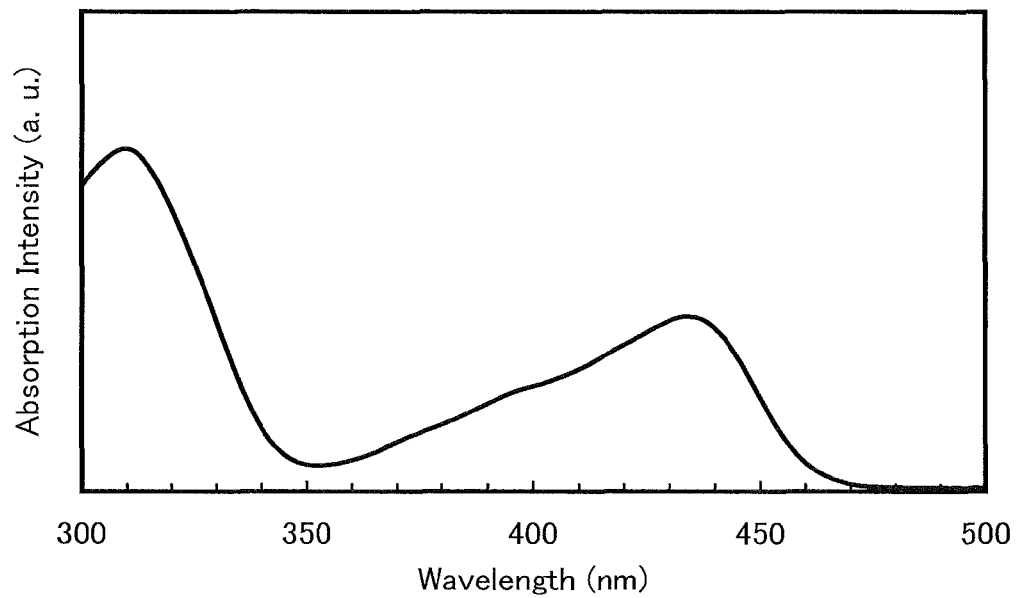
FIGS. 41A and 41B show an absorption spectrum and an emission spectrum of a toluene solution of 1,6DMeFLPAPrn.
Figure 41B:
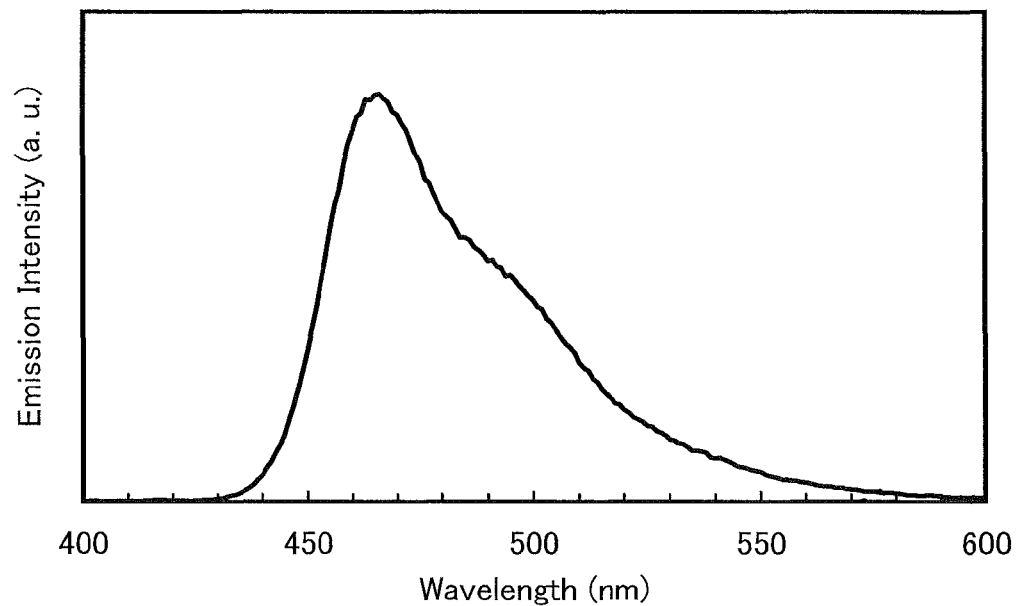
Figure 42A:
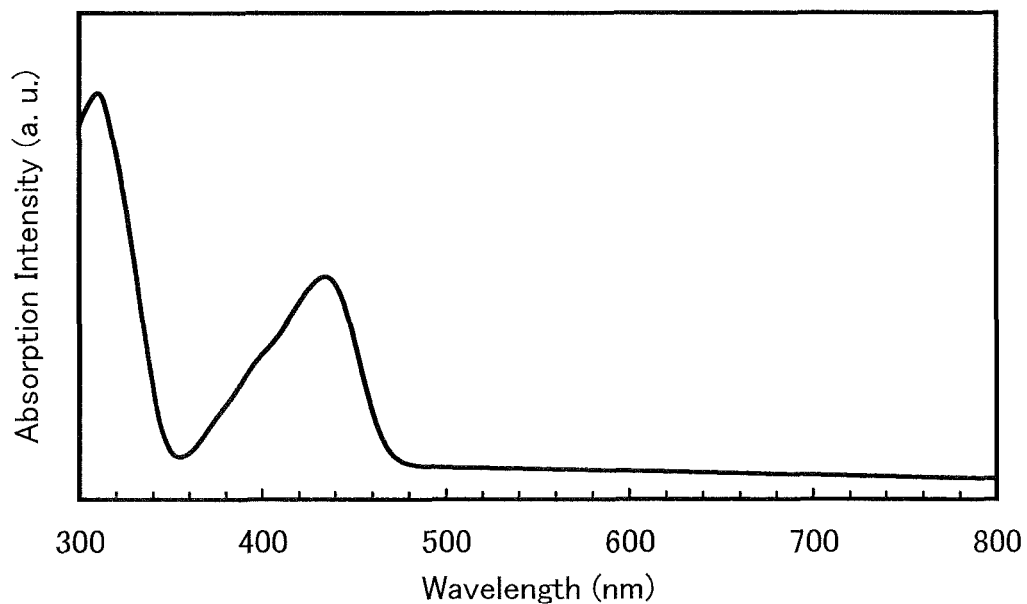
FIGS. 42A and 42B show an absorption spectrum and an emission spectrum of a thin film of 1,6DMeFLPAPrn.
Figure 42B:
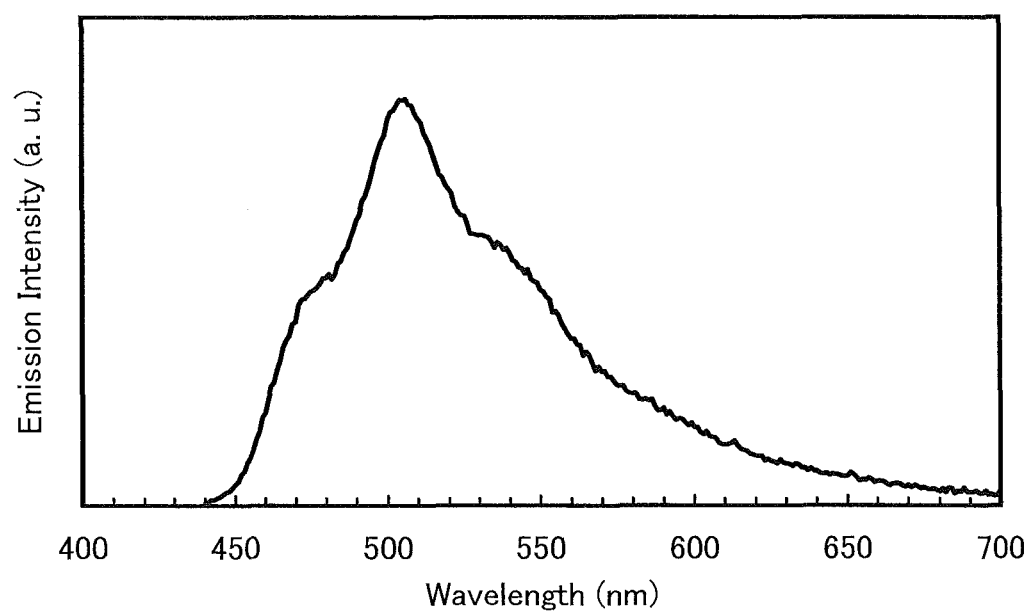

Further, FIG. 41A shows an absorption spectrum of a toluene solution of 1,6DMeFLPAPrn, and FIG. 41B shows an emission spectrum thereof. FIG. 42A shows an absorption spectrum of a thin film of 1,6DMeFLPAPrn, and FIG. 42B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 41A show the absorption spectrum of the solution which was obtained by subtracting the absorption spectra of quartz and toluene, and FIG. 42A shows the absorption spectrum of the thin film which was obtained by subtracting the absorption spectrum of a quartz substrate. In FIGS. 41A and 41B and FIGS. 42A and 42B, the horizontal axis represents wavelength (nm) and the vertical axis represents absorption intensity (arbitrary unit). In the case of the toluene solution, absorption was observed at around 434 nm, and the maximum emission wavelength was 466 nm (excitation wavelength: 370 nm). In the case of the thin film, absorption was observed at around 435 nm, and the maximum emission wavelength was 505 nm (excitation wavelength: 424 nm).

The HOMO level and the LUMO level of the thin film of 1,6DMeFLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6DMeFLPAPrn which is shown in FIG. 42B, was regarded as an optical energy gap and added to the value of the HOMO level. As a result, the HOMO level and LUMO level of 1,6DMeFLPAPrn were found to be −5.43 eV and −2.74 eV, respectively, and the energy gap was found to be 2.69 eV.

Thermogravimetry-differential thermal analysis (TG-DTA) of obtained 1,6DMeFLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

EXAMPLE 10

In this example, N,N'-bis[3-(9-phenyl-9H-fluoren-9-yl)phenyl]-N,N'-diphenyl-pyrene-1,6-diamine (abbreviation: 1,6mFLPAPrn) represented by Structural Formula (200) in Embodiment 2 was produced.

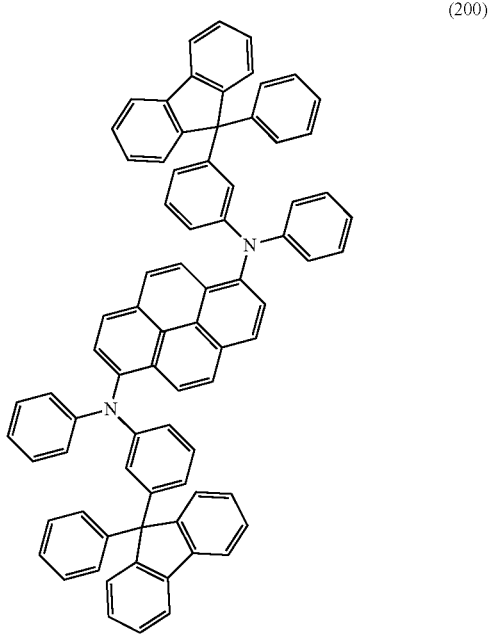

(200)

Step 1: Synthesis method of 9-(3-bromophenyl)-9-phenylfluorene

The air in a 500 mL three-neck flask was replaced with nitrogen, and then 80 mL of tetrahydrofuran and 3.7 mL (22.2 mmol) of 2-bromobiphenyl were put in the flask. The temperature of the mixture was set to −80° C. To this mixture was added 14.2 mL (22.3 mmol) of n-butyllithium, and the mixture was stirred for 1.5 hours. After that, 5.8 g (22.3 mmol) of 3-bromobenzophenone dissolved in 60 mL of tetrahydrofuran was added to the mixture, and the mixture was stirred for 4 hours. After that, the temperature of the mixture was set to room temperature, and the mixture was stirred for 20 hours. After that, an aqueous hydrochloric acid solution (1 mol/L) was added to this mixture. The organic layer and the aqueous layer of this mixture were separated. The aqueous layer was extracted with ethyl acetate three times. The ethyl acetate layer and the organic layer were washed with saturated brine once, and dried with magnesium sulfate. The obtained mixture was gravity filtered so that magnesium sulfate was removed, and the filtrate was concentrated to give an oily substance.

In a 200-mL recovery flask were put the obtained oily substance, 25 mL of glacial acetic acid, and 0.5 mL of hydrochloric acid. The mixture was heated and stirred at 110° C. for 2.0 hours. After the stirring, 100 mL of water was added to this mixture, and then 100 mL of ethyl acetate was added to the mixture. The organic layer and the aqueous layer of this mixture were separated. The aqueous layer was extracted with ethyl acetate three times. The organic layer and the ethyl acetate layer were combined, washed once with a saturated aqueous solution of sodium hydrogen carbonate and saturated brine, and then dried with magnesium sulfate. The obtained mixture was gravity filtered so that magnesium sulfate was removed, and the obtained filtrate was concentrated. Recrystallization from a mixed solvent of ethyl acetate and methanol gave 6.8 g of a white solid in 74% yield, which was the substance to be produced. The synthesis scheme of this Step 1 is shown in (E10-1) given below.

(E10-1)

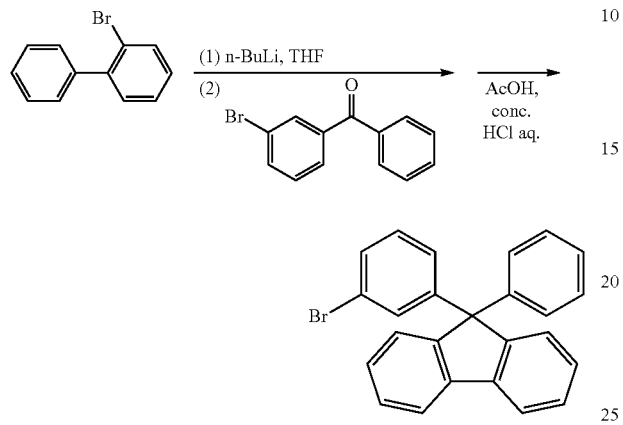

Step 2: Synthesis method of 3-(9-phenyl-9H-fluoren-9-yl)diphenylamine (abbreviation: mFLPA)

In a 200 mL three-neck flask were put 3.2 g (8.1 mmol) of 9-(3-bromophenyl)-9-phenylfluorene and 2.3 g (24.2 mmol) of sodium tert-butoxide. The air in the flask was replaced with nitrogen. To this mixture were added 40.0 mL of toluene, 0.75 mL (8.2 mmol) of aniline, and 0.2 mL of a 10% hexane solution of tri(tert-butyl)phosphine. The temperature of this mixture was set to 60° C., and 40.6 mg (0.1 mmol) of bis(dibenzylideneacetone)palladium(0) was added to the mixture. The temperature of the mixture was raised to 80° C., followed by stirring for 2.0 hours. After the stirring, toluene was added to this mixture, and the mixture was heated. Suction filtration through Florisil, Celite, and alumina gave a filtrate. The filtrate was concentrated to give a solid, which was then purified by silica gel column chromatography (the developing solvent has a 1:1 ratio of hexane to toluene). Accordingly, 3.2 g of a white solid was obtained in 96% yield, which was the substance to be produced. The synthesis scheme of this Step 2 is shown in (E10-2) given below.

-continued

Step 3: Synthesis method of N,N'-bis[3-(9-phenyl-9H-fluoren-9-yl)phenyl]-N,N'-diphenyl-pyrene-1,6-diamine (abbreviation: 1,6mFLPAPrn)

In a 100 mL three-neck flask were put 0.6 g (1.7 mmol) of 1,6-dibromopyrene, 1.4 g (3.4 mmol) of 3-(9-phenyl-9H-fluoren-9-yl)diphenylamine, and 0.5 g (5.1 mmol) of sodium tert-butoxide. The air in the flask was replaced with nitrogen. To this mixture were added 21.0 mL of toluene and 0.2 mL of a 10% hexane solution of tri(tert-butyl)phosphine. The temperature of this mixture was set to 80° C., and 38.1 mg (0.1 mmol) of bis(dibenzylideneacetone)palladium(0) was added to the mixture, followed by stirring for 3.0 hours. After the stirring, 500 mL of toluene was added to the mixture, and the mixture was heated. While the mixture was kept hot, it was suction-filtered through Florisil, Celite, and alumina to give a filtrate. The filtrate was concentrated to give a solid, which was then purified by silica gel column chromatography (the developing solvent has a 1:1 ratio of hexane to toluene) to give a yellow solid, which was the substance to be produced. Recrystallization of the obtained yellow solid from a mixed solvent of toluene and hexane gave 1.1 g of a yellow solid in 64% yield, which was the substance to be produced.

Because the substance produced (1,6mFLPAPrn) has a structure in which a fluorene skeleton is bonded to the meta position of a benzene ring in an amine skeleton, 1,6mFL-PAPrn has higher solubility in an organic solvent such as toluene than 1,6FLPAPrn obtained in Example 2. Such improvement of the solubility in a solvent facilitates purification of the fluorene derivative of this example (1,6mFL-PAPrn), demonstrating the easiness of its synthesis.

By a train sublimation method, 1.1 g of the obtained yellow solid was purified. In the purification, the yellow solid was heated at 320° C. under a pressure of 2.3 Pa with a flow rate of argon gas of 5.0 mL/min. After the purification, 1.0 g of a yellow solid was obtained in a yield of 91%, which was the substance to be produced. The synthesis scheme of Step 3 is shown by the following (E10-3).

(E10-2)

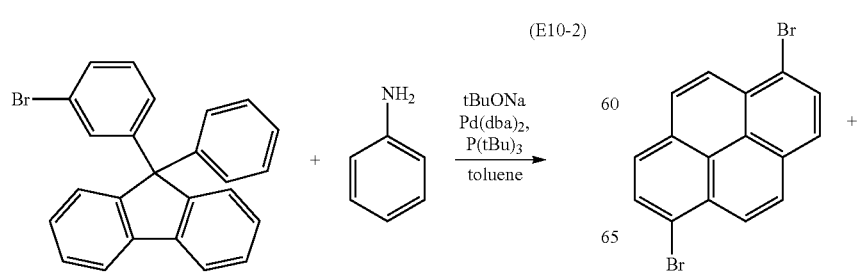

(E10-3)

-continued

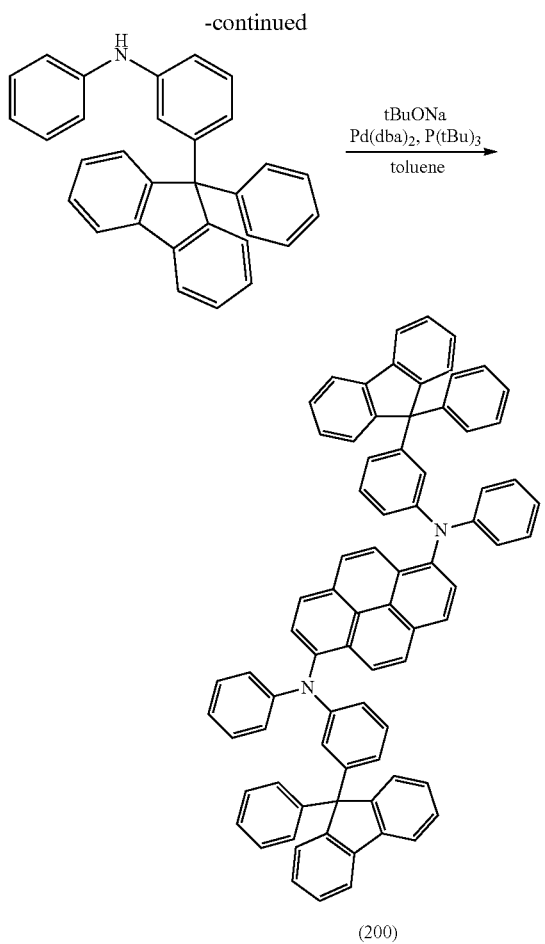

(200)

A nuclear magnetic resonance (NMR) method and a mass spectrometry identified this compound as N,N'-bis[3-(9-phenyl-9H-fluoren-9-yl)phenyl]-diphenyl-pyrene-1,6-diamine (abbreviation: 1,6mFLPAPrn), which was the substance to be produced.

$^1$H NMR data of the obtained compound are: $^1$H NMR (CDCl$_3$, 300 MHz): δ=6.68 (d, J=7.8 Hz, 2H), 6.87-7.23 (m, 38H), 7.61 (d, J=7.2 Hz, 4H), 7.74 (d, J=7.8 Hz, 2H), 7.85 (d, J=8.7 Hz, 2H), 8.03 (d, J=8.7 Hz, 4H).

Figure 43A:
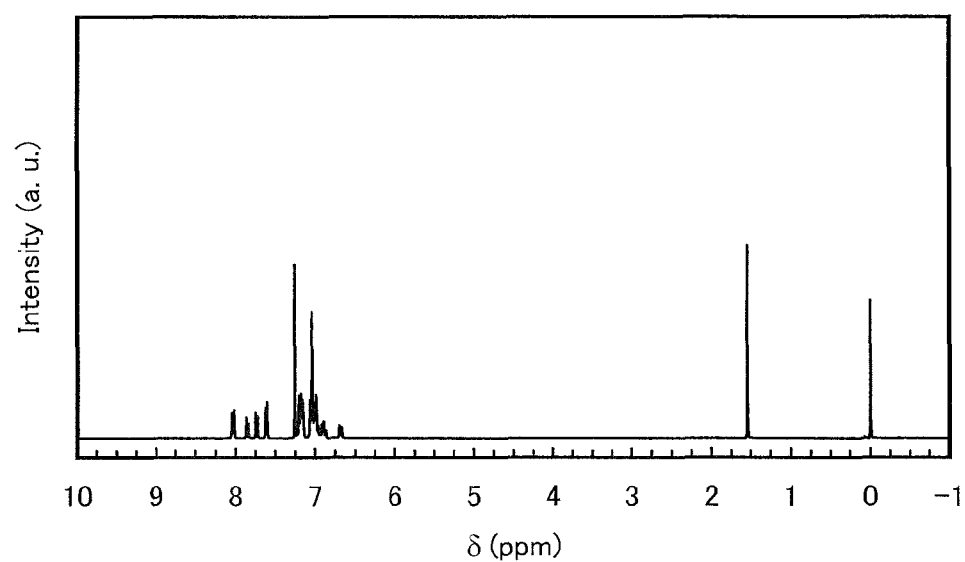
FIGS. 43A and 43B show $^1$H NMR charts of 1,6mFLPAPrn.
Figure 43B:
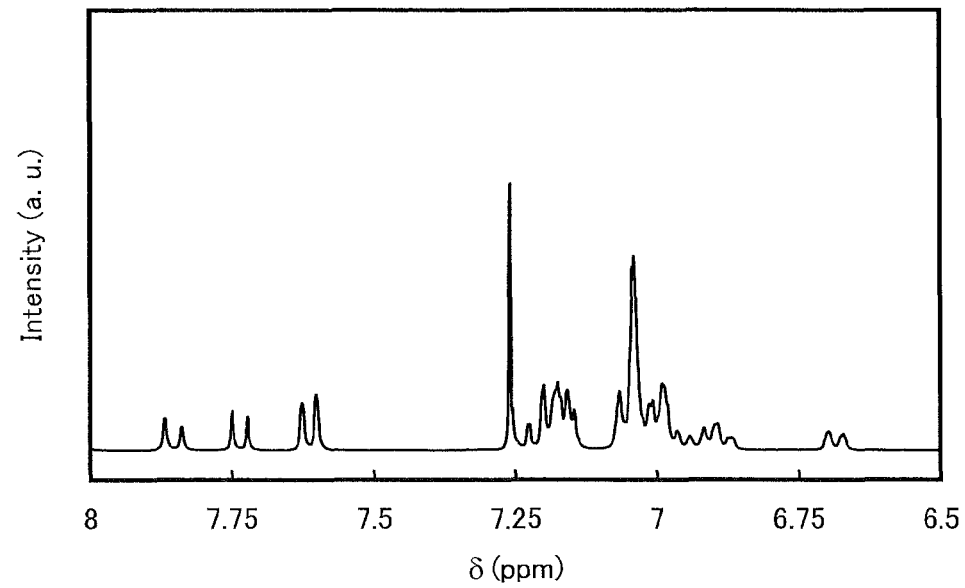

FIGS. 43A and 43B show the $^1$H NMR charts. Note that FIG. 43B is a chart showing an enlarged part of FIG. 43A in the range of 6.5 to 8.25 ppm.

The measurement result of the mass spectrometry of the obtained compound is: MS (ESI-MS): m/z=1017 (M+H)$^+$; C$_{78}$H$_{52}$N$_2$ (1016.41).

Figure 44A:
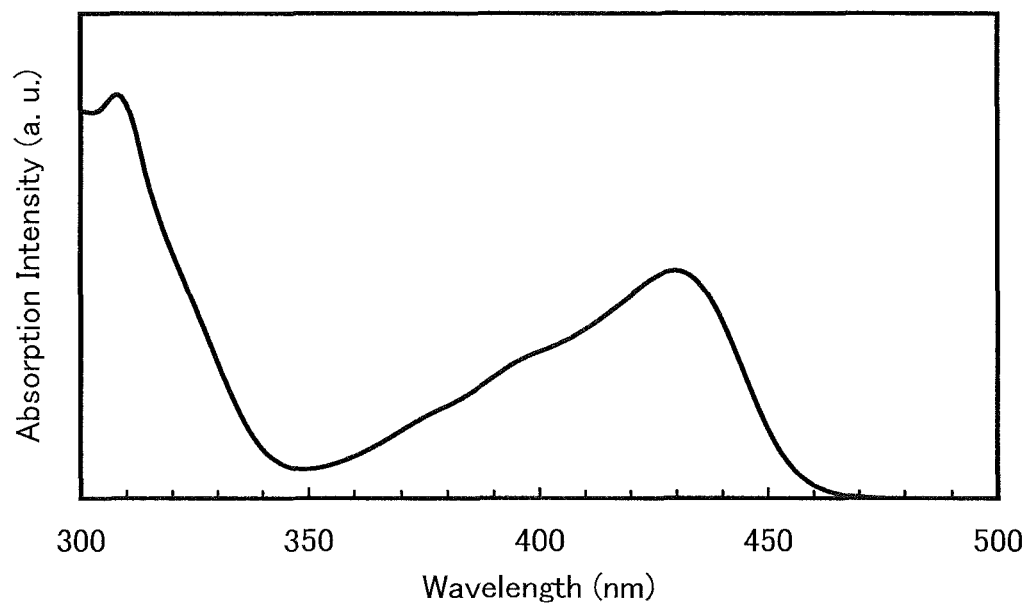
FIGS. 44A and 44B show an absorption spectrum and an emission spectrum of a toluene solution of 1,6mFLPAPrn.
Figure 44B:
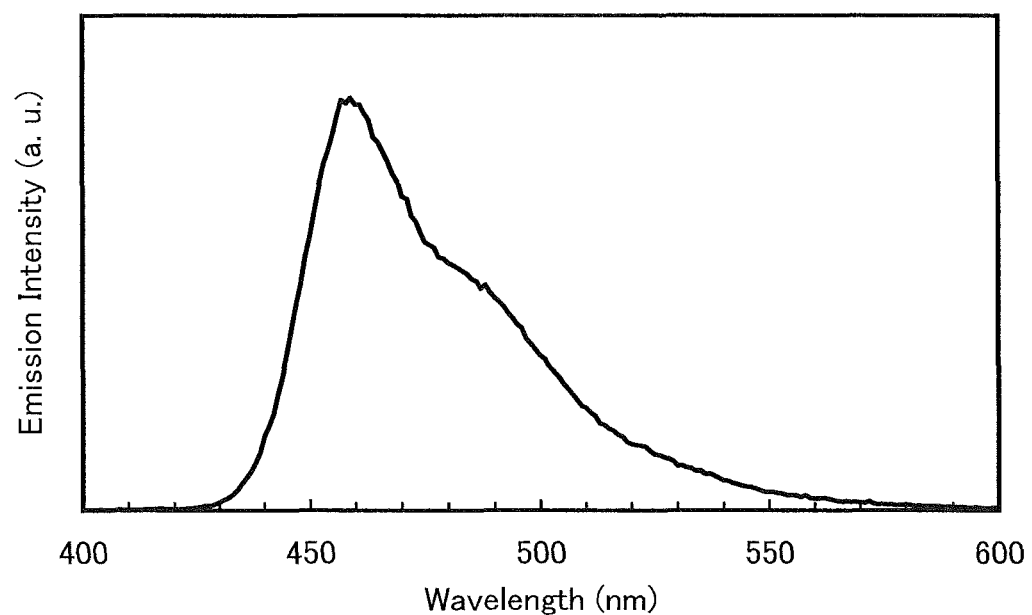
Figure 45A:
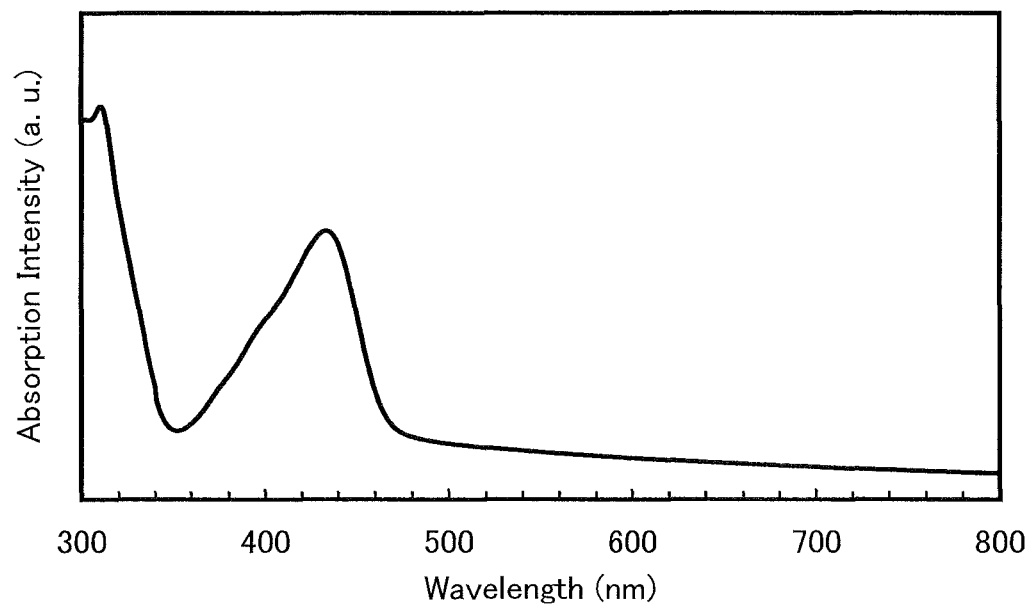
FIGS. 45A and 45B show an absorption spectrum and an emission spectrum of a thin film of 1,6mFLPAPrn.
Figure 45B:
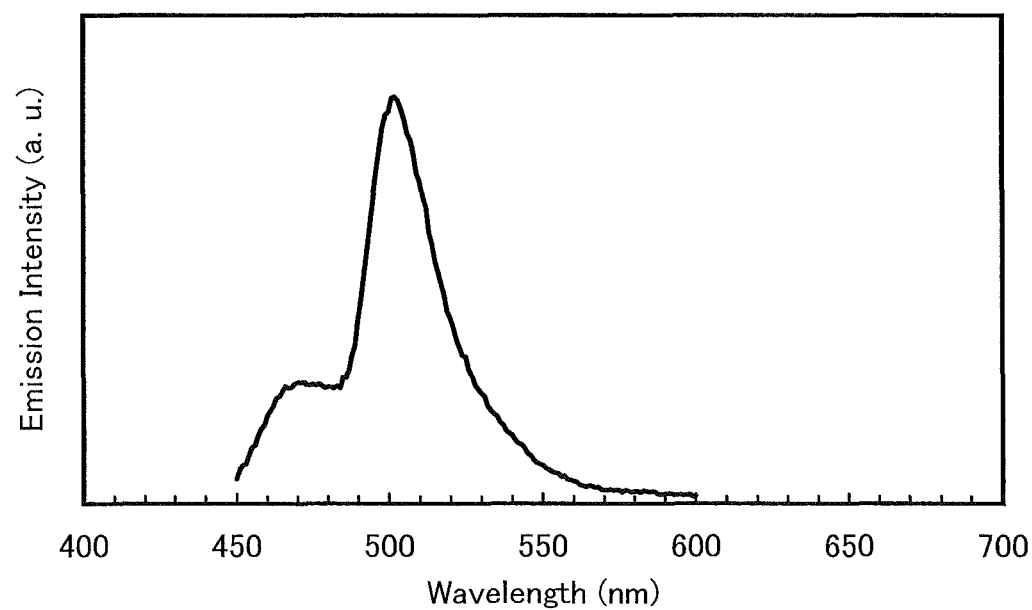

Further, FIG. 44A shows an absorption spectrum of a toluene solution of 1,6mFLPAPrn, and FIG. 44B shows an emission spectrum thereof. FIG. 45A shows an absorption spectrum of a thin film of 1,6mFLPAPrn, and FIG. 45B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 44A show the absorption spectrum of the solution which was obtained by subtracting the absorption spectra of quartz and toluene, and FIG. 45A shows the absorption spectrum of the thin film which was obtained by subtracting the absorption spectrum of a quartz substrate. In FIGS. 44A and 44B and FIGS. 45A and 45B, the horizontal axis represents wavelength (nm) and the vertical axis represents intensity (arbitrary unit). In the case of the toluene solution, absorption was observed at around 430 nm, and the maximum emission wavelength was 459 nm (excitation wavelength: 370 nm). In the case of the thin film, absorption was observed at around 434 nm, and the maximum emission wavelength was 502 nm (excitation wavelength: 432 nm).

The HOMO level and the LUMO level of the thin film of 1,6mFLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mFLPAPrn which is shown in FIG. 45B, was regarded as an optical energy gap and added to the value of the HOMO level. As a result, the HOMO level and LUMO level of 1,6mFLPAPrn were found to be −5.5 eV and −2.81 eV, respectively, and the energy gap was found to be 2.69 eV.

Thermogravimetry-differential thermal analysis (TG-DTA) of obtained 1,6mFLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 476° C. or more, which is indicative of high heat resistance.

The measurement was carried out under a pressure of 8.7×10$^{-4}$ Pa at a temperature rising rate of 10° C./min. The relationship between weight and temperature (thermogravimetry) shows that the 5% weight loss temperature is 316° C., which is indicative of a good sublimation property. Thus, it is understood that the fluorene derivative (1,6mFLPAPrn) of one embodiment of the present invention is a material having a low sublimation temperature and a good sublimation property despite its high molecular weight. Further, the lower sublimation temperature and the better sublimation property are found to result from the structure in which a fluorene skeleton is bonded to the meta position of a benzene ring in an amine skeleton.

EXAMPLE 11

In this example, N,N'-bis{3-[9-(3-methylphenyl)-9H-fluoren-9-yl]phenyl}-N,N'-diphenyl-pyrene-1,6-diamine (abbreviation: 1,6mFLPAPrn-II) represented by Structural Formula (215) in Embodiment 2 was produced.

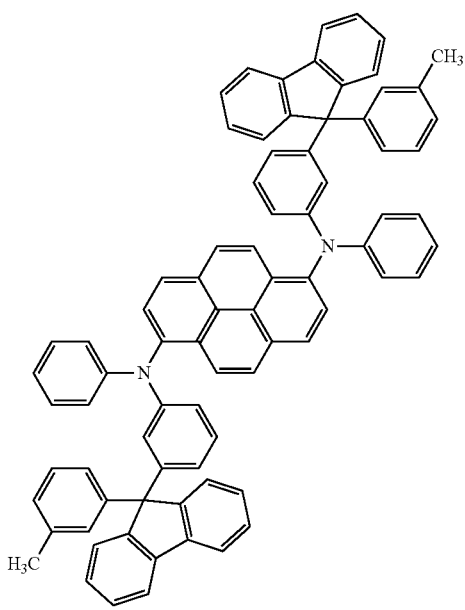

(215)

Step 1: Synthesis method of 9-(3-bromophenyl)-9-(3-methylphenyl)fluorene

The air in a 500 mL three-neck flask was replaced with nitrogen, and then 80 mL of tetrahydrofuran and 3.8 mL (22.8 mmol) of 2-bromobiphenyl were put in the flask. The temperature of the mixture was set to −80° C. To this mixture was added 14.5 mL (22.8 mmol) of n-butyllithium, and the mixture was stirred for 0.5 hours. After that, 6.3 g (22.8 mol) of 3-bromo-3' methyl-benzophenone dissolved in 71 mL of tetrahydrofuran was added to the mixture, and the mixture was stirred for 1.8 hours. After that, the temperature of the mixture was set to room temperature, and the mixture was stirred overnight. Then, an aqueous hydrochloric acid solution (1 mol/L) was added to this mixture. The organic layer and the aqueous layer of this mixture were separated. The aqueous layer was extracted with ethyl acetate three times. The ethyl acetate layer and the organic layer were washed with saturated brine once, and dried with magnesium sulfate. The obtained mixture was gravity filtered so that magnesium sulfate was removed, and the filtrate was concentrated to give an oily substance.

In a 200-mL recovery flask were put the obtained oily substance, 25 mL of glacial acetic acid, and 0.5 mL of hydrochloric acid, and the mixture was heated and stirred at 110° C. for 6.0 hours. After the stirring, water and ethyl acetate were added to the mixture. The organic layer and the aqueous layer of this mixture were separated. The aqueous layer was extracted with ethyl acetate three times. The organic layer and the ethyl acetate layer were combined, washed once with a saturated aqueous solution of sodium hydrogen carbonate and saturated brine, and then dried with magnesium sulfate. The obtained mixture was gravity filtered so that magnesium sulfate was removed, and the obtained filtrate was concentrated. Recrystallization from a mixed solvent of ethyl acetate and methanol gave 5.8 g of a white solid in 63% yield, which was the substance to be produced. The synthesis scheme of this Step 1 is shown in (E11-1) given below.

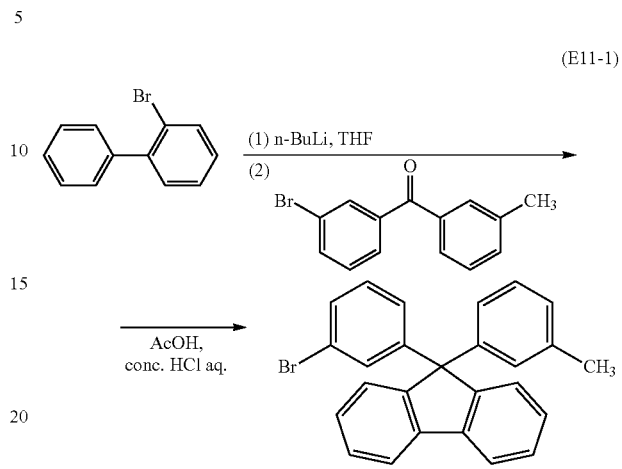

(E11-1)

Step 2: Synthesis method of 3-[9-(3-methylphenyl)-9H-fluoren-9-yl]diphenylamine (abbreviation: mFLPA-II)

In a 200 mL three-neck flask were put 2.8 g (6.8 mmol) of 9-(3-bromophenyl)-9-(3-methylphenyl)-fluorene and 2.0 g (20.6 mmol) of sodium tert-butoxide. The air in the flask was replaced with nitrogen. To this mixture were added 34.0 mL of toluene, 0.7 mL (7.1 mmol) of aniline, and 0.2 mL of a 10% hexane solution of tri(tert-butyl)phosphine. The temperature of this mixture was set to 60° C., and 33.0 mg (0.1 mmol) of bis(dibenzylideneacetone)palladium(0) was added to the mixture. The temperature of this mixture was raised to 80° C., followed by stirring for 2.0 hours. After the stirring, the mixture was suction-filtered through Florisil, Celite, and alumina to give a filtrate. The filtrate was concentrated to give a solid, which was then purified by silica gel column chromatography (the developing solvent has a 3:2 ratio of hexane to toluene). The obtained fractions were concentrated to give 2.8 g of a solid in 96% yield, which was the substance to be produced. The synthesis scheme of this Step 2 is shown in (E11-2) given below.

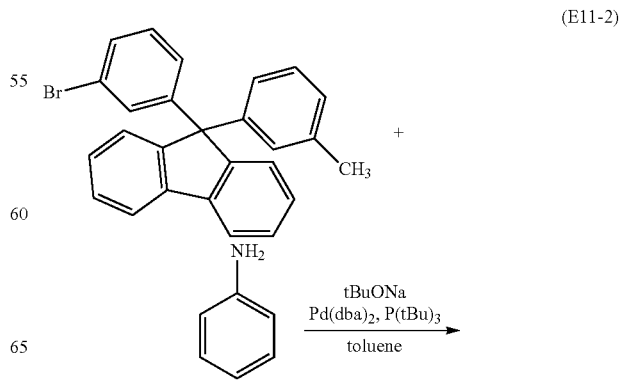

(E11-2)

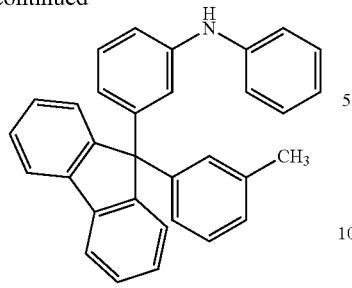

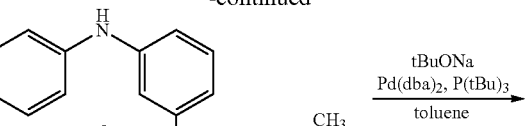

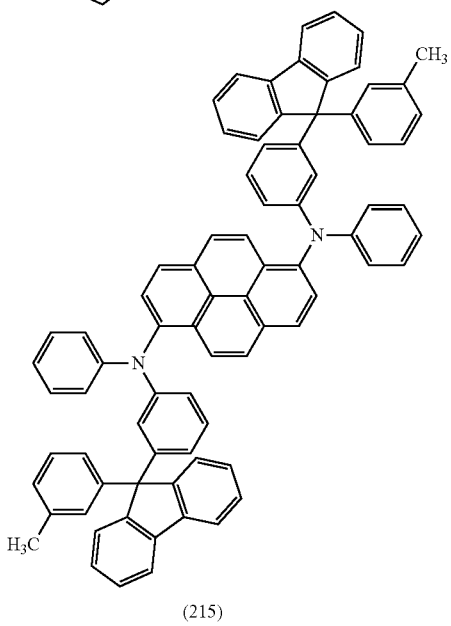

(215)

Step 3: Synthesis method of N,N'-bis{3-[9-(3-methylphenyl)-9H-fluoren-9-yl]phenyl}-N,N'-diphenyl-pyrene-1,6-diamine (abbreviation: 1,6mFLPAPrn-II)

In a 100 mL three-neck flask were put 0.5 g (1.4 mmol) of 1,6-dibromopyrene, 1.2 g (2.9 mmol) of 3-[9-(3-methylphenyl)-9H-fluoren-9-yl]diphenylamine, and 0.4 g (4.3 mmol) of sodium tert-butoxide. The air in the flask was replaced with nitrogen. To this mixture were added 19.0 mL of toluene and 0.2 mL of a 10% hexane solution of tri(tert-butyl)phosphine. The temperature of this mixture was set to 80° C., and 32.7 mg (0.1 mmol) of bis(dibenzylideneacetone)palladium(0) was added to the mixture, followed by stirring for 2.5 hours. After the stirring, the mixture was suction-filtered through Florisil, Celite, and alumina to give a filtrate. The filtrate was concentrated to give a solid, which was then purified by silica gel column chromatography (the developing solvent has a 4:5 ratio of hexane to toluene). The obtained fractions were concentrated to give a yellow solid. Recrystallization of the obtained yellow solid from a mixed solvent of toluene and hexane gave 0.7 g of a yellow solid in 46% yield, which was the substance to be produced.

Because the substance produced (1,6mFLPAPrn-II) has a structure in which a fluorene skeleton is bonded to the meta position of a benzene ring in an amine skeleton and a methyl group which is an alkyl group is bonded to a benzene ring bonded to the 9-position of fluorene, 1,6mFLPAPrn-II has higher solubility in an organic solvent such as toluene than 1,6FLPAPrn obtained in Example 2. Such improvement of the solubility in a solvent facilitates purification of the fluorene derivative of this example (1,6mFLPAPrn-II), demonstrating the easiness of its synthesis.

By a train sublimation method, 0.7 g of the obtained yellow solid was purified. In the purification, the yellow solid was heated at 312° C. under a pressure of 2.9 Pa with a flow rate of argon gas of 5.0 mL/min. After the purification, 0.6 g of a yellow solid was obtained in a yield of 89%, which was the substance to be produced. The synthesis scheme of Step 3 is shown by the following (E11-3).

(E11-3)

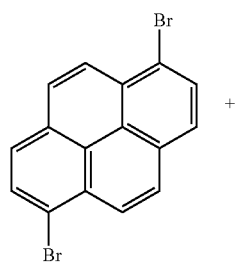

+

A nuclear magnetic resonance (NMR) method identified this compound as N,N'-bis{3-[9-(3-methylphenyl)-9H-fluoren-9-yl]phenyl}-N,N'-diphenyl-pyrene-1,6-diamine (abbreviation: 1,6mFLPAPrn-II), which was the substance to be produced.

$^1$H NMR data of the obtained compound are: $^1$H NMR (CDCl$_3$, 300 MHz): δ=2.14 (s, 6H), 6.68 (d, J=8.1 Hz, 2H), 6.86-7.23 (m, 36H), 7.61 (d, J=7.8 Hz, 4H), 7.73 (d, J=7.8 Hz, 2H), 7.85 (d, J=9.3 Hz, 2H), 8.02-8.05 (m, 4H).

Figure 46A:
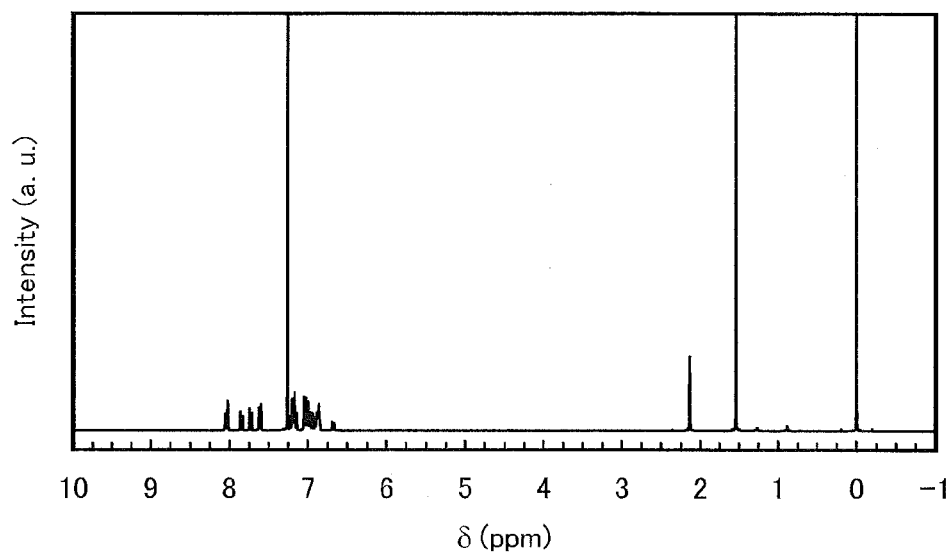
FIGS. 46A and 46B show $^1$H NMR charts of 1,6mFLPAPrn-II.
Figure 46B:
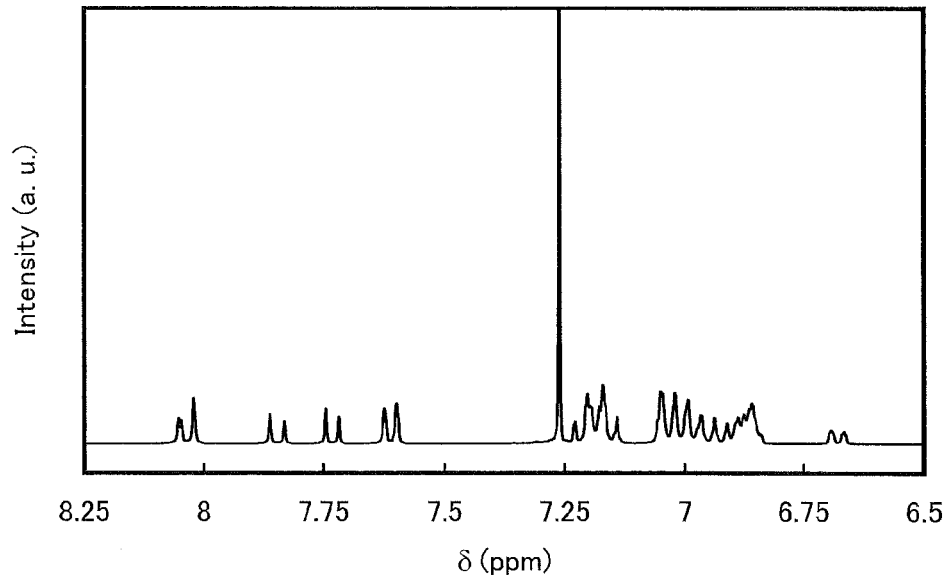

FIGS. 46A and 46B show the $^1$H NMR charts. Note that FIG. 46B is a chart showing an enlarged part of FIG. 46A in the range of 6.5 to 8.25 ppm.

Figure 47A:
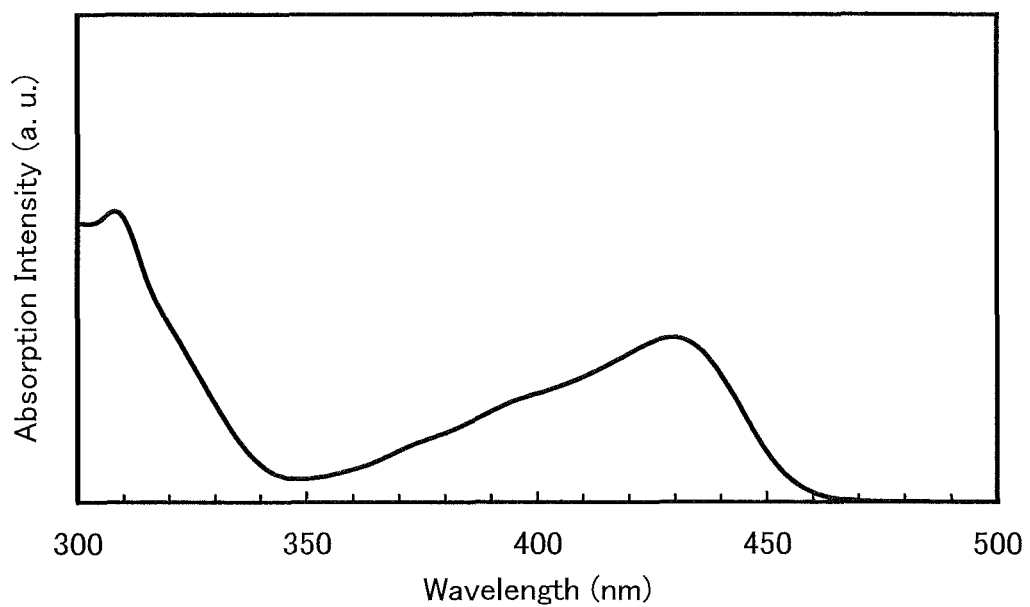
FIGS. 47A and 47B show an absorption spectrum and an emission spectrum of a toluene solution of 1,6mFLPAPrn-II.
Figure 47B:
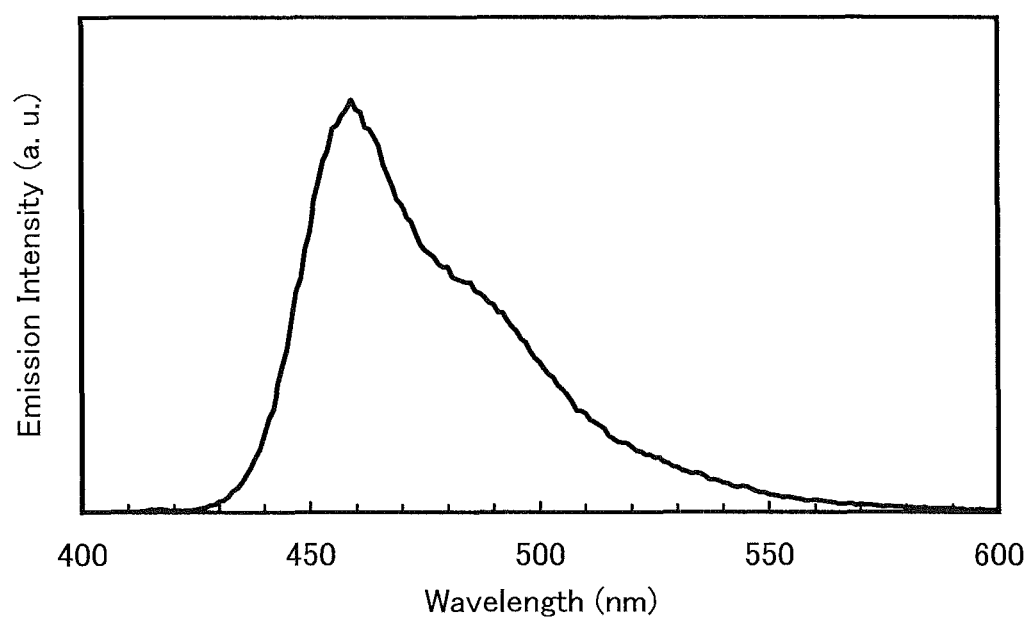
Figure 48A:
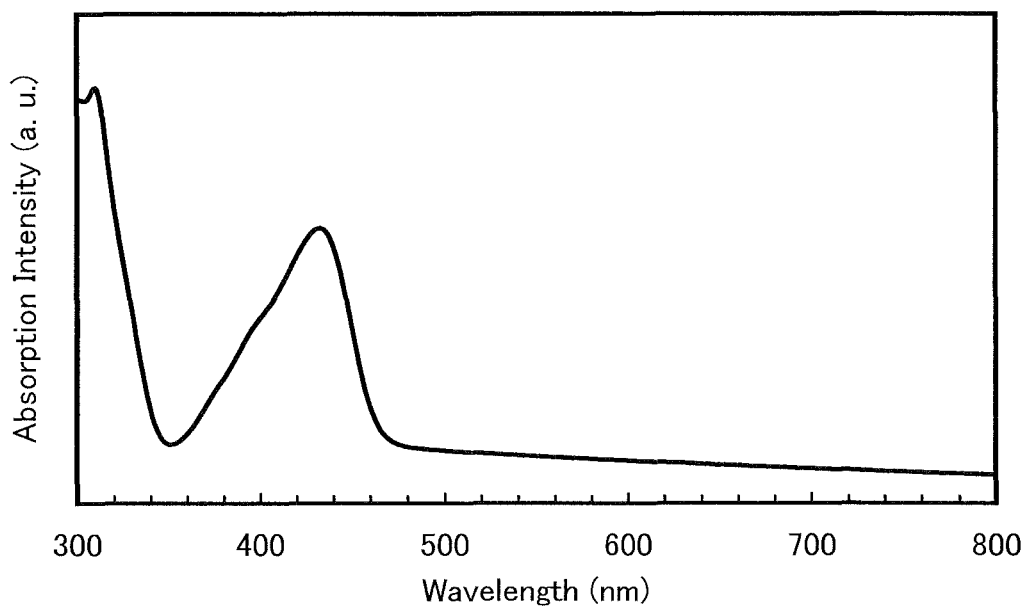
FIGS. 48A and 48B show an absorption spectrum and an emission spectrum of a thin film of 1,6mFLPAPrn-II.
Figure 48B:
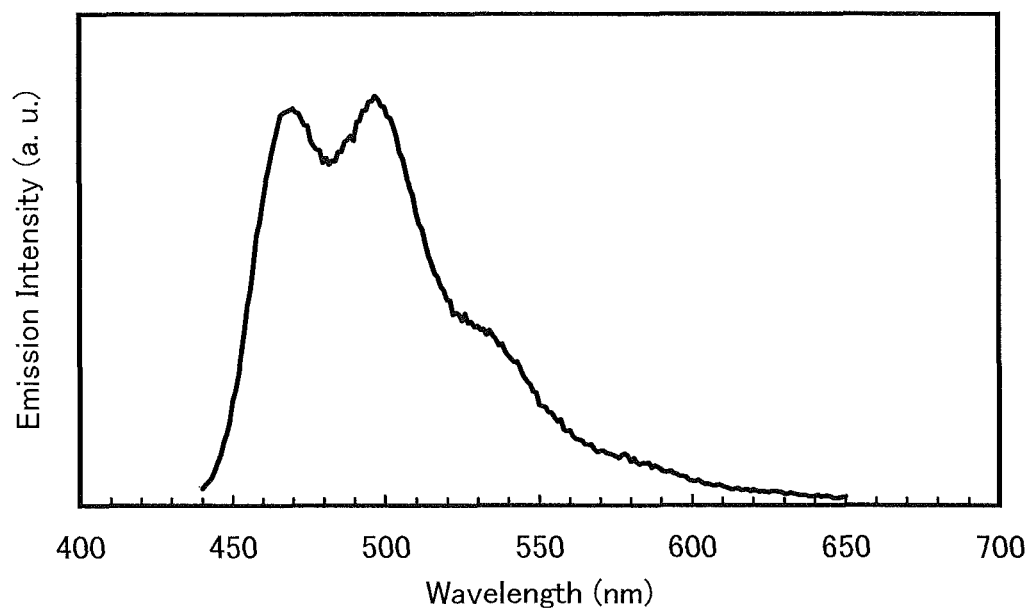

Further, FIG. 47A shows an absorption spectrum of a toluene solution of 1,6mFLPAPrn-II, and FIG. 47B shows an emission spectrum thereof. FIG. 48A shows an absorption spectrum of a thin film of 1,6mFLPAPrn-II, and FIG. 48B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 47A show the absorption spectrum of the solution which was obtained by subtracting the absorption spectra of quartz and toluene, and FIG. 48A shows the absorption spectrum of the thin film which was obtained by subtracting the absorption spectrum of a quartz substrate. In FIGS. 47A and 47B and FIGS. 48A and 48B, the horizontal axis represents wavelength (nm) and the vertical axis represents intensity (arbitrary unit). In the case of the toluene solution, absorption was observed at around 430 nm, and the maximum emission wavelength was 459 nm (excitation wavelength: 370 nm). In the case of the thin film, absorption was observed at around 433 nm, and the maximum emission wavelength was 497 nm (excitation wavelength: 434 nm).

The HOMO level and the LUMO level of the thin film of 1,6mFLPAPrn-II were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mFLPAPrn-II which is shown in FIG. 48B, was regarded as an optical energy gap and added to the value of the HOMO level. As a result, the HOMO level and LUMO level of 1,6mFLPAPrn-II were found to be −5.49 eV and −2.78 eV, respectively, and the energy gap was found to be 2.71 eV.

Thermogravimetry-differential thermal analysis (TG-DTA) of obtained 1,6mFLPAPrn-II was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 476° C., which is indicative of high heat resistance.

EXAMPLE 12

In this example, N,N'-bis{3-[9-(4-methylphenyl)-9H-fluoren-9-yl]phenyl}-N,N'-diphenyl-pyrene-1,6-diamine (abbreviation: 1,6mFLPAPrn-III) represented by Structural Formula (216) in Embodiment 2 was produced.

(216)

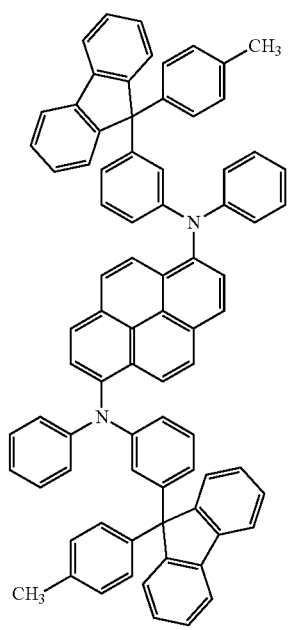

Step 1: Synthesis method of 9-(3-bromophenyl)-9-(4-methylphenyl)fluorene

The air in a 500 mL three-neck flask was replaced with nitrogen, and then 80 mL of tetrahydrofuran and 3.8 mL (22.8 mmol) of 2-bromobiphenyl were put in the flask. The temperature of the mixture was set to −80° C. To this mixture was added 13.5 mL (22.5 mmol) of n-butyllithium, and the mixture was stirred for 2.1 hours. After that, 5.8 g (22.8 mol) of 3-bromo-4' methyl-benzophenone dissolved in 70 mL of tetrahydrofuran was added to the mixture, and the mixture was stirred for 4.3 hours. After that, the temperature of the mixture was set to room temperature, and the mixture was stirred overnight. After that, an aqueous hydrochloric acid solution (1 mol/L) was added to this mixture. The organic layer and the aqueous layer of this mixture were separated. The aqueous layer was extracted with ethyl acetate three times. This ethyl acetate layer and the organic layer were dried with magnesium sulfate. The obtained mixture was gravity filtered so that magnesium sulfate was removed, and the filtrate was concentrated to give an oily substance.

In a 200 mL recovery flask were put the obtained oily substance, 30 mL of glacial acetic acid, and 0.5 mL of hydrochloric acid. The mixture was heated and stirred at 110° C. for 4.5 hours. After the stirring, water and ethyl acetate were added to the mixture. The organic layer and the aqueous layer of this mixture were separated. The aqueous layer was extracted with ethyl acetate three times. The organic layer and the ethyl acetate layer were combined, washed once with a saturated aqueous solution of sodium hydrogen carbonate and saturated brine, and then dried with magnesium sulfate. The obtained mixture was gravity filtered so that magnesium sulfate was removed to give a filtrate. The filtrate was concentrated to give an oily substance, which was then purified by silica gel column chromatography (the developing solvent has a 10:1 ratio of hexane to toluene). The obtained fractions were concentrated to give 4.9 g of a white solid in 50% yield, which was the substance to be produced. The synthesis scheme of this Step 1 is shown in (E12-1) given below.

(E12-1)

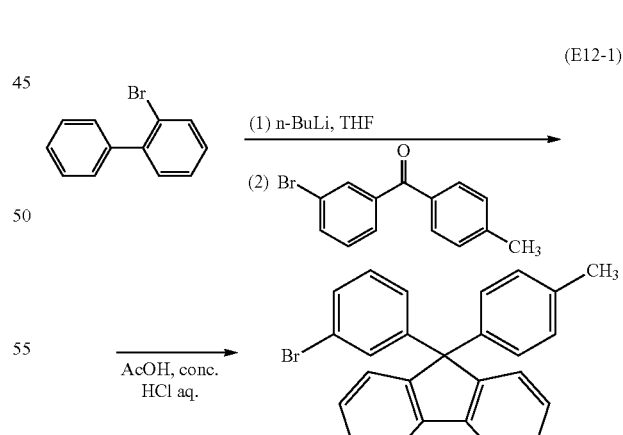

Step 2: Synthesis method of 3-[9-(4-methylphenyl)-9H-fluoren-9-yl]diphenylamine (abbreviation: mFLPA-III)

In a 50 mL three-neck flask were put 1.4 g (3.5 mmol) of 9-(3-bromophenyl)-9-(4-methylphenyl)-fluorene and 1.0 g (10.4 mmol) of sodium tert-butoxide. The air in the flask was replaced with nitrogen. To this mixture were added 18.0 mL of toluene, 0.4 mL (3.8 mmol) of aniline, and 0.2 mL of a 10% hexane solution of tri(tert-butyl)phosphine. The temperature of this mixture was set to 60° C., and 33.7 mg (0.1 mmol) of bis(dibenzylideneacetone)palladium(0) was added to the mixture. The temperature of this mixture was raised to 80° C., followed by stirring for 3.0 hours. After the stirring, the mixture was suction-filtered through Florisil, Celite, and alumina to give a filtrate. The filtrate was concentrated to give a solid, which was then purified by silica gel column chromatography (the developing solvent has a 3:2 ratio of hexane to toluene). The obtained fractions were concentrated. Accordingly, 1.5 g of a white solid was obtained in 99% yield, which was the substance to be produced. The synthesis scheme of this Step 2 is shown in (E12-2) given below.

solvent of toluene and hexane gave 0.8 g of a yellow solid in 46% yield, which was the substance to be produced.

Because the substance produced (1,6mFLPAPrn-III) has a structure in which a fluorene skeleton is bonded to the meta position of a benzene ring in an amine skeleton and a methyl group which is an alkyl group is bonded to a benzene ring bonded to the 9-position of fluorene, 1,6mFLPAPrn-III has higher solubility in an organic solvent such as toluene than 1,6FLPAPrn obtained in Example 2. Such improvement of the solubility in a solvent facilitates purification of the fluorene derivative of this example (1,6mFLPAPrn-III), demonstrating the easiness of its synthesis.

By a train sublimation method, 0.8 g of the obtained yellow solid was purified. In the purification, the yellow solid was heated at 314° C. under a pressure of 3.1 Pa with a flow rate of argon gas of 5.0 mL/min. After the purification, 0.7 g of a yellow solid was obtained in a yield of 84%, which was the substance to be produced. The synthesis scheme of Step 3 is shown by the following (E12-3).

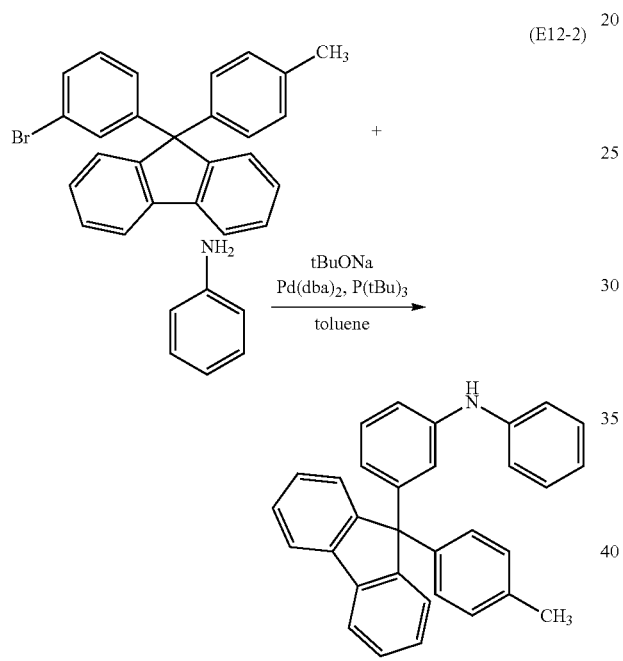

(E12-2)

Step 3: Synthesis method of N,N'-bis{3-[9-(4-methylphenyl)-9H-fluoren-9-yl]phenyl}-N,N'-diphenyl-pyrene-1,6-diamine (abbreviation: 1,6mFLPAPrn-III)

In a 100 mL three-neck flask were put 0.6 g (1.8 mmol) of 1,6-dibromopyrene, 1.5 g (3.5 mmol) of 3-[9-(4-methylphenyl)-9H-fluoren-9-yl]diphenylamine, and 0.5 g (5.3 mmol) of sodium tert-butoxide. The air in the flask was replaced with nitrogen. To this mixture were added 20.0 mL of toluene and 0.2 mL of a 10% hexane solution of tri(tert-butyl)phosphine. The temperature of this mixture was set to 80° C., and 33.1 mg (0.1 mmol) of bis(dibenzylideneacetone)palladium(0) was added to the mixture, followed by stirring for 3.5 hours. After the stirring, the mixture was suction-filtered through Florisil, Celite, and alumina to give a filtrate. The filtrate was concentrated to give a solid, which was then purified by silica gel column chromatography (the developing solvent has a 3:2 ratio of hexane to toluene). The obtained fractions were concentrated to give a yellow solid. Recrystallization of the obtained yellow solid from a mixed

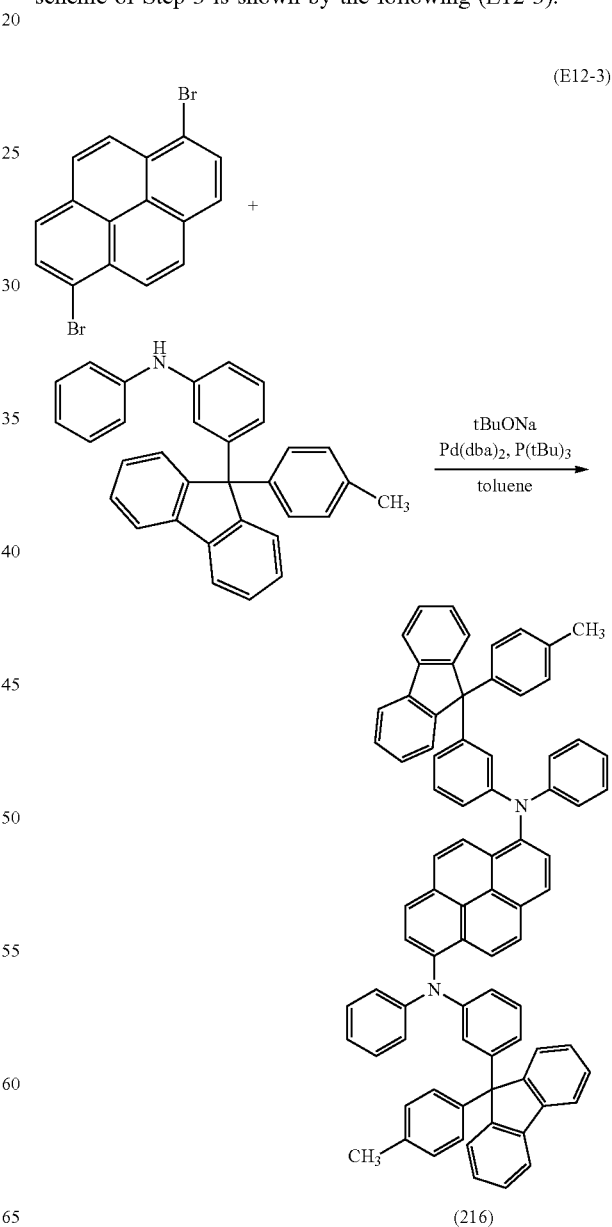

(E12-3)

(216)

A nuclear magnetic resonance (NMR) method identified this compound as N,N'-bis{3-[9-(4-methylphenyl)-9H-fluoren-9-yl]phenyl}-N,N'-diphenyl-pyrene-1,6-diamine (abbreviation: 1,6mFLPAPrn-III), which was the substance to be produced.

$^1$H NMR data of the obtained compound are: $^1$H NMR (CDCl$_3$, 300 MHz): δ=2.14 (s, 6H), 6.68 (d, J=7.5 Hz, 2H), 6.81-7.21 (m, 36H), 7.60 (d, J=7.2 Hz, 4H), 7.73 (d, J=8.4 Hz, 2H), 7.85 (d, J=9.3 Hz, 2H), 8.04 (d, J=9.0 Hz, 4H)

Figure 49A:
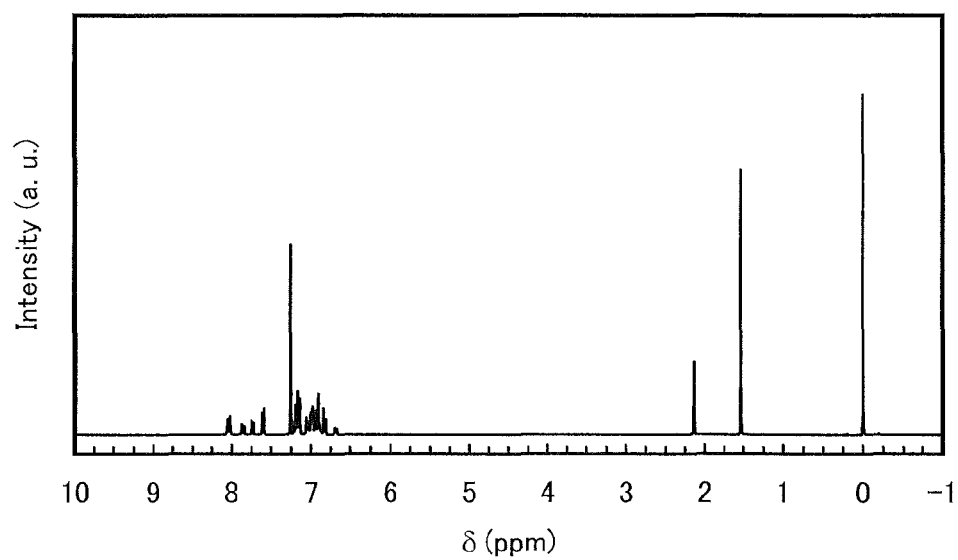
FIGS. 49A and 49B show $^1$H NMR charts of 1,6mFLPAPrn-III.
Figure 49B:
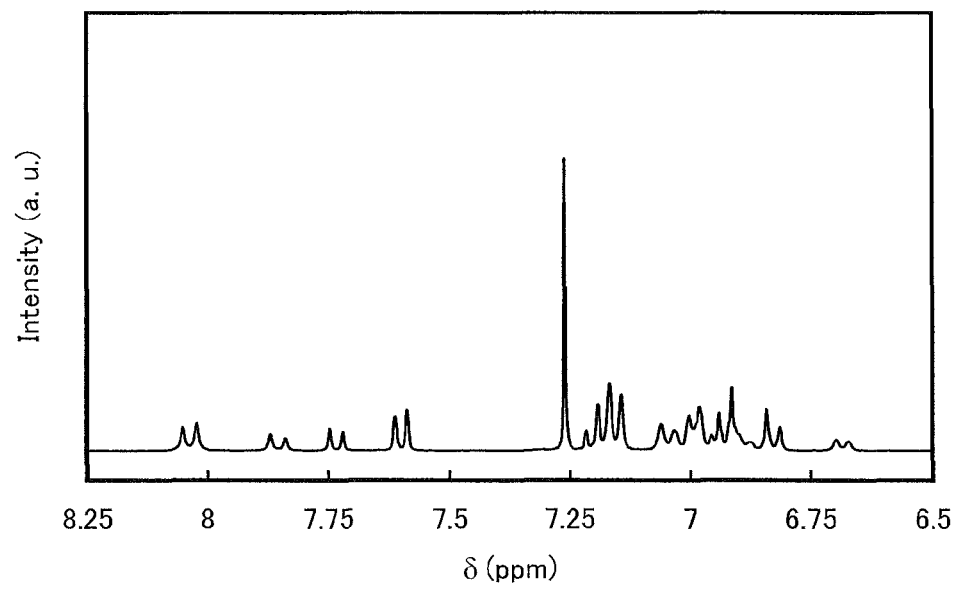

FIGS. 49A and 49B show the $^1$H NMR charts. Note that FIG. 49B is a chart showing an enlarged part of FIG. 49A in the range of 6.5 to 8.25 ppm.

Figure 50A:
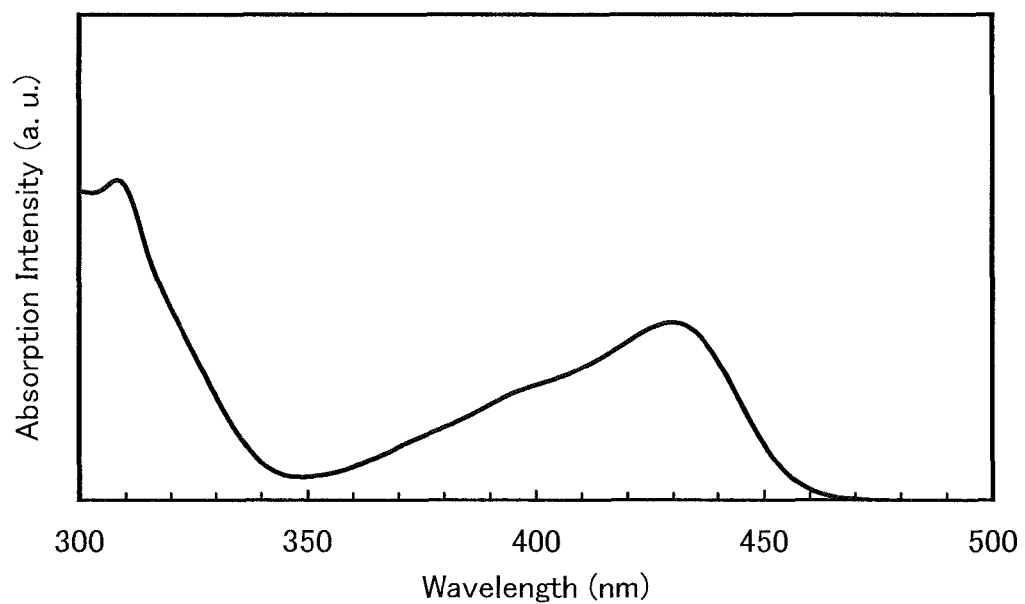
FIGS. 50A and 50B show an absorption spectrum and an emission spectrum of a toluene solution of 1,6mFLPAPrn-III.
Figure 50B:
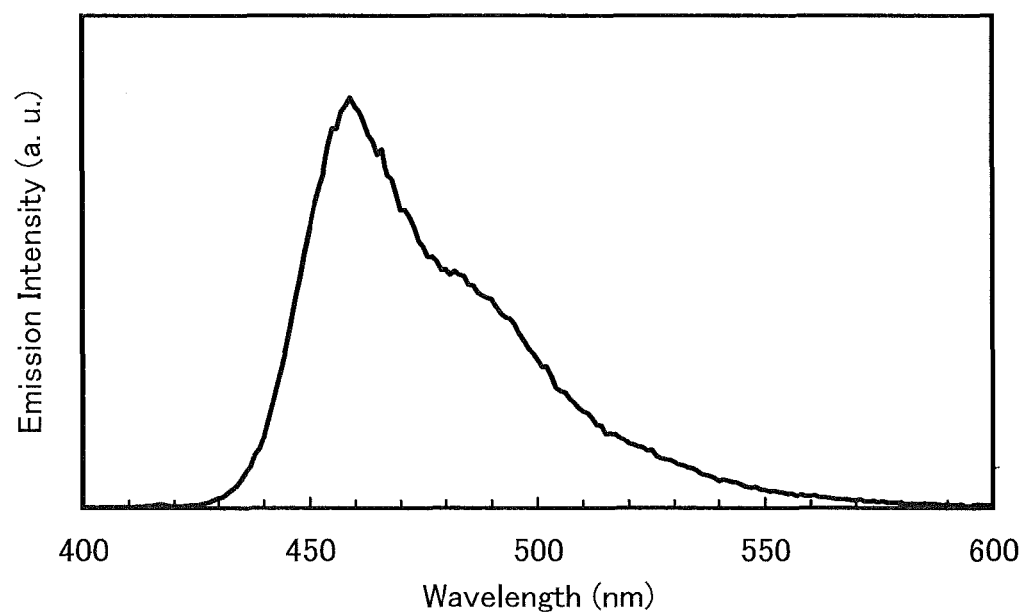
Figure 51A:
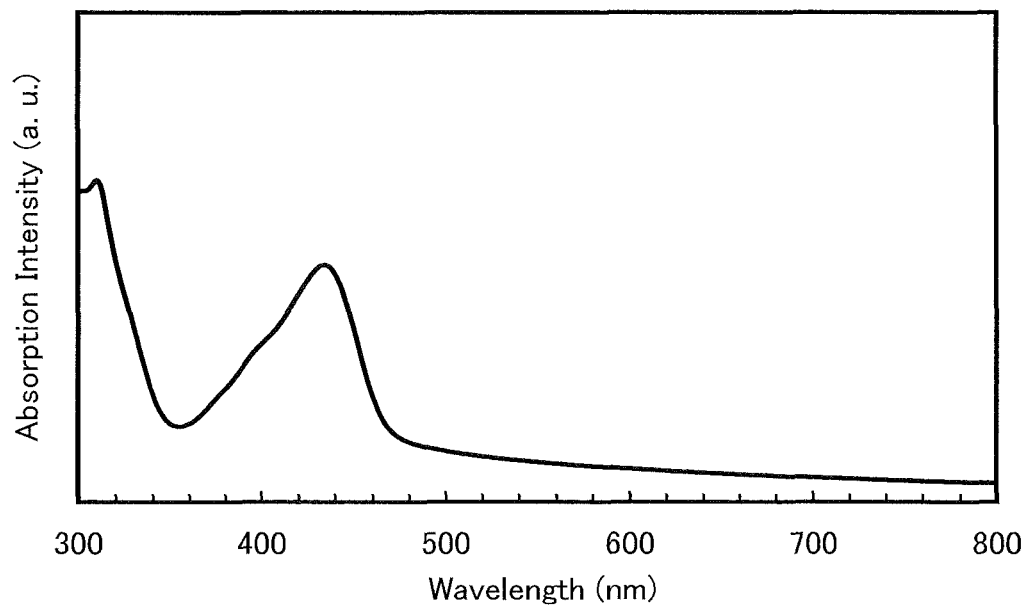
FIGS. 51A and 51B show an absorption spectrum and an emission spectrum of a thin film of 1,6mFLPAPrn-III.
Figure 51B:
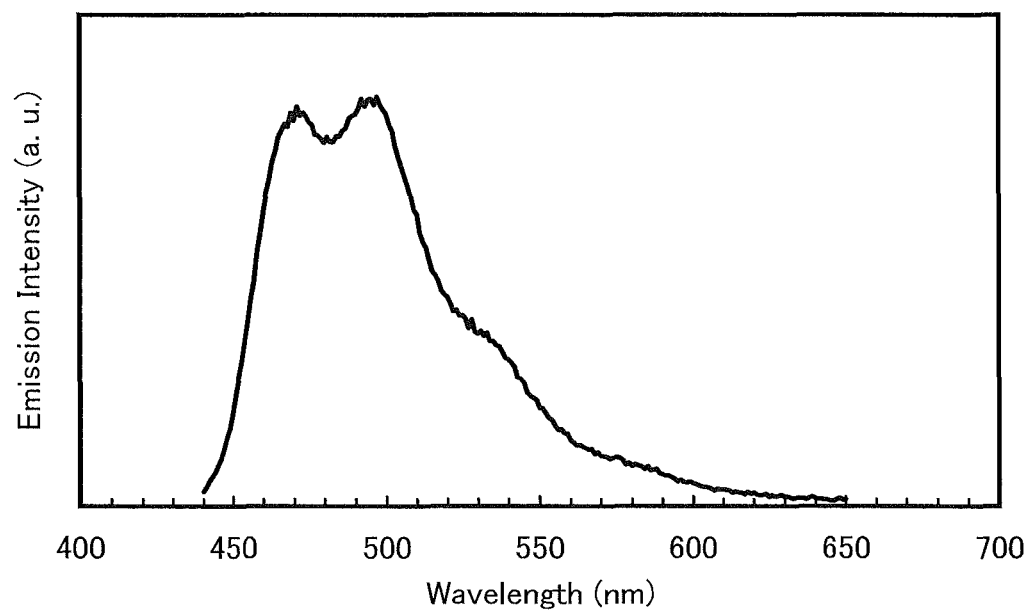

Further, FIG. 50A shows an absorption spectrum of a toluene solution of 1,6mFLPAPrn-III, and FIG. 50B shows an emission spectrum thereof. FIG. 51A shows an absorption spectrum of a thin film of 1,6mFLPAPrn-III, and FIG. 51B shows an emission spectrum thereof. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 50A show the absorption spectrum of the solution which was obtained by subtracting the absorption spectra of quartz and toluene, and FIG. 51A shows the absorption spectrum of the thin film which was obtained by subtracting the absorption spectrum of a quartz substrate. In FIGS. 50A and 50B and FIGS. 51A and 51B, the horizontal axis represents wavelength (nm) and the vertical axis represents intensity (arbitrary unit). In the case of the toluene solution, absorption was observed at around 430 nm, and the maximum emission wavelength was 459 nm (excitation wavelength: 370 nm). In the case of the thin film, absorption was observed at around 435 nm, and the maximum emission wavelength was 495 nm (excitation wavelength: 438 nm).

The HOMO level and the LUMO level of the thin film of 1,6mFLPAPrn-III were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mFLPAPrn-III which is shown in FIG. 51B, was regarded as an optical energy gap and added to the value of the HOMO level. As a result, the HOMO level and LUMO level of 1,6mFLPAPrn-III were found to be −5.49 eV and −2.8 eV, respectively, and the energy gap was found to be 2.69 eV.

Thermogravimetry-differential thermal analysis (TG-DTA) of obtained 1,6mFLPAPrn-III was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

EXAMPLE 13

In this example, N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (201) in Embodiment 2 was produced.

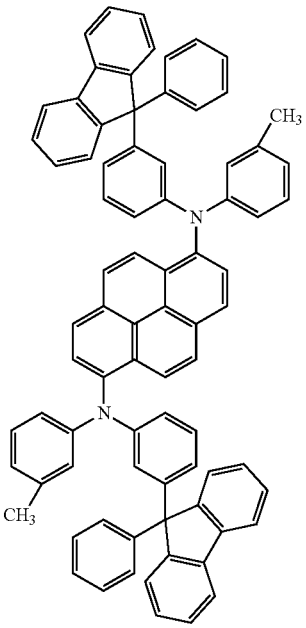

(201)

Step 1: Synthesis method of 3-methylphenyl-3-(9-phenyl-9H-fluoren-9-yl)phenylamine (abbreviation: mMemFLPA)

In a 200 mL three-neck flask were put 3.2 g (8.1 mmol) of 9-(3-bromophenyl)-9-phenylfluorene and 2.3 g (24.1 mmol) of sodium tert-butoxide. The air in the flask was replaced with nitrogen. To this mixture were added 40.0 mL of toluene, 0.9 mL (8.3 mmol) of m-toluidine, and 0.2 mL of a 10% hexane solution of tri(tert-butyl)phosphine. The temperature of this mixture was set to 60° C., and 44.5 mg (0.1 mmol) of bis(dibenzylideneacetone)palladium(0) was added to the mixture. The temperature of the mixture was raised to 80° C., followed by stirring for 2.0 hours. After the stirring, the mixture was suction-filtered through Florisil, Celite, and alumina to give a filtrate. The filtrate was concentrated to give a solid, which was then purified by silica gel column chromatography (the developing solvent has a 1:1 ratio of hexane to toluene). Accordingly, 2.8 g of a white solid was obtained in 82% yield, which was the substance to be produced. The synthesis scheme of this Step 1 is shown in the following (E13-1).

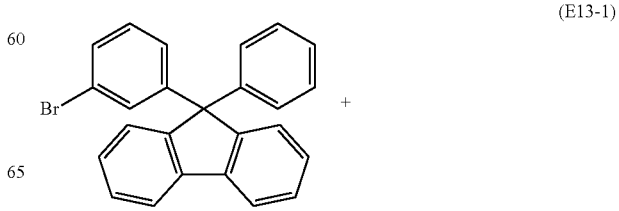

(E13-1)

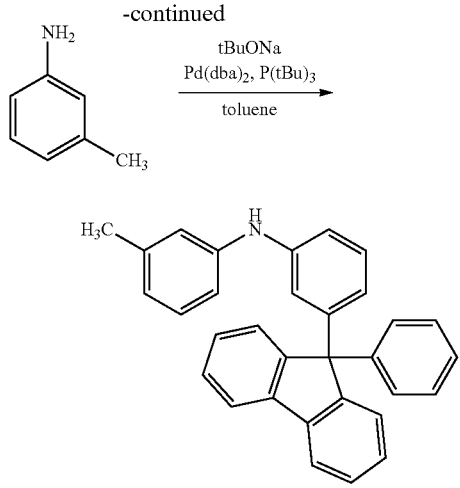

Step 2: Synthesis method of N,N'-bis(3-methylphenyl)-N,N'-bis[3-(9-phenyl-9H-fluoren-9-yl)phenyl]-pyrene-1,6-diamine (abbreviation: 1,6mMemFLPA-Prn)

In a 100 mL three-neck flask were put 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone)palladium(0) was added to the mixture. The temperature of this mixture was raised to 80° C., followed by stirring for 3.0 hours. After the stirring, 400 mL of toluene was added to the mixture, and the mixture was heated. While the mixture was kept hot, it was suction-filtered through Florisil, Celite, and alumina to give a filtrate. The filtrate was concentrated to give a solid, which was then purified by silica gel column chromatography (the developing solvent has a 3:2 ratio of hexane to toluene) to give a yellow solid. Recrystallization of the obtained yellow solid from a mixed solvent of toluene and hexane gave 1.2 g of a yellow solid in 67% yield, which was the substance to be produced.

Because the substance produced (1,6mMemFLPAPrn) has a structure in which a fluorene skeleton is bonded to the meta position of a benzene ring in an amine skeleton and a methyl group which is an alkyl group is bonded to a benzene ring in an amine skeleton, 1,6mMemFLPAPrn has higher solubility in an organic solvent such as toluene than 1,6FLPAPrn obtained in Example 2. Such improvement of the solubility in a solvent facilitates purification of the fluorene derivative of this example (1,6mMemFLPAPrn), demonstrating the easiness of its synthesis.

By a train sublimation method, 1.0 g of the obtained yellow solid was purified. In the purification, the yellow solid was heated at 317° C. under a pressure of 2.2 Pa with a flow rate of argon gas of 5.0 mL/min. After the purification, 1.0 g of a yellow solid was obtained in a yield of 93%, which was the substance to be produced. The synthesis scheme of Step 2 is shown by the following (E13-2).

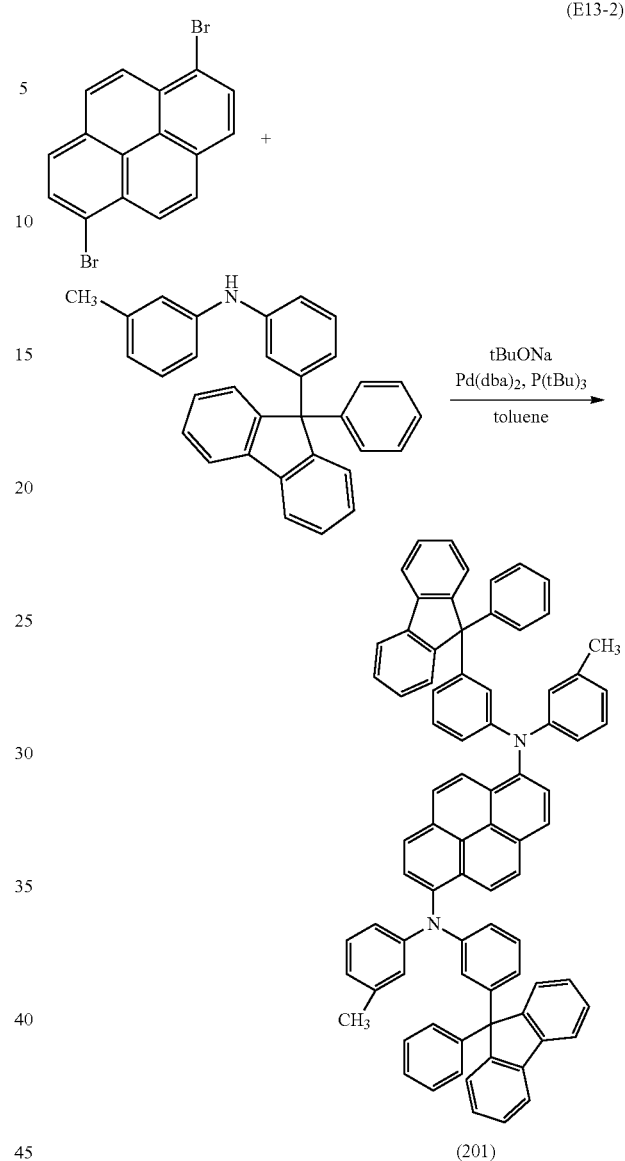

A nuclear magnetic resonance (NMR) method and a mass spectrometry identified this compound as N,N'-bis(3-methylphenyl)-N,N'-bis[3-(9-phenyl-9H-fluoren-9-yl)phenyl]-pyrene-1,6-diamine (abbreviation: 1,6mMemFLPAPrn), which was the substance to be produced.

$^1$H NMR data of the obtained compound are: $^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H)

Figure 52A:
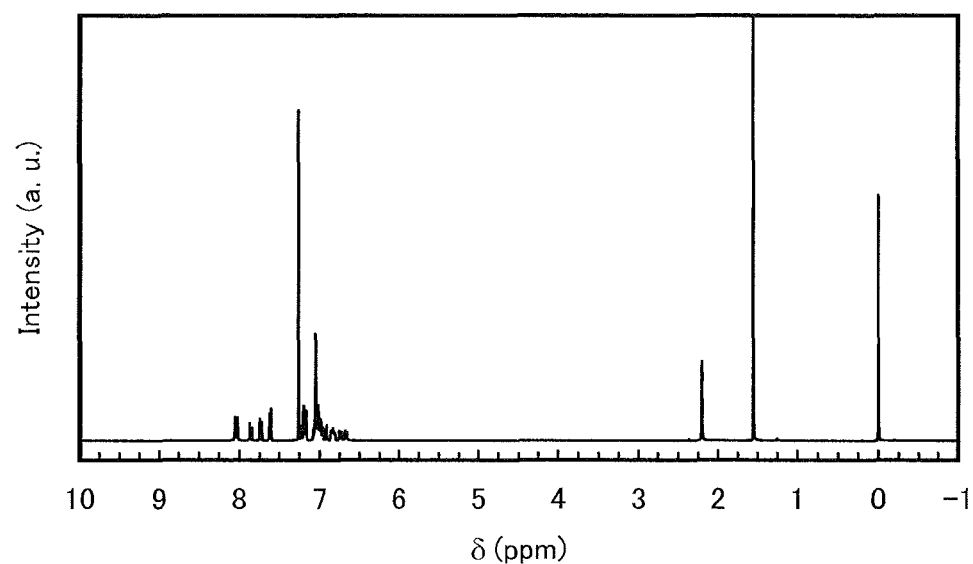
FIGS. 52A and 52B show $^1$H NMR charts of 1,6mMem-FLPAPrn.
Figure 52B:
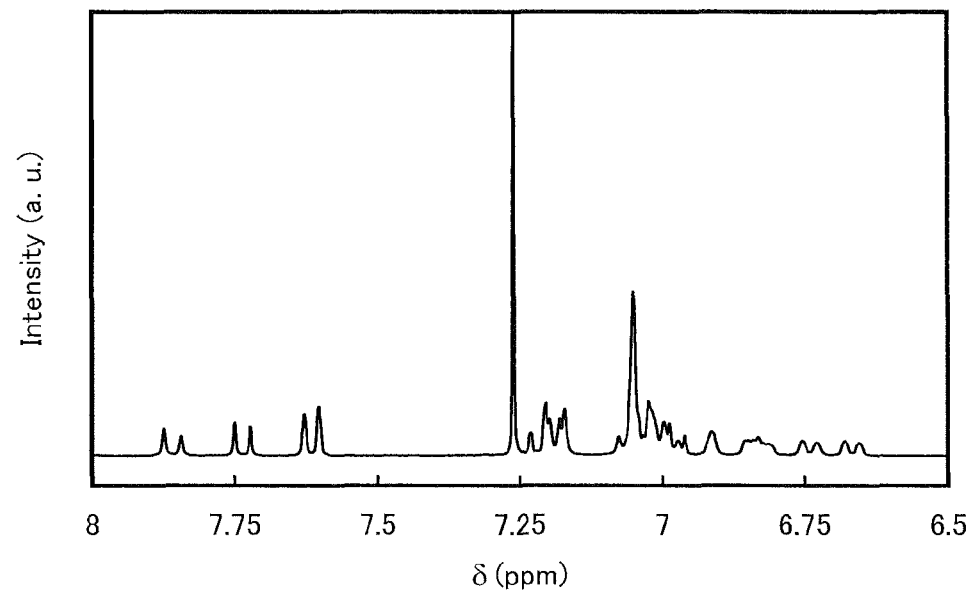

FIGS. 52A and 52B show the $^1$H NMR charts. Note that FIG. 52B is a chart showing an enlarged part of FIG. 52A in the range of 6.5 to 8.25 ppm.

The measurement result of the mass spectrometry of the obtained compound is: MS (ESI-MS): m/z=1045 (M+H)$^+$; C$_{80}$H$_{56}$N$_2$ (1044.44).

Figure 53A:
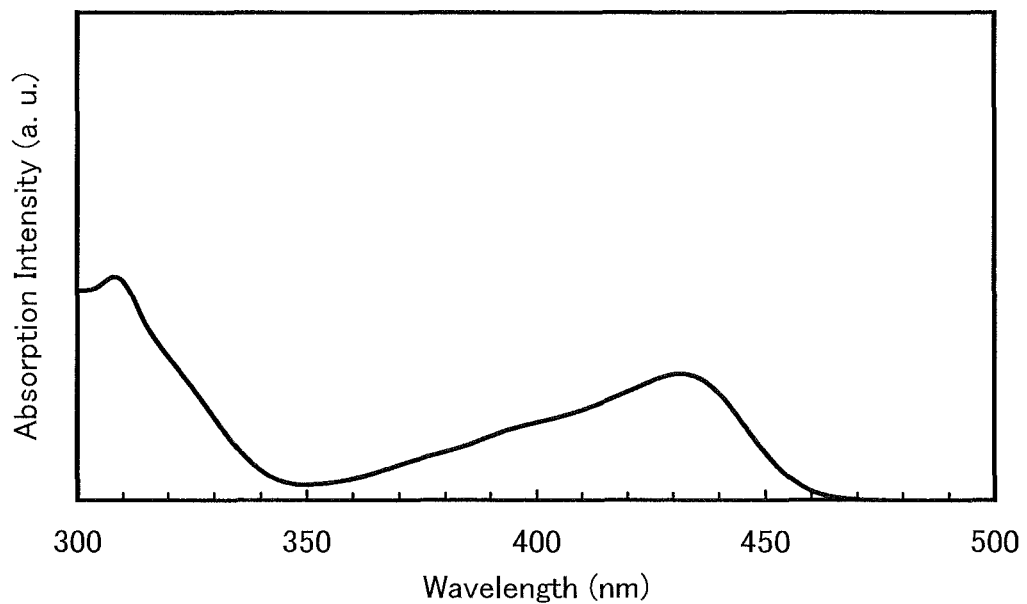
FIGS. 53A and 53B show an absorption spectrum and an emission spectrum of a toluene solution of 1,6mMemFL-PAPrn.
Figure 53B:
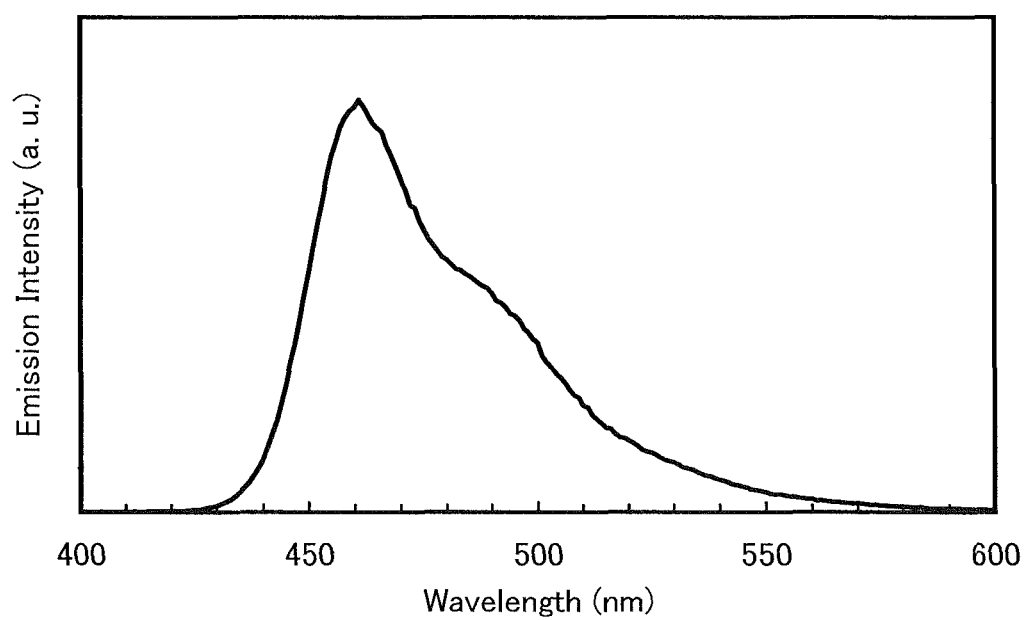
Figure 54A:
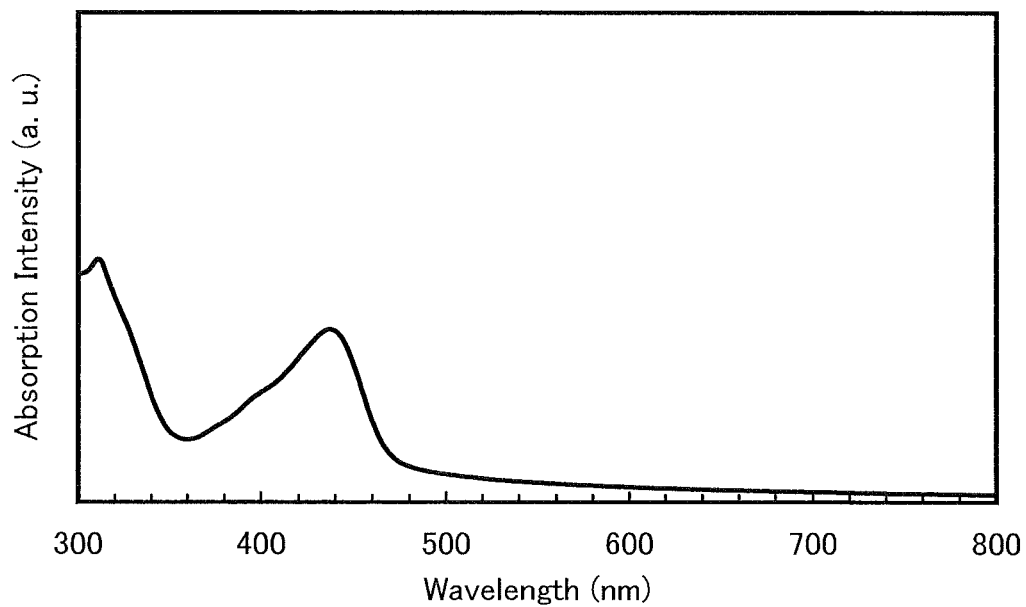
FIGS. 54A and 54B show an absorption spectrum and an emission spectrum of a thin film of 1,6mMemFLPAPrn.
Figure 54B:
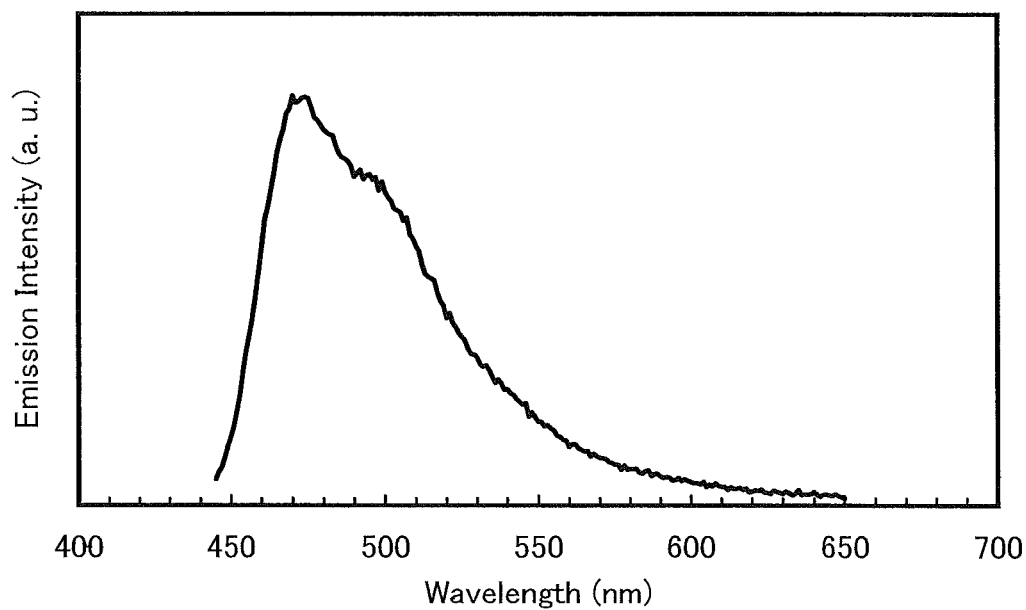

Further, FIG. 53A shows an absorption spectrum of a toluene solution of 1,6mMemFLPAPrn, and FIG. 53B shows an emission spectrum thereof. FIG. 54A shows an absorption spectrum of a thin film of 1,6mMemFLPAPrn, and FIG. 54B shows an emission spectrum thereof. The absorption spectrum was measured using an ultraviolet-visible spectrophotometer (V-553, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 53A show the absorption spectrum of the solution which was obtained by subtracting the absorption spectra of quartz and toluene, and FIG. 54A shows the absorption spectrum of the thin film which was obtained by subtracting the absorption spectrum of a quartz substrate. In FIGS. 53A and 53B and FIGS. 54A and 54B, the horizontal axis represents wavelength (nm) and the vertical axis represents intensity (arbitrary unit). In the case of the toluene solution, absorption was observed at around 432 nm, and the maximum emission wavelength was 461 nm (excitation wavelength: 370 nm). In the case of the thin film, absorption was observed at around 437 nm, and the maximum emission wavelength was 474 nm (excitation wavelength: 436 nm).

The HOMO level and the LUMO level of the thin film of 1,6mMemFLPAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mMemFLPAPrn which is shown in FIG. 54B, was regarded as an optical energy gap and added to the value of the HOMO level. As a result, the HOMO level and LUMO level of 1,6mMemFLPAPrn were found to be −5.5 eV and −2.82 eV, respectively, and the energy gap was found to be 2.68 eV.

Thermogravimetry-differential thermal analysis (TG-DTA) of obtained 1,6mMemFLPAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 479° C., which is indicative of high heat resistance.

EXAMPLE 14

In this example, N,N'-bis{3-[9-(3-methylphenyl)-9H-fluoren-9-yl]phenyl}-N,N'-bis(3-methylphenyl)-pyrene-1,6-diamine (abbreviation: 1,6mMemFLPAPrn-II) represented by Structural Formula (235) in Embodiment 2 was produced.

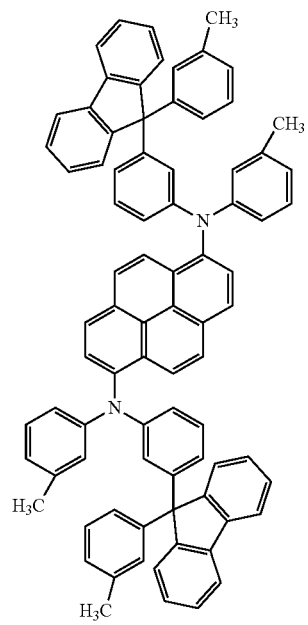

(235)

Step 1: Synthesis method of 3-methylphenyl-3-[9-(3-methylphenyl)-9H-fluoren-9-yl]phenylamine (abbreviation: mMemFLPA-II)

In a 200 mL three-neck flask were put 3.0 g (7.3 mmol) of 9-(3-bromophenyl)-9-(3-methylphenyl)-fluorene and 2.1 g (22.0 mmol) of sodium tert-butoxide. The air in the flask was replaced with nitrogen. To this mixture were added 37.0 mL of toluene, 0.8 mL (7.4 mmol) of m-toluidine, and 0.2 mL of a 10% hexane solution of tri(tert-butyl)phosphine. The temperature of this mixture was set to 85° C., and 29.8 mg (0.1 mmol) of bis(dibenzylideneacetone)palladium(0) was added to the mixture. The temperature of the mixture was raised to 90° C., followed by stirring for 4.0 hours. After the stirring, the mixture was suction-filtered through Florisil, Celite, and alumina to give a filtrate. The filtrate was concentrated to give an oily substance, which was then purified by silica gel column chromatography (the developing solvent has a 2:1 ratio of hexane to toluene). Accordingly, 3.1 g of a compound was obtained in 98% yield, which was the substance to be produced. The synthesis scheme of this Step 1 is shown in the following (E14-1).

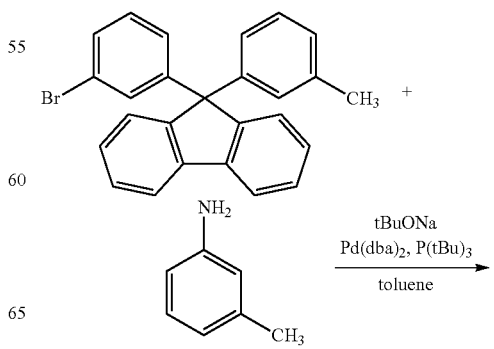

(E14-1)

-continued

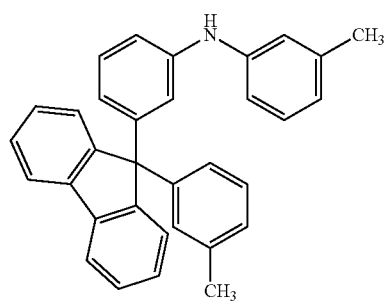

Step 2: Synthesis method of N,N'-bis{3-[9-(3-methylphenyl)-9H-fluoren-9-yl]phenyl}-N,N'-bis(3-methylphenyl)-pyrene-1,6-diamine (abbreviation: 1,6mMemFLPAPrn-II)

In a 100 mL three-neck flask were put 0.5 g (1.4 mmol) of 1,6-dibromopyrene and 0.4 g (4.2 mmol) of sodium tert-butoxide. The air in the flask was replaced with nitrogen. To this mixture were added 3.0 mL of toluene, 1.2 g (2.8 mmol) of 3-methylphenyl-3-[9-(3-methylphenyl)-9H-fluoren-9-yl]phenylamine dissolved in 14.0 mL of toluene, and 0.2 mL of a 10% hexane solution of tri(tert-butyl)phosphine. The temperature of this mixture was set to 80° C., and 30.4 mg (0.1 mmol) of bis(dibenzylideneacetone)palladium(0) was added to the mixture, followed by stirring for 3.5 hours. After the stirring, the mixture was suction-filtered through Florisil, Celite, and alumina to give a filtrate. The filtrate was concentrated to give a solid, which was then purified by silica gel column chromatography (the developing solvent has a 1:1 ratio of hexane to toluene). The obtained fractions were concentrated to give a yellow solid. Recrystallization of the obtained yellow solid from a mixed solvent of toluene and hexane gave 0.6 g of a yellow solid in 43% yield, which was the substance to be produced.

The substance produced (1,6mMemFLPAPrn-II) has a structure in which a fluorene skeleton is bonded to the meta position of a benzene ring in an amine skeleton, a methyl group which is an alkyl group is bonded to a benzene ring bonded to the 9-position of fluorene, and a methyl group which is an alkyl group is bonded to the benzene ring in the amine skeleton; therefore, 1,6mMemFLPAPrn-II has higher solubility in an organic solvent such as toluene than 1,6FL-PAPrn obtained in Example 2. Such improvement of the solubility in a solvent facilitates purification of the fluorene derivative of this example (1,6mMemFLPAPrn-II), demonstrating the easiness of its synthesis.

By a train sublimation method, 0.6 g of the obtained yellow solid was purified. In the purification, the yellow solid was heated at 298° C. under a pressure of 3.0 Pa with a flow rate of argon gas of 5.0 mL/min. After the purification, 0.4 g of a yellow solid was obtained in a yield of 61%, which was the substance to be produced. The synthesis scheme of this Step 2 is shown by the following (E14-2).

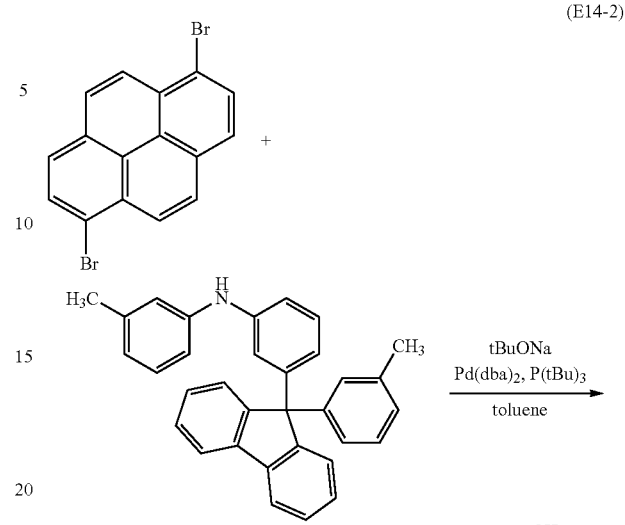

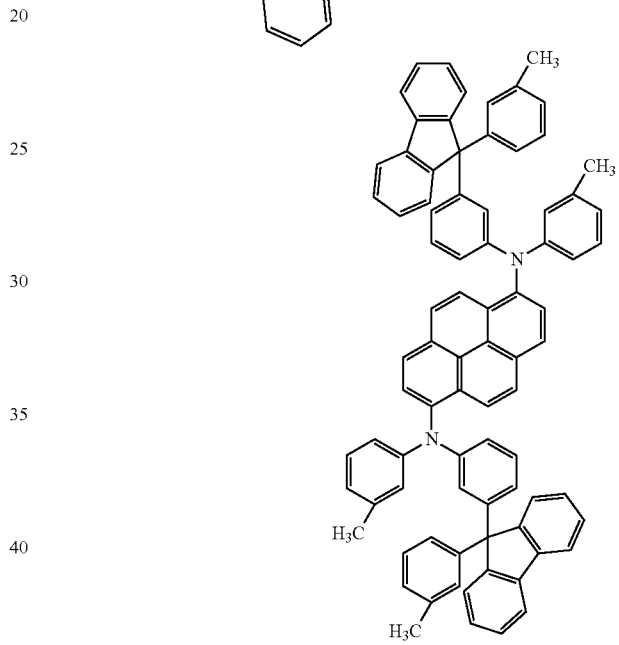

(235)

A nuclear magnetic resonance (NMR) method and a mass spectrometry identified this compound as N,N'-bis{3-[9-(3-methylphenyl)-9H-fluoren-9-yl]phenyl}-N,N'-bis(3-methylphenyl)-pyrene-1,6-diamine (abbreviation: 1,6mMemFL-PAPrn-II), which was the substance to be produced.

$^1$H NMR data of the obtained compound are: $^1$H NMR (CDCl$_3$, 300 MHz): δ=2.14 (s, 6H), 2.20 (s, 6H), 6.66-7.25 (m, 36H), 7.61 (d, J=7.2 Hz, 4H), 7.73 (d, J=7.8 Hz, 2H), 7.86 (d, J=9.3 Hz, 2H), 8.03-8.06 (m, 4H)

Figure 55A:
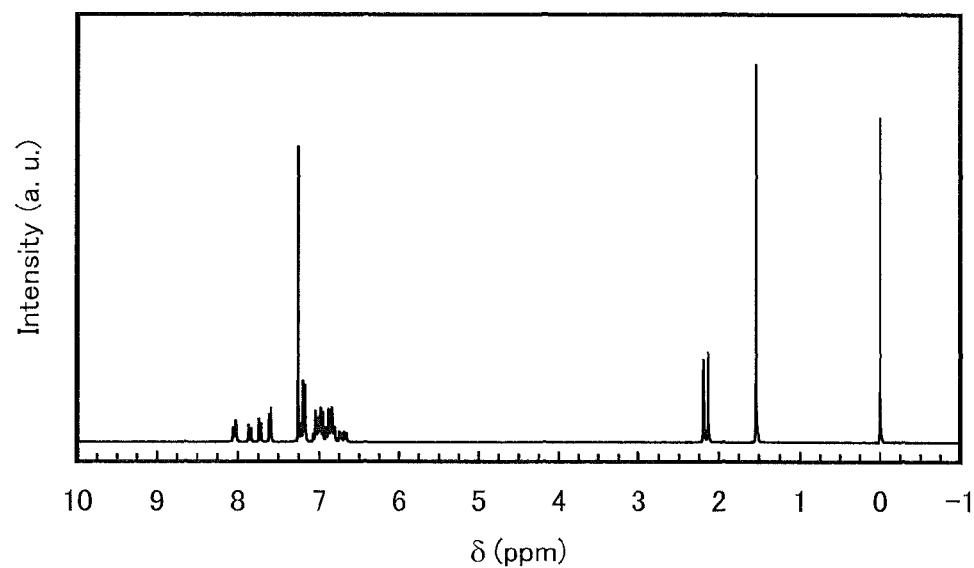
FIGS. 55A and 55B show $^1$H NMR charts of 1,6mMem-FLPAPrn-II.
Figure 55B:
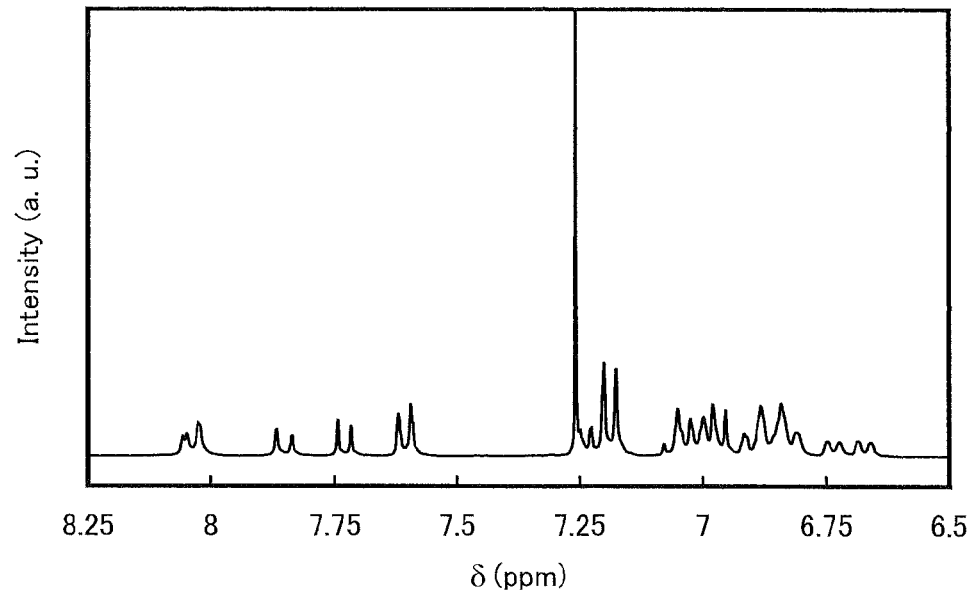

FIGS. 55A and 55B show the $^1$H NMR charts. Note that FIG. 55B is a chart showing an enlarged part of FIG. 55A in the range of 6.5 to 8.25 ppm.

The measurement result of the mass spectrometry of the obtained compound is: MS (ESI-MS): m/z=1073 (M+H)$^+$; C$_{82}$H$_{60}$N$_2$ (1072.48).

Figure 56A:
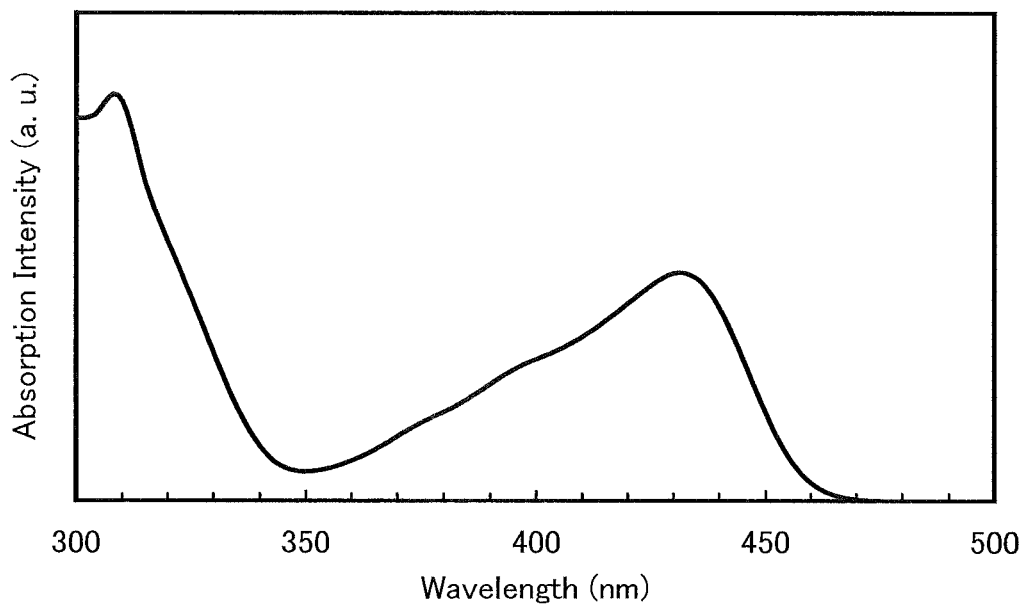
FIGS. 56A and 56B show an absorption spectrum and an emission spectrum of a toluene solution of 1,6mMemFL-PAPrn-II.
Figure 56B:
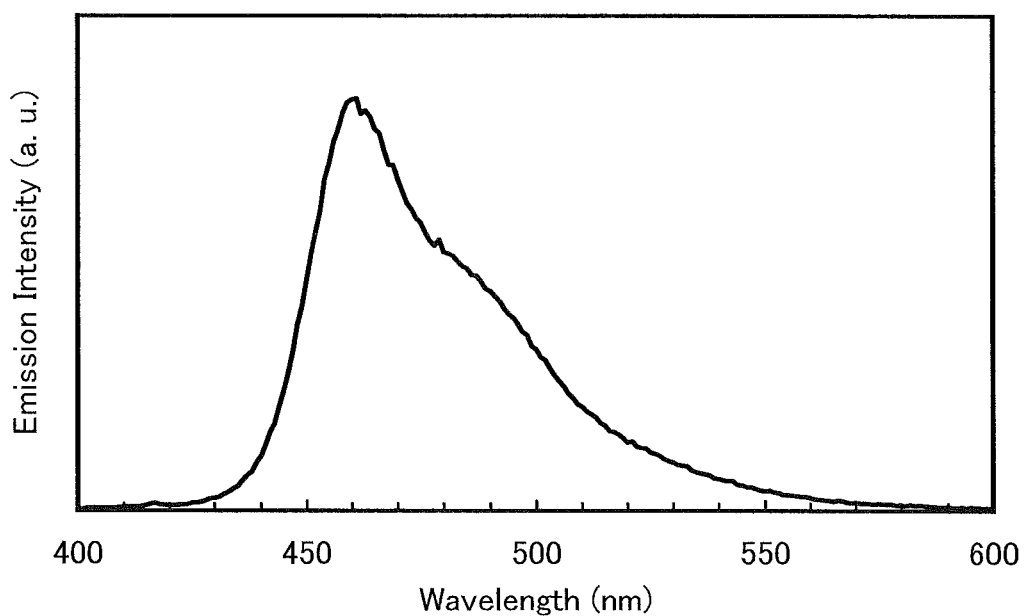
Figure 57A:
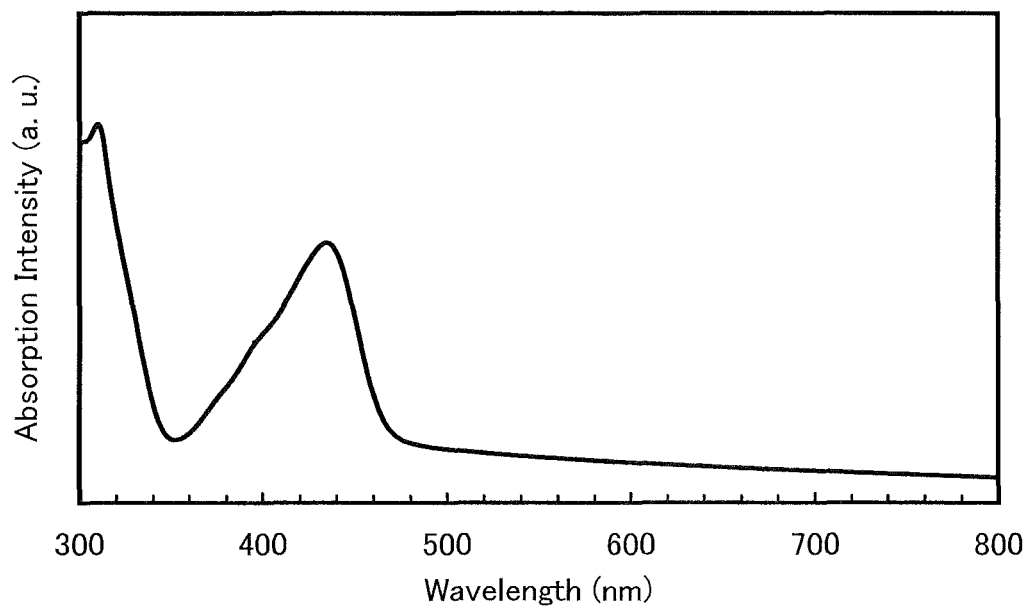
FIGS. 57A and 57B show an absorption spectrum and an emission spectrum of a thin film of 1,6mMemFLPAPrn-II.
Figure 57B:
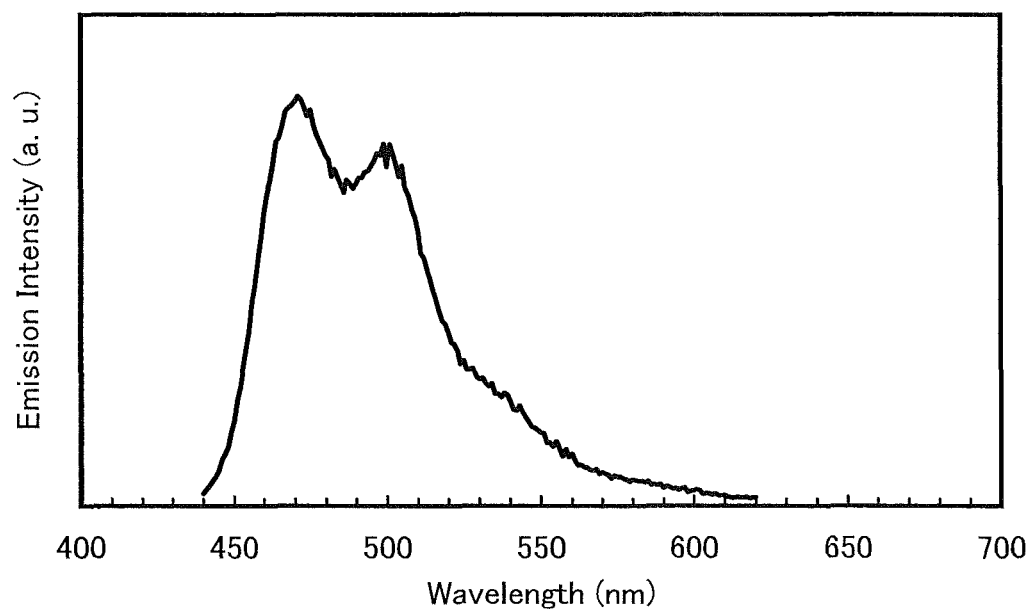

Further, FIG. 56A shows an absorption spectrum of a toluene solution of 1,6mMemFLPAPrn-II, and FIG. 56B shows an emission spectrum thereof. FIG. 57A shows an absorption spectrum of a thin film of 1,6mMemFLPAPrn-II, and FIG. 57B shows an emission spectrum thereof. The absorption spectrum was measured using an ultraviolet-visible spectrophotometer (V-556, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 56A show the absorption spectrum of the solution which was obtained by subtracting the absorption spectra of quartz and toluene, and FIG. 57A shows the absorption spectrum of the thin film which was obtained by subtracting the absorption spectrum of a quartz substrate. In FIGS. 56A and 56B and FIGS. 57A and 57B, the horizontal axis represents wavelength (nm) and the vertical axis represents intensity (arbitrary unit). In the case of the toluene solution, absorption was observed at around 431 nm, and the maximum emission wavelength was 461 nm (excitation wavelength: 370 nm). In the case of the thin film, absorption was observed at around 435 nm, and the maximum emission wavelength was 471 nm (excitation wavelength: 432 nm).

The HOMO level and the LUMO level of the thin film of 1,6mMemFLPAPrn-II were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mMemFLPAPrn-II which is shown in FIG. 57B, was regarded as an optical energy gap and added to the value of the HOMO level. As a result, the HOMO level and LUMO level of 1,6mMemFLPAPrn-II were found to be −5.47 eV and −2.78 eV, respectively, and the energy gap was found to be 2.69 eV.

Thermogravimetry-differential thermal analysis (TG-DTA) of obtained 1,6mMemFLPAPrn-II was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 456° C., which is indicative of high heat resistance.

EXAMPLE 15

In this example, N,N'-bis{3-[9-(4-methylphenyl)-9H-fluoren-9-yl]phenyl}-N,N'-bis(3-methylphenyl)-pyrene-1,6-diamine (abbreviation: 1,6mMemFLPAPrn-III) represented by Structural Formula (219) in Embodiment 2 was produced.

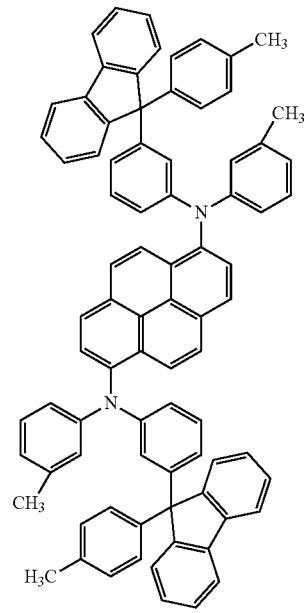

(219)

Step 1: Synthesis method of 3-methylphenyl-3-[9-(4-methylphenyl)-9H-fluoren-9-yl]phenylamine (abbreviation: mMemFLPA-III)

In a 200 mL three-neck flask were put 3.0 g (7.3 mmol) of 9-(3-bromophenyl)-9-(3-methylphenyl)-fluorene, 0.8 mL (7.3 mmol) of m-toluidine, and 2.1 g (21.9 mmol) of sodium tert-butoxide. The air in the flask was replaced with nitrogen. To this mixture were added 37.0 mL of toluene and 0.2 mL of a 10% hexane solution of tri(tert-butyl)phosphine. The temperature of this mixture was set to 85° C., and 36.0 mg (0.1 mmol) of bis(dibenzylideneacetone)palladium(0) was added to the mixture. The temperature of the mixture was raised to 90° C., followed by stirring for 4.0 hours. After the stirring, the mixture was suction-filtered through Florisil, Celite, and alumina to give a filtrate. The filtrate was concentrated to give an oily substance, which was then purified by silica gel column chromatography (the developing solvent has a 2:1 ratio of hexane to toluene). The obtained fractions were concentrated to give 2.9 g of a white solid in 91% yield, which was the substance to be produced. The synthesis scheme of this Step 1 is shown in (E15-1) given below.

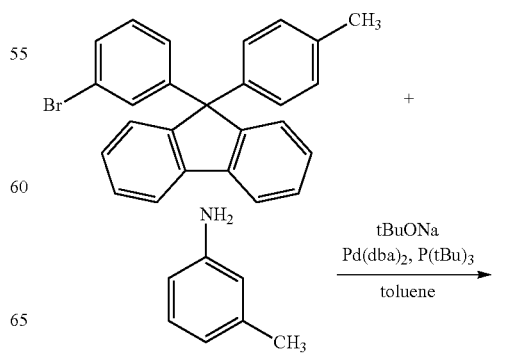

(E15-1)

-continued

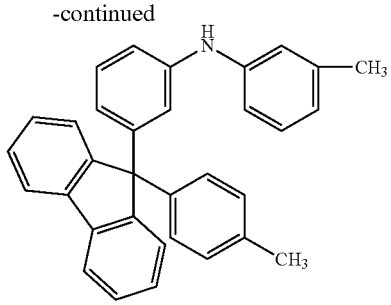

Step 2: Synthesis method of N,N'-bis{3-[9-(4-methylphenyl)-9H-fluoren-9-yl]phenyl}-N,N'-bis(3-methylphenyl)-pyrene-1,6-diamine (abbreviation: 1,6mMemFLPAPrn-III)

In a 100 mL three-neck flask were put 0.5 g (1.4 mmol) of 1,6-dibromopyrene and 0.4 g (4.3 mmol) of sodium tert-butoxide. The air in the flask was replaced with nitrogen. To this mixture were added 2.0 mL of toluene, 1.2 g (2.8 mmol) of 3-methylphenyl-3-[9-(4-methylphenyl)-9H-fluoren-9-yl]phenylamine dissolved in 15.0 mL of toluene, and 0.2 mL of a 10% hexane solution of tri(tert-butyl)phosphine. The temperature of this mixture was set to 80° C., and 30.8 mg (0.1 mmol) of bis(dibenzylideneacetone)palladium(0) was added to the mixture, followed by stirring for 4.0 hours. After the stirring, 250 mL of toluene was added to the mixture, and the mixture was heated. While the mixture was kept hot, it was suction-filtered through Florisil, Celite, and alumina to give a filtrate. The filtrate was concentrated to give a solid, which was then purified by silica gel column chromatography (the developing solvent has a 3:2 ratio of hexane to toluene). The obtained fractions were concentrated to give a yellow solid. Recrystallization of the obtained yellow solid from toluene gave 0.7 g of a yellow solid in 49% yield, which was the substance to be produced.

The substance produced (1,6mMemFLPAPrn-III) has a structure in which a fluorene skeleton is bonded to the meta position of a benzene ring in an amine skeleton, a methyl group which is an alkyl group is bonded to a benzene ring bonded to the 9-position of fluorene, and a methyl group which is an alkyl group is bonded to the benzene ring in the amine skeleton; therefore, 1,6mMemFLPAPrn-III has higher solubility in an organic solvent such as toluene than 1,6FLPAPrn obtained in Example 2. Such improvement of the solubility in a solvent facilitates purification of the fluorene derivative of this example (1,6mMemFLPAPrn-III), demonstrating the easiness of its synthesis.

By a train sublimation method, 0.7 g of the obtained yellow solid was purified. In the purification, the yellow solid was heated at 312° C. under a pressure of 3.1 Pa with a flow rate of argon gas of 5.0 mL/min. After the purification, 0.7 g of a yellow solid was obtained in a yield of 90%, which was the substance to be produced. The synthesis scheme of this Step 3 is shown by the following (E15-2).

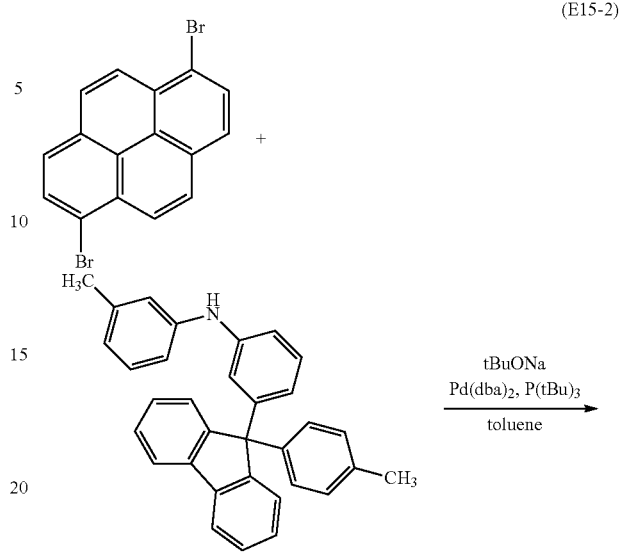

(E15-2)

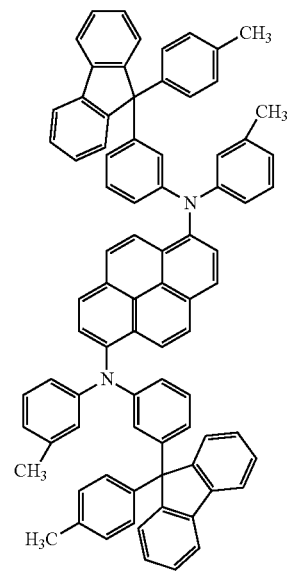

(219)

A nuclear magnetic resonance (NMR) method and a mass spectrometry identified this compound as N,N'-bis{3-[9-(4-methylphenyl)-9H-fluoren-9-yl]phenyl}-N,N'-bis(3-methylphenyl)-pyrene-1,6-diamine (abbreviation: 1,6mMemFLPAPrn-III), which was the substance to be produced.

$^1$H NMR data of the obtained compound are: $^1$H NMR (CDCl$_3$, 300 MHz): δ=2.15 (s, 6H), 2.21 (s, 6H), 6.66-7.25 (m, 36H), 7.61 (d, J=7.5 Hz, 4H), 7.73 (d, J=7.8 Hz, 2H), 7.86 (d, J=9.0 Hz, 2H), 8.04 (d, J=8.7 Hz, 4H)

Figure 58A:
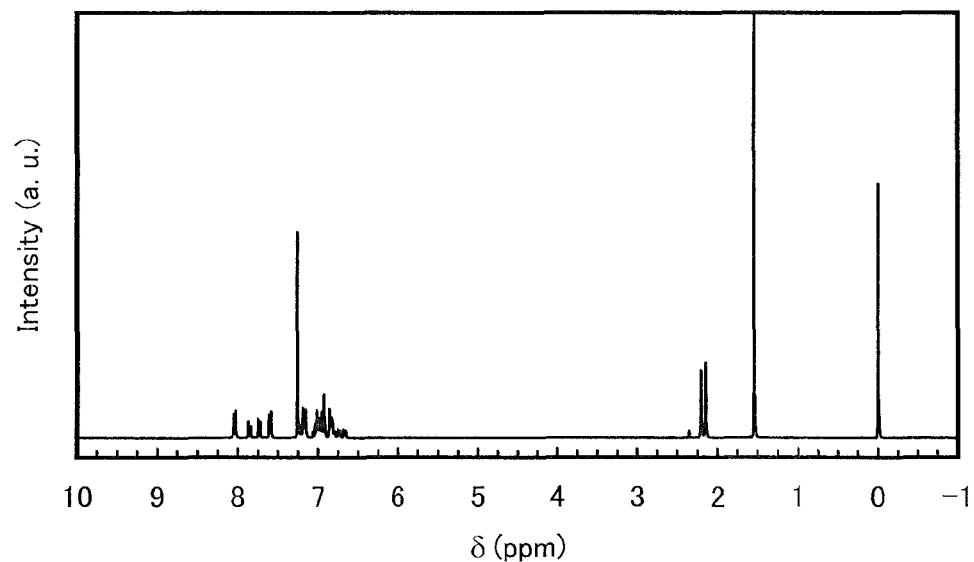
FIGS. 58A and 58B show $^1$H NMR charts of 1,6mMem-FLPAPrn-III.
Figure 58B:
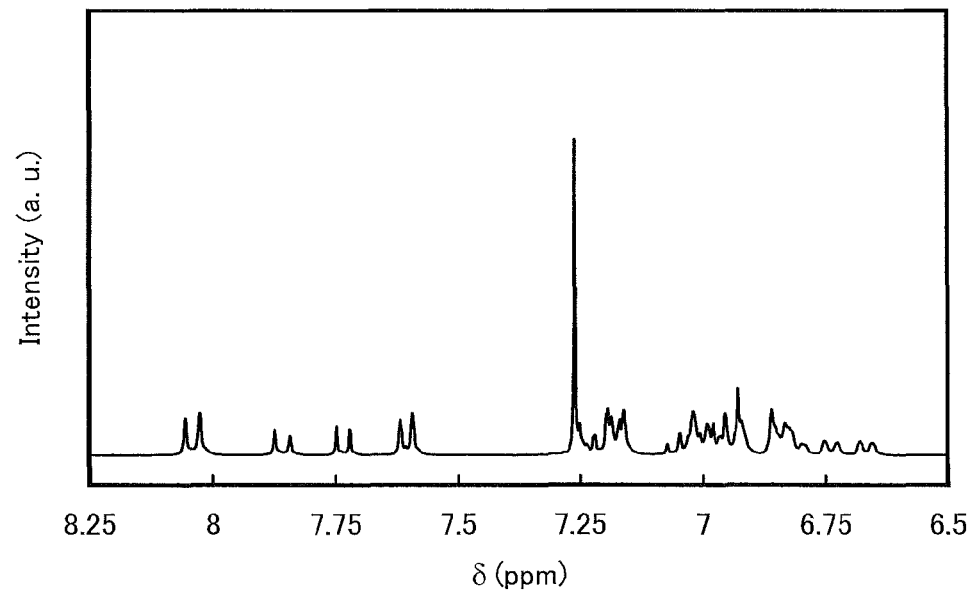

FIGS. 58A and 58B show the NMR charts. Note that FIG. 58B is a chart showing an enlarged part of FIG. 58A in the range of 6.5 to 8.25 ppm.

The measurement result of the mass spectrometry of the obtained compound is: MS (ESI-MS): m/z=1073 (M+H)$^+$; C$_{82}$H$_{60}$N$_2$ (1072.48).

Figure 59A:
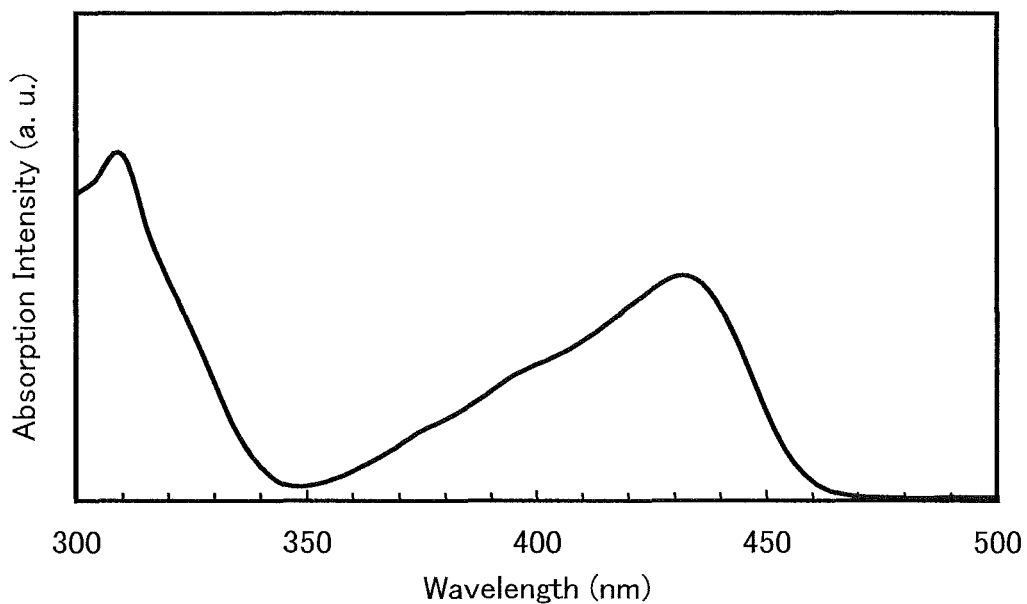
FIGS. 59A and 59B show an absorption spectrum and an emission spectrum of a toluene solution of 1,6mMemFL-PAPrn-III.
Figure 59B:
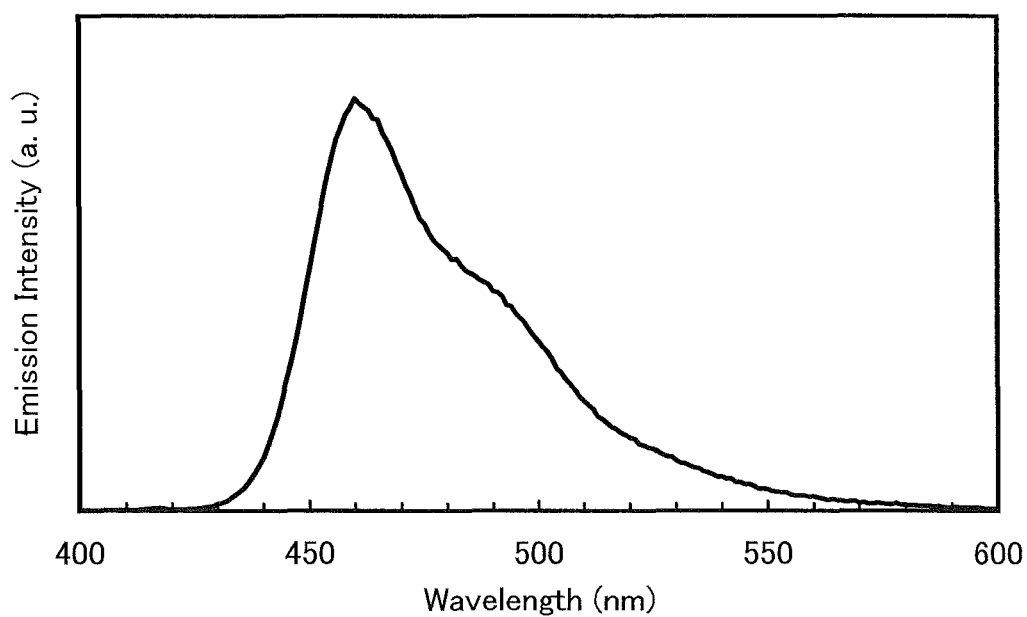
Figure 60A:
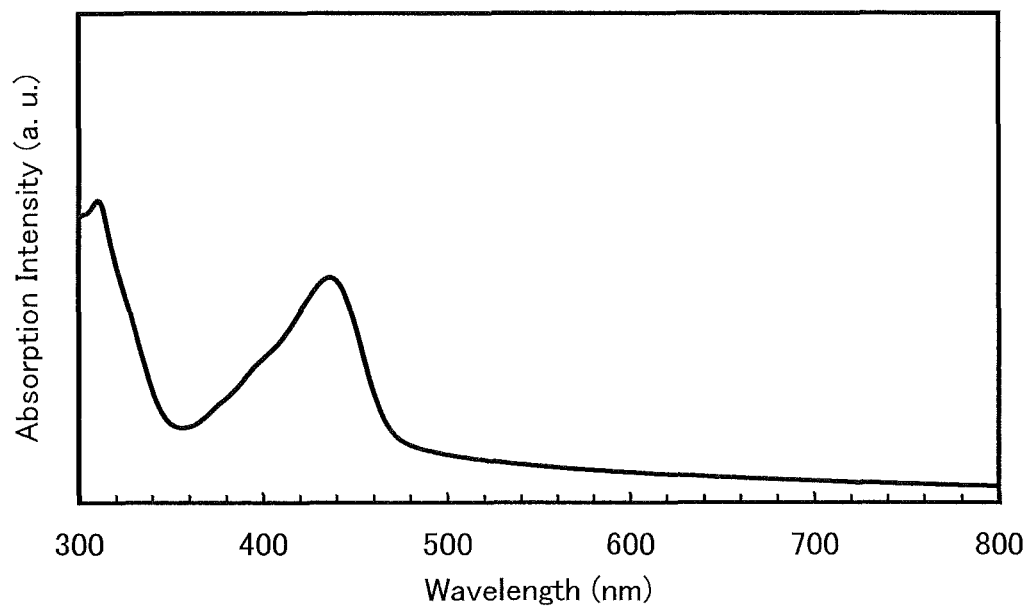
FIGS. 60A and 60B show an absorption spectrum and an emission spectrum of a thin film of 1,6mMemFLPAPrn-III.
Figure 60B:
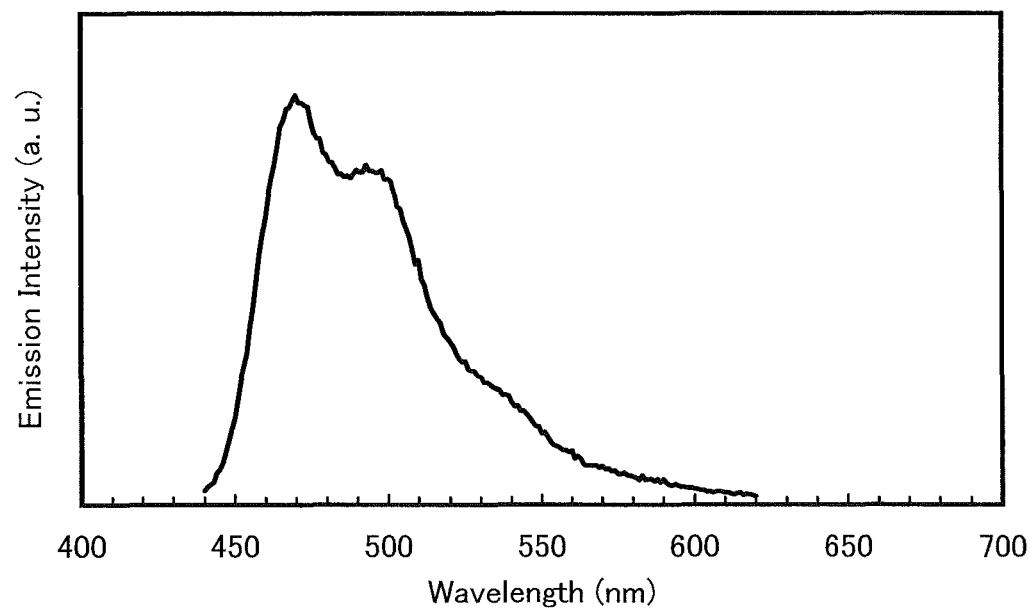

Further, FIG. 59A shows an absorption spectrum of a toluene solution of 1,6mMemFLPAPrn-III, and FIG. 59B shows an emission spectrum thereof. FIG. 60A shows an absorption spectrum of a thin film of 1,6mMemFLPAPrn-III, and FIG. 60B shows an emission spectrum thereof. The absorption spectrum was measured using an ultraviolet-visible spectrophotometer (V-559, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 59A show the absorption spectrum of the solution which was obtained by subtracting the absorption spectra of quartz and toluene, and FIG. 60A shows the absorption spectrum of the thin film which was obtained by subtracting the absorption spectrum of a quartz substrate. In FIGS. 59A and 59B and FIGS. 60A and 60B, the horizontal axis represents wavelength (nm) and the vertical axis represents intensity (arbitrary unit). In the case of the toluene solution, absorption was observed at around 432 nm, and the maximum emission wavelength was 460 nm (excitation wavelength: 370 nm). In the case of the thin film, absorption was observed at around 437 nm, and the maximum emission wavelength was 470 nm (excitation wavelength: 435 nm).

The HOMO level and the LUMO level of the thin film of 1,6mMemFLPAPrn-III were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mMemFLPAPrn-III which is shown in FIG. 60B, was regarded as an optical energy gap and added to the value of the HOMO level. As a result, the HOMO level and LUMO level of 1,6mMemFLPAPrn-III were found to be −5.47 eV and −2.79 eV, respectively, and the energy gap was found to be 2.68 eV.

Thermogravimetry-differential thermal analysis (TG-DTA) of obtained 1,6mMemFLPAPrn-III was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 475° C., which is indicative of high heat resistance.

EXAMPLE 16

This example will show a method for manufacturing light-emitting elements using the fluorene derivatives described in Embodiment 1 as light-emitting materials, and measurement results of their element characteristics. Specifically, the light-emitting elements described here were formed using N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn) represented by Structural Formula (109) described in Example 7, N,N'-bis(3-methylphenyl)-N,N'-bis[4-(9-phenyl-9H-fluoren-9-yl)phenyl]-pyrene-1,6-diamine (abbreviation: 1,6mMeFLPAPrn) represented by Structural Formula (103) described in Example 8, and N,N'-bis(3,5-dimethylphenyl)-N,N'-bis[4-(9-phenyl-9H-fluoren-9-yl)phenyl]-pyrene-1,6-diamine (abbreviation: 1,6DMeFLPAPrn) represented by Structural Formula (117) described in Example 9.

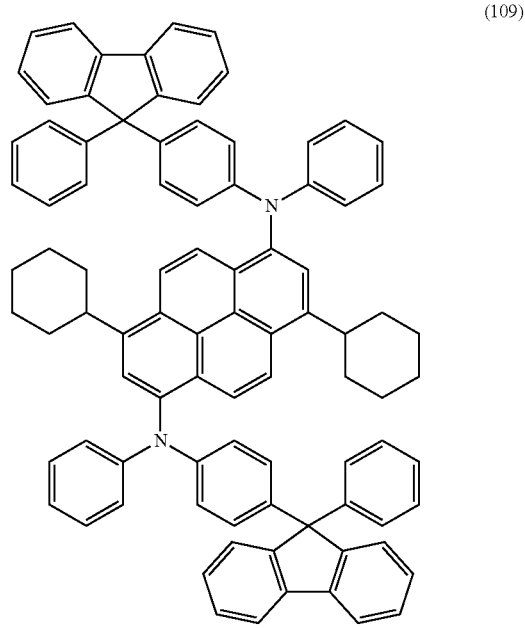 [SMILES: c1ccc(N(c2ccc(C3(c4ccccc4)c4ccccc4-c4ccccc43)cc2)c2cc(C3CCCCC3)c3ccc4c(N(c5ccccc5)c5ccc(C6(c7ccccc7)c7ccccc7-c7ccccc76)cc5)cc(C5CCCCC5)c5ccc2c3c54)cc1]

(109)

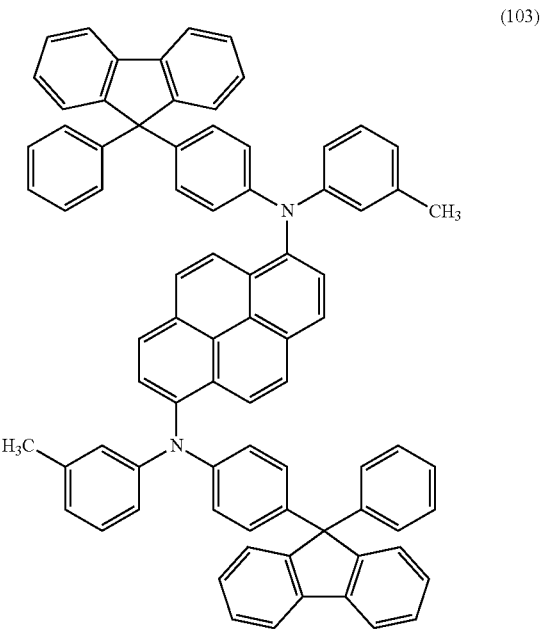 [SMILES: Cc1cccc(N(c2ccc(C3(c4ccccc4)c4ccccc4-c4ccccc43)cc2)c2ccc3ccc4c(N(c5ccc(C6(c7ccccc7)c7ccccc7-c7ccccc76)cc5)c5cccc(C)c5)ccc5ccc2c3c54)c1]

(103)

-continued

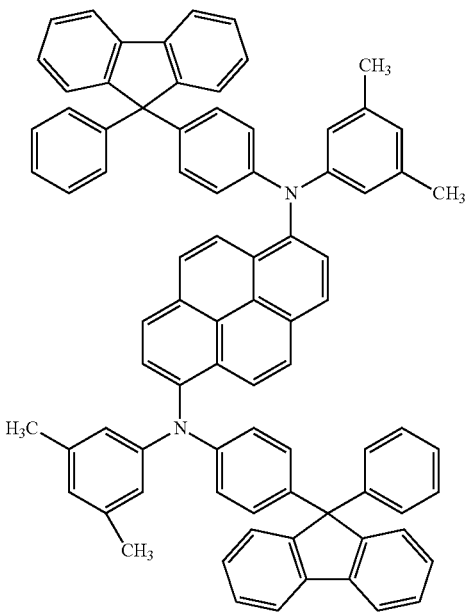

(117)

Fabrication methods of Light-emitting Elements 4 to 6 of this example will be now described. In addition, structural formulas of the organic compounds used in this example are shown below. Note that the organic compounds whose molecular structures are already shown in the above examples are not detailed here. The structure of the elements, which is the same as that in Example 4, can be found in FIG. 17A.

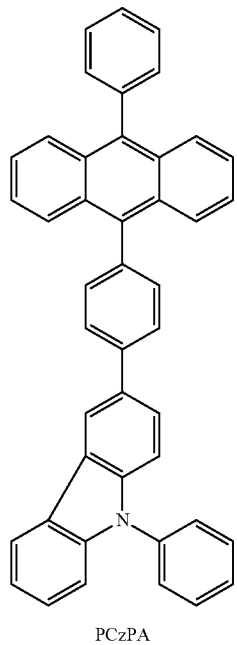 [SMILES: c1ccc(-c2c3ccccc3c(-c3ccc(-c4ccc5c(c4)c4ccccc4n5-c4ccccc4)cc3)c3ccccc23)cc1]

PCzPA (Light-emitting Element 4)

Light-emitting Element 4 of this example was fabricated in the same way as Light-emitting Element 1 of Example 4 except for the hole-injection layer 2103, the hole-transport layer 2104, and the light-emitting layer 2105.

The hole-injection layer 2103 of Light-emitting Element 4 was formed in the following manner: the substrate 2101 was fixed to a substrate holder in a vacuum evaporation apparatus so that a surface of the substrate 2101 on which the anode 2102 was formed faced downward, the pressure in the vacuum evaporation apparatus was reduced to about $10^{-4}$ Pa, and then 9-[4-(9-phenylcarbazol-3-yl)]phenyl-10-phenylanthracene (abbreviation: PCzPA), and molybdenum (VI) oxide were co-evaporated on the anode 2102. The thickness of the hole-injection layer 2103 was 50 nm, and the evaporation rate was controlled so that the weight ratio of PCzPA to molybdenum(VI) oxide was 4:2 (=PCzPA: molybdenum(VI) oxide).

Next, a 10-nm-thick film of a hole-transport material was formed on the hole-injection layer 2103 by an evaporation method using resistance heating, whereby the hole-transport layer 2104 was formed. Note that PCzPA was used for the hole-transport layer 2104.

Next, the light-emitting layer 2105 was formed on the hole-transport layer 2104 by an evaporation method using resistance heating. As the light-emitting layer 2105, a 30-nm-thick film was formed by co-evaporation of 9-[4-(10-phenyl-9-anthryl)phenyl]-9H-carbazole (abbreviation: CzPA) and N,N'-bis[4-(9-phenyl-9H-fluoren-9-yl)phenyl]-N,N'-diphenyl-3,8-dicyclohexylpyrene-1,6-diamine (abbreviation: ch-1,6FLPAPrn). Here, the evaporation rate was controlled so that the weight ratio of CzPA to ch-1,6FLPAPrn was 1:0.05 (=CzPA:ch-1,6FLPAPrn).

(Light-emitting Element 5)

Light-emitting Element 5 of this example was manufactured in the same way as Light-emitting Element 4 except for the light-emitting layer 2105.

As the light-emitting layer 2105 of Light-emitting Element 5, a 30-nm-thick film was formed by co-evaporation of 9-[4-(10-phenyl-9-anthryl)phenyl]-9H-carbazole (abbreviation: CzPA) and N,N'-bis(3-methylphenyl)-N,N'-bis[4-(9-phenyl-9H-fluoren-9-yl)phenyl]-pyrene-1,6-diamine (abbreviation: 1,6mMeFLPAPrn). Here, the evaporation rate was controlled so that the weight ratio of CzPA to 1,6mMeFLPAPrn was 1:0.05 (=CzPA:1,6mMeFLPAPrn).

(Light-emitting Element 6)

Light-emitting Element 6 of this example was manufactured in the same way as Light-emitting Element 4 except for the light-emitting layer 2105.

For Light-emitting Elements 5, the light-emitting layer 2105 was formed to a thickness of 30 nm by co-evaporation of 9-[4-(10-phenyl-9-anthryl)phenyl]-9H-carbazole (abbreviation: CzPA) and N,N'-bis(3,5-dimethylphenyl)-N,N'-bis [4-(9-phenyl-9H-fluoren-9-yl)phenyl]-pyrene-1,6-diamine (abbreviation: 1,6DMeFLPAPrn). Here, the evaporation rate was controlled such that the weight ratio of CzPA to 1,6DMeFLPAPrn was 1:0.05 (=CzPA:1,6DMeFLPAPrn).

Table 7 shows element structures of Light-emitting Elements 4 to 6 manufactured in this example. In Table 7, all the mixture ratios are weight ratios.

TABLE 7

|  | Light-Emitting Element 4 | Light-Emitting Element 5 | Light-Emitting Element 6 |
|---|---|---|---|
| Anode 2102 | ITSO 110 nm | ITSO 110 nm | ITSO 110 nm |
| Hole-injection layer 2103 | PCzPA:MoOx (=4:2) 50 nm | PCzPA:MoOx (=4:2) 50 nm | PCzPA:MoOx (=4:2) 50 nm |
| Hole-transport layer 2104 | PCzPA 10 nm | PCzPA 10 nm | PCzPA 10 nm |
| Light-emitting layer 2105 | CzPA:ch-1,6FLPAPrn (=1:0.05) 30 nm | CzPA:1,6mMeFLPAPrn (=1:0.05) 30 nm | CzPA:1,6DMeFLPAPrn (=1:0.05) 30 nm |
| Electron-transport layer 2106 | Alq 10 nm Bphen 15 nm | Alq 10 nm Bphen 15 nm | Alq 10 nm Bphen 15 nm |
| Electron-injection layer 2107 | LiF 1 nm | LiF 1 nm | LiF 1 nm |
| Cathode 2108 | Al 200 nm | Al 200 nm | Al 200 nm |

All the mixture ratios are weight ratios.

Light-emitting Elements 4 to 6 thus obtained were sealed in a glove box having a nitrogen atmosphere without being exposed to the air. Then, the operating characteristics of the elements were measured. Note that the measurement was carried out at room temperature (in an atmosphere kept at 25° C.).

Figure 61:
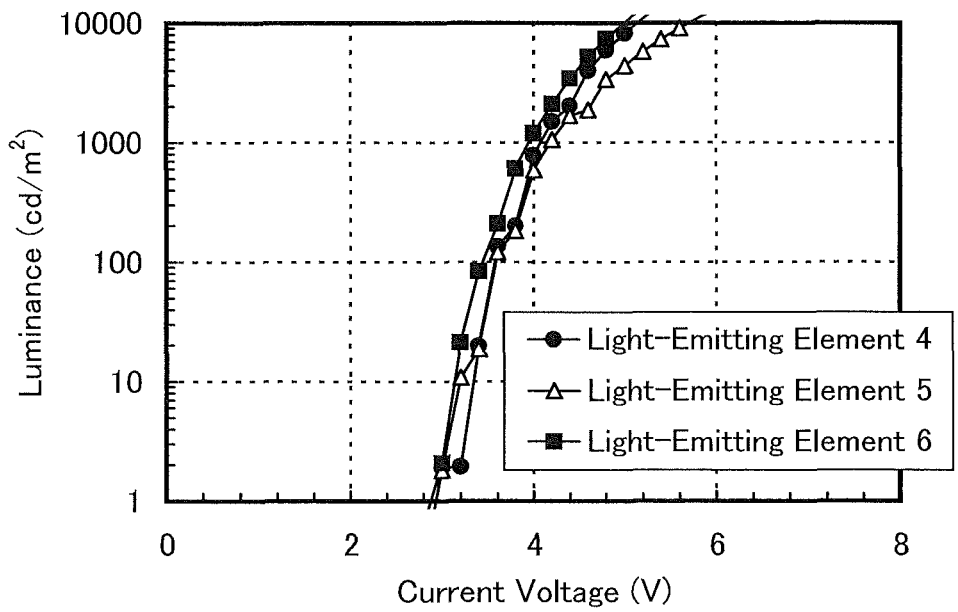
FIG. 61 shows characteristics of Light-emitting Elements 4 to 6.
Figure 62:
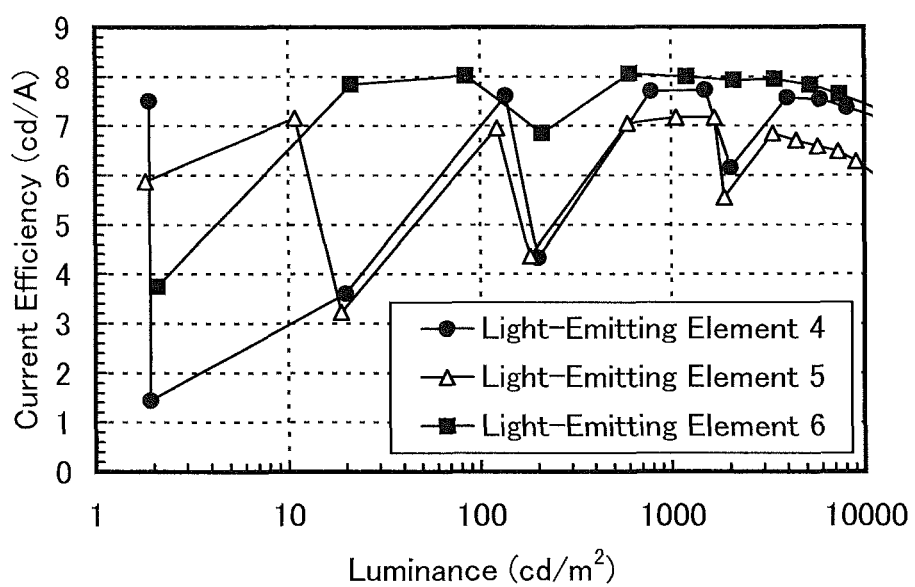
FIG. 62 shows characteristics of Light-emitting Elements 4 to 6.

FIG. 61 shows voltage vs luminance characteristics of Light-emitting Elements 4 to 6, and FIG. 62 shows luminance vs. current efficiency characteristics thereof. In FIG. 61, the vertical axis represents luminance (cd/m$^2$) and the horizontal axis represents current voltage (V). In FIG. 62, the vertical axis represents current efficiency (cd/A) and the horizontal axis represents luminance (cd/m$^2$). Further, Table 8 shows the chromaticity of the light-emitting elements at around 1000 cd/m$^2$.

TABLE 8

|  | Chromaticity coordinates (x, y) |
|---|---|
| Light-Emitting Element 4 | (0.15, 0.21) |
| Light-Emitting Element 5 | (0.15, 0.19) |
| Light-Emitting Element 6 | (0.15, 0.24) |

Figure 63:
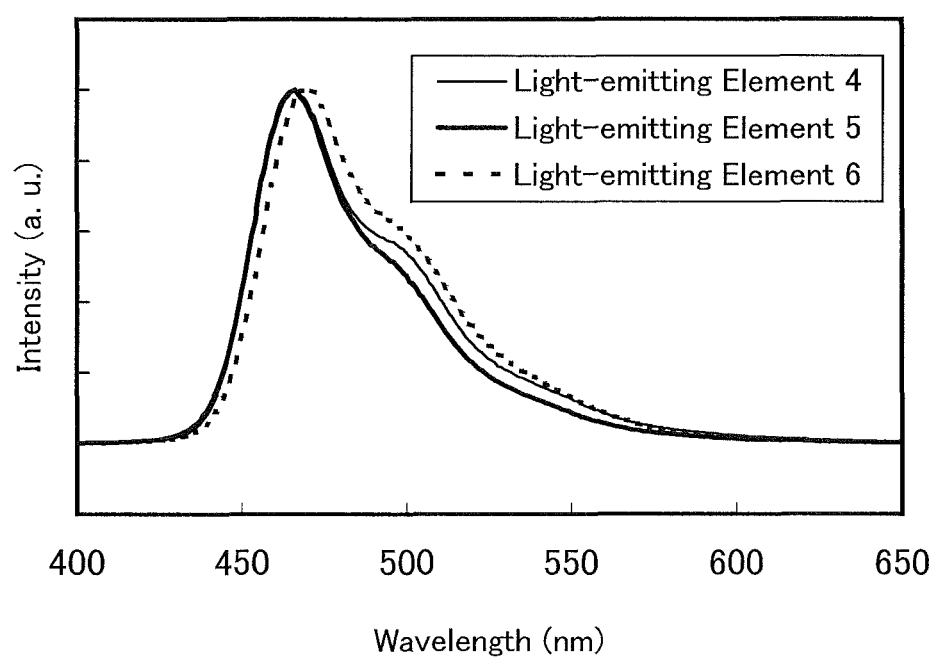
FIG. 63 shows characteristics of Light-emitting Elements 4 to 6.

FIG. 63 shows emission spectra of Light-emitting Elements 4 to 6.

As apparent from FIG. 63 and Table 8, Light-emitting Elements 4 to 6 of this example exhibit good blue emission. In addition, FIG. 62 shows that Light-emitting Elements 4 to 6 of this example has high emission efficiency.

Figure 64:
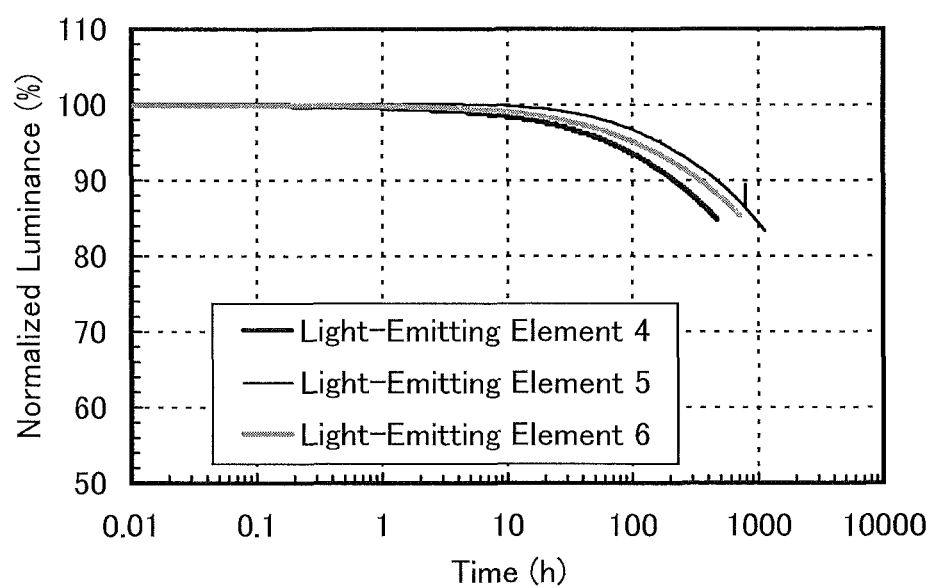
FIG. 64 shows characteristics of Light-emitting Elements 4 to 6.

Fabricated Light-emitting Elements 4 to 6 underwent reliability tests. In the reliability tests, the initial luminance was set at 1000 cd/m$^2$, these elements were operated at a constant current density, and the luminance was measured at regular intervals. Results of the reliability tests are shown in FIG. 64. In FIG. 64, the horizontal axis represents current flow time (hour), and the vertical axis represents the proportion of luminance at each time in the initial luminance, i.e., normalized luminance (%).

As shown in FIG. 64, Light-emitting Element 4 kept 85% of the initial luminance after driving for 470 hours, and Light-emitting Element 5 kept 83% of the initial luminance after driving for 1100 hours. In addition, Light-emitting Element 6 kept 85% of the initial luminance after driving for 700 hours. Therefore, the luminances of Light-emitting Elements 4 to 6 do not easily deteriorate over time, indicating that they have a long lifetime.

As described above, it is found that light-emitting elements of this example can be a light-emitting element that achieves a long lifetime, high reliability, high color purity, and high emission efficiency.

EXAMPLE 17

This example will show a method for manufacturing light-emitting elements using the fluorene derivatives described in Embodiment 1 as a light-emitting material, and measurement results of their element characteristics. Specifically, the light-emitting elements described here were formed using N,N'-bis[3-(9-phenyl-9H-fluoren-9-yl)phenyl]-N,N'-diphenyl-pyrene-1,6-diamine (abbreviation: 1,6mFLPAPrn) represented by Structural Formula (200) described in Example 10, N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by Structural Formula (201) described in Example 13, N,N'-bis{3-[9-(3-methylphenyl)-9H-fluoren-9-yl]phenyl}-N,N'-bis(3-methylphenyl)-pyrene-1,6-diamine (abbreviation: 1,6mMemFLPAPrn-II) represented by Structural Formula (215) described in Example 14, and N,N'-bis{3-[9-(4-methylphenyl)-9H-fluoren-9-yl]phenyl}-N,N'-bis(3-methylphenyl)-pyrene-1,6-diamine (abbreviation: 1,6mMemFLPAPrn-III) represented by Structural Formula (219) described in Example 15.

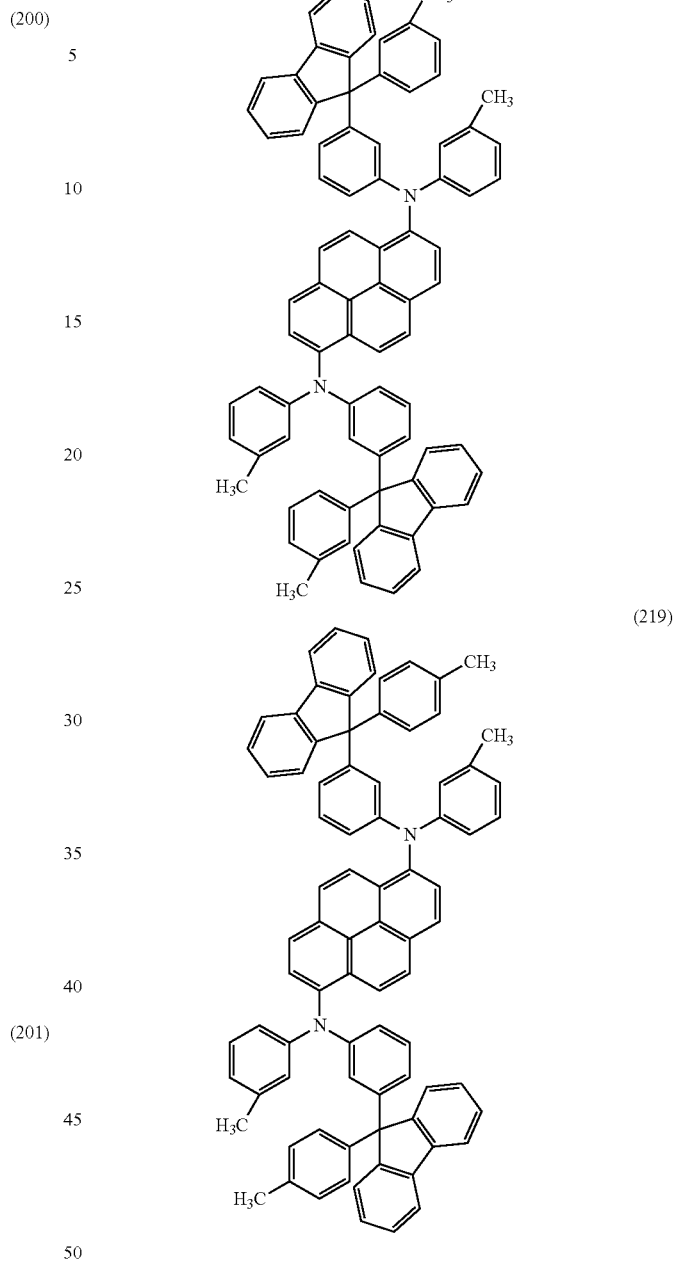

Fabrication methods of Light-emitting Elements 7 to 10 of this example will be now described. Note that the organic compounds used in this example, the molecular structures of which are already shown in the above examples, are not detailed here. The structure of the elements, which is the same as that in Example 4, can be found in FIG. 17A.

Light-emitting Elements 7 to 10 of this example were manufactured in the same way as Light-emitting Element 4 of Example 17 except for the light-emitting layer 2105.

(Light-emitting Element 7)

As the light-emitting layer 2105 of Light-emitting Element 7, a 30-nm-thick film was formed by co-evaporation of 9-[4-(10-phenyl-9-anthryl)phenyl]-9H-carbazole (abbreviation: CzPA) and N,N'-bis[3-(9-phenyl-9H-fluoren-9-yl)phenyl]-N,N'-diphenyl-pyrene-1,6-diamine (abbreviation:

1,6mFLPAPrn). Here, the evaporation rate was controlled so that the weight ratio of CzPA to 1,6mFLPAPrn was 1:0.05 (=CzPA:1,6mFLPAPrn).

(Light-emitting Element 8)

As the light-emitting layer 2105 of Light-emitting Element 8, a 30-nm-thick film was formed by co-evaporation of 9-[4-(10-phenyl-9-anthryl)phenyl]-9H-carbazole (abbreviation: CzPA) and N,N'-bis(3-methylphenyl)-N,N'-b is [3-(9-phenyl-9H-fluoren-9-yl)phenyl]-pyrene-1,6-diamine (abbreviation: 1,6mMemFLPAPrn). Here, the evaporation rate was controlled so that the weight ratio of CzPA to 1,6mMemFLPAPrn was 1:0.05 (=CzPA:1,6mMemFLPAPrn).

(Light-emitting Element 9)

As the light-emitting layer 2105 of Light-emitting Element 9, a 30-nm-thick film was formed by co-evaporation of 9-[4-(10-phenyl-9-anthryl)phenyl]-9H-carbazole (abbreviation: CzPA) and N,N'-bis{3-[9-(3-methylphenyl)-9H-fluoren-9-yl]phenyl}-N,N'-bis(3-methylphenyl)-pyrene-1,6-diamine (abbreviation: 1,6mMemFLPAPrn-II). Here, the evaporation rate was controlled so that the weight ratio of CzPA to 1,6mMemFLPAPrn-II was 1:0.05 (=CzPA:1,6mMemFLPAPrn-II).

(Light-emitting Element 10)

As the light-emitting layer 2105 of Light-emitting Element 10, a 30-nm-thick film was formed by co-evaporation of 9-[4-(10-phenyl-9-anthryl)phenyl]-9H-carbazole (abbreviation: CzPA) and N,N'-bis{3-[9-(4-methylphenyl)-9H-fluoren-9-yl]phenyl}-N,N'-bis(3-methylphenyl)-pyrene-1,6-diamine (abbreviation: 1,6mMemFLPAPrn-III). Here, the evaporation rate was controlled so that the weight ratio of CzPA to 1,6mMemFLPAPrn-III was 1:0.05 (=CzPA:1,6mMemFLPAPrn-III).

Table 9 shows element structures of Light-emitting Elements 7 to 10 manufactured in this example. In Table 9, all the mixture ratios are weight ratios.

Figure 66:
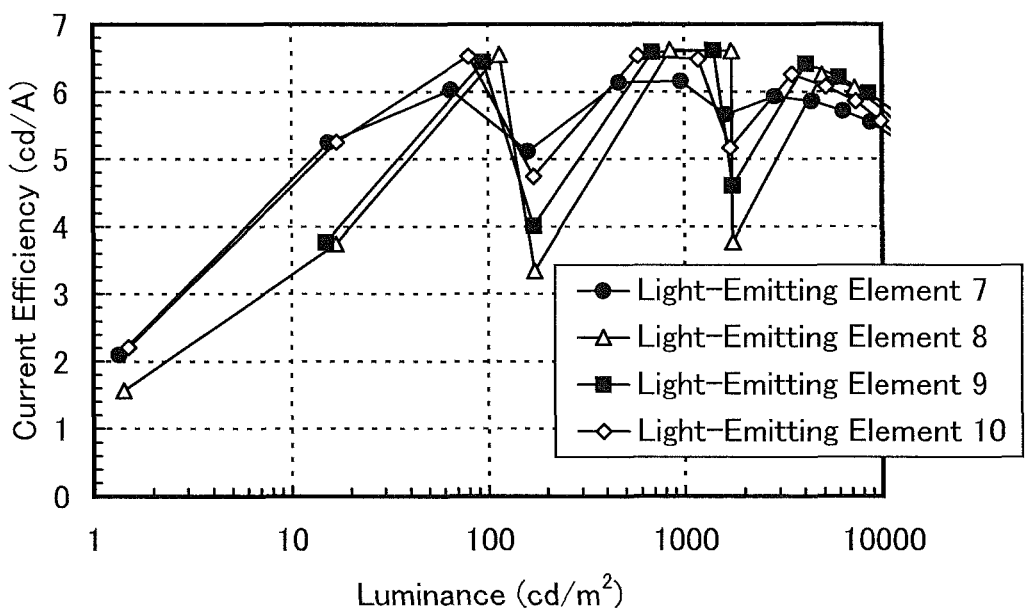
FIG. 66 shows characteristics of Light-emitting Elements 7 to 10.

65, the vertical axis represents luminance (cd/m$^2$) and the horizontal axis represents current voltage (V). In FIG. 66, the vertical axis represents current efficiency (cd/A) and the horizontal axis represents luminance (cd/m$^2$). Further, Table 10 shows the chromaticity of the light-emitting elements at around 1000 cd/m$^2$.

TABLE 10

|  | Chromaticity coordinates (x, y) |
|---|---|
| Light-Emitting Element 7 | (0.14, 0.15) |
| Light-Emitting Element 8 | (0.14, 0.16) |
| Light-Emitting Element 9 | (0.14, 0.16) |
| Light-Emitting Element 10 | (0.14, 0.17) |

Figure 67:
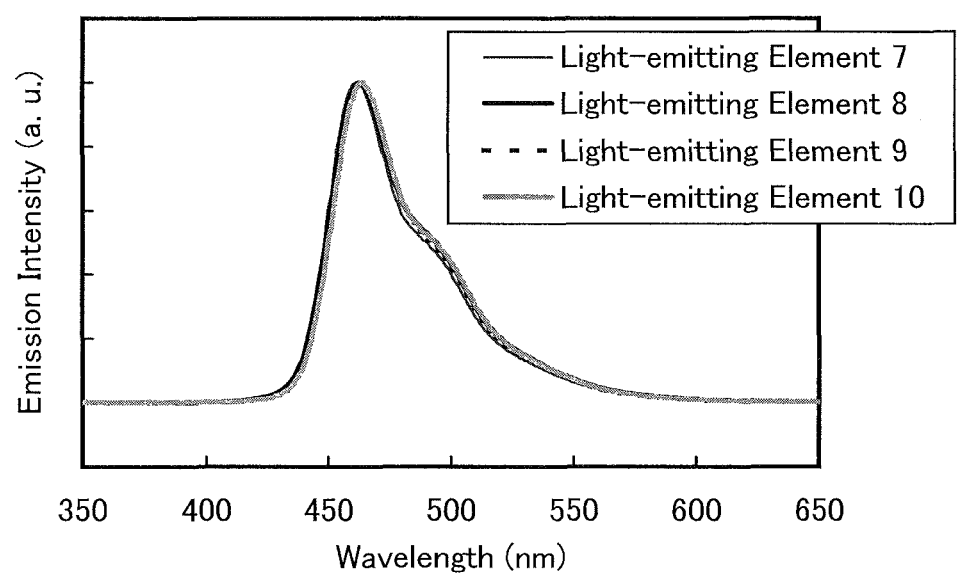
FIG. 67 shows characteristics of Light-emitting Elements 7 to 10.

FIG. 67 shows emission spectra of Light-emitting Elements 7 to 10.

As apparent from FIG. 67 and Table 10, Light-emitting Elements 7 to 10 of this example exhibit good blue emission. In addition, FIG. 66 shows that Light-emitting Elements 7 to 10 of this example has high emission efficiency.

Light-emitting Element 7 differs from Light-emitting Elements 8 to 10 in that 1,6mFLPAPrn used as a dopant of Light-emitting Element 7 has no substituent in a fluorene skeleton while 1,6mMemFLPAPrn, 1,6mMemFLPAPrn-II, and 1,6mMemFLPAPrn-III, which were used as dopants of Light-emitting Elements 8 to 10, each have a methyl group in a fluorene skeleton. However, FIG. 65, FIG. 66, FIG. 67, Table 8 and the like indicate no significant difference in initial characteristics among Light-emitting Elements 7 to 10. Thus, in the fluorene derivatives of one embodiment of the present invention, introduction of a substituent into a fluorene skeleton does not affect initial characteristics.

Fabricated Light-emitting Elements 7 to 10 underwent reliability tests. In the reliability tests, the initial luminance

TABLE 9

|  | Light-Emitting Element 7 | Light-Emitting Element 8 | Light-Emitting Element 9 | Light-Emitting Element 10 |
|---|---|---|---|---|
| Anode 2102 | ITSO 110 nm | ITSO 110 nm | ITSO 110 nm | ITSO 110 nm |
| Hole-injection layer 2103 | PCzPA:MoOx (=4:2) 50 nm | PCzPA:MoOx (=4:2) 50 nm | PCzPA:MoOx (=4:2) 50 nm | PCzPA:MoOx (=4:2) 50 nm |
| Hole-transport layer 2104 | PCzPA 10 nm | PCzPA 10 nm | PCzPA 10 nm | PCzPA 10 nm |
| Light-emitting layer 2105 | CzPA:1,6mFLPAPrn (=1:0.05) 30 nm | CzPA:1,6mMemFLPAPrn (=1:0.05) 30 nm | CzPA:1,6mMemFLPAPrn-II (=1:0.05) 30 nm | CzPA:1,6mMemFLPAPrn-III (=1:0.05) 30 nm |
| Electron-transport layer 2106 | Alq 10 nm Bphen 15 nm | Alq 10 nm Bphen 15 nm | Alq 10 nm Bphen 15 nm | Alq 10 nm Bphen 15 nm |
| Electron-injection layer 2107 | LiF 1 nm | LiF 1 nm | LiF 1 nm | LiF 1 nm |
| Cathode 2108 | Al 200 nm | Al 200 nm | Al 200 nm | Al 200 nm |

All the mixture ratios are weight ratios.

Light-emitting Elements 7 to 10 thus obtained were sealed in a glove box having a nitrogen atmosphere without being exposed to the air. Then, the operating characteristics of the elements were measured. Note that the measurement was carried out at room temperature (in an atmosphere kept at 25° C.).

Figure 65:
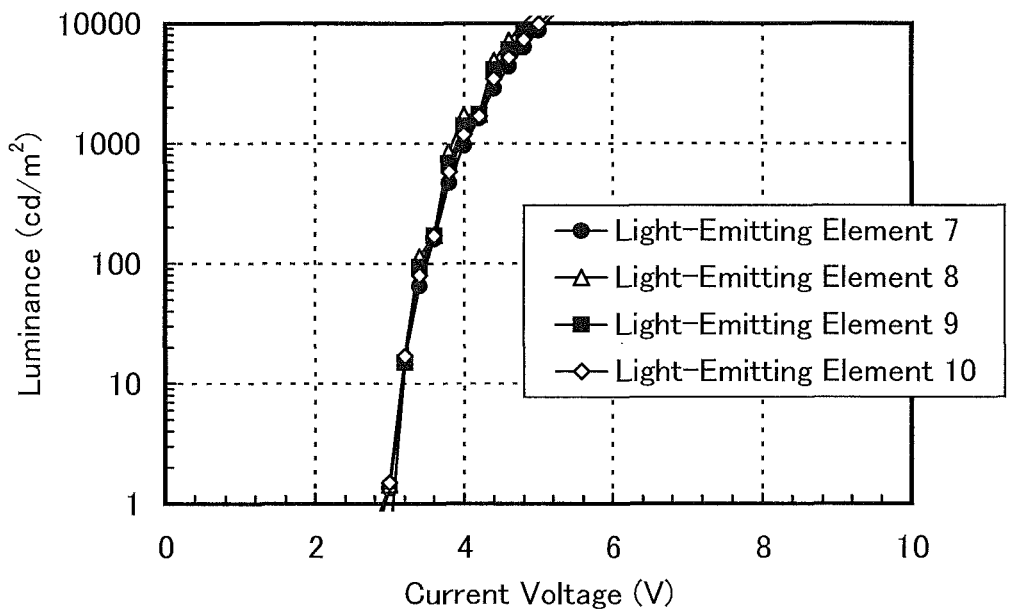
FIG. 65 shows characteristics of Light-emitting Elements 7 to 10.
Figure 68:
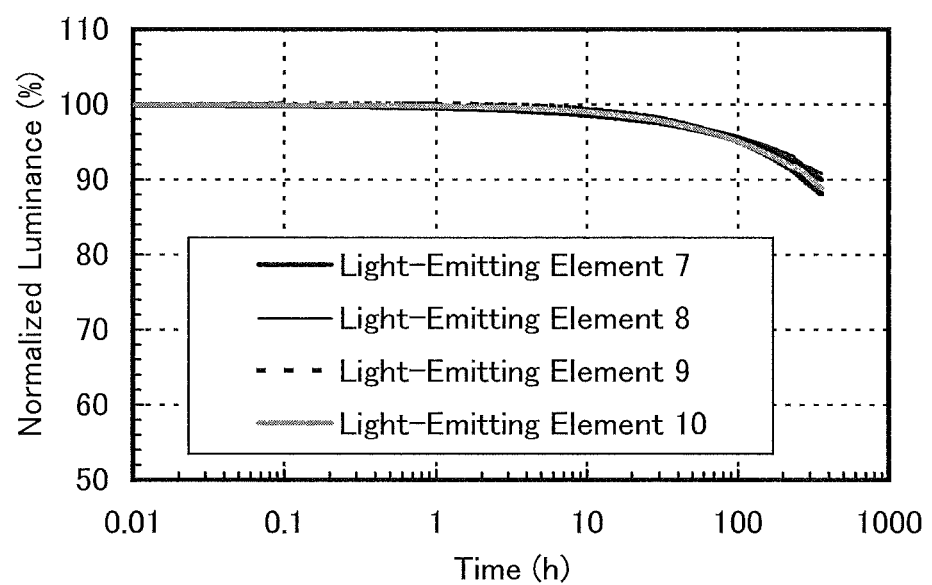
FIG. 68 shows characteristics of Light-emitting Elements 7 to 10.

FIG. 65 shows voltage vs. luminance characteristics of Light-emitting Elements 7 to 10, and FIG. 66 shows luminance vs. current efficiency characteristics thereof. In FIG.

was set at 1000 cd/m$^2$, these elements were operated at a constant current density, and the luminance was measured at regular intervals. Results of the reliability tests are shown in FIG. 68. In FIG. 68, the horizontal axis represents current flow time (hour), and the vertical axis represents the proportion of luminance at each time in the initial luminance, i.e., normalized luminance (%).

As shown in FIG. 68, Light-emitting Element 7 kept 90% of the initial luminance after driving for 360 hours, and Light-emitting Element 8 kept 91% of the initial luminance after driving for 360 hours. In addition, Light-emitting Element 9 kept 88% of the initial luminance after driving for 360 hours, and Light-emitting Element 10 kept 89% of the initial luminance after driving for 360 hours. Therefore, the luminances of Light-emitting Elements 7 to 10 do not easily deteriorate over time, indicating that they have a long lifetime.

As described above, it is found that light-emitting elements of this example can be a light-emitting element that achieves a long lifetime, high reliability, high color purity, and high emission efficiency.

EXAMPLE 18

In this example, N,N'-bis(3-methylphenyl)-N,N'-bis{3-[3-(9-phenyl-9H-fluoren-9-yl)phenyl]phenyl}-pyrene-1,6-diamine (abbreviation: 1,6mMemFLBiAPrn) represented by Structural Formula (234) in Embodiment 2 was produced.

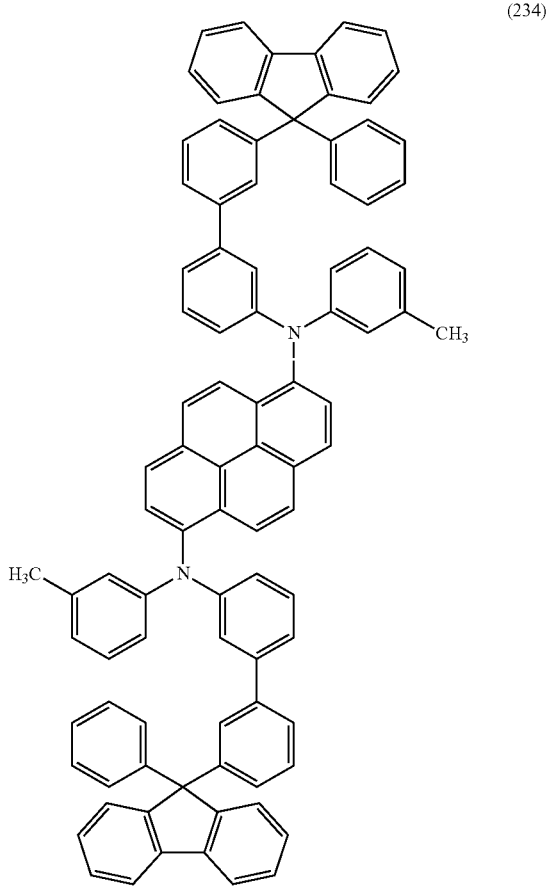

Step 1: Synthesis method of [3-(9-phenyl-9H-fluoren-9-yl)phenyl]boronic acid

In a 100 mL three-neck flask was put 1.4 g (3.6 mmol) of 9-(3-bromophenyl)-9-phenyl-9H-fluorene. The air in the flask was replaced with nitrogen. Then, 36.0 mL of tetrahydrofuran was added to the mixture, and the mixture was stirred at 80° C. for 30 minutes. After the stirring, 2.4 mL (4.0 mmol) of a 1.65 mol/L hexane solution of n-butyllithium was dripped with a syringe, followed by stirring at −80° C. for 2 hours. Then, 0.6 mL (4.8 mmol) of trimethyl borate was added, and the mixture was stirred overnight while the temperature thereof was gradually increased from −80° C. to room temperature. After the stirring, an aqueous solution of hydrochloric acid (1 mol/L) was added to this mixture, and it was then stirred at room temperature for 30 minutes. Then, ethyl acetate was added to separate the organic layer and the aqueous layer of this mixture, and the aqueous layer was extracted with ethyl acetate three times. This ethyl acetate layer and the organic layer were combined, washed with saturated brine, and dried with magnesium sulfate. The obtained mixture was gravity filtered so that magnesium sulfate was removed, and the obtained filtrate was concentrated to give a white solid. Recrystallization of the obtained white solid from a mixed solvent of ethyl acetate and hexane gave 1.2 g of a white solid in 90% yield, which was the substance to be produced. The synthesis scheme of this Step 1 is shown in (E18-1) given below.

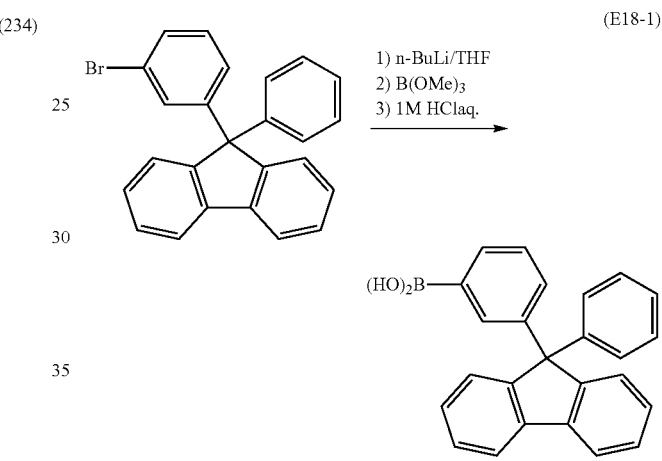

Step 2: Synthesis method of 9-[3-(3-bromophenyl)phenyl]-9-phenylfluorene

In a 50 mL three-neck flask were put 1.2 g (3.2 mmol) of [3-(9-phenyl-9H-fluoren-9-yl)phenyl]boronic acid and 54.7 mg (0.2 mmol) of tris(2-methylphenyl)phosphine. The air in the flask was replaced with nitrogen. To this mixture were added 12.0 mL of toluene, 4.0 mL of ethanol, 0.5 mL (3.5 mmol) of 1-bromo-3-iodobenzene, and 3.2 mL of an aqueous solution of potassium carbonate (2 mol/L). The temperature of this mixture was set to 60° C., and then 13.9 mg (0.1 mmol) of palladium(II) acetate was added to the mixture. The temperature of this mixture was set to 80° C., followed by reflux for 3.0 hours. After the reflux, toluene and water were added to this mixture, the organic layer and the aqueous layer were separated, and the aqueous layer was extracted three times with toluene. This toluene layer and the organic layer were combined, washed with saturated brine, and dried with magnesium sulfate. The obtained mixture was gravity filtered so that magnesium sulfate was removed, and the obtained filtrate was concentrated to give a solid. Recrystallization of the solid from a mixed solvent of toluene and methanol gave 1.2 g of a white solid in 80% yield, which was the substance to be produced. The synthesis scheme of this Step 2 is shown in (E18-2) given below.

(E18-2)

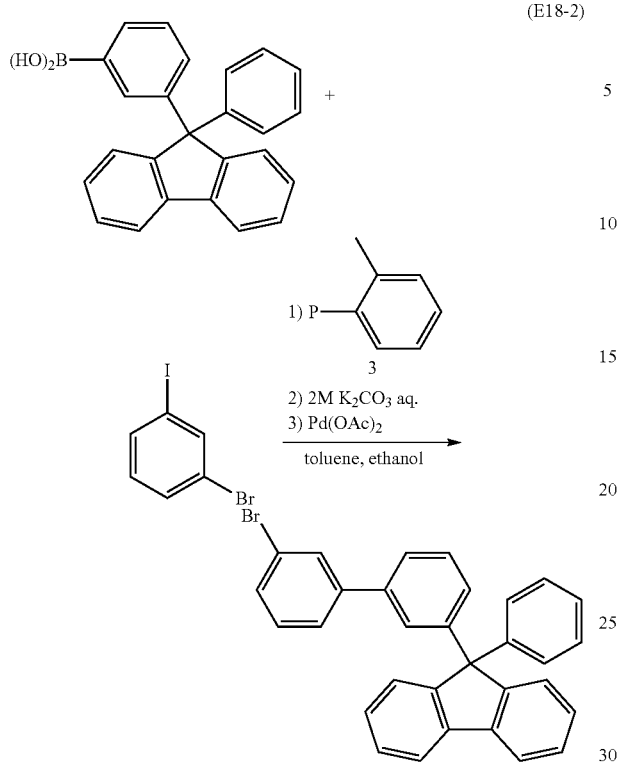

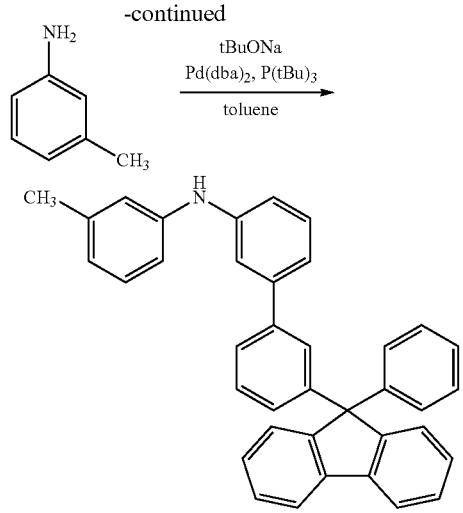

Step 3: Synthesis method of 3-methylphenyl-3-[3-(9-phenyl-9H-fluoren-9-yl)phenyl]phenylamine (abbreviation: mMemFLBiA)

In a 50 mL three-neck flask were put 1.2 g (2.5 mmol) of 9-[3-(3-bromophenyl)phenyl]-9-phenylfluorene and 0.7 g (7.4 mmol) of sodium tert-butoxide. The air in the flask was replaced with nitrogen. To this mixture were added 12.5 mL of toluene, 0.3 mL (2.5 mmol) of m-toluidine, and 0.2 mL of a 10% hexane solution of tri(tert-butyl)phosphine. The temperature of this mixture was set to 60° C., and 20.0 mg (0.03 mmol) of bis(dibenzylideneacetone)palladium(0) was added to the mixture. The temperature of the mixture was raised to 80° C., followed by stirring for 2.5 hours. After the stirring, the mixture was suction-filtered through Florisil, Celite, and alumina to give a filtrate. The filtrate was concentrated to give a solid, which was then purified by silica gel column chromatography (the developing solvent has a 2:3 ratio of hexane to toluene). Accordingly, 1.1 g of a solid was obtained in 91% yield, which was the substance to be produced. The synthesis scheme of this Step 3 is shown in the following (E18-3).

(E18-3)

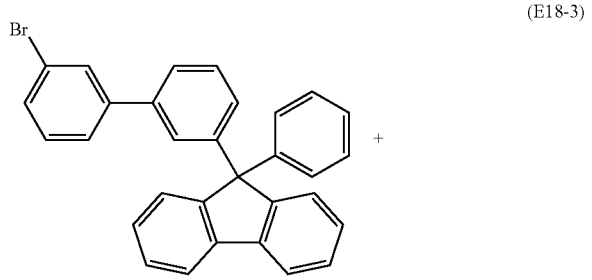

Step 4: Synthesis method of N,N'-bis(3-methylphenyl)-N,N'-bis{3-[3-(9-phenyl-9H-fluoren-9-yl)phenyl]phenyl}-pyrene-1,6-diamine (abbreviation: 1,6mMemFLBiAPrn)

In a 100 mL three-neck flask were put 1.1 g (2.2 mmol) of 3-methylphenyl-3-[3-(9-phenyl-9H-fluoren-9-yl)phenyl]phenylamine, 0.4 g (1.1 mmol) of 1,6-dibromopyrene, and 0.3 g (3.3 mmol) of sodium tert-butoxide. The air in the flask was replaced with nitrogen. To this mixture were added 13.0 mL of toluene and 0.2 mL of a 10% hexane solution of tri(tert-butyl)phosphine. The temperature of this mixture was set to 80° C., and 16.3 mg (0.03 mmol) of bis(dibenzylideneacetone)palladium(0) was added to the mixture, followed by stirring for 3.5 hours. After the stirring, the mixture was suction-filtered through Florisil, Celite, and alumina to give a filtrate. The filtrate was concentrated to give a solid, which was then purified by silica gel column chromatography (the developing solvent has a 1:1 ratio of hexane to toluene), whereby a yellow solid was obtained. Recrystallization of the obtained yellow solid from a mixed solvent of toluene and hexane gave 0.7 g of a yellow solid in 53% yield, which was the substance to be produced.

Because the substance produced (1,6mMemFLBiAPrn) has a structure in which a benzene ring bonded to the 9-position of fluorene is bonded to the meta position of a benzene ring in an amine skeleton, 1,6mMemFLBiAPrn has higher solubility in an organic solvent such as toluene than 1,6FLPAPrn obtained in Example 2 and 1,6mMemFLPAPrn obtained in Example 13. Such improvement of the solubility in a solvent facilitates purification of the fluorene derivative of this example (1,6mMemFLBiAPrn), demonstrating the easiness of its synthesis.

By a train sublimation method, 0.4 g of the obtained yellow solid was purified. In the purification, the yellow solid was heated at 363° C. under a pressure of 2.8 Pa with a flow rate of argon gas of 4.0 mL/min. After the purification, 0.2 g of a yellow solid was obtained in a yield of 65%, which was the substance to be produced. The synthesis scheme of Step 4 is shown by the following (E18-4).

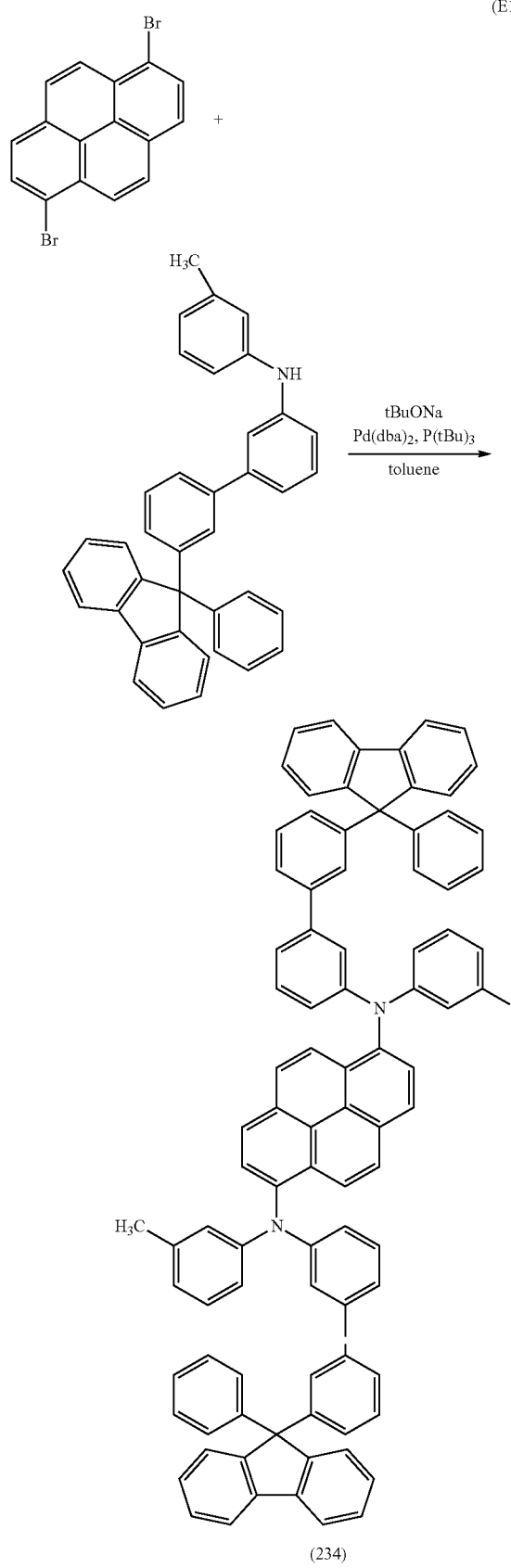

A nuclear magnetic resonance (NMR) method and a mass spectrometry identified this compound as N,N'-bis(3-methylphenyl)-N,N'-bis{3-[3-(9-phenyl-9H-fluoren-9-yl)phenyl]phenyl}-pyrene-1,6-diamine (abbreviation: 1,6mMemFLBiAPrn), which was the substance to be produced.

$^1$H NMR data of the obtained compound are: $^1$H NMR (DMSO-d$_6$, 300 MHz): δ=2.10 (s, 6H), 6.80-7.30 (m, 46H), 7.70 (d, J=7.2 Hz, 4H), 7.86 (d, J=8.1 Hz, 2H), 8.11 (s, 4H), 8.28 (d, J=7.8 Hz, 2H)

Figure 69A:
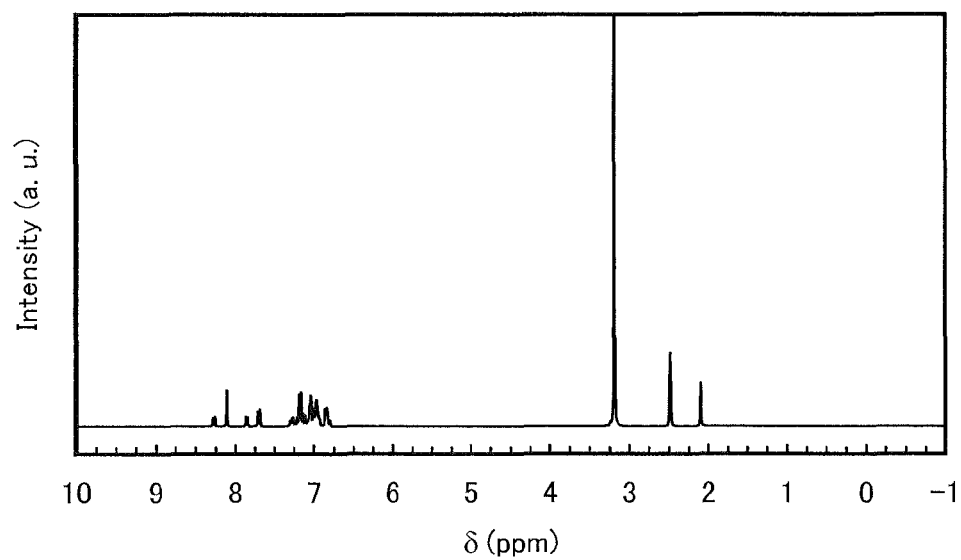
FIGS. 69A and 69B show $^1$H NMR charts of 1,6mMem-FLBiAPrn.
Figure 69B:
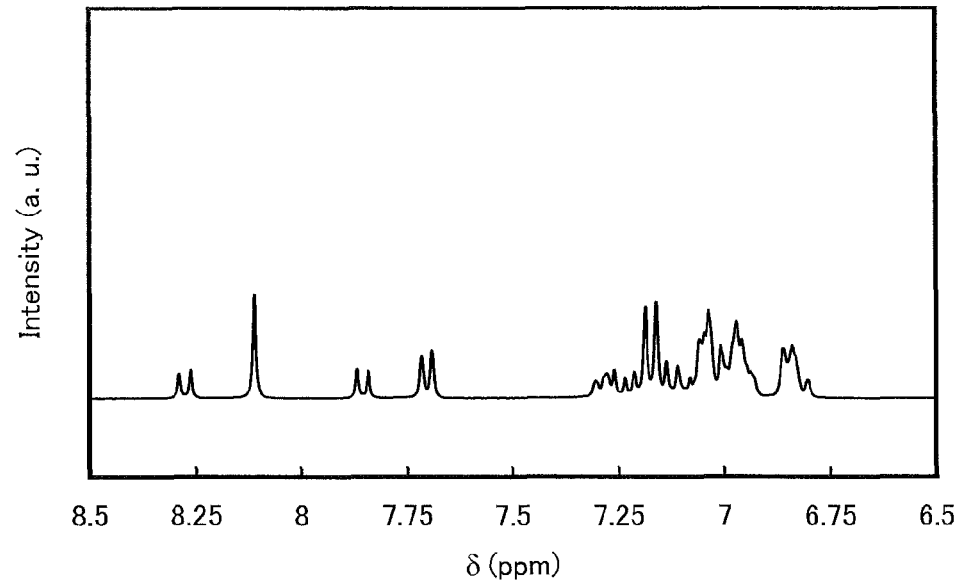

FIGS. 69A and 69B show the NMR charts. Note that FIG. 69B is a chart showing an enlarged part of FIG. 69A in the range of 6.5 to 8.5 ppm.

The measurement result of the mass spectrometry of the obtained compound is: MS (ESI-MS): m/z=1198 (M+H)$^+$; C$_{92}$H$_{64}$N$_2$ (1196.51).

Figure 70A:
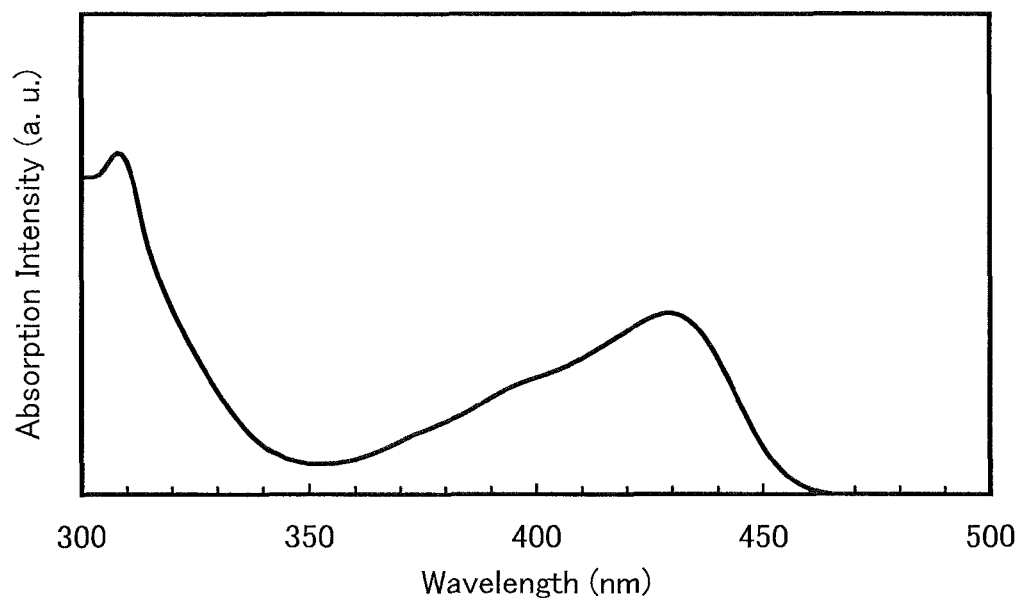
FIGS. 70A and 70B show an absorption spectrum and an emission spectrum of a toluene solution of 1,6mMemFLBi-APrn.
Figure 70B:
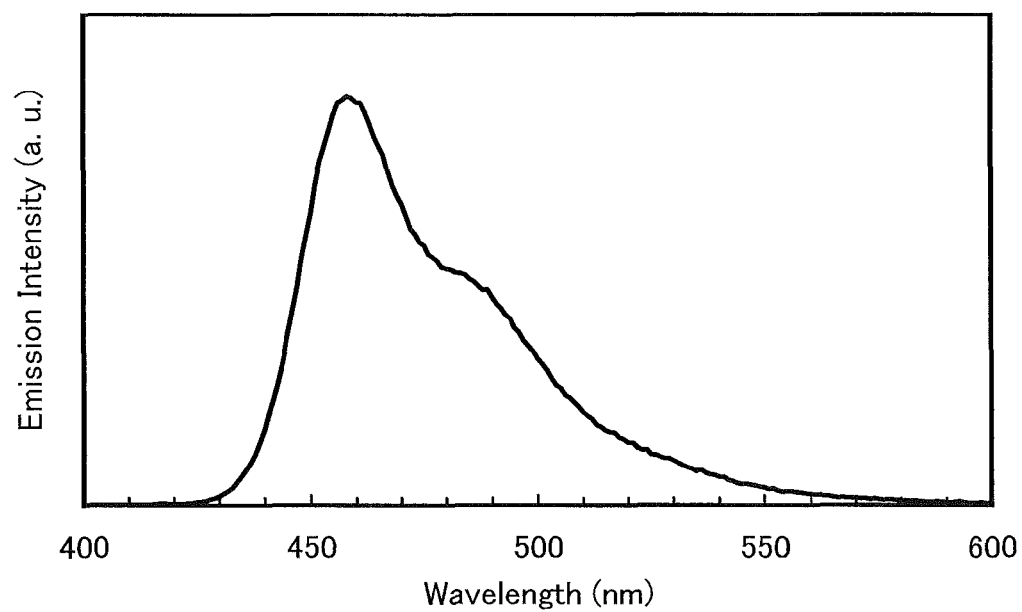
Figure 71A:
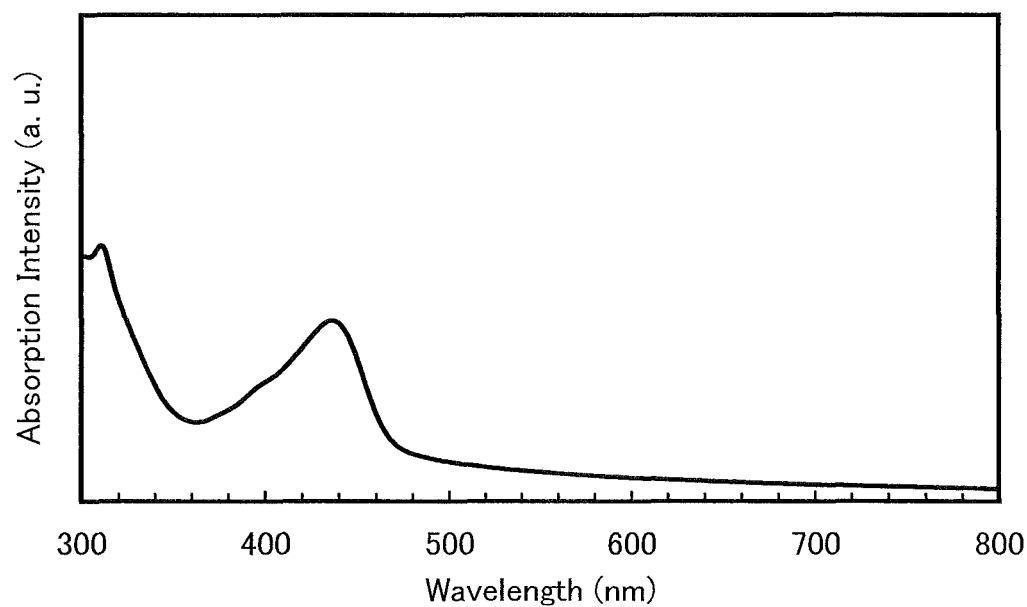
FIGS. 71A and 71B show an absorption spectrum and an emission spectrum of a thin film of 1,6mMemFLBiAPrn.
Figure 71B:
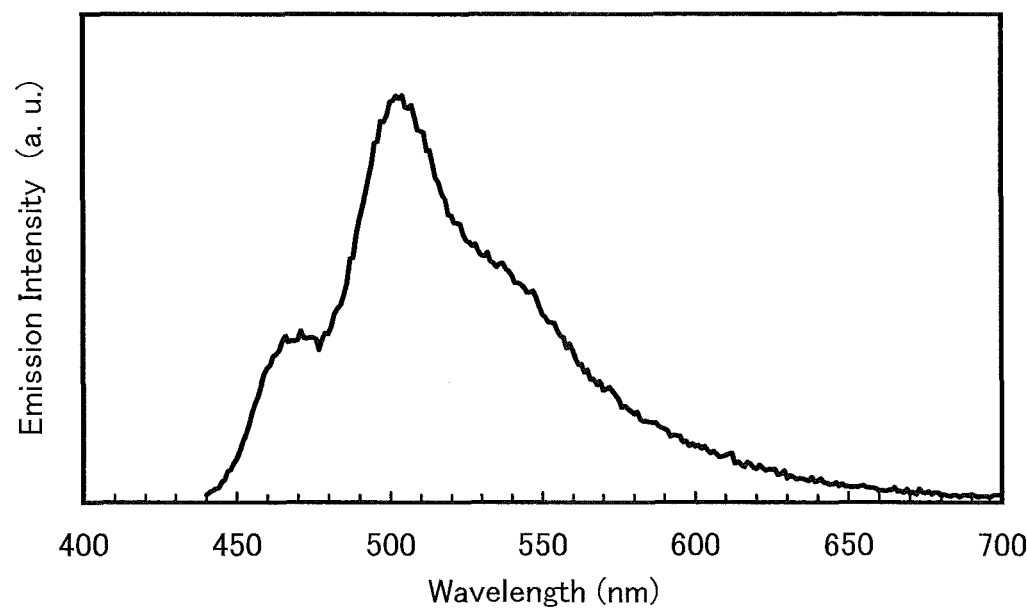

Further, FIG. 70A shows an absorption spectrum of a toluene solution of 1,6mMemFLBiAPrn, and FIG. 70B shows an emission spectrum thereof. FIG. 71A shows an absorption spectrum of a thin film of 1,6mMemFLBiAPrn, and FIG. 71B shows an emission spectrum thereof. The absorption spectrum was measured using an ultraviolet-visible spectrophotometer (V-570, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 70A show the absorption spectrum of the solution which was obtained by subtracting the absorption spectra of quartz and toluene, and FIG. 71A shows the absorption spectrum of the thin film which was obtained by subtracting the absorption spectrum of a quartz substrate. In FIGS. 70A and 70B and FIGS. 71A and 71B, the horizontal axis represents wavelength (nm) and the vertical axis represents intensity (arbitrary unit). In the case of the toluene solution, absorption was observed at around 429 nm, and the maximum emission wavelength was 458 nm (excitation wavelength: 370 nm). In the case of the thin film, absorption was observed at around 436 nm, and the maximum emission wavelength was 503 nm (excitation wavelength: 434 nm).

The HOMO level and the LUMO level of the thin film of 1,6mMemFLBiAPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6mMemFLBiAPrn which is shown in FIG. 71B, was regarded as an optical energy gap and added to the value of the HOMO level. As a result, the HOMO level and LUMO level of 1,6mMemFLBiAPrn were found to be −5.44 eV and −2.76 eV, respectively, and the energy gap was found to be 2.68 eV.

Thermogravimetry-differential thermal analysis (TG-DTA) of obtained 1,6mMemFLBiAPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

EXAMPLE 19

In this example, N,N'-bis[4-(9-phenyl-9H-fluoren-9-yl)phenyl]-N,N'-dinaphthyl-pyrene-1,6-diamine (abbreviation: 1,6FLPNPrn) represented by the following Structural Formula (251) was produced.

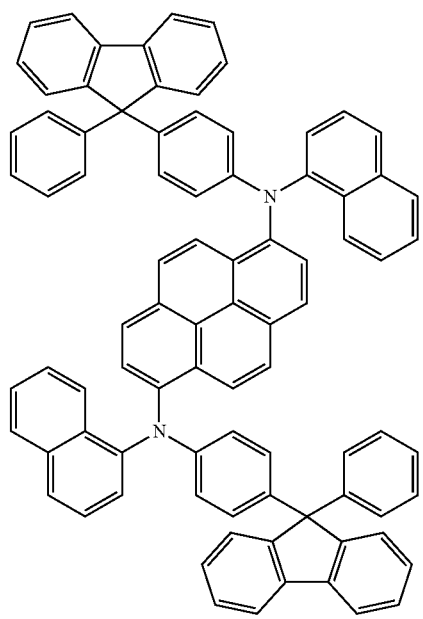

(251)

Step 1: Synthesis method of 1-naphthyl-4-(9-phenyl-9H-fluoren-9-yl)phenylamine (abbreviation: FLPN)

In a 200 mL three-neck flask were put 3.2 g (8.7 mmol) of 9-(4-bromophenyl)-9-phenyl-9H-fluorene, 1.2 g (8.7 mmol) of 1-naphthylamine, and 2.5 g (26.2 mmol) of sodium tert-butoxide. The air in the flask was replaced with nitrogen. To this mixture were added 43.0 mL of toluene and 0.2 mL of a 10% hexane solution of tri(tert-butyl)phosphine. The temperature of this mixture was set to 60° C., and 35.1 mg (0.1 mmol) of bis(dibenzylideneacetone)palladium(0) was added to the mixture. The temperature of the mixture was raised to 80° C., followed by stirring for 2.5 hours. After the stirring, the mixture was suction-filtered through Florisil, Celite, and alumina to give a filtrate. The filtrate was concentrated to give a solid, which was then purified by silica gel column chromatography (the developing solvent has a 1:1 ratio of hexane to toluene). Accordingly, 2.1 g of a white solid was obtained in 52% yield, which was the substance to be produced. The synthesis scheme of this Step 1 is shown in the following (E19-1).

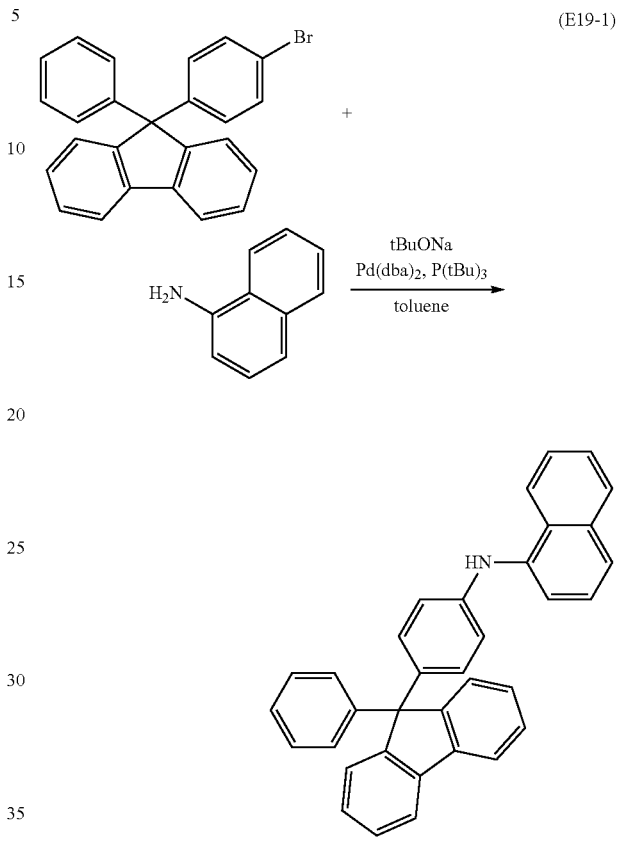

(E19-1)

Step 2: Synthesis method of N,N'-bis[4-(9-phenyl-9H-fluoren-9-yl)phenyl]-N,N'-dinaphthyl-pyrene-1,6-diamine (abbreviation: 1,6FLPNPrn)

In a 100 mL three-neck flask were put 0.6 g (1.8 mmol) of 1,6-dibromopyrene, 1.6 g (3.6 mmol) of 1-naphthyl-4-(9-phenyl-9H-fluoren-9-yl)phenylamine, and 0.5 g (5.6 mmol) of sodium tert-butoxide. The air in the flask was replaced with nitrogen. To this mixture were added 20.0 mL of toluene and 0.2 mL of a 10% hexane solution of tri(tert-butyl)phosphine. The temperature of this mixture was set to 80° C., and 34.9 mg (0.1 mmol) of bis(dibenzylideneacetone)palladium(0) was added to the mixture, followed by stirring for 0.3 hours. After the stirring, 10.4 mg (0.02 mmol) of bis(dibenzylideneacetone)palladium(0) was added to the mixture, followed by stirring for 1.5 hours. This mixture was suction-filtered while being kept at 80° C., whereby a solid was obtained. Toluene was added to the obtained solid, and the resulting mixture was heated to 110° C. and suction-filtered through alumina, Florisil, and Celite to give a filtrate. The filtrate was concentrated to give a solid, which was then recrystallized from a mixed solvent of toluene and hexane. Accordingly, 0.7 g of a yellow solid was obtained in 37% yield, which was the substance to be produced. The synthesis scheme of this Step 2 is shown in the following (E19-2).

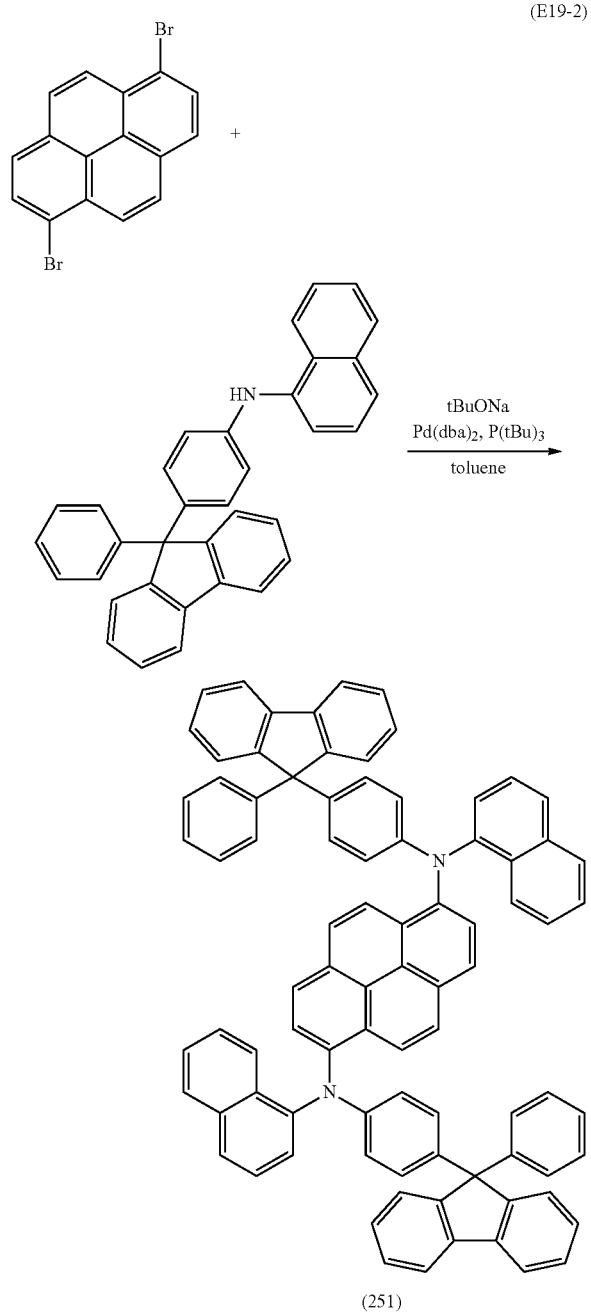

A nuclear magnetic resonance (NMR) method and a mass spectrometry identified this compound as N,N'-bis[4-(9-phenyl-9H-fluoren-9-yl)phenyl]-N,N'-dinaphthyl-pyrene-1,6-diamine (abbreviation: 1,6FLPNPrn), which was the substance to be produced.

$^1$H NMR data of the obtained compound are: NMR (CDCl$_3$, 300 MHz): δ=6.59 (d, J=8.4 Hz, 4H), 6.95 (d, J=8.7 Hz, 4H), 7.11-7.23 (m, 15H), 7.28-7.48 (m, 15H), 7.64-7.74 (m, 8H), 7.79 (d, J=9.3 Hz, 2H), 7.85 (d, J=7.8 Hz, 2H), 7.93 (d, J=8.1 Hz, 2H), 8.09-8.16 (m, 4H)

Figure 72A:
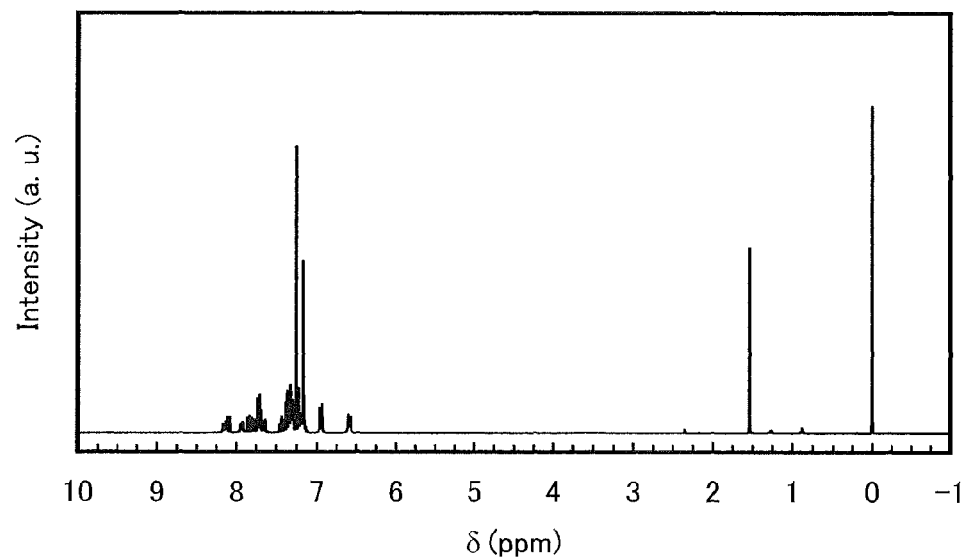
FIGS. 72A and 72B show $^1$H NMR charts of 1,6FLPN-Prn.
Figure 72B:
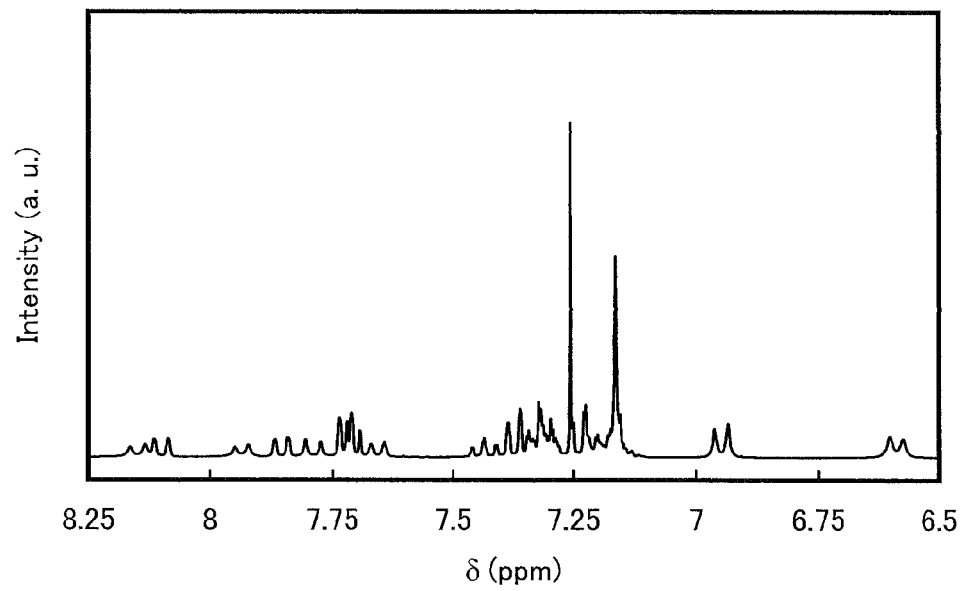

FIGS. 72A and 72B show the NMR charts. Note that FIG. 72B is a chart showing an enlarged part of FIG. 72A in the range of 6.5 to 8.25 ppm.

The measurement result of the mass spectrometry of the obtained compound is: MS (ESI-MS): m/z=1171 (M+H)$^+$; C$_{86}$H$_{56}$N$_2$ (1116.44).

Figure 73A:
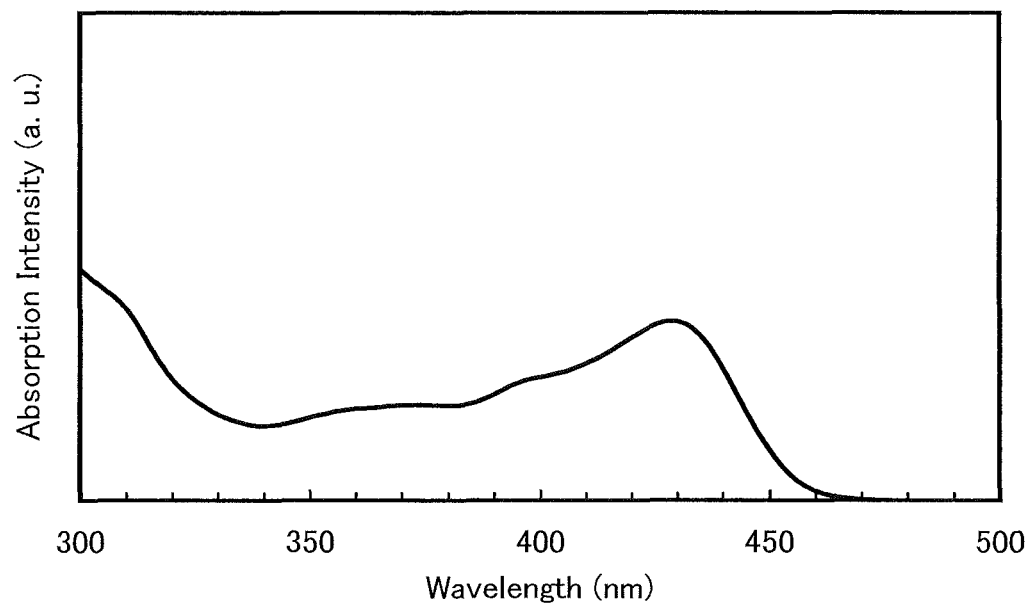
FIGS. 73A and 73B show an absorption spectrum and an emission spectrum of a toluene solution of 1,6FLPNPrn.
Figure 73B:
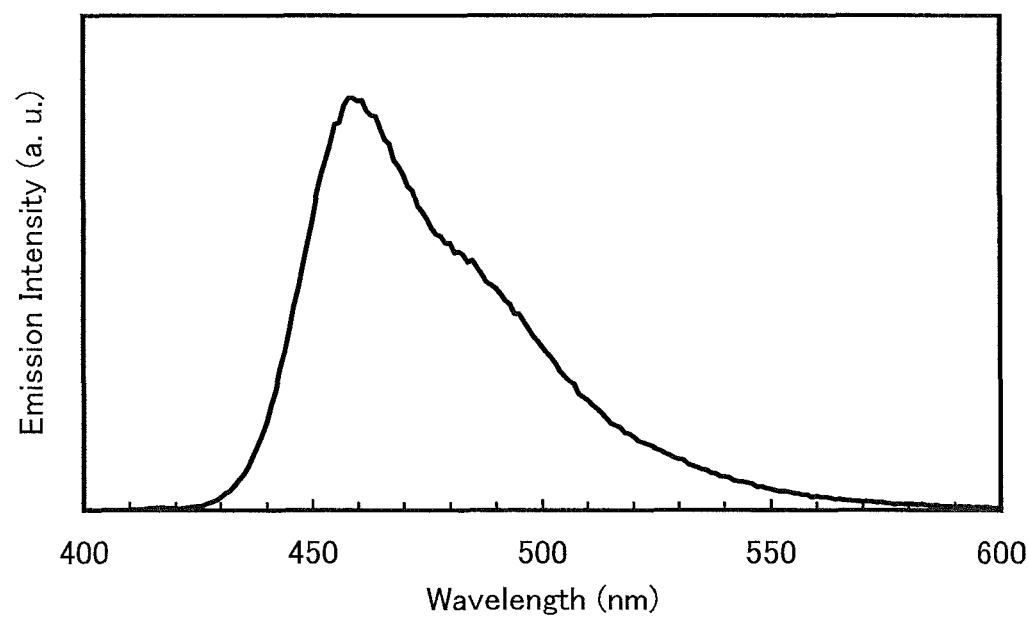
Figure 74A:
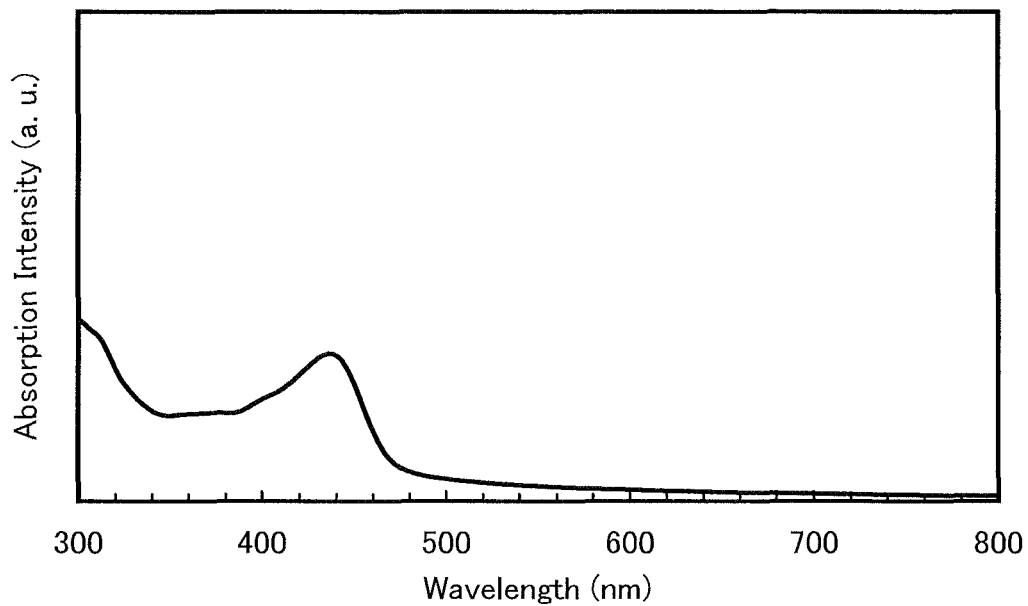
FIGS. 74A and 74B show an absorption spectrum and an emission spectrum of a thin film of 1,6FLPNPrn.
Figure 74B:
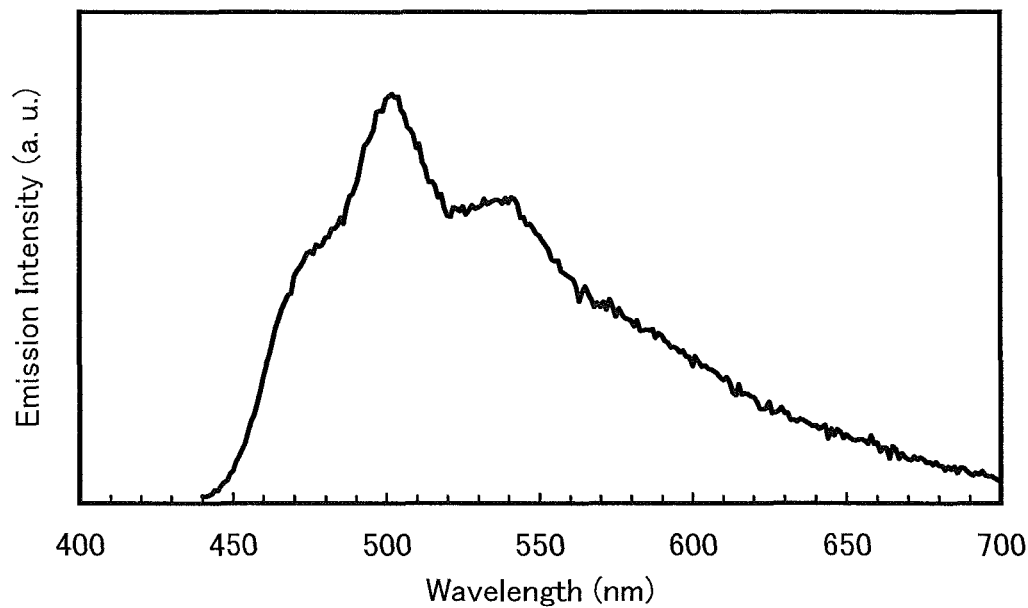

Further, FIG. 73A shows an absorption spectrum of a toluene solution of 1,6FLPNPrn, and FIG. 73B shows an emission spectrum thereof. FIG. 74A shows an absorption spectrum of a thin film of 1,6FLPNPrn, and FIG. 74B shows an emission spectrum thereof. The absorption spectrum was measured using an ultraviolet-visible spectrophotometer (V-573, produced by JASCO Corporation). The emission spectrum was measured using a fluorescence spectrophotometer (FS920, produced by Hamamatsu Photonics Corporation). The measurements were performed with samples prepared in such a manner that the solution was put in a quartz cell and the thin film was obtained by evaporation onto a quartz substrate. FIG. 73A show the absorption spectrum of the solution which was obtained by subtracting the absorption spectra of quartz and toluene, and FIG. 74A shows the absorption spectrum of the thin film which was obtained by subtracting the absorption spectrum of a quartz substrate. In FIGS. 73A and 73B and FIGS. 74A and 74B, the horizontal axis represents wavelength (nm) and the vertical axis represents intensity (arbitrary unit). In the case of the toluene solution, absorption was observed at around 429 nm, and the maximum emission wavelength was 459 nm (excitation wavelength: 370 nm). In the case of the thin film, absorption was observed at around 436 nm, and the maximum emission wavelength was 502 nm (excitation wavelength: 435 nm).

The HOMO level and the LUMO level of the thin film of 1,6FLPNPrn were measured. The value of the HOMO level was obtained by conversion of a value of the ionization potential measured with a photoelectron spectrometer (AC-2, manufactured by Riken Keiki Co., Ltd.) in the atmosphere into a negative value. The value of the LUMO level was obtained in such a manner that the absorption edge, whish was obtained from Tauc plot with an assumption of direct transition using data on the absorption spectrum of the thin film of 1,6FLPNPrn which is shown in FIG. 74B, was regarded as an optical energy gap and added to the value of the HOMO level. As a result, the HOMO level and LUMO level of 1,6FLPNPrn were found to be −5.41 eV and −2.73 eV, respectively, and the energy gap was found to be 2.68 eV.

Thermogravimetry-differential thermal analysis (TG-DTA) of obtained 1,6FLPNPrn was performed. A high vacuum differential type differential thermal balance (manufactured by Bruker AXS K.K., TG/DTA 2410SA) was used for the measurement. The measurement was carried out under a nitrogen stream (a flow rate of 200 mL/min) and a normal pressure at a temperature rising rate of 10° C./min. The relationship between weight and temperature (thermogravimetry) shows that the 5% weight loss temperature is 500° C. or more, which is indicative of high heat resistance.

This application is based on Japanese Patent Application Serial No. 2009-243646 filed with the Japan Patent Office on Oct. 22, 2009, Japanese Patent Application Serial No. 2009-264300 filed with the Japan Patent Office on Nov. 19, 2009, and Japanese Patent Application Serial No. 2010-167352 filed with the Japan Patent Office on Jul. 26, 2010, the entire contents of which are hereby incorporated by reference.

What is claimed is:
1. A compound represented by Formula (G1),

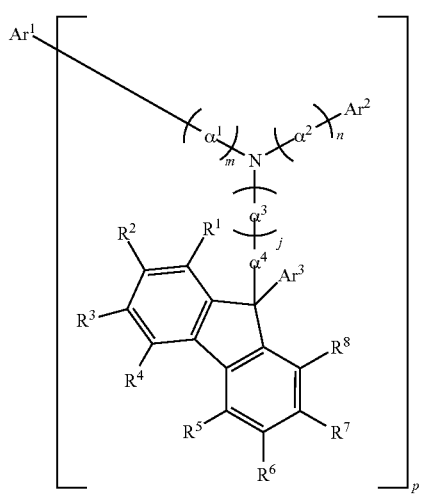

(G1)

wherein $R^1$ to $R^8$ separately represent any one of a hydrogen atom, an alkyl group having 1 to 6 carbon atoms, an unsubstituted phenyl group; an unsubstituted biphenyl group; a phenyl group substituted by a methyl group, an ethyl group, a propyl group, a pentyl group, a hexyl group, or a biphenyl group; and a biphenyl group substituted by a methyl group, an ethyl group, a propyl group, a pentyl group, a hexyl group, or a biphenyl group, wherein $\alpha^1$ to $\alpha^4$ separately represent an unsubstituted phenylene group or a phenylene group substituted by a methyl group, an ethyl group, a propyl group, a pentyl group, a hexyl group, a phenyl group, or a biphenyl group, wherein $Ar^1$ represents an unsubstituted condensed aromatic hydrocarbon having 14 to 18 carbon atoms forming a ring or a condensed aromatic hydrocarbon having 14 to 18 carbon atoms forming a ring substituted by a methyl group, an ethyl group, a propyl group, a pentyl group, a hexyl group, a phenyl group, or a biphenyl group, wherein $Ar^2$ is represented by any one of Formulas (Ar2-1) to (Ar2-4)

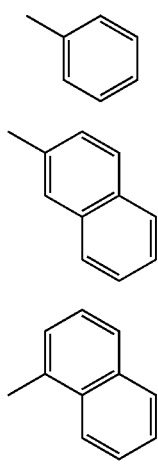

(Ar2-1)

(Ar2-2)

(Ar2-3)

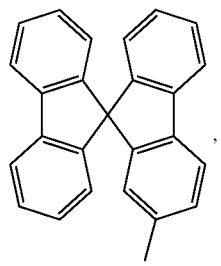

(Ar2-4)

wherein $Ar^3$ is represented by any one of Formulas (Ar3-1) to (Ar3-8)

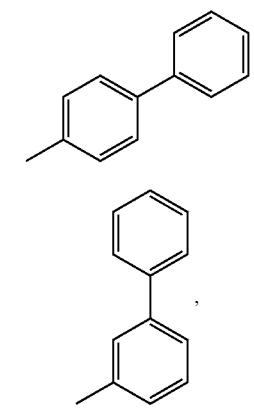

(Ar3-1)

(Ar3-2)

(Ar3-3)

(Ar3-4)

(Ar3-5)

(Ar3-6)

(Ar3-7)

(Ar3-8)

wherein j, m, and n separately represent 0 or 1, and wherein p represents 1 or 2.

2. The compound according to claim 1, wherein $Ar^1$ is any one of an unsubstituted phenanthryl group; an unsubstituted pyrenyl group; an unsubstituted triphenylenyl group; an unsubstituted chrysenyl group; an unsubstituted anthryl group; an unsubstituted tetracenyl group; a phenanthryl group substituted by a methyl group, an ethyl group, a propyl group, a pentyl group, a hexyl group, a phenyl group, or a biphenyl group; a pyrenyl group substituted by a methyl group, an ethyl group, a propyl group, a pentyl group, a hexyl group, a phenyl group, or a biphenyl group; a triphenylenyl group substituted by a methyl group, an ethyl group, a propyl group, a pentyl group, a hexyl group, a phenyl group, or a biphenyl group; a chrysenyl group substituted by a methyl group, an ethyl group, a propyl group, a pentyl group, a hexyl group, a phenyl group, or a biphenyl group; an anthryl group substituted by a methyl group, an ethyl group, a propyl group, a pentyl group, a hexyl group, a phenyl group, or a biphenyl group; and a tetracenyl group substituted by a methyl group, an ethyl group, a propyl group, a pentyl group, a hexyl group, a phenyl group, or a biphenyl group.

3. The compound according to claim 1,
wherein $Ar^1$ is represented by any one of Formulas (Ar1-1) to (Ar1-4)

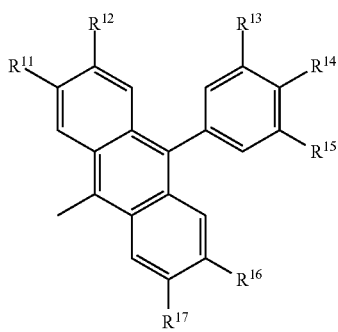
(Ar1-1)

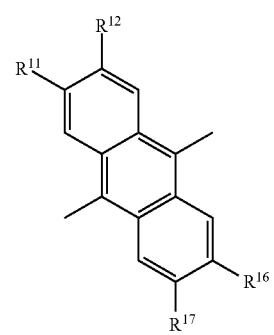
(Ar1-2)

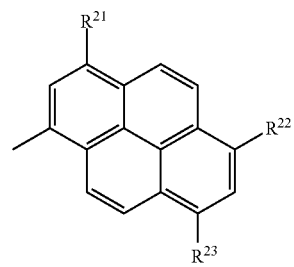
(Ar1-3)

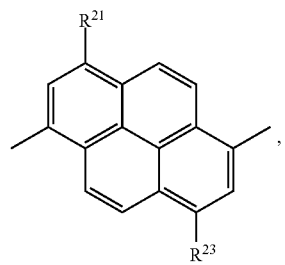
(Ar1-4)

wherein $R^{11}$ to $R^{17}$ and $R^{21}$ to $R^{23}$ separately represent a hydrogen atom or an alkyl group having 1 to 6 carbon atoms, and wherein p is 1 when $Ar^1$ is represented by Formula (Ar1-1) or (Ar1-3), and p is 2 when $Ar^1$ is represented by Formula (Ar1-2) or (Ar1-4).

4. The compound according to claim 1, wherein $\alpha^1$ to $\alpha^4$ are separately represented by any one of Formulas ($\alpha$-1) to ($\alpha$-3)

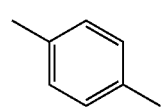
($\alpha$-1)

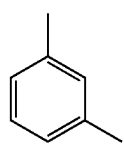
($\alpha$-2)

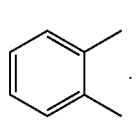
($\alpha$-3)

5. The compound according to claim 1, wherein $R^1$ to $R^8$ are separately represented by any one of Formulas (R-1) to (R-9)

(R-1)

(R-2)

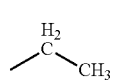
(R-3)

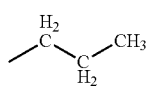
(R-4)

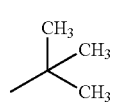
(R-5)

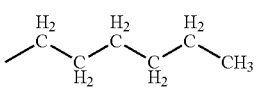
(R-6)

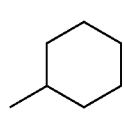
(R-7)

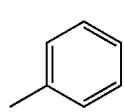
(R-8)

-continued (R-9)

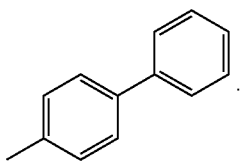

6. A light-emitting element comprising:
   a pair of electrodes; and
   a light-emitting layer including the compound according to claim 1 between the pair of electrodes.
7. A light-emitting device comprising the light-emitting element according to claim 6.
8. A compound represented by Formula (G2),

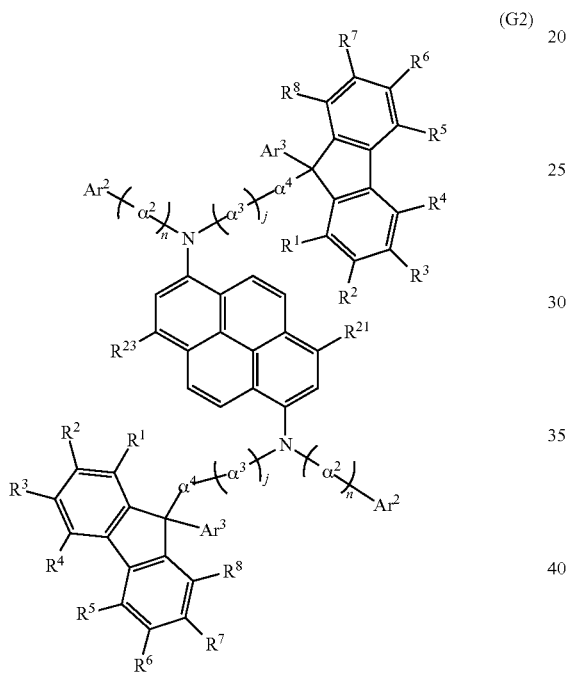

(G2)

wherein $R^1$ to $R^8$ separately represent any one of a hydrogen atom, an alkyl group having 1 to 6 carbon atoms, an unsubstituted phenyl group; an unsubstituted biphenyl group; a phenyl group substituted by a methyl group, an ethyl group, a propyl group, a pentyl group, a hexyl group, or a biphenyl group; and a biphenyl group substituted by a methyl group, an ethyl group, a propyl group, a pentyl group, a hexyl group, or a biphenyl group, wherein $R^{21}$ and $R^{23}$ separately represent a hydrogen atom or an alkyl group having 1 to 6 carbon atoms, wherein $\alpha^2$ to $\alpha^4$ separately represent an unsubstituted phenylene group or a phenylene group substituted by a methyl group, an ethyl group, a propyl group, a pentyl group, a hexyl group, a phenyl group, or a biphenyl group, wherein $Ar^2$ represents an unsubstituted aryl group having 6 to 13 carbon atoms forming a ring or an aryl group having 6 to 13 carbon atoms forming a ring substituted by a methyl group, an ethyl group, a propyl group, a pentyl group, a hexyl group, a phenyl group, or a biphenyl group, wherein $Ar^3$ represents an alkyl group having 1 to 6 carbon atoms or an unsubstituted aryl group having 6 to 12 carbon atoms, and wherein j and n separately represent 0 or 1.

9. The compound according to claim 8, wherein $\alpha^2$ to $\alpha^4$ are separately represented by any one of Formulas ($\alpha$-1) to ($\alpha$-3)

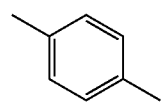

($\alpha$-1)

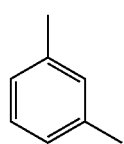

($\alpha$-2)

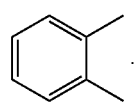

($\alpha$-3)

10. The compound according to claim 8, wherein $Ar^2$ is represented by any one of Formulas (Ar2-1) to (Ar2-6)

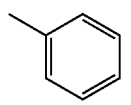

(Ar2-1)

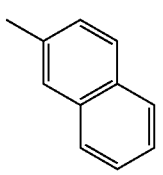

(Ar2-2)

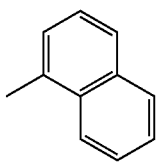

(Ar2-3)

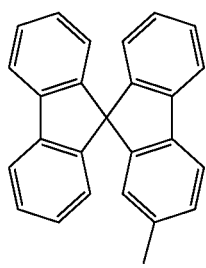

(Ar2-4)

-continued (Ar2-5)
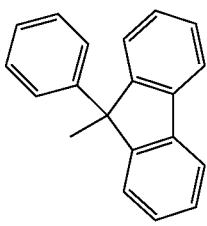

(Ar2-6)
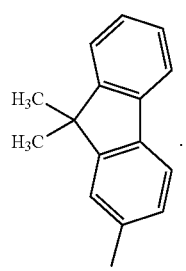

11. The compound according to claim 8, wherein $Ar^3$ is represented by any one of Formulas (Ar3-1) to (Ar3-8)

(Ar3-1)
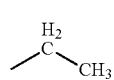

(Ar3-2)
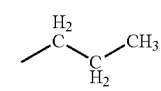

(Ar3-3)
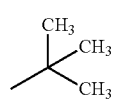

(Ar3-4)
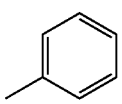

(Ar3-5)
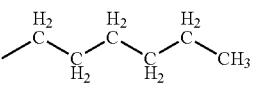

(Ar3-6)
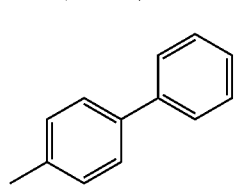

(Ar3-7)

(Ar3-8)
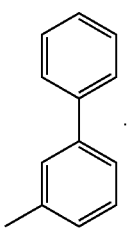

12. The compound according to claim 8, wherein $R^1$ to $R^8$ are separately represented by any one of Formulas (R-1) to (R-9)

(R-1)

(R-2)

(R-3)
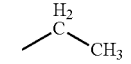

(R-4)
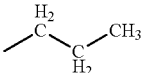

(R-5)
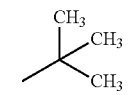

(R-6)
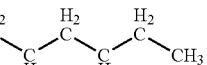

(R-7)
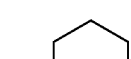

(R-8)
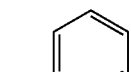

(R-9)

13. A light-emitting element comprising:
a pair of electrodes; and
a light-emitting layer including the compound according to claim 8 between the pair of electrodes.

14. A light-emitting device comprising the light-emitting element according to claim 13.

15. An electronic device comprising the light-emitting device according to claim 14.

16. A lighting device comprising the light-emitting device according to claim 14.

17. A light-emitting element comprising:
a first electrode;
a first light-emitting unit over the first electrode, the first light-emitting unit comprising a first light-emitting layer;
a second light-emitting unit over the first light-emitting unit, the second light-emitting unit comprising a second light-emitting layer;
a charge-generation layer between the first light-emitting unit and the second light-emitting unit; and
a second electrode over the second light-emitting unit,
wherein at least one of the first light-emitting layer and the second light-emitting layer comprises the compound according to claim 9 between the first electrode and the second electrode.

18. The light-emitting element according to claim 17, wherein the charge-generation layer is configured to inject electrons into one of the first light-emitting layer and the second light-emitting layer and to inject holes into the other of the first light-emitting layer and the second light-emitting layer.

19. The light-emitting element according to claim 17,
wherein the charge-generation layer comprises a first layer injecting holes and a second layer injecting electrons,
wherein the first layer comprises an acceptor substance and a substance having a hole-transport property, and
wherein the second layer comprises a donor substance and a substance having an electron-transport property.

20. The light-emitting element according to claim 19,
wherein the acceptor substance is any one of vanadium oxide, molybdenum oxide, and tungsten oxide,
wherein the substance having the hole-transport property is any one of an aromatic amine compound, a carbazole derivative, an aromatic hydrocarbon, an oligomer, a dendrimer, and a polymer,
wherein the donor substance is any one of an oxide of an alkali metal, an alkaline earth metal, a rare-earth metal, and a metal that belongs to Group 13, and
wherein the substance having the electron-transport property is a metal complex or a heterocyclic compound.

* * * * *

UNITED STATES PATENT AND TRADEMARK OFFICE
CERTIFICATE OF CORRECTION

PATENT NO. : 9,553,273 B2  
APPLICATION NO. : 14/161847  
DATED : January 24, 2017  
INVENTOR(S) : Kaori Ogita et al.

Page 1 of 11

It is certified that error appears in the above-identified patent and that said Letters Patent is hereby corrected as shown below:

In the Specification

Column 21, Lines 33-65, replace

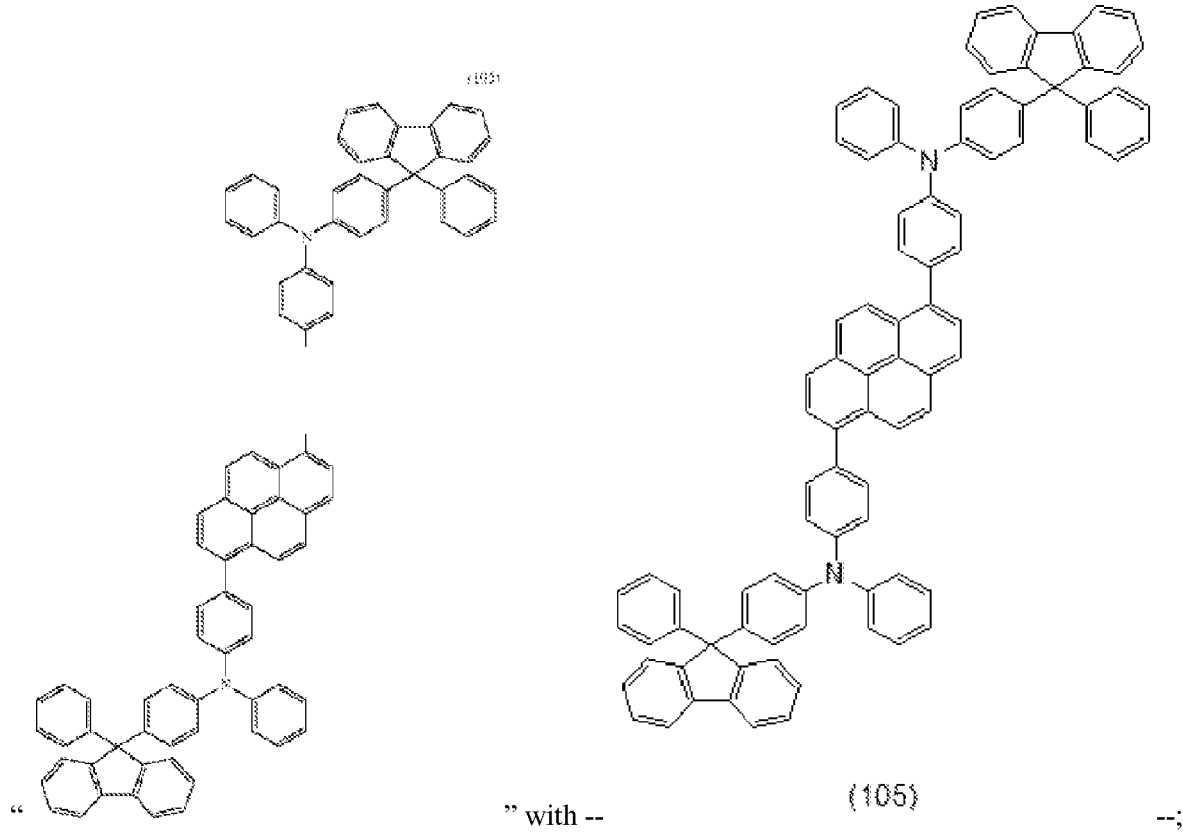

" with -- --;

Signed and Sealed this  
Twenty-seventh Day of June, 2017

Joseph Matal  
*Performing the Functions and Duties of the*  
*Under Secretary of Commerce for Intellectual Property and*  
*Director of the United States Patent and Trademark Office*

Column 41, Lines 1-44, replace
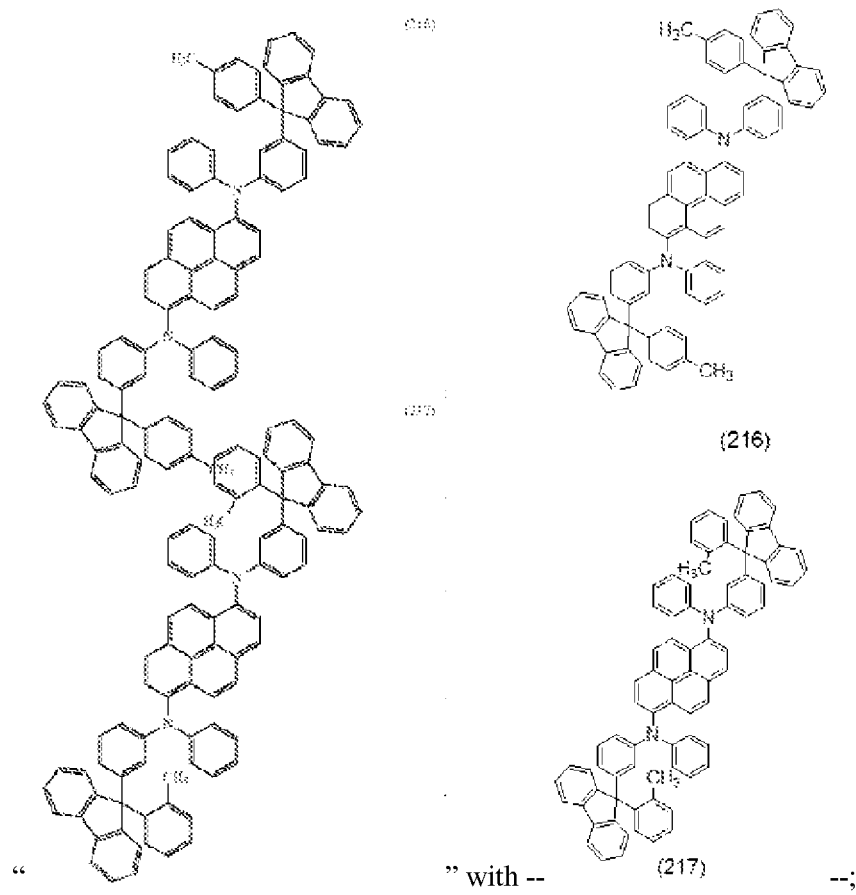
" with -- (217) --;

CERTIFICATE OF CORRECTION (continued)
U.S. Pat. No. 9,553,273 B2

Column 46, Lines 53-65, and Column 47, Lines 1-21, replace

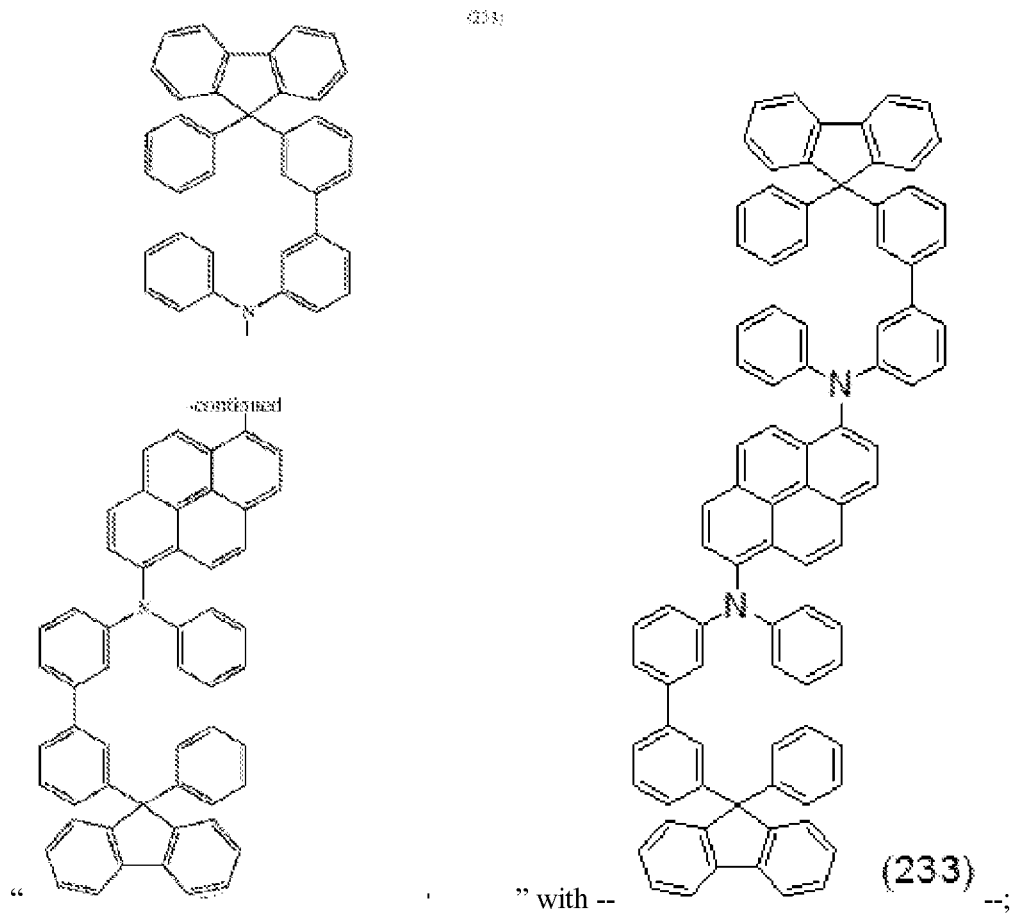

CERTIFICATE OF CORRECTION (continued)
U.S. Pat. No. 9,553,273 B2

Column 47, Lines 54-65, and Column 47, Lines 1-23, replace

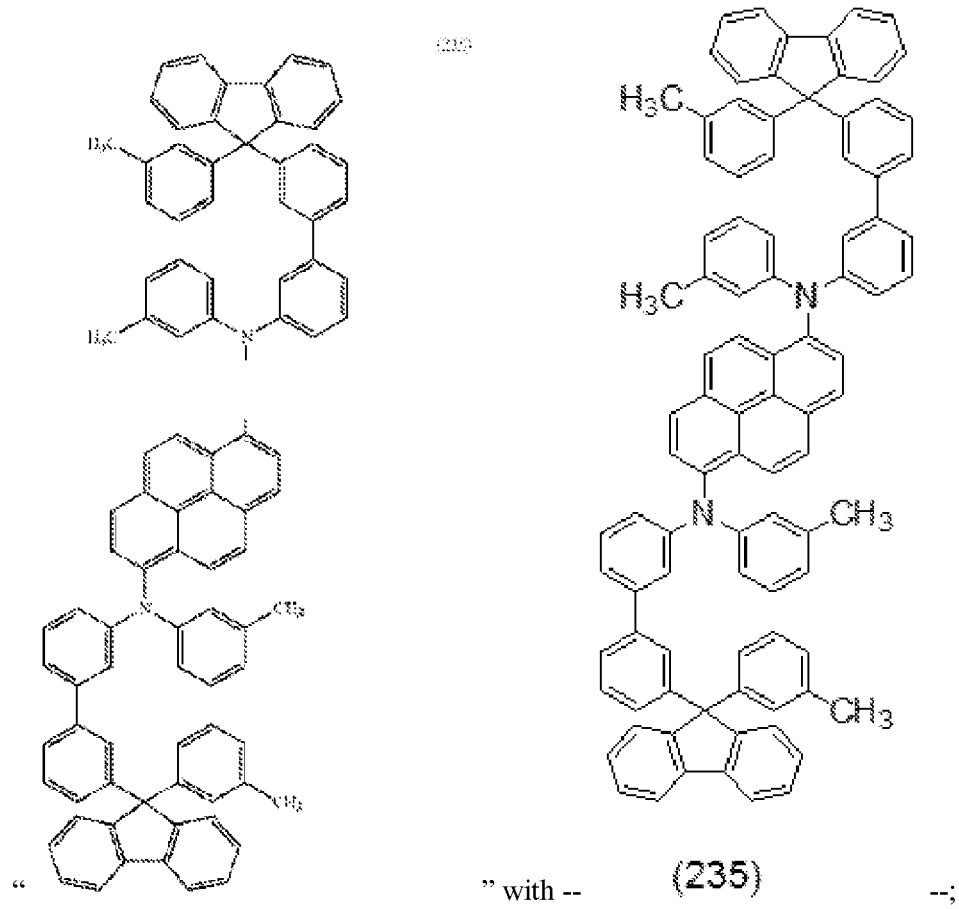

" with --    (235)    --;

CERTIFICATE OF CORRECTION (continued)
U.S. Pat. No. 9,553,273 B2

Column 48, Lines 27-65, replace

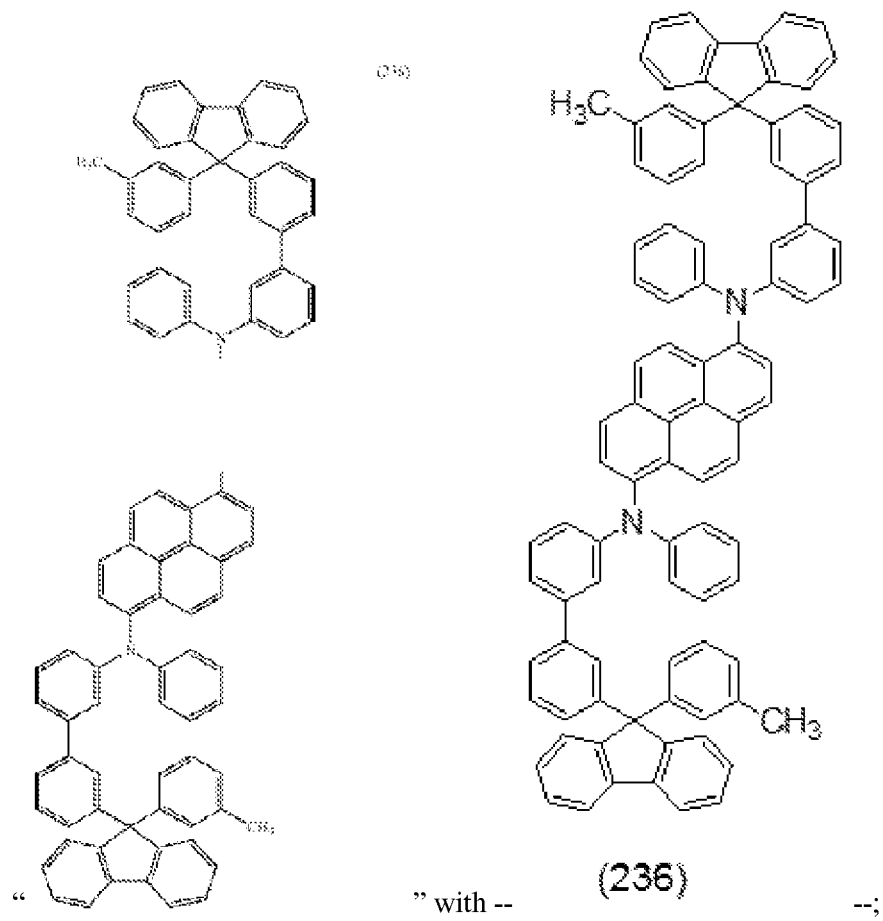

" with -- (236) --;

CERTIFICATE OF CORRECTION (continued)

U.S. Pat. No. 9,553,273 B2

Column 49, Lines 1-35, replace

" 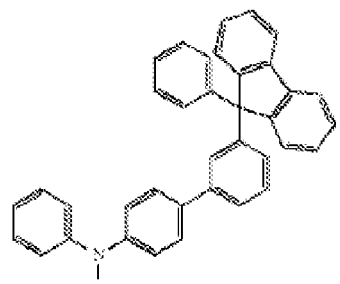 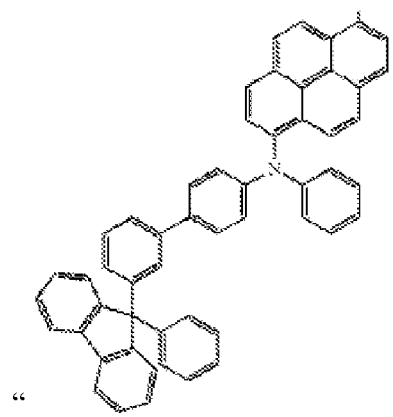 " with

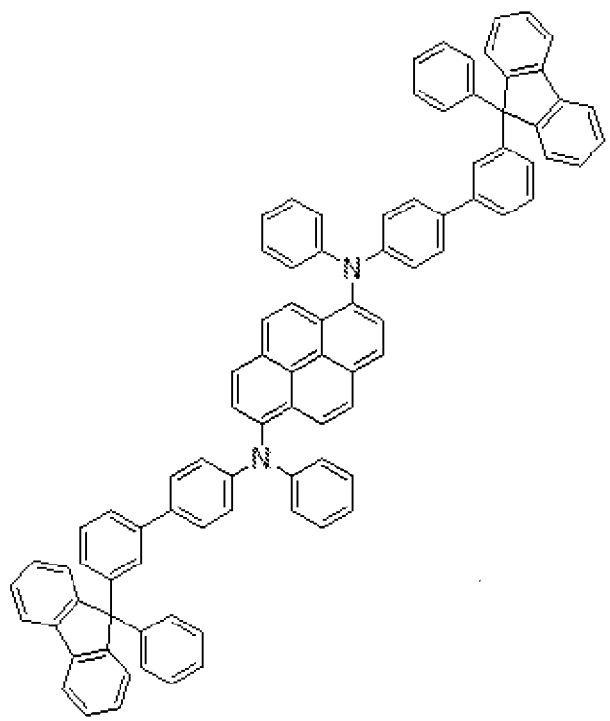

-- (237) --;

Column 49, Lines 39-65, replace
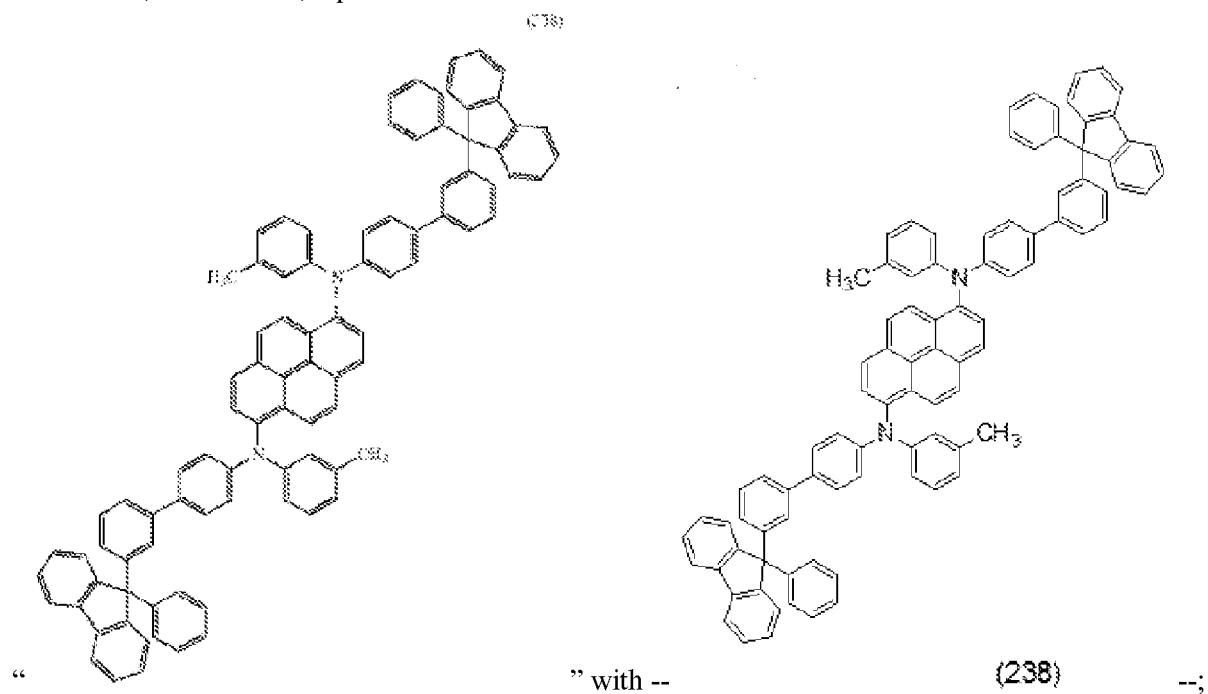
" with --
Column 50, Lines 1-35, replace
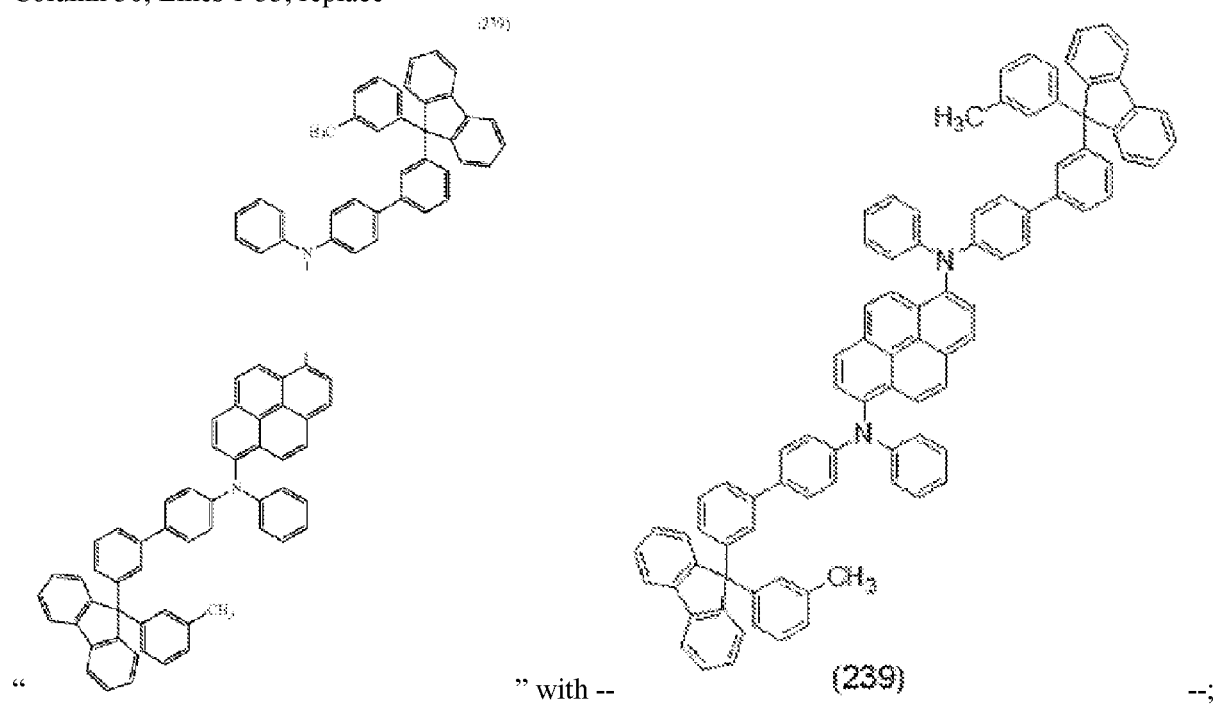
" with --

CERTIFICATE OF CORRECTION (continued)
U.S. Pat. No. 9,553,273 B2

Column 50, Lines 39-65, replace

" 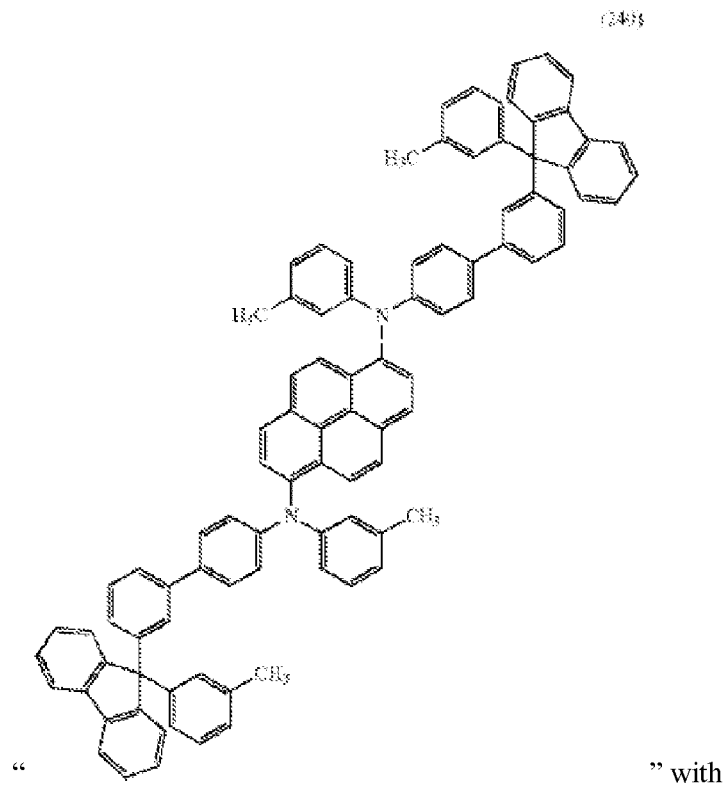 " with

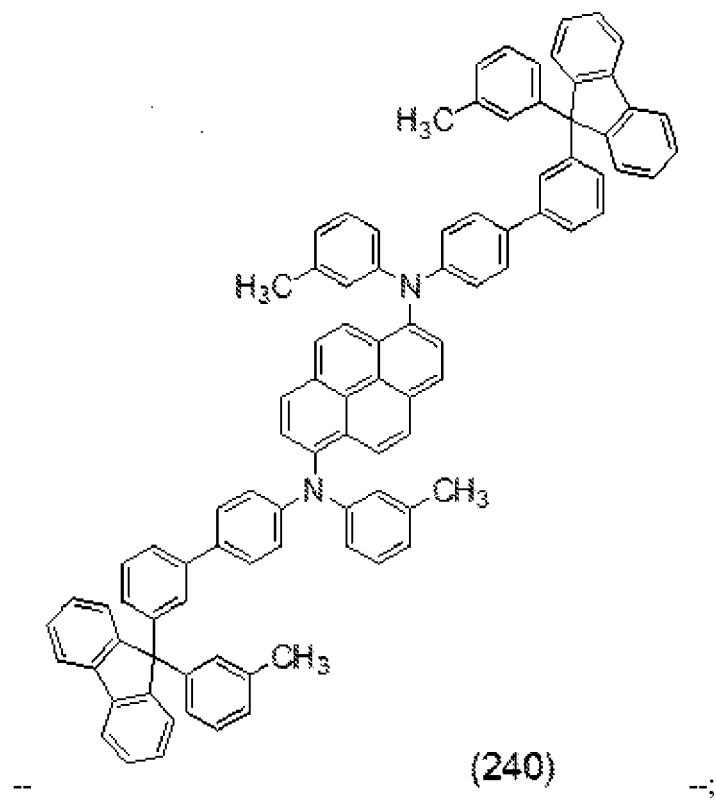

-- (240) --;

CERTIFICATE OF CORRECTION (continued)
U.S. Pat. No. 9,553,273 B2

Column 51, Lines 1-47, replace

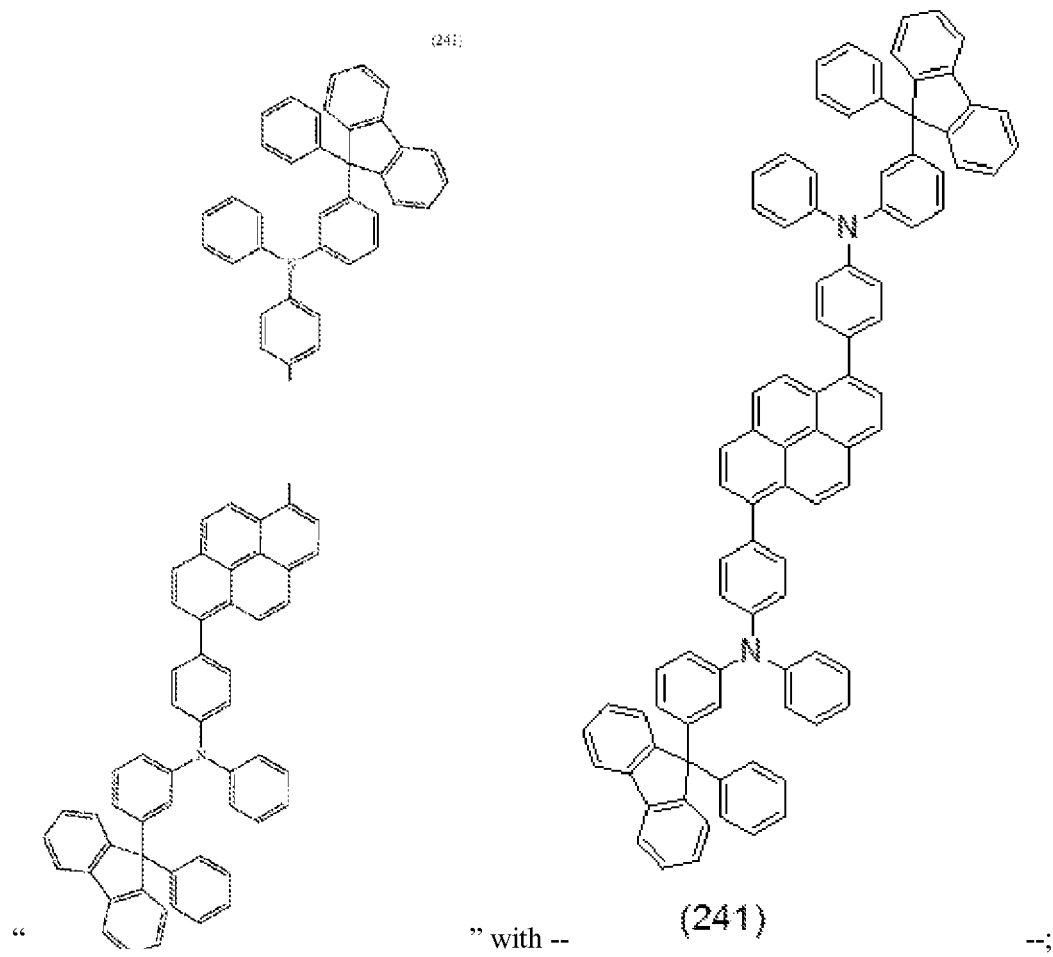

Column 51, Lines 51-65, and Column 52, Lines 1-24, replace

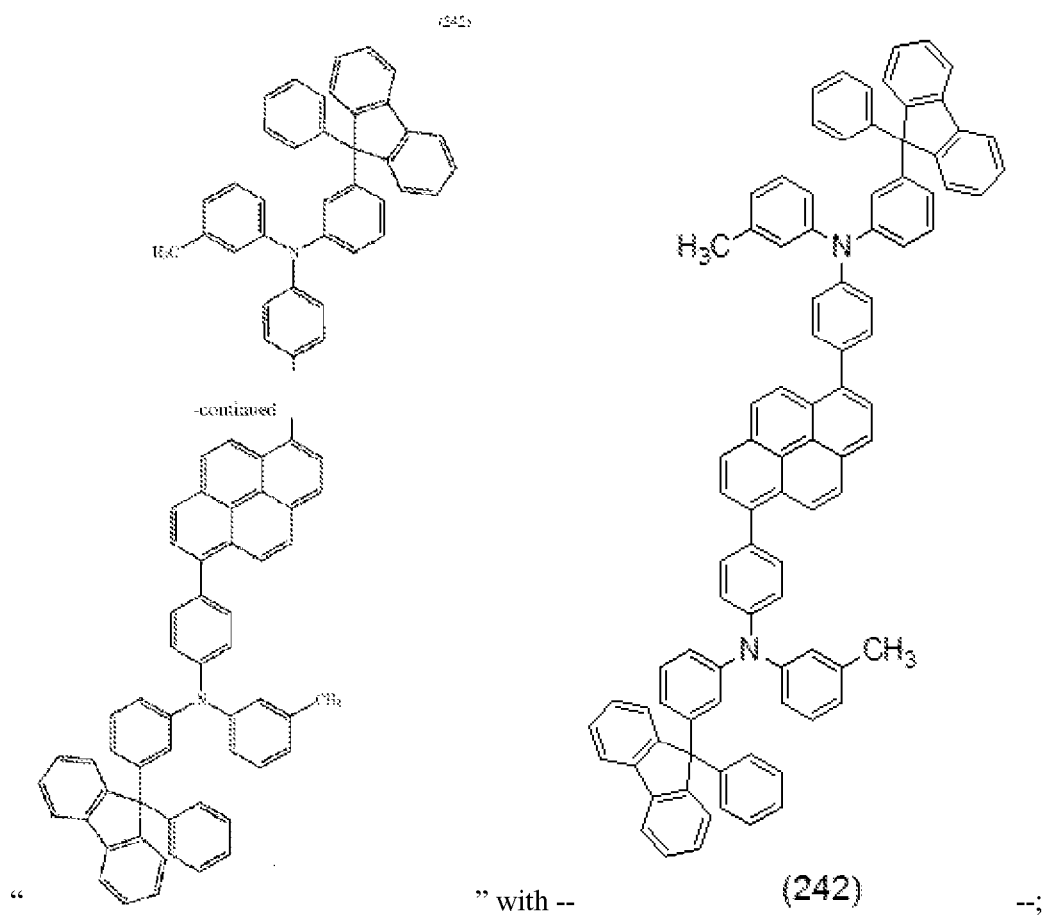

" with --            (242)          --;

Column 57, Line 32, replace "4-[N-" with --4-[N'- --;

Column 57, Line 32, replace ")-N-" with --)-N'- --;

Column 58, Line 31, replace "(2-naphthyeanthracene" with --(2-naphthyl)anthracene--;

Column 59, Line 54, replace "(2-benzothiaxolyephenolato" with --(2-benzothiazolyl)phenolato--;

Column 60, Line 6, replace "-diyediphenanthrene" with -- -diyl)diphenanthrene--;

Column 60, Line 7, replace "-diyediphenanthrene" with -- -diyl)diphenanthrene--;

Column 60, Line 9, replace "-triyetripyrene" with -- -triyl)tripyrene--;

Column 77, Line 66, after "spectrometry is" insert --:--;

Column 78, Line 29, after "45 nm" insert --.--;

CERTIFICATE OF CORRECTION (continued)
U.S. Pat. No. 9,553,273 B2

Column 88, Line 49, replace "1,6FLPAPm" with --1,6FLPAPrn--;

Column 92, Line 1, replace "1,6FLPAPm" with --1,6FLPAPrn--;

Column 94, Line 54, replace "1,6FLPAPm" with --1,6FLPAPrn--;

Column 103, Line 6, replace "NMR" with --$^1$H NMR--;

Column 107, Line 40, replace "phenyl]-diphenyl" with --phenyl]-N, N'-diphenyl--;

Column 128, Line 59, replace "the NMR" with --the $^1$H NMR--;

Column 133, Line 30, after "vs" insert --.--;

Column 137, Line 8, replace "N' b is [" with --N'-bis[--;

Column 144, Line 11, replace "the NMR" with --the $^1$H NMR--;

Column 147, Line 53, replace "NMR" with --$^1$H NMR--;

Column 147, Line 58, replace "the NMR" with --the $^1$H NMR--; and

In the Claims

Column 156, Line 66, in Claim 17, replace "9" with --8--.